US010947289B2

(12) United States Patent
Iwamoto et al.

(10) Patent No.: US 10,947,289 B2
(45) Date of Patent: Mar. 16, 2021

(54) GLYCO-MODIFIED ATRIAL NATRIURETIC PEPTIDE

(71) Applicant: Daiichi Sankyo Company, Limited, Tokyo (JP)

(72) Inventors: Mitsuhiro Iwamoto, Tokyo (JP); Takahiro Yamaguchi, Tokyo (JP); Yutaka Mori, Tokyo (JP); Keiji Saito, Tokyo (JP); Takeshi Honda, Tokyo (JP); Takahiro Nagayama, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 21 days.

(21) Appl. No.: 14/806,487

(22) Filed: Jul. 22, 2015

(65) Prior Publication Data
US 2016/0017015 A1  Jan. 21, 2016

Related U.S. Application Data

(63) Continuation of application No. PCT/JP2014/051357, filed on Jan. 23, 2014.

(30) Foreign Application Priority Data

Jan. 23, 2013 (JP) .............................. JP2013-010612

(51) Int. Cl.
| A61K 47/54 | (2017.01) |
| C07K 14/58 | (2006.01) |
| A61K 38/00 | (2006.01) |
| A61K 47/65 | (2017.01) |
| A61K 47/60 | (2017.01) |
| A61K 38/22 | (2006.01) |

(52) U.S. Cl.
CPC .............. *C07K 14/58* (2013.01); *A61K 38/00* (2013.01); *A61K 38/2242* (2013.01); *A61K 47/549* (2017.08); *A61K 47/60* (2017.08); *A61K 47/65* (2017.08)

(58) Field of Classification Search
None
See application file for complete search history.

(56) References Cited

U.S. PATENT DOCUMENTS

| 2003/0036181 | A1* | 2/2003 | Okkels | ............... | A61K 38/24 435/184 |
| 2009/0306349 | A1* | 12/2009 | Hutchins | ............ | C07K 16/2863 530/391.1 |
| 2010/0062973 | A1* | 3/2010 | Frank | ............... | A61K 47/61 514/11.4 |
| 2010/0305301 | A1 | 12/2010 | Yeh et al. | | |
| 2013/0059780 | A1* | 3/2013 | DeFrees | ............... | C07K 14/605 514/11.7 |

FOREIGN PATENT DOCUMENTS

| JP | H07-059587 A | 3/1995 |
| JP | 2002-509898 A | 4/2002 |
| JP | 2005-523723 A | 8/2005 |
| JP | 2010-530222 A | 9/2010 |
| JP | 2012-530119 A | 11/2012 |
| WO | WO-99/49897 A1 | 10/1999 |
| WO | WO-03/093465 A1 | 11/2003 |
| WO | WO-2004/047871 A2 | 6/2004 |
| WO | WO-2006/076471 A2 | 7/2006 |
| WO | WO-2008/154226 A1 | 12/2008 |
| WO | WO-2009/142307 A1 | 11/2009 |
| WO | WO-2010/146362 A2 | 12/2010 |

OTHER PUBLICATIONS

Kenny, A. John and Stephenson, Sally L., "Role of endopeptdiase-24-11 in the inactivation of atrial natriuretic peptide." FEBS (1988) 232(1) p. 1-8.*
Zhang, Xiao-Lian, "ROles of glycans and glycopeptides in immune system and immune related diseases." Curr. Med. Chem. (2006) 13(10) p. 1141-1147.*
Tomabechi, Yusuke et al, "Chemo-enzymatic synthesis of glycosylated insulin using a glcnac tag." Bioorg. Med. Chem. (2010) 18 p. 1259-1264.*
Kitov, Pavel I and Bundle, David R.; "On the nature of the multivalency effect: a tehrmodynamic model." J. Am. Chem. Soc. (2003) 125 p. 16271-16284.*
Haubner, Roland et al, "Glyosylated rgd-containing peptides: tracer for tumor trageting and angiogenesis imaging with improved biokinetics." J. Nuc. Med. (2001) 42 p. 326-336.*
Yamamoto, Kenji et al, "Chemoenzymatic synthesis of a novel glycopeptide using a microbial endoglycosidase." Carb. Res. (1998) 305(2) p. 415-422.*
Baudyš, Miroslav et al, "Physical stabilization of insulin by glycosylation." J. Pharmaceut. Sci. (1995) 84(1) p. 28-33.*
Gregoriadis, G. et al, "Polysialic acids: potential in drug delivery." FEBS (1993) 315(3) p. 271-276.*
Kubetzko, Susanne et al, "Protein pegylation decreases observed target association rates via a dual blocking mechanism." Mol. Pharmacol. (2005) 68(5) p. 1439-1454.*
Tsuyuki, Hideaki et al, "Purification and characterization of streptomyces griseus metalloendopeptidases I and II." J. Biochem. (1991) 110 p. 339-344.*
Lee, S. et al; "Pegylated glucagon like peptide 1 displays preserved effects on insulin release in isolated pancreatic islets and improved biological activity in db/db mice." Diabetologia (2006) 49 p. 1608-1611.*

(Continued)

*Primary Examiner* — Fred H Reynolds
(74) *Attorney, Agent, or Firm* — Foley & Lardner LLP

(57) ABSTRACT

The present invention provides a modified atrial natriuretic peptide that exhibits prolonged duration in blood and maintains cGMP elevating activity. The present invention provides a modified peptide in which at least one sugar substance is linked directly through a glycosidic bond or via a linker structure to at least one hANP peptide, or a pharmaceutically acceptable salt thereof, a medicament comprising the modified peptide or the salt thereof as an active ingredient, etc.

12 Claims, 1 Drawing Sheet
Specification includes a Sequence Listing.

(56) References Cited

OTHER PUBLICATIONS

Veronese, Francesco M. et al, "Branched and linear poly(ehtylene glycol): influence of the polymer structure on enzymological, pharmacokinetic, and immunological properteis of protein conjugates." J. Bioactive Compat. Poly (1997) 12 p. 197-208.*

Jiang, Jingjing et al, "Effect of sialyated o-glycans in pro-brain natriuretic peptide stability." Clin. Chem. (2010) 56(6) p. 959-966.*

Oefner, Christian et al, "Structure of human neutral endopeptidase (neprilysin) complexed with phosphorannidon." J. Mol. Biol. (2000) 296 p. 341-349.*

Turner, Anthony J. et al, "THe neprilysin(nep) family of zinc metalloendopeptidases: genomics and function." BioEssays (2001) 23 p. 261-269.*

Ceaglio et al., "Highly glycosylated human alpha interferon: An insight into a new therapeutic candidate," Journal of Biotechnology, vol. 146, 2010, pp. 74-83.

Chang et al., "Subtiligase: A tool for semisynthesis of proteins" Proc. Natl. Acad. Sci., vol. 91, 1994, pp. 12544-12548.

Flintegaard et al., "N-Glycosylation Increases the Circulator Half-Life of Human Growth Hormone," Endocrinology, vol. 151, No. 11, 2010, pp. 5326-5336.

Mezo et al., "Atrial Natriuretic Peptide-Fc, ANP-Fc, Fusion Proteins: Semisynthesis, In Vitro Activity, and Pharmacokinetics in Rats," Bioconjugate Chemistry, vol. 23, 2012, pp. 518-526.

Nesher et al., "Reversible Pegylation Prolongs the Hypotensive Effect of Atrial Natriuretic Peptide", Biconjugate Chemistry, vol. 19, 2008, pp. 342-348.

Nishi et al., "Qualitative Improvement of Therapeutic Glycoproteins by Glycotechnology," Trends in Glycoscience and Glycotechnology, vol. 4, No. 18, Jul. 1992, pp. 336-344.

Tomabechi et al., "Chemo-enzymatic synthesis of glycosylated insulin using a GlcNAc tag," Bioorganic & Medicinal Chemistry, vol. 18, 2010, pp. 1259-1264.

International Search Report issued in PCT/JP2014/051357 dated Apr. 15, 2015.

Extended European Search Report issued in Application No. 14743069.8 dated Jul. 21, 2016.

The Extended European Search Report issued in Application No. 14743069.8 dated Jul. 21, 2016.

\* cited by examiner

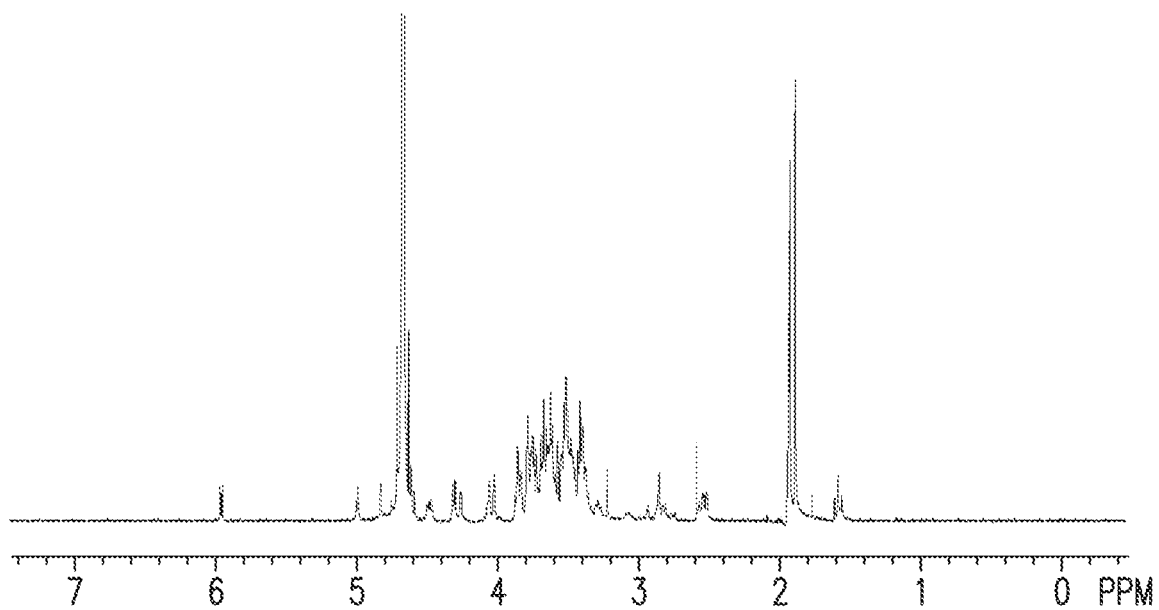

GLYCO-MODIFIED ATRIAL NATRIURETIC PEPTIDE

TECHNICAL FIELD

The present invention relates to a glyco-modified atrial natriuretic peptide that has a glycochain linkage and exhibits an improved duration time in blood, a medicament comprising the modified peptide as an active ingredient, etc.

BACKGROUND ART

Atrial natriuretic peptides are biologically active peptides having a vasodilatory effect, a diuretic effect, a cell growth inhibitory effect, a venous return lowering effect, and a sympathetic activity inhibitory effect. Native hANP loses its activity upon cleavage by neutral endopeptidase (NEP) in blood and therefore has a short half-life in blood. For such reasons, the native hANP needs to be continuously administered by drip infusion or the like in current clinical practice.

Examples of attempts to prolong the half-lives in blood of such biologically active peptides having a short half-life in blood include various methods such as utilization of sustained-release formulations, amino acid substitution or modification, fusion peptides containing linked albumin, an immunoglobulin Fc portion, or the like, and modified peptides containing an added polymer (e.g., PEG). When applying the biologically active peptides to medicaments for reason of their biological activity, it is required to prolong their half-lives in blood while maintaining the biological activity possessed by the peptide at pharmacologically necessary levels. Attempts to apply such biologically active peptides having a prolonged half-life in blood to medicaments have been made on many peptides.

Non Patent Literature 1 (Proc. Natl. Acad. Sci. USA 1994, 91, 12544-12548) and Non Patent Literature 2 (Bioconjugate Chem. 2008, 19, 342-348) disclose a modified peptide in which PEG is bonded to atrial natriuretic peptide (ANP).

Patent Literature 1 (WO2006/076471 A2) discloses a modified peptide in which PEG is bonded to brain natriuretic peptide (BNP).

Patent Literature 2 (WO2008/154226 A1) and Non Patent Literature 3 (Bioconjugate Chem. 2012, 23, 518-526) describe a fusion protein in which an immunoglobulin Fc fragment is bonded to ANP.

Patent Literature 3 (WO2004/047871 (A2,A3) and Patent Literature 4 (WO2009/142307 A1) disclose a mutant having an altered amino acid sequence of ANP.

However, these techniques are not always successful. In particular, it is not possible to predict whether or not a sufficient duration time in blood and maintenance of activity necessary for pharmacological effects can both be attained, unless a large number of tests are actually conducted.

CITATION LIST

Patent Literature

Patent Literature 1: International Publication No. WO2006/076471
Patent Literature 2: International Publication No. WO2008/154226
Patent Literature 3: International Publication No. WO2004/047871
Patent Literature 4: International Publication No. WO2009/142307

Non Patent Literature

Non Patent Literature 1: Proc. Natl. Acad. Sci. USA 1994, 91, 12544-12548
Non Patent Literature 2: Bioconjugate Chem. 2008, 19, 342-348)
Non Patent Literature 3: Bioconjugate Chem. 2012, 23, 518-526

SUMMARY OF INVENTION

Technical Problem

An object of the present invention is to find a modified peptide that exhibits a prolonged duration time in blood compared with native human atrial natriuretic peptide (hANP) and maintains cGMP elevating activity.

Solution to Problem

The present inventors have conducted diligent studies on the modification of hANP so as to prolong the duration time in blood and to maintain the cGMP elevating activity. As a result, the present inventors have completed the present invention by finding, for example, that modified peptides, in which a glycochain is bonded to hANP by various methods, elevated the intracellular cGMP concentration of GC-A receptor-expressing cells, exhibited a prolonged duration time in blood when administered to mice, and persistently elevated the cGMP concentration in blood even 60 minutes or later after the administration of the modified peptide.

The present invention provides the following:
(1) A modified peptide in which at least one sugar substance is linked directly through a glycosidic bond or via a linker structure to at least one hANP peptide, or a pharmaceutically acceptable salt thereof.
(2) The modified peptide according to (1) or a pharmaceutically acceptable salt thereof, wherein the sugar substance is linked directly through a glycosidic bond or via a linker structure to at least one of the N terminus of the hANP peptide, the C terminus of the hANP peptide, and the side chain of at least one amino acid constituting the peptide.
(3) The modified peptide according to (1) or a pharmaceutically acceptable salt thereof, wherein the hANP peptide is hANP(1-28), hANP(2-28), hANP(3-28), hANP(1-27), hANP(2-27), or hANP(3-27).
(4) The modified peptide according to (1) or a pharmaceutically acceptable salt thereof, wherein the sugar substance is selected from at least one type of monosaccharide, disaccharide, trisaccharide, and glycochain of 4 or more monosaccharides bonded through glycosidic bonds, and when a plurality of sugar substances are contained in one molecule, the sugar substances may be the same as or different from each other.
(5) The modified peptide according to (1) or a pharmaceutically acceptable salt thereof, wherein the sugar substance is a glycochain of 4 or more monosaccharides bonded through glycosidic bonds.
(6) The modified peptide according to (5) or a pharmaceutically acceptable salt thereof, wherein the sugar substance is a glycoprotein-derived N-linked glycochain or O-linked glycochain, or an altered glycochain thereof.
(7) The modified peptide according to (6) or a pharmaceutically acceptable salt thereof, wherein the sugar substance is an N-linked glycochain comprising a glycochain structure represented by the following formula, or a glycochain altered at the reducing end thereof:

[Formula 1]

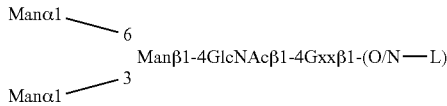

wherein Gxx is GlcNAc, Glc, or Man (hereinafter, glycochains having the above structure are referred to as "AG(5)", "AG(5-Glc)", and "AG(5-Man)", respectively, according to the type of Gxx), and "O/N-L" represents binding to the linker structure or the hANP peptide through an O-glycosidic bond or a N-glycosidic bond.
(8) The modified peptide according to (7) or a pharmaceutically acceptable salt thereof, wherein the sugar substance is a glycochain comprising a glycochain structure represented by the following formula:

[Formula 2]

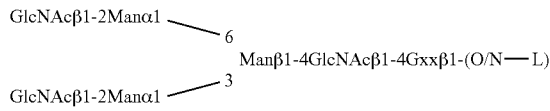

wherein Gxx is GlcNAc, Glc, or Man (hereinafter, glycochains having the above structure are referred to as "AG(7)", "AG(7-Glc)", and "AG(7-Man)", respectively, according to the type of Gxx), and "O/N-L" represents binding to the linker structure or the hANP peptide through an O-glycosidic bond or a N-glycosidic bond. (9) The modified peptide according to (8) or a pharmaceutically acceptable salt thereof, wherein the sugar substance is a glycochain comprising a glycochain structure represented by the following formula:

[Formula 3]

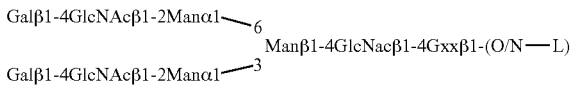

wherein Gxx is GlcNAc, Glc, or Man (hereinafter, glycochains having the above structure are referred to as "AG(9)", "AG(9-Glc)", and "AG(9-Man)", respectively, according to the type of Gxx), and "O/N-L" represents binding to the linker structure or the hANP peptide through an O-glycosidic bond or a N-glycosidic bond.
(10) The modified peptide according to (9) or a pharmaceutically acceptable salt thereof, wherein the sugar substance is a glycochain comprising a glycochain structure represented by the following formula:

[Formula 4]

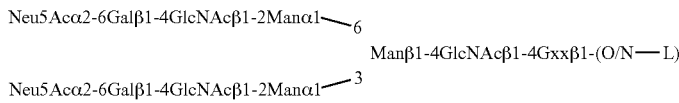

wherein Gxx is GlcNAc, Glc, or Man (hereinafter, glycochains having the above structure are referred to as "SG", "SG(Glc)", and "SG(Man)", respectively, according to the type of Gxx), and "O/N-L" represents binding to the linker structure or the hANP peptide through an O-glycosidic bond or a N-glycosidic bond.

(11) The modified peptide according to any of (7) to (10) or a pharmaceutically acceptable salt thereof, wherein in the sugar substance, Gxx is GlcNAc.

(12) The modified peptide according to (11) or a pharmaceutically acceptable salt thereof, wherein the sugar substance is SG.

(13) The modified peptide according to (1) or a pharmaceutically acceptable salt thereof, wherein 10 or fewer sugar substances are linked to one hANP peptide.

(14) The modified peptide according to (1) or a pharmaceutically acceptable salt thereof, wherein 1, 2, or 3 sugar substances are linked to one hANP peptide,

(15) The modified peptide according to (1) or a pharmaceutically acceptable salt thereof, wherein each molecule of the modified peptide contains a divalent or higher hANP peptide.

(16) The modified peptide according to (3) or a pharmaceutically acceptable salt thereof, wherein the sugar substance is linked via a linker structure to the hANP peptide, and the linker structure is a chemical structure that has a linking chain of 3 or more atoms and is bonded at least one site to the reducing end of the sugar substance through a glycosidic bond and bonded at at least one site to the hANP peptide.

(17) The modified peptide according to (16) or a pharmaceutically acceptable salt thereof, wherein the sugar substance is linked to either the N terminus or the C terminus, or both, of the hANP peptide via a linker structure.

(18) The modified peptide according to (17) or a pharmaceutically acceptable salt thereof, wherein the linker structure is a structure having a linking chain of 15 or fewer atoms.

(19) The modified peptide according to (18) or a pharmaceutically acceptable salt thereof, wherein the modified peptide is SG-hANP(1-28) (compound 2-1), hANP(1-28)-SG (compound 2-2), SG-hANP(1-28)-SG (compound 2-7), AG(9)-hANP(1-28) (compound 2-10), SG-triazole-hANP (1-28) (compound 2-12), SG-thioacetamide-hANP(1-28) (compound 2-25), or AG(5)-hANP(1-28) (compound 2-26), or is derived from any of these modified peptides by the replacement of the sugar substance with SG, SG(Glc), SG(Man), AG(5), AG(5-Glc), AG(5-Man), AG(7), AG(7-Glc), AG(7-Man), AG(9), AG(9-Glc), AG(9-Man), or GlcNAc and/or the replacement of the hANP peptide with hANP(1-28), hANP(2-28), hANP(3-28), hANP(1-27), hANP(2-27), or hANP(3-27).

(20) The modified peptide according to (16) or a pharmaceutically acceptable salt thereof, wherein the linker structure comprises at least one structure selected from a polyoxyalkylene chain, an amino acid, and an oligopeptide chain consisting of 2 or more amino acids.

(21) The modified peptide according to (20) or a pharmaceutically acceptable salt thereof, wherein the polyoxyalkylene chain, the amino acid, and/or the oligopeptide chain contained in the linker structure is bonded through an amide bond to the N terminus and/or the C terminus of the hANP peptide.

(22) The modified peptide according to (21) or a pharmaceutically acceptable salt thereof, wherein the polyoxyalkylene chain is PEG.

(23) The modified peptide according to (21) or a pharmaceutically acceptable salt thereof, wherein the modified peptide is SG-PEG(3)-(SG-)Asn-hANP(1-28) (compound 2-16), AG(9)-(AG(9)-)Asn-PEG(3)-hANP(1-28) (compound 2-21), AG(7)-(AG(7)-)Asn-PEG(3)-hANP(1-28) (compound 2-22), SG-PEG(3)-hANP(1-28)-PEG(3)-SG (compound 2-24), SG-(SG-)Asn-PEG(11)-hANP(1-28) (compound 2-27), SG-(SG-)Asn-PEG(11)-PEG(11)-hANP(1-28) (compound 2-28), SG-PEG(3)-hANP(1-28) (compound 2-29), SG-PEG(11)-hANP(1-28) (compound 2-30), SG-*(SG-)Gln-Mal-PEG(3)-hANP(1-28) (compound 2-31), SG-(SG-)Gln-PEG(3)-Mal-hANP(1-28) (compound 2-32), SG-(SG-)Asn-(Ser-Gly)3-hANP(1-28) (compound 2-36), or SG-(SG-)Asn-Gly$_6$-hANP(1-28) (compound 2-37), or is derived from any of these modified peptides by the replacement of the sugar substance with SG, SG(Glc), SG(Man), AG(5), AG(5-Glc), AG(5-Man), AG(7), AG(7-Glc), AG(7-Man), AG(9), AG(9-Glc), AG(9-Man), or GlcNAc and/or the replacement of the hANP peptide with hANP(1-28), hANP(2-28), hANP(3-28), hANP(1-27), hANP(2-27), or hANP(3-27).

(24) The modified peptide according to (20) or a pharmaceutically acceptable salt thereof, wherein the linker structure comprises at least one amino acid having a functional group on the side chain selected from an amino acid having an amino group on the side chain, an amino acid having SH on the side chain, an amino acid having a carboxyl group on the side chain, an amino acid having a hydroxy group on the side chain, and an amino acid having phenol on the side chain and is linked at the side chain of the amino acid having a functional group on the side chain to the sugar substance or the hANP peptide.

(25) The modified peptide according to (24) or a pharmaceutically acceptable salt thereof, wherein the linker structure comprises at least one amino acid having an amino group on the side chain and has a structure of the following general formula (C) in which the sugar substance is linked to the side chain of the amino acid having an amino group on the side chain:

[Formula 5]

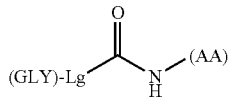

wherein GLY represents the sugar substance; Lg represents a structure on the glycochain side in the linker structure and may be linear or have two or more branches; GLY and L are bonded through an O- or N-glycosidic bond; when Lg is branched, there are the same number of GLY as the number of branch ends that are capable of being linked thereto; and N-(AA) represents a nitrogen atom derived from the side chain amino group of the amino acid having an amino group on the side chain.

(26) The modified peptide according to (25) or a pharmaceutically acceptable salt thereof, wherein the side chain amino group and the α amino group of the amino acid having an amino group on the side chain form amide bonds with the α carboxyl groups of other amino acids.

(27) The modified peptide according to (25) or (26) or a pharmaceutically acceptable salt thereof, wherein the amino acid having an amino group on the side chain is Lys.

(28) The modified peptide according to (27) or a pharmaceutically acceptable salt thereof, wherein the modified peptide is SG-(SG-)Lys-Gly-hANP(1-28) (compound 2-14), [(SG-)Cys-Gly]$_3$-hANP(1-28) (compound 2-15), SG-Mal-(SG-Mal-)Lys-[SG-Mal-(SG-Mal)Lys-]Lys-PEG(3)-hANP(1-28) (compound 2-19), [SG$_2$-Mal-(SG$_2$-Mal-)Lys-[SG$_2$-Mal-(SG$_2$-Mal-)-Lys-]Lys-PEG(3)-hANP(1-28) (compound 2-20), SG-Mal-(SG-Mal-)Lys-hANP(1-28) (compound 2-33), SG-thioacetamide-(SG-thioacetamide-)Lys-PEG-(3)-hANP(1-28) (compound 2-34), or SG-(SG-)Lys-PEG(3)-hANP(1-28) (compound 2-35), or is derived from any of these modified peptides by the replacement of the sugar substance with SG, SG(Glc), SG(Man), AG(5), AG(5-Glc), AG(5-Man), AG(7), AG(7-Glc), AG(7-Man), AG(9), AG(9-Glc), AG(9-Man), or GlcNAc and/or the replacement of the hANP peptide with hANP(1-28), hANP(2-28), hANP(3-28), hANP(1-27), hANP(2-27), or hANP(3-27).

(29) The modified peptide according to (24) or a pharmaceutically acceptable salt thereof, wherein the linker structure comprises at least one amino acid having an SH group on the side chain and has a structure of the following general formula in which the sugar substance is linked to the side chain of the amino acid having an SH group on the side chain:

[Formula 6]

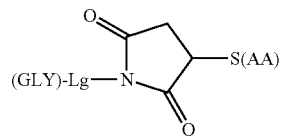

wherein GLY represents the sugar substance; Lg represents a structure on the glycochain side in the linker structure and may be linear or have two or more branches; GLY and L are bonded through an O- or N-glycosidic bond; when Lg is branched, there are the same number of GLY as the number of branch ends that are capable of being linked thereto; and S represents a sulfur atom derived from the side chain SH group of the amino acid having a SH group on the side chain.

(30) The modified peptide according to (29) or a pharmaceutically acceptable salt thereof, wherein the amino acid having an SH group on the side chain is Cys.

(31) The modified peptide according to (30) or a pharmaceutically acceptable salt thereof, wherein the modified peptide is [(SG-)Cys-Gly]$_5$-hANP(1-28) (compound 2-17), [(SG$_2$-)Cys-Gly]$_5$-hANP(1-28) (compound 2-18), or SG-Mal-(SG-Mal-)Lys-[SG-Mal-(SG-Mal-)Lys-]Lys-PEG(11)-hANP(1-28) (compound 2-23), or is derived from any of these modified peptides by the replacement of the sugar substance with SG, SG(Glc), SG(Man), AG(5), AG(5-Glc), AG(5-Man), AG(7), AG(7-

Glc), AG(7-Man), AG(9), AG(9-Glc), AG(9-Man), or GlcNAc and/or the replacement of the hANP peptide with hANP(1-28), hANP(2-28), hANP(3-28), hANP(1-27), hANP(2-27), or hANP(3-27).

(32) The modified peptide according to (24) or a pharmaceutically acceptable salt thereof, wherein the linker structure comprises at least one amino acid having a carboxyl group on the side chain and has a structure of the following general formula in which the sugar substance is linked to the side chain of the amino acid having carboxylic acid on the side chain:

[Formula 7]

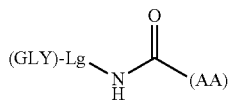

wherein GLY represents the sugar substance; Lg represents a structure on the glycochain side in the linker structure and may be linear or have two or more branches; GLY and L are bonded through an O- or N-glycosidic bond; when Lg is branched, there are the same number of GLY as the number of branch ends that are capable of being linked thereto; and CO represents CO derived from the side chain of the amino acid having carboxylic acid on the side chain.

(33) The modified peptide according to (32) or a pharmaceutically acceptable salt thereof, wherein the sugar substance is bonded through an N-glycosidic bond to both of the side chain carboxyl group and the a carboxyl group of the amino acid having a carboxyl group on the side chain and bonded to another linker structure or the hANP peptide via the α amino group.

(34) The modified peptide according to (32) or (33) or a pharmaceutically acceptable salt thereof, wherein the amino acid having a carboxylic acid group on the side chain is Glu, Gln, Asp, or Asn.

(35) The modified peptide according to (34) or a pharmaceutically acceptable salt thereof, wherein the modified peptide is (SG-)Asn-hANP(1-28) (compound 2-3), (SG-)Asn-hANP(2-28) (compound 2-4), (SG-)Asn-hANP(3-28) (compound 2-8), SG-(SG-)Asn-hANP(1-28) (compound 2-9), or SG-(SG-)Asn-PEG(3)-hANP(1-28) (compound 2-13), or is derived from any of these modified peptides by the replacement of the sugar substance with SG, SG(Glc), SG(Man), AG(5), AG(5-Glc), AG(5-Man), AG(7), AG(7-Glc), AG(7-Man), AG(9), AG(9-Glc), AG(9-Man), or GlcNAc and/or the replacement of the hANP peptide with hANP(1-28), hANP(2-28), hANP(3-28), hANP(1-27), hANP(2-27), or hANP(3-27).

(36) The modified peptide according to (24) or a pharmaceutically acceptable salt thereof, wherein the linker structure comprises at least one amino acid having phenol on the side chain and has a structure of the following general formula in which the sugar substance is linked to the side chain of the amino acid having phenol on the side chain:

[Formula 8]

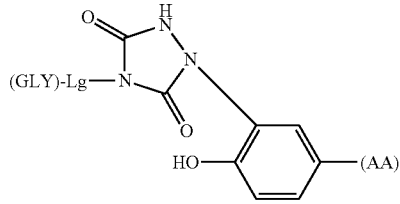

wherein GLY represents the sugar substance; Lg represents a structure on the glycochain side in the linker structure and may be linear or have two or more branches; GLY and L are bonded through an O- or N-glycosidic bond; when Lg is branched, there are the same number of GLY as the number of branch ends that are capable of being linked thereto; and the phenol group represents a phenol group derived from the side chain of the amino acid having a phenol group on the side chain.

(37) The modified peptide according to (36) or a pharmaceutically acceptable salt thereof, wherein the amino acid having a phenol group on the side chain is Tyr.

(38) The modified peptide according to (37) or a pharmaceutically acceptable salt thereof, wherein the modified peptide is hANP(1-27)-(SG-)Tyr (compound 2-6), or is derived from the modified peptide by the replacement of the sugar substance with SG, SG(Glc), SG(Man), AG(5), AG(5-Glc), AG(5-Man), AG(7), AG(7-Glc), AG(7-Man), AG(9), AG(9-Glc), AG(9-Man), or GlcNAc and/or the replacement of the hANP peptide with hANP(1-28), hANP(2-28), hANP(3-28), hANP(1-27), hANP(2-27), or hANP(3-27).

(39) The modified peptide according to (24) or a pharmaceutically acceptable salt thereof, wherein the linker structure comprises at least one amino acid having a hydroxy group on the side chain and has a structure of the following general formula in which the sugar substance is bonded through an O-glycosidic bond to the side chain of the amino acid having a hydroxy group on the side chain:

[Formula 9]

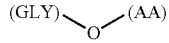

wherein GLY represents the sugar substance; and O represents an oxygen atom derived from the side chain hydroxy group of the amino acid having a hydroxy group on the side chain.

(40) The modified peptide according to (39) or a pharmaceutically acceptable salt thereof, wherein the amino acid having a hydroxy group on the side chain is Ser.

(41) The modified peptide according to (40) or a pharmaceutically acceptable salt thereof, wherein the modified peptide is (SG-)Ser-hANP(2-28) (compound 2-5), or is derived from the modified peptide by the replacement of the sugar substance with SG, SG(Glc), SG(Man), AG(5), AG(5-Glc), AG(5-Man), AG(7), AG(7-Glc), AG(7-Man), AG(9), AG(9-Glc), AG(9-Man), or GlcNAc and/or the replacement of the hANP peptide with hANP(1-28), hANP(2-28), hANP(3-28), hANP(1-27), hANP(2-27), or hANP(3-27).

(42) The modified peptide according to any of (16) to (41) or a pharmaceutically acceptable salt thereof, wherein the modified peptide has one or two SG molecules as the sugar substance and one hANP(1-28) (SEQ ID NO: 1) as the hANP peptide, and the SG is linked to the N terminus of the hANP(1-28) via a linker structure having a linking chain of 10 or fewer atoms. In this context, the pharmaceutically acceptable salt of the modified peptide of the present invention is preferably trifluoroacetate or an acetate.

(43) The modified peptide according to (1) or a pharmaceutically acceptable salt thereof, wherein the modified peptide has a structure represented by the formula of the one of following compounds 2-1, 2-3, 2-10, 2-11, 2-12, 2-13, 2-14, 2-15, 2-16, 2-25, 2-26, 2-27, 2-29, or 2-30:

[Formula 10]

(Compound 2-1)

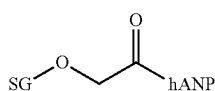

[Formula 11]

(Compound 2-3)

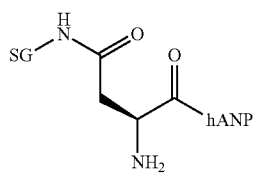

[Formula 12]

(Compound 2-10)

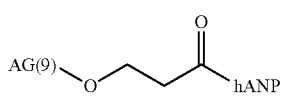

[Formula 13]

(Compound 2-11)

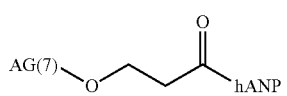

[Formula 14]

(Compound 2-12)

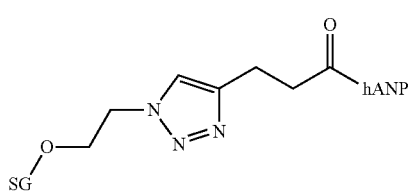

[Formula 15]

(Compound 2-13)

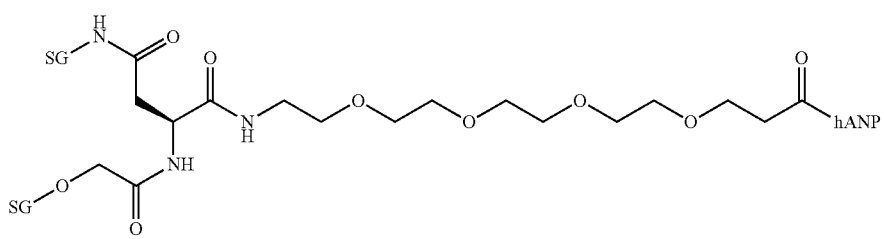

[Formula 16]

(Compound 2-14)

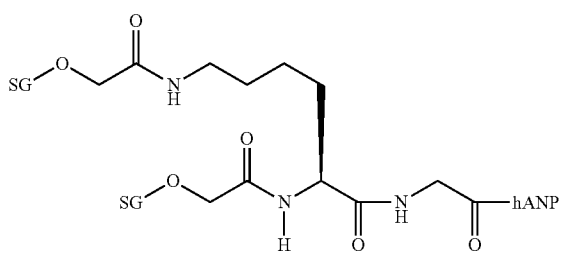

-continued
[Formula 17]
(Compound 2-15)
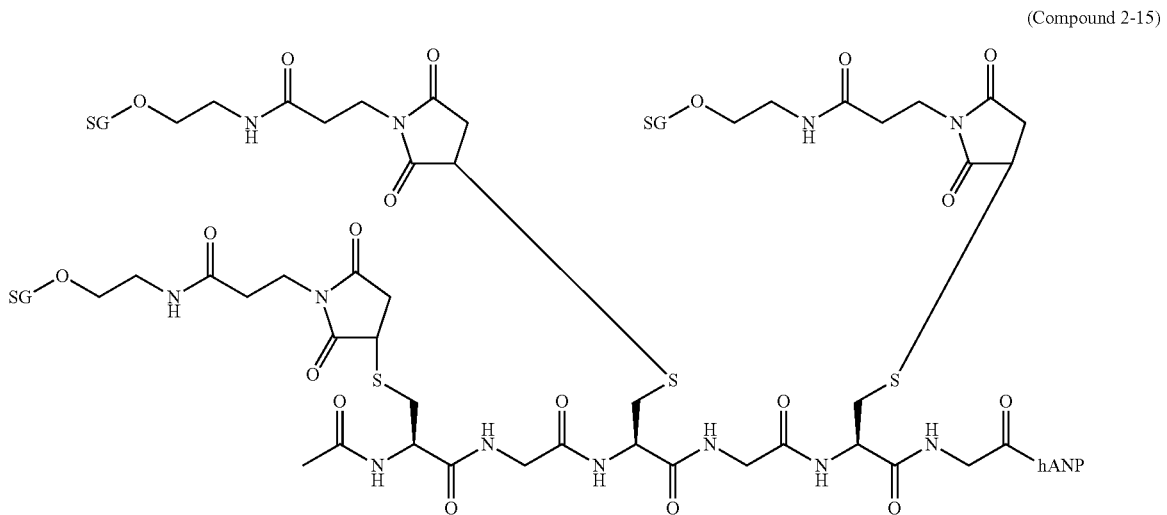
[Formula 18]
(Compound 2-16)
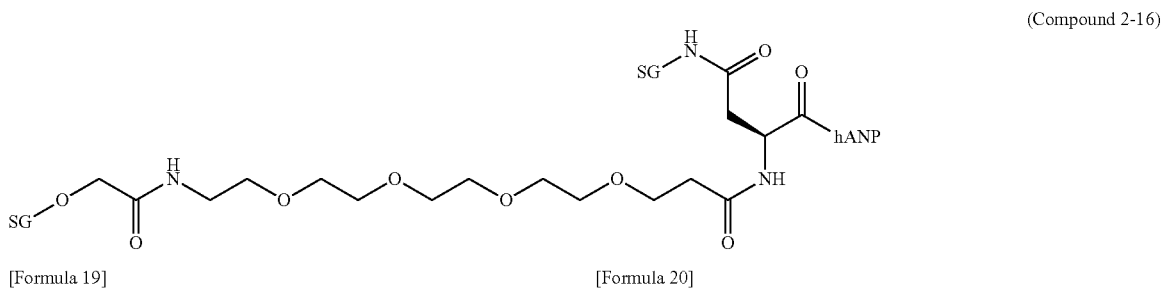
[Formula 19]     [Formula 20]
(Compound 2-25)     (Compound 2-26)
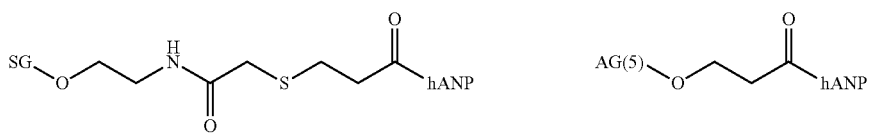 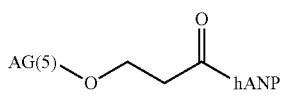
[Formula 21]
(Compound 2-27)
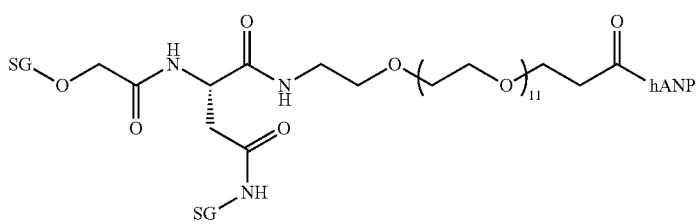
[Formula 22]
(Compound 2-29)
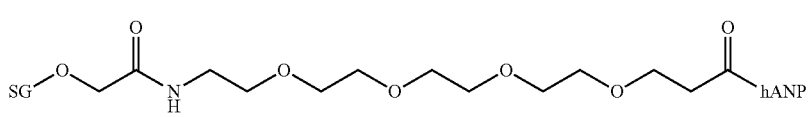

[Formula 23]

(Compound 2-30)

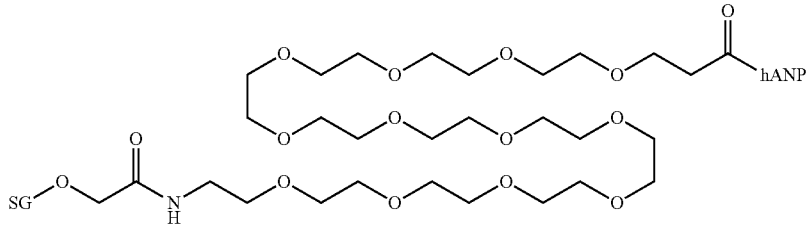

wherein hANP is hANP(1-28) consisting of the amino acid sequence of SEQ ID NO: 1 and is bonded at the N terminus of the amino acid sequence to the linker structure through an amide bond.
(44) The salt of the modified peptide according to any of (1) to (43), preferably (42) or (43), wherein the pharmaceutically acceptable salt is trifluoroacetate or an acetate.
(45) The modified peptide according to (3) or a pharmaceutically acceptable salt thereof, wherein the sugar substance is linked to the side chain of an amino acid in the hANP peptide, and the linked amino acid is an amino acid other than amino acids at amino acid positions 7 to 23 of SEQ ID NO: 1 contained in the hANP peptide.
(46) The modified peptide according to (1) or a pharmaceutically acceptable salt thereof, wherein the modified peptide or the pharmaceutically acceptable salt thereof exhibits a prolonged duration time in blood compared with unmodified hANP(1-28) and maintains cGMP elevating activity.
(47) The modified peptide according to (1) or a pharmaceutically acceptable salt thereof, wherein the modified peptide or the pharmaceutically acceptable salt thereof has resistance to the degradation of the hANP peptide by neutral endopeptidase.
(48) The modified peptide according to (1) or a pharmaceutically acceptable salt thereof, wherein the modified peptide or the pharmaceutically acceptable salt thereof exhibits 3 or more times the water solubility of unmodified hANP(1-28).
(49) A medicament comprising a modified peptide according to any of (1) to (48) or a pharmaceutically acceptable salt thereof.
(50) The medicament according to (49), wherein the medicament is an agent for treating or alleviating a cardiovascular disease.
(51) A method for treating or alleviating a cardiovascular disease, comprising administering an effective amount of a modified peptide according to any of (1) to (48) or a pharmaceutically acceptable salt thereof.
(52) A method for producing a modified peptide according to any of (1) to (48) or a pharmaceutically acceptable salt thereof, comprising the step of linking an hANP peptide, a sugar substance, and, if necessary, a linker molecule and an acceptor compound.
(53) The method according to (52), further comprising the step of transferring a glycochain to a GlcNAc compound, a Glc compound, or a Man compound by use of Endo-M or a mutant enzyme thereof.

Advantageous Effects of Invention

The modified peptide of the present invention exhibits a prolonged duration time in blood compared with unmodified hANP(1-28) (hereinafter, also referred to as "native hANP") and maintains cGMP elevating activity. The modified peptide of the present invention is therefore clinically capable of exhibiting efficacy by non-continuous administration and is applicable to diseases on which native hANP has no therapeutic effect. In addition, this modified peptide is superior in water solubility to native hANP and is therefore susceptible to diverse administration methods based on higher doses, higher concentrations, etc., of formulations. This modified peptide can therefore meet diverse medical needs, which cannot be attained by native hANP.

BRIEF DESCRIPTION OF DRAWING

FIG. 1 shows the NMR chart of SG-oxa/compound 1-12A.

DESCRIPTION OF EMBODIMENTS

Hereinafter, the present invention will be described in detail.

The present invention provides a modified peptide in which at least one sugar substance is linked directly through a glycosidic bond or via a linker structure to at least one hANP peptide. The modified peptide of the present invention exhibits a prolonged duration time in blood compared with unmodified hANP(1-28) and maintains cGMP elevating activity possessed by hANP(1-28). The modified peptide of the present invention is a modified peptide that has been isolated from the natural world and artificially produced by the control of the production process and has a substantially homogeneous structure. The modified peptide of the present invention does not encompass a peptide that may be found in nature and is biologically produced in vivo or in cultured cells. Such a naturally occurring substance itself is definitely excluded from the scope of the present invention.

In the present invention, the term "linked" described for a plurality of structural units (e.g., hANP peptide, sugar substance, and linker structure) means that these structural units are bonded directly through a covalent bond or indirectly via a linker structure so that the structural units exist in one molecule. The chemical structure that links the structural units is not particularly limited. In the case of linking via a linear structure, one each of the structural units is contained in one molecule. In the case of linking via a branched structure, a plurality of either or both of the structural units may be contained in one molecule. The binding pattern between the linker structure and each structural unit is not particularly limited and is selected according to the type of the structural unit to be linked.

<hANP Peptide>

In the present invention, the "hANP peptide" means a peptide consisting of an amino acid sequence comprising at least amino acids at the 7- to 27-positions in the amino acid sequence of human atrial natriuretic peptide (SEQ ID NO: 1; hereinafter, also referred to as hANP or hANP(1-28)), which is a biologically active peptide consisting of 28 amino acids. The hANP exhibits its biological activity by binding to the GC-A receptor (Chinkers M, et al., Nature 338; 78-83, 1989)) expressed on the cell surface, activating guanylate cyclase present in the intracellular domain of the receptor, and elevating the intracellular cGMP concentration. As for the native hANP, α-hANP described in Biochem. Biophys. Res. Commun., vol. 118, p. 131, 1984, has been approved for manufacture and sale under the generic name of "carperitide" in Japan and is commercially available (trade name: HANP). α-hANP is also generally known as Human pro-ANP[99-126].

hANP has an intramolecular ring structure formed by Cys residues at the 7- and 23-positions of SEQ ID NO: 1 through a disulfide bond. It is known that this ring structure and the C-terminal amino acids up to the Arg residue at the 27-position are important for activation of the GC-A receptor by hANP (Silver, M A, Curr. Opin. Nephrol. Hypertens. (2006), 15, p. 14-21; and A. Calderone, Minerva Endocrinol. (2004), 29, p. 113-127). hANP(7-27) consisting of this ring structure is therefore considered as the minimum unit for activating GC-A. The hANP peptide of the present invention is a peptide consisting of an amino acid sequence that may lack 1 to 6 amino acids consecutively from the N-terminal amino acid and/or an amino acid at the 28-position in SEQ ID NO: 1, and is preferably a peptide that may lack at least one of the amino acids at the 1-position, the 1- and 2-positions, and the 28-position of SEQ ID NO: 1, more preferably a peptide (hANP(2-28), hANP(3-28), etc.) consisting of an amino acid sequence that may lack an amino acid at the 1-position or amino acids at the 1- and 2-positions of SEQ ID NO: 1, most preferably a peptide (hANP(1-28)) consisting of the amino acid sequence of SEQ ID NO: 1.

Examples of the modified peptide of the present invention in which the hANP peptide and the sugar substance are bonded directly without the medium of the linker structure can include modified peptides in which any one or two or more of the hydroxy groups on the side chains of Ser at the 1-, 5-, 6-, and 25-positions and Tyr at the 28-position of SEQ ID NO: 1 are bonded directly through an O-glycosidic bond to the sugar substance, and modified peptides in which an amide group on the side chain of Asn at the 26-position of SEQ ID NO: 1 is bonded directly through an N-glycosidic bond to the sugar substance (in production, the amide bond can also be formed by converting the amino acid at the position to Asp and reacting the sugar substance with an azidated reducing end).

In the case of the modified peptide of the present invention in which the hANP peptide and the sugar substance are linked via a linker structure, as mentioned below in detail, the sugar substance can be linked to: a functional group on the side chain of an amino acid constituting the hANP peptide, the N terminus, and/or the C terminus by the adoption of diverse linker structures. The site on the hANP peptide to which the sugar substance is linked is preferably the N terminus and/or the C terminus, more preferably the N terminus.

The modified peptide of the present invention may comprise one hANP peptide in one molecule or may be a polyvalent modified peptide of hANP comprising two or more hANP peptides. The polyvalent modified peptide of hANP can be appropriately produced by the selection of a linker molecule having a plurality of functional groups capable of binding to the hANP peptides such that a plurality of hANP molecules can be linked to the linker structure.

<Sugar Substance>

In the present invention, the "sugar substance" means a structural unit consisting of one monosaccharide or a structural unit of two or more monosaccharides bonded to each other through a glycosidic bond. In the present invention, the sugar substance is also referred to as "GLY". Alternatively, a specific monosaccharide or glycochain is also indicated by an abbreviation, for example, "GlcNAc-" or "SG-". The sugar substance represented by a structural formula with these abbreviations is bonded at the carbon atom at the 1-position, which is a reducing end, to the linker structure or the hANP peptide through an O- or N-glycosidic bond, unless otherwise specified. An oxygen atom or a nitrogen atom belonging to the glycosidic bond is not included in the abbreviations indicating the sugar substance, unless otherwise defined.

In the present specification, the monosaccharide serving as the basic unit of the sugar substance is indicated in its ring structure in which a carbon atom bonded to an oxygen atom constituting the ring and directly bonded to the hydroxy group (or the oxygen atom belonging to the glycosidic bond) is defined as the 1-position (2-position only for sialic acid) for the sake of convenience, unless otherwise specified. The compounds described in the Examples are named in the light of their whole chemical structures, so that this rule is not necessarily applicable thereto.

The monosaccharide contained in the sugar substance is not particularly limited as long as the monosaccharide has the basic structure of a sugar. Various monosaccharides such as 6-membered and 5-membered sugars can be used. The monosaccharide may be a sugar found in nature or may be an artificially synthesized sugar. A sugar found in nature is preferred. Examples of the monosaccharide can include glucose (Glu), fructose (Flu), mannose (Man), galactose (Gal), glucosamine (Glc), N-acetylglucosamine (GlcNAc), glucuronic acid (GlucA), neuraminic acid (Neu), sialic acid/N-acetylneuraminic acid (NeuNAc/Neu5Ac), galactosamine, N-acetylgalactosamine (GalNAc), xylose (Xyl), iduronic acid (IdoA), fucose (Fuc), aldotriose, glyceraldehyde, aldotetrose, erythrose, threose, aldopentose, ribose, lyxose, arabinose, aldohexose, allose, talose, gulose, aldose, idose, ketotriose, dihydroxyacetone, ketotetrose, erythrulose, ketopentose, xylulose, ribulose, ketohexose, psicose, sorbose, and tagatose.

An oligosaccharide or a polysaccharide composed of a plurality of monosaccharides bonded through glycosidic bonds may be used as the sugar substance of the present invention. The oligosaccharide is not particularly limited as long as a desired number of monosaccharides are bonded through glycosidic bonds. Examples thereof can include: disaccharides such as sucrose, maltose, lactose, and trehalose; trisaccharides such as maltotriose, melezitose, and raffinose; and tetrasaccharides such as nystose, nigerotetraose, and stachyose. Examples of the polysaccharide can include amylose, glycogen, cellulose, chitin, chitosan, chondroitin, chondroitin sulfate, hyaluronic acid, dextran, and dextran sulfate.

The sugar substance of the present invention may be a glycochain. The "glycochain" may be a natural glycochain that is produced in vivo or generated by metabolism and is composed of two or more monosaccharides bonded through a glycosidic bond or may be an altered glycochain having an artificial alteration added with reference to the structure of the natural glycochain. The natural glycochain exists as a glycochain (carbohydrate) or in the form of a glycoprotein or a glycolipid in animals, plants, microorganisms, etc., and can be obtained by isolation and purification therefrom. The altered glycochain is a glycochain artificially altered from the glycochain structure of the natural glycochain. The alteration method can be by way of a synthesis chemical or enzyme chemical addition, substitution, and/or deletion of one or more monosaccharides in a naturally derived glycochain and is preferably an alteration to delete a sugar at the non-reducing end by use of a glycosidase appropriate for the sugar at the non-reducing end. The number of monosaccharides contained in the glycochain is not particularly limited as long as the number is two or more. An arbitrary number of monosaccharides can be selected from, for example, approximately 50 or fewer, approximately 40 or fewer, and approximately 30 or fewer monosaccharides. The number of monosaccharides contained in the glycochain is preferably approximately 25 or fewer, more preferably approximately 20 or fewer, even more preferably approximately 15 or fewer, further preferably 11 or fewer.

The glycochain of the present invention may be linear or branched. The linear glycochain is a glycochain in which all the monosaccharides contained in the glycochain except for the sugar at the non-reducing end are linked in a linear form such that each monosaccharide is bonded at one carbon atom other than the carbon atom at the 1-position in its ring structure, either directly or via a substituent, to the carbon atom at the 1-position (2-position for sialic acid) of another monosaccharide through a glycosidic bond.

On the other hand, the branched glycochain is a glycochain in which one or more monosaccharides contained in the glycochain are linked in a branched form such that at least one monosaccharide is bonded at two or more carbon atoms other than the carbon atom at the 1-position in its ring structure, either directly or via a substituent, to the carbon atoms at the 1-positions (2-positions for sialic acid) of other monosaccharides through glycosidic bonds. For both of the linear and branched glycochains, the end (reducing end) on the 1-position carbon side of the ring structure is constituted by one monosaccharide, and the carbon atom at the 1-position (2-position for sialic acid) of the sugar at this reducing end is bonded through an O- or N-glycosidic bond to the linker structure or the hANP peptide.

On the other hand, the monosaccharide at the non-reducing end of the glycochain does not form a glycosidic bond with another sugar at a site other than the carbon atom at the 1-position (2-position for sialic acid). The glycochain has the same number of non-reducing ends as the number of branches and is altered mainly at this non-reducing end.

Glycochains contained in natural glycoproteins are broadly classified into N-linked glycochains attached to asparagine of a glycoprotein and O-linked glycochains attached to serine or threonine thereof, both of which have their characteristic basic structures. Naturally, the N-linked glycochain is bonded through an N-glycosidic bond to the amino acid side chain of a protein, while the O-linked glycochain is bonded through an O-glycosidic bond thereto. Artificial glycochains can be bonded to other compounds through any glycosidic bond. Thus, the type of glycosidic bond is not limited by structure of such glycochain. For example, the sugar substance is azidated at its reducing end, and this azidated sugar substance can be reacted with a compound having a carboxyl group in the presence of triphenylphosphine to bond the compound having the desired structure to the sugar substance through an N-glycosidic bond.

Alternatively, the sugar substance can be reacted with a compound having a hydroxy group, such as an alcohol, to bond the sugar substance to the desired compound through an O-glycosidic bond.

The basic structure of the N-linked glycochain is represented by the following formula (structural formula (I) and sequence (II)). A glycochain having this glycochain structure is designated as AG(5).

[Formula 24]

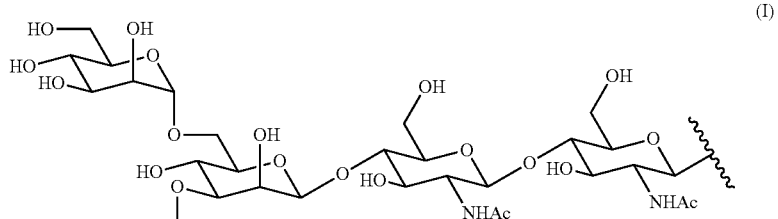

(I)

[Formula 25]

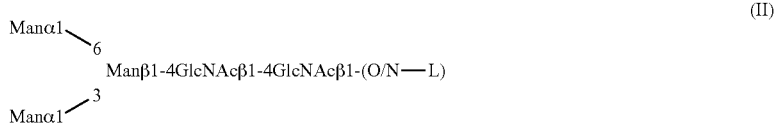

(II)

In the above formula, "O/N-L" represents binding to the linker structure through an O-glycosidic bond or an N-glycosidic bond. In the above formula, glycochains altered at the reducing end by the replacement of GlcNAc at the reducing end with Glc or Man are referred to as AG(5-Glc) and AG(5-Man), respectively.

Most of the N-linked glycochains have this basic structure. Its non-reducing end or branched sugar may be further bonded to a glycochain.

Human glycochains or human-compatible glycochains are glycochains known to exhibit no antigenicity in the bodies of humans. For example, high-mannose, complex, and composite forms of N-linked glycochains are known.

The high-mannose form is a glycochain having a mannose-rich structure composed of a plurality of mannose molecules at the non-reducing end of the N-linked basic structure. The complex form is a glycochain having a Galβ1-4GlcNAc motif structure at the non-reducing end of the N-linked basic structure. The composite glycochain is a glycochain having a Gal1β-4GlcNAc motif structure at the non-reducing end of the N-linked basic structure and also having a mannose-rich structure composed of a plurality of mannose molecules.

<SG,AG(n)>

The N-linked complex glycochain is typically a glycochain contained in sialylglycopeptide (hereinafter, referred to as "SGP") contained in chicken egg yolk. Examples thereof can include sialyl glycan (hereinafter, referred to as "SG") having a structure represented by the following structural formula (III) and sequence (IV):

0278681. Alternatively, a purified product of SGP is commercially available (Tokyo Chemical Industry Co., Ltd. or Fushimi Pharmaceutical Co., Ltd.) and can be purchased.

The glycochain altered at the reducing end by the replacement of GlcNAc at the reducing end of SG with another sugar can be prepared by use of the transglycosylation reaction mentioned later. The glycochain altered at the reducing end by the replacement of GlcNAc at the reducing end of SG with Glc is referred to as SG(Glc). The glycochain altered at the reducing end by the replacement of GlcNAc at the reducing end of SG with Man is referred to as SG(Man).

Specific examples of the altered glycochain that may be used as the sugar substance of the present invention can include AG(9) (structural formula (V) and sequence (VI) given below) that lacks two non-reducing end Neu5Ac residues as a result of the neuraminidase treatment of SG, AG(7) (structural formula (VII) and sequence (VIII) given below) that lacks two non-reducing end Gal residues as a result of the galactosidase treatment of AG(9), and AG(5)

[Formula 26]

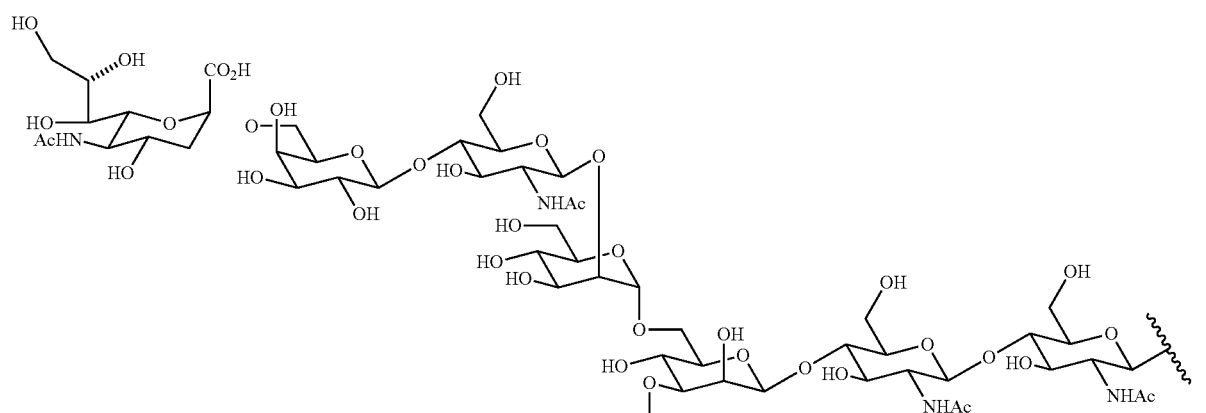

(III)

[Formula 27]

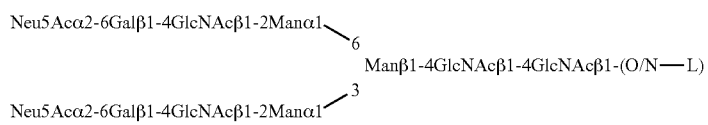

(IV)

In the above formula, "O/N-L" represents binding to the linker structure through an O-glycosidic bond or a N-glycosidic bond. In the above formula, glycochains altered at the reducing end by the replacement of GlcNAc at the reducing end with Glc or Man are referred to as SG(Glc) and SG(Man), respectively.

SG can be obtained, as mentioned later, by reacting SGP with an enzyme (Endo-M, a mutant thereof, etc.) by a method known in the art, followed by hydrolytic cleavage or transfer to a desired compound. SGP can be isolated and purified from chicken egg yolk according to a conventional method, for example, a method described in WO2011/

(glycochain having the aforementioned N-linked basic structure) that lacks two non-reducing end GlcNAc residues as a result of the further treatment of AG(7) with N-acetylglucosaminidase. Also, glycochains altered at the reducing end of AG(9), AG(7), and AG(5) (e.g. AG(9-Glc) with GlcNAc at the reducing end of AG(9) replaced with Glc, and AG(9-Man) with GlcNAc at the reducing end of AG(9) replaced with Man) can be obtained by the same treatment as above using the glycochain altered at the reducing end of SG (e.g., SG(Glc) or SG(Man)) instead of SG and can be adopted as the sugar substance of the present invention.

[Formula 28]

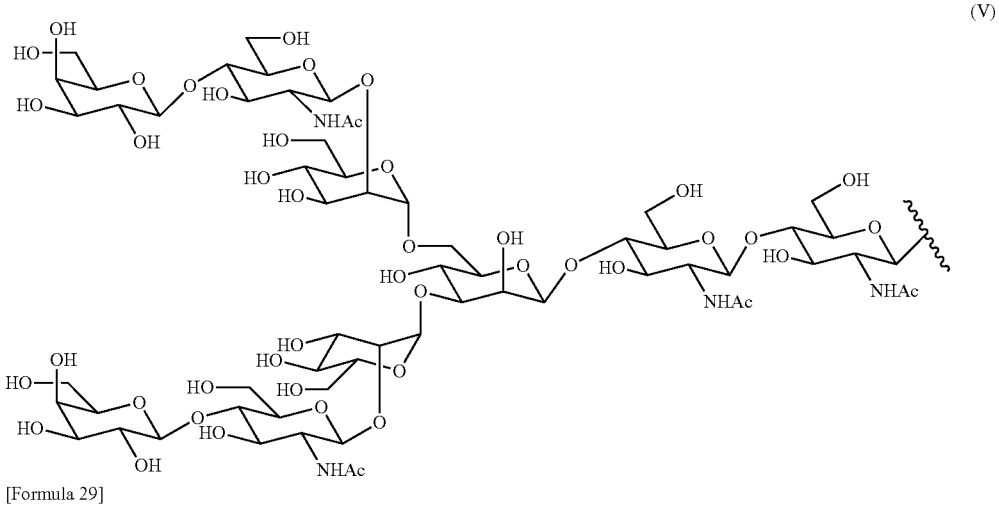
(V)

[Formula 29]

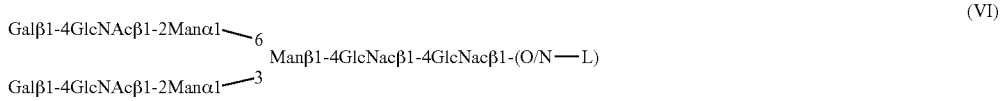
(VI)

In the above formula, "O/N-L" represents binding to the linker structure through an O-glycosidic bond or an N-glycosidic bond. In the above formula, glycochains altered at the reducing end by the replacement of GlcNAc at the reducing end with Glc or Man are referred to as AG(9-Glc) and AG(9-Man), respectively.

the reducing end by the replacement of GlcNAc at the reducing end with Glc or Man are referred to as AG(7-Glc) and AG(7-Man), respectively.

The modified peptide of the present invention is not limited by the maximum number of sugar substances as long as, in one molecule, at least one sugar substance is linked to

[Formula 30]

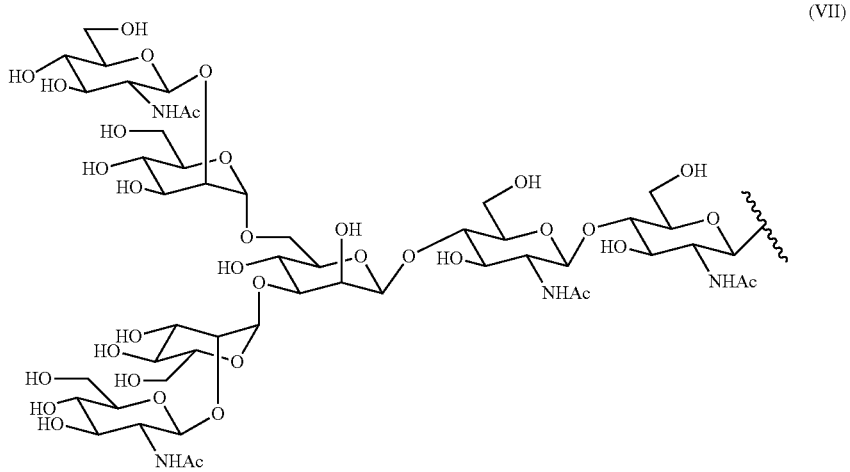
(VII)

[Formula 31]

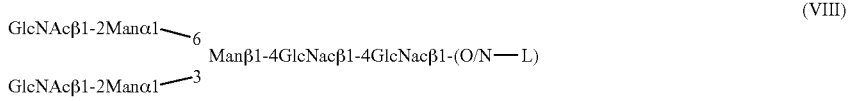
(VIII)

In the above formula, "O/N-L" represents binding to the linker structure through an O-glycosidic bond or an N-glycosidic bond. In the above formula, glycochains altered at the hANP peptide. The number of sugar substances is, for example, 20 or fewer, more preferably 15 or fewer, even more preferably 12 or fewer, further preferably 10 or fewer, still further preferably 5 or fewer, still further preferably 1, 2, 3, or 4, most preferably 1 or 2. The sugar substances contained in one molecule may have the same structure or may be a mixture of sugar substances differing in structure. Preferably, all of these sugar substances are identical sugar substances.

In the present invention, in the case of using a glycoprotein- or glycolipid-derived glycochain found in nature as the sugar substance, the glycochain can be used after being cleaved or isolated or transferred to a desired compound (acceptor compound) through transglycosylation by use of an enzyme. The enzyme for use in such a reaction can be selected from diverse enzymes known in the art according to the structure of the glycochain used (Endo-A: Li, B., et al, J. Am. Chem. Soc. 127 (2005), pp. 9692-9693; Endo-F: Wei Huang., et al, ChemBioChem 12 (2011), pp. 932-941; Endo-D: Shu-Quan Fan, et al, J. Biol. Chem. 287 (2012), pp. 11272-11281; and Endo-S: Wei Huang, et al, J. Am. Chem. Soc. 134 (2012), pp. 12308-12318). As an example of such an enzyme, for example, endo-β-N-acetylglucosaminidases are known as a series of enzyme families that hydrolyze β-glycosidic bonds in chitobiose structures and are known as Endo-A, Endo-D, Endo-F, Endo-M, Endo-S, etc., according to their origins.

Of them, Endo-M derived from *Mucor hiemalis* has the activity of hydrolyzing the glycosidic bond between GlcNAc-GlcNAc on the reducing end side in a glycochain having an N-linked basic structure. In addition, this enzyme even has the activity of transferring and bonding a glycochain on the non-reducing end side containing the second reducing end GlcNAc cleaved by this hydrolysis from the N-linked glycochain basic structure, to the 4-position of GlcNAc of another acceptor compound having a GlcNAc site (see e.g., Y. Tomabechi, et al, Bioorg. Med. Chem., 18 (2010), pp. 1259-1264). Also, it is known that when a compound having the structure of a different sugar unit (e.g., Glc or Man) instead of GlcNAc is used as an acceptor compound in similar transglycosylation reactions using Endo-M, the similar transfer reaction proceeds at a position in the sugar unit corresponding to the 4-position of GlcNAc (Endoglycosidases—Biochemistry, Biotechnology, Application, Masahiko Endo et al. Kodansha, Tokyo (2006)).

The glycochain structure serving as a substrate of Endo-M can be any glycochain structure having an N-linked basic structure, and diverse glycochains such as high-mannose, complex, and composite forms can be used as the substrate. AG(5), AG(7), AG(9), and SG also serve as substrates of Endo-M. Endo-M N175Q, which is a mutant of Endo-M, is a mutant that exhibits reduced hydrolysis activity while maintaining the substrate specificity and transglycosylation activity of Endo-M. Endo-M N175Q is particularly preferred for bonding a glycochain to a desired compound through a transglycosylation reaction. In the case of using Endo-M N175Q, for example, an excised glycochain moiety such as SG-Oxa can be used as a glycochain donor, or a glycopeptide or a glycoprotein such as SGP may be used (Midori Umekawa et al. JOURNAL OF BIOLOGICAL CHEMISTRY, 285, 2010, pp. 511-521 (which also describes reports of other mutants)). Endo-M and mutant enzymes thereof can be produced by genetic engineering by methods known in the art. Alternatively, Endo-M and Endo-M N175Q may be purchased as commercially available reagents (distributor: Tokyo Chemical Industry Co., Ltd.).

In the case of using a glycochain excised by use of hydrolase, the substrate can be reacted with hydrolase at an appropriate temperature for an appropriate time, and the glycochain can be isolated from the obtained reaction solution.

The excised glycochain may be used as it is or may be modified at its reducing end for use. For example, in the case of a glycochain having GlcNAc at the reducing end, this glycochain can be treated with DMC and isolated as GLY (GlcNAc)-oxa (specifically, SG-Oxa having an oxazoline ring formed between a hydroxy group bonded to the carbon atom at the 1-position and a N-acetyl group bonded to the carbon atom at the 2-position in the ring structure of GlcNAc). The glycochain thus excised can be used as a substrate for the transfer reaction to the linker molecule (GlcNAc compound) and thereby bonded to a desired compound.

In the case of transferring a glycochain to a desired compound by use of a glycosyltransferase, a substrate (glycochain donor), an acceptor compound, and a glycosyltransferase are reacted at an appropriate temperature for an appropriate time, and the compound of interest is obtained from the resulting reaction solution by the isolation of the compound made by the transfer and binding of the glycochain of interest to the acceptor compound. For example, in the case of using SGP as the substrate, a GlcNAc compound as the acceptor compound, and Endo-M N175Q as the glycosyltransferase, an appropriate amount of the GlcNAc compound and SGP at a dose appropriate for the GlcNAc valence of the GlcNAc compound are shaken at 20 to 40° C. (preferably 20 to 30° C., more preferably 22 to 27° C., most preferably 25° C.) for 1 to 10 hours (preferably 2 to 8 hours, more preferably 3 to 6 hours) in the presence of Endo-M-N175Q and, if desired, an appropriate amount of DMSO, and the resulting reaction product can be purified by use of reverse-phase HPLC (ODS; which employs a 0.1% aqueous trifluoroacetic acid solution and a 0.1% solution of trifluoroacetic acid in acetonitrile as eluents).

A functional group such as an amino group (SG-NH$_2$, etc.), a carboxyl group (SG-A, etc.), an azide group (SG-N$_3$, etc.), a maleimide group (SG-M), or an α-iodoacetylamide group (SG-I) can be bonded to the reducing end of the glycochain through such a transfer reaction by use of various GlcNAc compounds mentioned later. The glycochain thus prepared can be linked to a desired linker structure.

The glycochain-bound compound thus obtained may be bonded directly to the hANP peptide or may be linked to the hANP peptide via another linker molecule.

In this context, the "acceptor compound" includes a sugar that has not undergone a modification except for the glycosidic bond at the 1-position carbon, and is not particularly limited as long as the compound functions as a sugar acceptor in the transglycosylation reaction. Preferably, a "GlcNAc compound" (which will be mentioned later in detail) containing GlcNAc as the sugar, a "Glc compound" containing Glc as the sugar, a "Man compound" containing Man as the sugar, or the like can be used as the acceptor compound. A GlcNAc compound is most preferred.

<Linker Structure>

In the present invention, the linker structure means a chemical structure that mediates the linking between the hANP peptide and the sugar substance in the modified peptide of the present invention. The linker structure is bonded at least one site to the hANP peptide and bonded at least one site to the sugar substance through a glycosidic bond.

For the link between the hANP peptide and the linker structure, the linker structure may be bonded to any position selected from the N-terminal amino group of the hANP peptide, the C-terminal carboxyl group of the hANP peptide, and at least one side chain of the constituent amino acids of hANP peptide. The number of binding positions may be one or two or more. In the case of binding to an amino acid side chain, a desired compound having a functional group appropriate for binding to each functional group which is a hydroxy group in the side chain of Ser at the 1-, 5-, 6-, or 25-position of SEQ ID NO: 1 or Tyr at the 28-position, or which is an amide group in the side chain of Asn at the 26-position, or the like may be provided.

In the notation of a modified peptide of the present invention or a partial structure thereof, the N terminus (amino group) and the C terminus (carboxyl group) of an amino acid or a peptide are indicated on the left and on the right, respectively, unless otherwise specified. An amino acid or a peptide with the symbol "*" on the right (e.g., Gln*) represents that contrary to this rule, the C terminus and the N terminus are indicated on the left and on the right, respectively.

In the notation of an amino acid, an amino group and a carboxyl group, which are structures essential to an amino acid, directly bonded to the central carbon atom (a carbon) are referred to as an "a amino group" and an "a carboxyl group", respectively.

When the sugar substance is linked to at least one of the N terminus (amino group) and the C terminus (carboxyl group) of the hANP peptide, the hANP peptide and the linker structure form an amide bond. A modified peptide in which the sugar substance is linked to the N terminus of the hANP peptide via a linker structure is represented as follows:

GLY-L-hANP                                                     (A)

wherein GLY represents the sugar substance; L represents the linker structure that is linear or has two or more branches; hANP represents the hANP peptide; L is bonded through an O- or N-glycosidic bond to GLY; when L is branched, there are the same number of GLY as the number of branch ends that are capable of being linked thereto; and L is bonded through an amide bond to the N terminus of the hANP peptide.

In the notation of a modified peptide or a partial structure thereof in the present specification, when an amino acid or a peptide is linked at its N-terminal amino group to another linker, a symbol representing the structural unit to be linked is indicated with a hyphen and without parentheses on the left side of a symbol representing this peptide or amino acid. In this case, the hyphen represents the amide bond formed between the amino group of the peptide or the amino acid and the carboxyl group carried by the linker structure. For example, a structure in which SG is linked to the amino group of Asn is referred to as "SG-Asn".

A modified peptide in which the sugar substance is linked to the C terminus of the hANP peptide via a linker structure is represented as follows:

hANP-L-GLY (B) wherein GLY represents the sugar substance; L represents the linker structure that is linear or has two or more branches; hANP represents the hANP peptide; L is bonded through an O- or N-glycosidic bond to GLY; when L is branched, there are the same number of GLY as the number of branch ends that are capable of being linked thereto; and L is bonded through an amide bond to the C terminus of the hANP peptide.

Specifically, in the notation of a modified peptide or a partial structure thereof in the present specification, when an amino acid or a peptide is linked at its C-terminal carboxyl group to another structural unit, a symbol representing the structural unit to be linked is indicated with a hyphen and without parentheses on the right side of a symbol representing this peptide or amino acid. In this case, the hyphen represents the amide bond formed between the C-terminal carboxyl group of the peptide or the amino acid and the amino group (or azide group) carried by the linker structure. For example, a structure in which SG is linked to the carboxyl group of Tyr is referred to as "Tyr-SG".

In the present invention, a modified peptide in which the sugar substance is linked to both of the N terminus and the C terminus of the hANP peptide is represented by the following formula C:

GLY-L1-hANP-L2-GLY                                             (C)

wherein GLY represents a sugar substance; L1 and L2 may be the same or different and each represent the linker structure that is linear or has two or more branches; hANP represents the hANP peptide; L1 and L2 are each bonded through an O- or N-glycosidic bond to GLY; when L1 or L2 is branched, there are the same number of GLY as the number of branch ends that are capable of being linked thereto; and L1 and L2 are bonded through amide bonds to each of the N terminus and the C terminus of the hANP peptide, respectively.

In a modified peptide of the present invention or a partial structure thereof, the partial structure in which the sugar substance is linked to an amino acid side chain is represented by the following formula D:

(GLY-)AA                                                       (D)

wherein GLY represents the sugar substance; AA represents an arbitrary amino acid; and the side chain of the amino acid is bonded through an O- or N-glycosidic bond, directly or via a linker structure, to GLY.

Specifically, in the notation of the modified peptide or a partial structure thereof in the present specification, when an amino acid or a peptide is linked at its side chain functional group to another structural unit, a symbol representing the structural unit to be linked is indicated with a hyphen and parentheses on the left side of a symbol representing the linked amino acid. In this case, the hyphen represents a chemical structure containing the glycosidic bond at the reducing end of the sugar substance. When this linking is mediated by a linker structure, a structural characteristic of the linker structure may also be described (e.g., (SG-PEG(3)-) Asn). However, when the linker structure has no such characteristic structure or is not defined, this may be omitted (e.g., (SG-)Lys). The names of the compounds described in the Examples represent specific compounds represented by the structural formulas provided therewith.

In accordance with such rules, a partial structure in which SG is linked to both of the side chain amino group and the α amino group of Lys is referred to as "SG-(SG-)Lys". Likewise, a partial structure in which SG is linked to both of the side chain carboxyl group and the α carboxyl group of Glu is referred to as "(SG-)Gln-SG" or "SG-(SG-)Gln*" (wherein Asp and Glu have the same structure as Asn/Gln when the side chain carboxyl group forms an amide bond; and Gln* means that the carboxyl group is located on the left and the amino group is located on the right).

When one molecule contains a plurality of hANP peptides, individual notations are adopted. For example, the structure in which the sugar substance is linked to the α carboxyl group of Lys and the N termini of the hANP peptides are respectively linked to the α amino group and the side chain amino group via PEG linkers is referred to as "GLY-Lys*(-PEG-hANP)$_2$".

The sugar substance and the linker structure are bonded through an N- or O-glycosidic bond at the carbon atom at the 1-position of the reducing end of the sugar substance. In this respect, the configuration of the glycosidic bond may be selected as any of the α-position and the β-position. Any binding pattern can be selectively synthesized according to a method known in the art (Tomoya Ogawa, et al, Agric. Biol. Chem. 47 (1983), pp. 281-285; and Mamoru Mizuno, et al, 121 (1999), pp. 284-290). In the case of using a glycochain derived from a natural glycoprotein, the same pattern as the naturally occurring binding pattern of this glycochain is desirably selected. When the sugar substance is, for example, SG or an altered glycochain thereof, the β-position is desirably selected for the glycosidic bond with the linker structure.

When the sugar substance is indicated by a symbol (e.g., GLY, SG, or GlcNAc) in the present specification, this symbol also includes carbon at the reducing end and excludes N or O belonging to the N- or O-glycosidic bond, unless otherwise defined. Likewise, when the hANP peptide is indicated by a symbol (e.g., hANP or hANP(1-28)), the symbol also includes N-terminal —NH and C-terminal C=O as a rule. The N terminus and the C terminus are indicated on the left and on the right, respectively, unless otherwise specified. Specifically, an unmodified hANP peptide is referred to as H-hANP-OH.

The chemical structure of the linker structure contained in the modified peptide of the present invention has an oxygen atom or a nitrogen atom bonded through a glycosidic bond to at least one sugar substance and a partial structure bonded to at least one hANP peptide (NH or C=O for an amide bond or a structure (which will be mentioned later) appropriate for the structure of each side chain for linking to a side chain of the hANP peptide). Other structures are not limited and may be derived from a single molecule or may be a plurality of partial structures in which a plurality of molecules are bonded. Such a molecule from which the linker structure is derived is referred to as a "linker molecule". When a plurality of partial structures are contained in the linker structure, these partial structures may be indicated by "Lx" according to the partial structures. For example, the partial structure directly bonded to the sugar substance is indicated by "Lg". This partial structure fully satisfies the definitions applied to the linker structure except for the structure directly bonded to the hANP peptide. Also, the partial structure directly bonded to the hANP peptide is indicated by "Lp". This partial structure fully satisfies the definitions applied to the linker structure except for the structure belonging to the glycosidic bond with the sugar substance.

In the linker structure of the present invention, the shortest chain of atoms that links N or O belonging to the glycosidic bond and the atom directly bonded to the hANP peptide (in the case of an amide bond, N or C belonging to the amide bond) is referred to as a "linking chain". The linking chain contains the atom belonging to each of the aforementioned bonds. For example, the modified peptide represented by (GLY)—O—CH2-C(=O)—(N term hANP) has a linker structure consisting of a linking chain of 3 atoms. Also, the modified peptide represented by (GLY)—NH—C(=O)—CH2-CH2-NH—(C term hANP) has a linker structure consisting of a linking chain of 5 atoms. The linker structure of the present invention is not particularly limited as long as the linker structure has a linking chain of 3 or more atoms. The linking chain can be, for example, of 200 or fewer atoms and is preferably of approximately 150 or fewer atoms, more preferably of 100 or fewer atoms, even more preferably of 70 or fewer atoms, 50 or fewer atoms, or 30 or fewer atoms, most preferably of 20 or fewer atoms, 15 or fewer atoms, or 10 or fewer atoms. For forming such a linker structure, a plurality of linker molecules can be used to create a linker structure having a complicated and long linking chain. Preferably, 5 or fewer linker molecules are adopted. A modified peptide containing a linker structure derived from 4, 3, 2, or 1 linker molecules is also preferred.

When the linker structure of the present invention is derived from one linker molecule, this linker molecule is a compound containing, in one molecule, both a functional group binding through a glycosidic bond to the sugar substance, and a functional group binding to the hANP peptide, and is preferably, for example, an amino acid or a peptide because of having an amino group and a carboxyl group, more preferably an amino acid having an amino group, a carboxyl group, a hydroxy group, or the like on the side chain. Specific examples of such a linker molecule can include HO—CH2-COOH, HO—CH2-CH2-NH2, aspartic acid, glutamic acid, serine, and lysine.

When the linker structure of the present invention is derived from a plurality of linker molecules, at least a compound containing a functional group capable of binding through a glycosidic bond to the sugar substance, and a compound having a functional group capable of binding to the hANP peptide are used as these linker molecules. These two compounds also have functional groups that permit the compounds to be bonded to each other directly. Alternatively, these two compounds may be linked to each other via an additional compound. A method known in the art can be applied to the binding between such linker molecules. Examples thereof can include, but are not particularly limited to, an amide bond between an amino group and a carboxyl group, a bond between an SH group and a maleimide group, a bond between an SH group and an iodoacetyl group, a bond between a phenol group and a triazoledione group (Hitoshi Ban, et al, 132 (2010), 1523-1525), an ester bond between an alcohol and a carboxyl group, and a bond between an azide group and an acetylene group through Huisgen reaction. The linker molecules used in the present invention can be appropriately selected from those having functional groups appropriate for these binding patterns and used in the formation of the linker structure.

The modified peptide of the present invention needs to exhibit a certain degree of hydrophilicity as a whole. It is therefore preferred to adopt a highly hydrophilic structure when the linker structure has a size above a certain level. Examples of such a structure include a polyoxyalkylene and a polyamide or other biologically applicable repeat structures.

Examples of the polyoxyalkylene can include polyethylene glycol (PEG), polypropylene glycol, polybutylene glycol, and polyvinyl alcohol (PVA). PEG is preferred. In the notation of the linker structure containing PEG in the present specification, the number of ethoxy repeats is represented by, for example, PEG(3) or PEG(11). Examples of a modified peptide having such a structure can include compounds 2-13 and 2-27 to 2-34 prepared in the working examples.

Alternatively, the linker structure of the present invention may contain an amino acid or an oligopeptide chain of two or more amino acids bonded through a peptide bond. Such an amino acid or oligopeptide chain can assume a structure that is directly bonded through an amide bond to the N terminus or the C terminus of the hANP peptide to extend the peptide chain of the hANP peptide. Alternatively, this structure may be linked to the hANP peptide via a non-peptide structure or may have both of these structures.

The amino acid contained in the linker structure of the present invention is not particularly limited as long as the amino acid has an amino acid structure in which a hydrogen atom, an amino group, and a carboxyl group are bonded to the same carbon atom. The amino acid may be a naturally occurring amino acid or may be an artificial amino acid. The artificial amino acid may be a synthetically produced amino acid such as a D amino acid or may be an altered amino acid having an artificially modified side chain of a naturally occurring amino acid. The amino acid is preferably a naturally occurring amino acid or an altered amino acid, more preferably a naturally occurring amino acid. When the modified peptide of the present invention is used as an active ingredient for a medicament, it is preferred that the amino acid contained in the linker structure should not have its own biological activity, and it is also preferred to adopt Gly or an amino acid whose side chain is bonded to another structure. Examples of the linker structure containing such an amino acid can include a linker structure that contains Gly or oligo-Gly consisting of two or more Gly residues and is linked at the N terminus and the C terminus to the hANP peptide and the sugar substance. Specific examples of such a modified peptide can include compound 2-40 in which SG(Glc) is used as the sugar substance and Gly is contained as the linker.

For example, an "amino acid having an amino group on the side chain", such as Lys, which has a side chain amino group, "an amino acid having an SH group on the side chain", such as Cys, which has a side chain SH group, "an amino acid having a carboxyl group on the side chain", such as aspartic acid or glutamic acid, which have a side chain carboxyl group, "an amino acid having a hydroxy group on the side chain", such as serine, which has a side chain hydroxy group, or "an amino acid having phenol on the side chain", such as tyrosine, which has a side chain p-phenol group, can be adopted as the amino acid having such a side chain structure. This amino acid having the side chain structure can attain linking at three sites, i.e., the amino group and the carboxyl group bonded to the α carbon and the side chain functional group. For forming a branched linker structure, it is therefore preferred to contain at least one of these amino acids having the side chain structure.

The amino acid having an amino group on the side chain is not particularly limited as long as the amino acid has at least one amino group (except for an amide group) on the side chain. The natural amino acid having an amino group on the side chain is Lys. Examples of the artificial amino acids having an amino group on the side chain can include altered amino acids obtained by the reaction of a divalent amine such as 1,2-diaminoethane with the side chain carboxyl group of Glu or Asp.

When the linker structure contains at least one amino acid having an amino group on the side chain and the sugar substance is linked to the side chain of the amino acid having an amino group on the side chain, a partial structure of the following general formula can be taken:

[Formula 32]

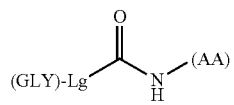

wherein GLY represents the sugar substance; Lg represents a structure on the glycochain side in the linker structure and may be linear or have two or more branches; GLY and L are bonded through an O- or N-glycosidic bond; when Lg is branched, there are the same number of GLY as the number of branch ends that are capable of being linked thereto; N-(AA) represents a nitrogen atom derived from the side chain amino group of the amino acid having an amino group on the side chain; and (AA) contains the basic structure of the amino acid and a structural moiety linked to the side chain amino group.

The linker structure having such a partial structure can be produced by introducing a protective group to the carboxyl group of the amino acid having an amino group on the side chain or a linker molecule containing this amino acid, subsequently reacting therewith a linker molecule represented by "GLY-Lg-COOH", deprotecting the carboxyl group, and bonding the resulting compound to the hANP peptide or Lp. In this reaction, when the amino acid having an amino group on the side chain has a free α amino group, Lg can form a linker structure having a branched structure through amide bonds to both of the side chain amino group and the α amino group. The modified peptide thus constituted is, for example, a modified peptide having a partial structure such as SG-(SG-)Lys. Specific examples of such a compound can include compounds 2-14 and 2-35 prepared in the working examples.

In similar production, a modified peptide having a partial structure in which the hANP peptide is linked to the side chain of the amino acid having an amino group on the side chain can be produced by the replacement of Lg(-sugar substance) with Lp(-hANP peptide). Such a partial structure can be produced by introducing a protective group to the carboxyl group of the amino acid having an amino group on the side chain or a linker molecule containing this amino acid, subsequently reacting therewith a linker molecule represented by "Lp-COOH", deprotecting the carboxyl group, and bonding Lg or the sugar substance to the carboxyl group. In this reaction, when the amino acid having an amino group on the side chain has a free α amino group, Lp can form a linker structure having a branched structure through amide bonds to both of the side chain amino group and the α amino group. The modified peptide thus constituted is, for example, a modified peptide having a partial structure such as Lp-(Lp-)Lys-Lg. Specific examples of such a compound can include compounds 2-38 and 2-39. In addition, a modified peptide containing a plurality of sugar substances and/or a plurality of hANP peptides in one molecule can be appropriately produced by the combined use with other linker molecules having diverse structures.

Alternatively, a structure having a large number of amino groups may be formed by repeatedly forming respective amide bonds from the side chain amino group and the α amino group of each amino acid having an amino group on the side chain with the α carboxyl groups of identical amino acids having an amino group on the side chain, and this structure can be bonded to Lg to form a linker structure linked to the same number of sugar substances as the number of amino groups. For example, a plurality of amino groups in such a branched peptide can be reacted with glycochains having carboxyl groups, for example, by use of a condensing agent such as HATU, to introduce a plurality of glycochains via the branched peptide. Examples of the modified peptide thus produced include linker structures such as "SG-[SG-(SG-)Lys-]Lys" and "SG-(SG-)Lys-[SG-(SG-)Lys-]Lys". Specific examples of such a modified peptide can include compounds 2-14 and 2-35.

The amino acid having an SH group on the side chain is not particularly limited as long as the amino acid has at least one SH group on the side chain. The natural amino acid having an SH group on the side chain is Cys. Examples of artificial amino acids having an SH group on the side chain can include SH group-containing altered amino acids obtained by the reaction of a compound having, for example, a HOOC—R-STr (trityl sulfide) structure with the side chain amino group of Lys or by the reaction of a compound having, for example, a H$_2$N—R-STr structure with the side chain carboxyl group of Glu or Asp.

When the linker structure contains at least one amino acid having an SH group on the side chain and the sugar substance is linked to the side chain of the amino acid having the SH group on the side chain, a partial structure of the following general formula can be taken:

[Formula 33]

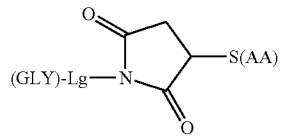

wherein GLY represents the sugar substance; Lg represents a structure on the glycochain side in the linker structure and may be linear or have two or more branches; GLY and L are bonded through an O- or N-glycosidic bond; when Lg is branched, there are the same number of GLY as the number of branch ends that are capable of being linked thereto; S represents a sulfur atom derived from the side chain SH group of the amino acid having the SH group on the side chain; and (AA) contains the basic structure of the amino acid and a structural moiety linked to the side chain SH group.

The linker structure having such a partial structure can be produced by reacting the amino acid having the SH group on the side chain or a linker molecule containing this amino acid with a linker molecule represented by (GLY)-Lg-N maleimide. In this reaction, the amino acid having the SH group on the side chain can be linked at its a amino group and/or a carboxyl group to another sugar substance, thereby forming a linker structure having a branched structure. For example, a plurality of glycochains can be introduced via such a branched peptide by: reacting a plurality of amino groups in the branched peptide with 3-mercaptopropionic acid having a protected SH group; deprotecting the C terminus of the peptide; after binding to the hANP peptide, deprotecting the SH group; and reacting therewith glycochains having maleimide groups in a 0.2 M phosphate buffer solution (pH 6.75). Specific examples of such a compound include compounds 2-19, 2-20, and 2-23.

In similar production, a modified peptide having a partial structure in which the hANP peptide is linked to the side chain of the amino acid having the SH group on the side chain can be produced by the replacement of Lg(-sugar substance) with Lp(-hANP peptide). In addition, a modified peptide containing a plurality of sugar substances and/or a plurality of hANP peptides in one molecule can be appropriately produced by the combined use with other linker molecules having diverse structures.

The amino acid having a carboxyl group on the side chain is not particularly limited as long as the amino acid has at least one carboxyl group on the side chain. The natural amino acids having carboxyl group on the side chain are Asp or Glu. Examples of an artificial amino acid having a carboxyl group on the side chain can include altered amino acids obtained by the reaction of a divalent carboxylic acid such as maleic acid with the side chain amino group of Lys.

When the linker structure contains at least one amino acid having a carboxylic acid group on the side chain and the sugar substance is linked to the side chain of the amino acid having the carboxylic acid group on the side chain, a partial structure of the following general formula can be taken:

[Formula 34]

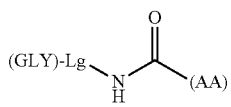

wherein GLY represents the sugar substance; Lg represents a structure on the glycochain side in the linker structure and may be linear or have two or more branches; GLY and L are bonded through an O- or N-glycosidic bond; when Lg is branched, there are the same number of GLY as the number of branch ends that are capable of being linked thereto; CO represents CO derived from the side chain of the amino acid having carboxylic acid on the side chain; and (AA) contains the basic structure of the amino acid and a structural moiety linked to the side chain carboxylic acid group.

The linker structure having such a partial structure can be produced by introducing, if necessary, a protective group to the amino group of the amino acid having the carboxyl group on the side chain or a linker molecule containing this amino acid, subsequently reacting therewith a linker molecule represented by "Lg-NH$_2$", then deprotecting the amino group, and bonding the resulting compound to Lg or the C terminus of the hANP peptide. In this reaction, when the amino acid having the carboxyl group on the side chain has a free a carboxyl group, Lg can form a linker structure having a branched structure through amide bonds to both of the side chain carboxyl group and the α carboxyl group. For example, a plurality of glycochains can be introduced via such a branched peptide by activating the carboxylic acids of the branched peptide having a plurality of carboxyl groups by use of trifluoroacetic anhydride and N-hydroxysuccinimide and reacting therewith glycochains (SG-NH$_2$, etc.) having amino groups. Such a partial structure in which Glu is used as the amino acid having the carboxyl group on the side chain and is linked to SG is represented by, for example, "-(SG(Lg)-)Gln-(Lg) SG" (wherein Glu and Asp have the same structure as Gln/Asn because their side chains form amide bonds). Specific examples of such a modified peptide can include compounds 2-31 and 2-32.

In similar production, a modified peptide having a partial structure in which the hANP peptide is linked to the side chain of the amino acid having the carboxyl group on the side chain can be produced by the replacement of Lg(sugar substance) with Lp(hANP peptide). The linker structure having such a partial structure can be produced by introducing, if necessary, a protective group to the amino group of the amino acid having the carboxyl group on the side chain or a linker molecule containing this amino acid, subsequently reacting therewith a linker molecule represented by "(hANP)-Lp-NH$_2$", then deprotecting the amino group, and bonding the resulting compound to Lg having an appropriate functional group. In this reaction, when the amino acid having a carboxyl group on the side chain has a free a carboxyl group, Lp can form a linker structure having a branched structure through amide bonds to both of the side chain carboxyl group and the α carboxyl group. For example, a polyvalent modified peptide of hANP in which a plurality of hANP peptides are introduced via such a branched peptide can be produced by activating the carboxylic acids of the branched peptide having a plurality of carboxyl groups by use of trifluoroacetic anhydride and N-hydroxysuccinimide and reacting therewith Lp having amino groups or the N-terminal amino groups of the hANP peptides. Such a partial structure in which Glu is used as the amino acid having a carboxyl group on the side chain and is linked to hANP is represented by, for example, "SG Gln-(Lp-hANP)$_2$" (wherein Glu and Asp have the same structure as Gln/Asn because their side chains form amide bonds). In addition, a modified peptide containing a plurality of sugar substances and/or a plurality of hANP peptides in one molecule can be appropriately produced by the combined use with other linker molecules having diverse structures.

Alternatively, a structure having a large number of carboxyl groups may be formed by repeatedly forming respective amide bonds from the side chain carboxyl group and the α carboxyl group of each amino acid having a carboxyl group on the side chain with the α amino groups of other amino acids (which may be of the same type or of different types and is preferably of the same type) having a carboxyl group on the side chain, and this structure can be bonded to Lg through the aforementioned reaction to form a linker structure linked to the same number of Lg as the number of carboxyl groups. Such a partial structure of the linker structure is, for example, "H-[(SG-)Gln-SG]Gln-SG".

The carboxyl group of the amino acid having the carboxyl group on the side chain can be further linked directly to the sugar substance through an N-glycosidic bond to form the following partial structure:

[Formula 35]

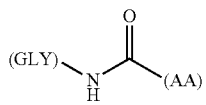

wherein GLY represents the sugar substance; NH—CO—(AA) represents an amide structure derived from the side chain of the amino acid having the carboxyl group on the side chain; and (AA) contains the basic structure of the amino acid and a structural moiety linked to the side chain carboxylic acid group.

Such a partial structure can be produced by reacting the amino acid having carboxylic acid on the side chain or a linker molecule containing this amino acid with a sugar substance azidated at the reducing end in the presence of triphenylphosphine, and bonding the reducing end of the sugar substance to the side chain through an N-glycosidic bond. Also, a compound having a structure in which the sugar substance is linked to the α carboxyl group of the amino acid having the carboxyl group on the side chain can be synthesized by a method based on the Examples. Specific examples of such a sugar-modified peptide include compounds 2-3, 2-4, 2-8, 2-9, 2-13, 2-21, 2-22, 2-27, 2-28, 2-38, and 2-39.

The amino acid having a phenol group on the side chain is not particularly limited as long as the amino acid has at least one p-phenol group on the side chain. The natural amino acid having a phenol group on the side chain is Tyr. Examples of an artificial amino acid having a phenol group on the side chain can include altered amino acids obtained by the reaction of p-aminophenol with the side chain carboxyl group of Glu or Asp.

When the linker structure contains at least one amino acid having a phenol group on the side chain and the sugar substance is linked to the side chain of this amino acid, a partial structure of the following general formula can be taken:

[Formula 36]

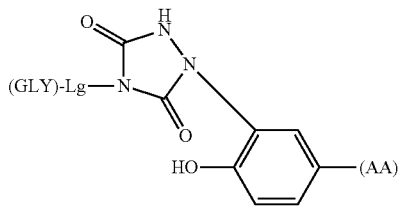

wherein GLY represents the sugar substance; Lg represents a structure on the glycochain side in the linker structure and may be linear or have two or more branches; GLY and L are bonded through an O- or N-glycosidic bond; when Lg is branched, there are the same number of GLY as the number of branch ends that are capable of being linked thereto; the phenol group represents a phenol group derived from the side chain of the amino acid having phenol on the side chain; and (AA) contains the basic structure of the amino acid and a structural moiety linked to the side chain phenol group.

The linker structure having such a partial structure can be produced by reacting the amino acid having the phenol group on the side chain or a linker molecule containing this amino acid with a linker molecule represented by (GLY)-Lg-N triazoledione(*). In this reaction, the amino acid having the phenol group on the side chain can be linked at its α amino group and/or a carboxyl group to another sugar substance, thereby forming a linker structure having a branched structure. For example, a GlcNAc structure can be selectively introduced to the phenolic side chain of Tyr corresponding to the 28-position of hANP by activating GlcNAc having a triazoledione structure by use of N-bromosuccinimide, and reacting therewith hANP. A transglycosylation reaction can be carried out with this compound as a starting material. Specific examples of such a compound include compound 2-6.

In similar production, a modified peptide having a partial structure in which the hANP peptide is linked to the side chain of the amino acid having the phenol group on the side chain can be produced by the replacement of Lg(sugar substance) with Lp(hANP peptide). In addition, a modified peptide containing a plurality of sugar substances and/or a plurality of hANP peptides in one molecule can be appropriately produced by the combined use with other linker molecules having diverse structures.

The amino acid having a hydroxy group on the side chain is not particularly limited as long as the amino acid has at least one hydroxy group on the side chain. A natural amino acid having a hydroxy group on the side chain is Ser or Tyr. Examples of an artificial amino acid having a hydroxy group on the side chain can include altered amino acids obtained by the reaction of an aminoalcohol such as 2-aminoethanol with the side chain carboxylic acid of Asp or Glu.

When the linker structure contains at least one amino acid having a hydroxy group on the side chain and the sugar substance is linked to the side chain of this amino acid, a partial structure of the following general formula can be taken:

[Formula 37]

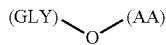

wherein GLY represents the sugar substance; O represents an oxygen atom derived from the side chain hydroxy group of the amino acid having a hydroxy group on the side chain; and (AA) contains the basic structure of the amino acid and a structural moiety linked to the side chain hydroxy group.

The linker structure having such a partial structure can be produced by reacting the amino acid having the hydroxy group on the side chain or a linker molecule containing this amino acid with the sugar substance under conditions that form an O-glycosidic bond. In this reaction, the amino acid having the hydroxy group on the side chain can be linked at its α amino group and/or a carboxyl group to another sugar substance, thereby forming a linker structure having a branched structure. For example, GlcNAc can be introduced to the side chain of serine via an O-glycosidic bond by reacting a glucosamine derivative having a trichloroacetimidate structure with the side chain hydroxy group of serine in the presence of trimethylsilyl trifluoromethanesulfonate, followed by several steps. Transglycosylation reactions can be carried out with this compound as a starting material. Specific examples of such a modified peptide include compound 2-5.

In similar production, a modified peptide having a partial structure in which the hANP peptide is linked to the side chain of the amino acid having a hydroxy group on the side chain can be produced by the replacement of Lg(sugar substance) with Lp(hANP peptide). In addition, a modified peptide containing a plurality of sugar substances and/or a plurality of hANP peptides in one molecule can be appropriately produced by the combined use with other linker molecules having diverse structures.

At least the same number of sugar substances as the number of these functional group-containing side chains can be linked through various reactions mentioned above using a linker molecule containing an oligopeptide containing a plurality of such amino acids having the side chain structure or a plurality of linker molecules each containing one or more each of these amino acids. Such an oligopeptide is not particularly limited as long as the oligopeptide comprises the aforementioned amino acids having the side chain. The oligopeptide may further contain a certain number of Gly and preferably has a repeat sequence in which these Gly residues are regularly arranged. When the amino acid having the side chain is defined as, for example, Xaa, an oligopeptide represented by (Xaa-Gly$_m$)$_n$ (wherein m and n each independently represent a natural number of 1 or larger) is preferred. Although there are no particular upper limits on n and m, each of n and m is preferably 10 or smaller, more preferably 7 or smaller. Even more preferably, m is 3 or smaller. Specific examples of the oligopeptide can include, but are not limited to, (Cys-Gly)$_3$, (Cys-Gly)$_5$, (Lys-Gly-Gly)$_3$, and (Tyr-Gly-Gly-Gly)$_3$. Specific examples of the modified peptide having such a structure can include compounds 2-15, 2-17, and 2-18.

Various linker molecules and GlcNAc compounds as described above can be bonded by an appropriate combination to synthesize a linker structure having a structure designed as desired. Such linker structures can be designed as very diverse structures and can also control the number of sugar substances to be bonded. Many variations of modified peptides can be produced by such design and synthesis.

<Production Method and GlcNAc Compound>

In the present invention, the modified peptide in which the sugar substance is bonded through an O-glycosidic bond to the linker structure can be produced by the reaction of GlcNAc-oxa (or its related substance, for example, in which three hydroxy groups contained at the GlcNAc moiety are protected by acetylation), which is an oxazoline derivative of N-acetylglucosamine (GlcNAc), with a linker molecule having a hydroxy group (e.g., benzyl glycolate or an amino acid having a hydroxy group on the side chain, such as serine or tyrosine). Also, the modified peptide in which the sugar substance is bonded through an N-glycosidic bond to the linker structure can be produced by the reaction of a sugar substance having an azide group with a linker molecule having a carboxyl group in the presence of triphenylphosphine.

In the modified peptide of the present invention, in the case of linking a sugar substance having a glycochain structure as the sugar substance, the reducing end of the glycochain may be appropriately modified and bonded to the linker molecule. Alternatively, an acceptor compound having a particular sugar unit and a desired structure (e.g., a GlcNAc compound) may be synthesized, and the modified peptide can also be produced by the transfer of a glycochain to the sugar unit (e.g., GlcNAc) by use of a glycosynthase (e.g., Endo-M N175Q).

In the present invention, a "GlcNAc compound" is a compound containing GlcNAc that has not undergone a modification except for the glycosidic bond at the 1-position carbon, and functional groups capable of binding to other molecules, or a compound linked to the hANP peptide. The GlcNAc compound may be, for example, a compound in which GlcNAc as a monosaccharide is bonded through a glycosidic bond to a desired compound, amino acid, or the like in one molecule, a glycochain (e.g., AG(5)) having GlcNAc at the non-reducing end, or a compound bonded thereto. The glycosidic bond between the compound and GlcNAc may have either of the α-position or the β-position, both of which promote the transfer reaction (Endoglycosidases: Masahiko Endo, et al., Biochemistry, Biotechnology, Application). For the glycochain structure after a transfer with respect to a natural glycochain, it is preferred to have the same binding pattern as in the naturally occurring glycochain. For example, when the sugar-bound compound after the transfer has SG, the β-position is also preferred for the GlcNAc compound as an acceptor of the SG.

The GlcNAc compound can be produced according to various methods known in the art. For example, glucosamine or 4,5-dihydro-2-methyloxazolo[5',4':1,2]-3,4,6-tri-O-acetyl-1,2-dideoxy-α-glucopyranose (the following formula; see Bull. Chem. Soc. Jpn., 2003, 76, 485-500)):

[Formula 38]

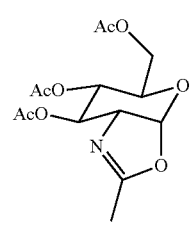

can be used as a starting material to synthesize a compound having a desired structure and functional group appropriately. Specific examples of such a GlcNAc compound can include compound 1-2C having a carboxyl group, compound 1-7A having an amino group, and compound 1-6D having a triazoledione group. Also, the GlcNAc compound in which an amino acid is linked to GlcNAc can be synthesized by the selective addition of a protective group to either the amino group or the carboxyl group. Specific examples thereof can include Boc-(GlcNAc-)Ser (compound 1-1D), Boc-(GlcNAc-)Asn (J. Am. Chem. Soc., 1999, 121, 284-290), and (GlcNAc-)Gln.

The GlcNAc compound as described above can be bonded to another linker molecule or to the peptide to synthesize GlcNAc compounds having diverse structures and linking functional groups. Such diverse GlcNAc compounds can be used in the production of the modified peptide of the present invention. For example, a GlcNAc compound having an amino group (or a carboxyl group) can be bonded to a linker molecule having a carboxyl group (or an amino group) and a desired structure and functional group in order to synthesize a GlcNAc compound having the desired functional group (specific examples: compound 1-7B having a maleimide group).

For example, a GlcNAc compound having an amino group (or a carboxyl group) can be bonded to a PEG linker molecule having a carboxyl group (or an amino group) to synthesize a GlcNAc compound having a desired length of PEG (specific examples: compounds 1-3A, 1-4B, 1-5A, and 1-19). Alternatively, a polyamide such as polyGly or poly (Ser-Gly) can be used instead of PEG to synthesize a GlcNAc compound having a desired length of polyamide linker (specific examples: compound 1-21B). In this context, an amino acid having a functional group on the side chain can be adopted as the amino acid contained in the polyamide to bond an additional GlcNAc compound to the functional group.

The GlcNAc compound used in the present invention may be a compound containing a plurality of individual GlcNAc residues in one molecule. Examples of such a polyvalent GlcNAc compound include compounds in which two GlcNAc residues are bonded through N-glycosidic bonds to the aforementioned amino acid, and compounds in which a plurality of the aforementioned GlcNAc compounds are bonded to the linker molecule. For example, an amino acid having an amino group on the side chain, such as Lys can be reacted as a linker molecule with 2 equivalents of a GlcNAc compound having a carboxyl group to synthesize a GlcNAc compound having two GlcNAc residues and one carboxyl group, such as GlcNAc-(GlcNAc-)Lys-OH. This GlcNAc-(GlcNAc-)Lys-OH can be further reacted with lysine (an amino acid having an amino group on the side chain) to synthesize a tetravalent GlcNAc compound. This step can be repeated to synthesize a GlcNAc compound containing a large number of GlcNAc residues. When the GlcNAc compound has a plurality of functional groups, a polyvalent GlcNAc compound can also be synthesized (specific examples: compound 1-5B) by introducing a protective group to a portion of these functional groups, linking GlcNAc thereto, then deprotecting the functional groups, and bonding additional GlcNAc compounds to the deprotected functional groups. These approaches can be appropriately repeated and/or combined according to conventional methods to synthesize diverse GlcNAc compounds.

Compounds derived from the GlcNAc compound by the replacement of GlcNAc as in the above definition, form, etc., with Glc or Man are defined as a Glc compound and a Man compound, respectively. These compounds are also preferably adopted as the acceptor compound for the production of the modified peptide of the present invention.

In the production of the modified peptide of the present invention, the modified peptide can be produced by the appropriate binding, transfer, etc. of intermediates (hANP, sugar substance, linker molecule, acceptor compound, etc.). The order in which these intermediates are produced is not particularly limited, and the intermediates can be produced by various methods according to conventional processes. The functional group carried by each intermediate is appropriately subjected to activation, deactivation, addition of a protective group, deprotection, etc., according to conventional methods depending on the production process.

The sugar substance can be linked by the adoption of various methods. For example, a glycochain is transferred to a linker molecule having GlcNAc, Glc, or the like, and this glycochain-bound linker molecule can be linked to the hANP peptide. Alternatively, an intermediate in which Glc or GlcNAc is linked to the hANP peptide may be used as an acceptor compound for the transfer of a glycochain in the production of the modified peptide. The hydroxy group carried by the sugar substance can be appropriately subjected to steps such as acetylation and deacetylation and thereby prevented from causing unnecessary side reactions.

<Function and Activity>

The modified peptide of the present invention exhibits a prolonged duration time in blood and excellent water solubility compared with unmodified hANP(1-28) and maintains cGMP elevating activity. hANP(1-28) disappears rapidly from blood and therefore needs to be continuously administered in clinical practice. By contrast, the modified peptide of the present invention can exert pharmacological effects even by non-continuous administration. Furthermore, the modified peptide of the present invention is superior in water solubility to native hANP and is therefore applicable to a formulation containing an active ingredient at a high concentration. Such characteristics of the modified peptide of the present invention allow for adoption of administration methods, administration routes, and formulation techniques, which cannot be attained by conventional native hANP, and also enable the modified peptide to be used in the treatment of acute cardiovascular diseases as well as chronic cardiovascular diseases (hypertension, chronic heart diseases, etc.). Moreover, the modified peptide of the present invention is also useful as a biological research tool. It is unclear how or whether native hANP migrates to a tissue when residing in blood for a long period. By contrast, such localization or the influence of the long-term residence of hANP in blood on living bodies can be examined by the administration of the modified peptide of the present invention. The duration time of the modified peptide of the present invention in blood can be tested according to the method of Test Example 3 by administering the modified peptide to an animal and then detecting the cGMP concentration in peripheral blood and/or the modified peptide contained in the peripheral blood sample. The modified peptide of the present invention maintains the effect of elevating the cGMP concentration in peripheral blood even approximately 15 minutes after intracorporeal administration, more preferably maintains this effect even approximately 30 minutes after the administration, even more preferably maintains this effect even approximately 45 minutes after the administration, and further preferably maintains this effect even approximately 60 minutes after the administration. As for the detection of the modified peptide from peripheral blood after the administration of the modified peptide, this peptide is preferably detected even approximately 30 minutes later, more preferably even approximately 45 minutes later, even more preferably even approximately 60 minutes later, further preferably even approximately 90 minutes later.

The modified peptide of the present invention exhibits excellent water solubility by virtue of the linked sugar substance. This excellent water solubility is also influenced by the chemical structure of the linker structure. The amount of native hANP dissolved per ml of water is 32 mmol at which point the peptide is gelled. By contrast, 60 mmol or more, preferably 80 mmol or more, more preferably 100 mmol (e.g., specifically, 112 mmol) of the modified peptide of the present invention is soluble per ml of water. Thus, the modified peptide of the present invention has approximately 2 or more times, preferably approximately 3 or more times the water solubility of native hANP.

The duration time in blood of the modified peptide of the present invention can be measured by administering the modified peptide to an organism, sampling blood at certain intervals of time, and detecting the modified peptide contained in the blood samples. Various methods, for example, detection by LC-MS and ELISA using an antibody specifically recognizing the ring structure of hANP, can be used as methods for detecting the modified peptide. In the case of administering the modified peptide of the present invention at a dose that produces its cGMP elevating activity, the cGMP levels of the blood samples are measured by use of a commercially available measurement kit and compared with the cGMP level in blood determined before the start of the administration. In this way, the duration time of the modified peptide in blood can be measured as biological activity. Alternatively, the modified peptide may be labeled with a radioisotope and detected by separating blood samples by SDS-PAGE or the like and detecting the radioactive signals.

In the present invention, the "prolonged duration time in blood" means that the modified peptide exhibits a longer duration time in blood than that of native hANP. Native hANP subcutaneously administered to a monkey is no longer detected in blood 30 minutes after the administration. Hence, if the modified peptide can be detected 30 minutes after the administration, its duration time in blood can be regarded as prolonged. Also, the elevation of the cGMP level in blood by the native hANP subcutaneously administered to a monkey returns, 60 minutes after the administration, to the same level as that before the administration. Hence, if the modified peptide exhibits, 60 minutes after the administration, a higher cGMP level than that before the administration, its duration time in blood can be regarded as prolonged.

The modified peptide of the present invention also has resistance to the degradation of the hANP peptide by NEP. This is probably responsible in part for the prolonged duration time. Such resistance to the NEP degradation can be measured by a method known in the art.

The cGMP elevating activity of the modified peptide of the present invention can be measured by stimulating GC-A receptor-expressing cells with a test substance prepared in concentration gradient up to a sufficient amount to provide the maximum activity, then lysing the cells, measuring cGMP concentrations in the cell lysates, and identifying the maximum cGMP concentration (Emax). The phrase "maintaining cGMP elevating activity" described for the modified peptide of the present invention means that the maximum cGMP concentration exhibited by the modified peptide is approximately 30% or more compared with the maximum cGMP concentration of native hANP. The maximum cGMP concentration exhibited by the modified peptide is preferably approximately 50% or more, more preferably approximately 70% or more. The modified peptide of the present invention can be formulated at a high concentration compared with native hANP and exhibits a prolonged duration time in blood. In this respect, it is not appropriate to define the activity of the modified peptide of the present invention on the basis of an index such as so-called EC50 values. If the maximum activity of a modified peptide at the elevated concentration can be activity equal to or greater than a certain level of activity of native hANP, the modified peptide can display sufficient efficacy when administered continuously and/or at a high concentration in clinical practice.

The present invention provides a medicament comprising the modified peptide of the present invention as an active ingredient.

<Medicament>

The substance that may be used as an active ingredient for the medicament according to the present invention may be a pharmaceutically acceptable salt of the modified peptide mentioned above. Specifically, in the present invention, an acid (an inorganic acid, for example, hydrochloric acid, sulfuric acid, or phosphoric acid, or an organic acid, for example, formic acid, acetic acid, butyric acid, trifluoroacetic acid (TFA), succinic acid, or citric acid)-addition salt of the substance may be used as the active ingredient. Alternatively, in the present invention, a metal (e.g., sodium, potassium, lithium, or calcium) salt of the substance or a salt form based on an organic base thereof may be used as the active ingredient. Such a salt of the modified peptide of the present invention may be a salt based on the hANP peptide moiety or may be a salt formed in the structure of the sugar substance. The salt of the modified peptide of the present invention is preferably a pharmaceutically acceptable salt formed at the hANP peptide moiety, more preferably trifluoroacetate or an acetate formed at the hANP peptide moiety. The pharmaceutical composition according to the present invention may contain a free form of the substance related to the active ingredient or a pharmaceutically acceptable salt thereof.

The substance that may be used as an active ingredient for the medicament according to the present invention, or the pharmaceutically acceptable salt thereof is preferably mixed with a pharmaceutically acceptable carrier, excipient, diluent, or the like known in the art and administered to an individual by an administration method generally used for medicaments, i.e., an oral administration method or a parenteral administration method such as transmucosal administration, intravenous administration, intramuscular administration, or subcutaneous administration.

The dose of the substance that may be used as an active ingredient for the medicament according to the present invention differs depending on the type of disease, the age, body weight, and severity of the individual's (patient's) condition, and the administration route, etc. In general, the upper limit of the daily dose is, for example, approximately 100 mg/kg or lower, preferably approximately 50 mg/kg or lower, more preferably 1 mg/kg or lower. The lower limit of the daily dose is, for example, approximately 0.1 µg/kg or higher, preferably 0.5 µg/kg or higher, more preferably 1 µg/kg or higher.

The frequency of administration of the medicament according to the present invention varies depending on the active ingredient used, the administration route, and the particular disease to be treated. In the case of orally administering, for example, a peptidic substance, this substance is preferably prescribed such that the number of doses per day is 4 or fewer. In the case of parenteral administration, for example, intravenous administration, the medicament can be injected by use of a normal syringe or may be continuously administered by use of an infusion pump, a catheter, or the like. Alternatively, administration through a route such as subcutaneous injection or intramuscular injection is also preferred. In this case, various administration devices that are usually used can be adopted.

When the active ingredient for the medicament of the present invention is prepared in a solution, the modified peptide of the present invention or the pharmaceutically acceptable salt thereof can be dissolved in an aqueous solvent and supplemented, if necessary, with a stabilizer, a pH adjuster, a surfactant, and the like to prepare the solution. When the active ingredient is prepared in a lyophilized formulation, the solution thus prepared can be lyophilized and dissolved in physiological saline, injectable water, or a glucose solution in use.

The medicament of the present invention is administered to a patient with a disease that is treatable by the activation on GC-A and the resulting elevation of the cGMP level, and is thereby effective for treating such a disease. In this context, the "treatment" of the disease or its symptoms means that the progression of a pathological condition expected to be normalized by the activation of GC-A is delayed, alleviated, reduced, and/or suppressed, thereby making the condition closer to a normal state. The medicament of the present invention is expected to be effective for preventing the aggravation or onset of a disease by starting its administration at an early stage of the disease or to an individual at a high risk of the disease. Although a patient who has developed the disease in the past is at risk of recurrence or chronicity, the medicament of the present invention can be expected to reduce the risk of recurrence or chronicity by continuous administration to such a patient. These effects are also included in the scope of the treatment.

Examples of such a disease include hypertension, acute heart failure (including the management of a medical condition after the onset of acute heart failure), chronic heart failure, ischemic heart diseases, acute nephritis (including the management of a medical condition after the onset of acute nephritis), chronic nephritis, acute renal failure (including the management of a medical condition after the onset of acute renal failure), chronic renal failure, ischemic heart diseases (myocardial infarction, etc.), metastasis of malignant tumor, hepatic fibrosis, hepatic cirrhosis, tissue adhesion caused by dialysis, and fibrosis.

EXAMPLES

Hereinafter, the present invention will be specifically described with reference to Examples. The embodiments of the present invention described in the Examples are given merely for illustrative purposes, and the present invention is not intended to be limited by these examples.

Example 1 is a production example of a linker molecule, a GlcNAc compound, a sugar substance, or a derivative thereof, which is an intermediate for the production of the modified peptide of the present invention. Example 2 is a production example of the modified peptide using these intermediates. Test Examples are examples of tests on the characteristics or effects of the modified peptide of the present invention.

Example 1

Example 1-1

(1-1A) Synthesis of [(2R,3S,4R,5R,6R)-3,4-diacetoxy-6-hydroxy-5-(2,2,2-trichloroethoxycarbonylamino)tetrahydropyran-2-yl]methyl Acetate (Compound 1-1A: Compound of the Following Formula)

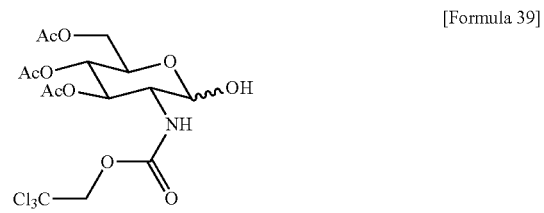

[Formula 39]

Glucosamine hydrochloride (10.0 g, 46.38 mmol) and sodium bicarbonate (11.7 g, 139 mmol) were dissolved in water (100 mL). To the solution, 2,2,2-trichloroethyl chloroformate (7.66 mL, 55.7 mmol) was added dropwise at room temperature, and the mixture was stirred for 1 hour. The reaction solution was neutralized by the addition of 1 N hydrochloric acid, and the resulting precipitates were collected by filtration. The solid was washed with water and then dried in a vacuum pump. The obtained solid was dissolved in pyridine (50 mL). To the solution, acetic anhydride (24.1 mL, 255 mmol) was added at room temperature, and the mixture was stirred overnight. The solvent was distilled off under reduced pressure to obtain a crude product. This product was purified by silica gel column chromatography (hexane:ethyl acetate=80:20-33:67, v/v) to obtain a crude product of the intermediate as a colorless oil (19.4 g).

The obtained crude product (19.4 g) of the intermediate was dissolved in N,N-dimethylformamide (200 mL). To the solution, hydrazine acetate (4.01 g, 44.5 mmol) was added at room temperature, and the mixture was stirred for 1 hour. The reaction solution was diluted with ethyl acetate and washed with 10% saline twice and saturated saline once. After drying over anhydrous sodium sulfate and filtering, the solvent was distilled off under reduced pressure to obtain a crude product. This product was purified by silica gel column chromatography (hexane:ethyl acetate=80:20-25:75, v/v) to obtain the title compound 1-1A as a white solid (11.6 g, yield through 2 steps: 52%).

$^1$H-NMR (CDCl$_3$) δ: 5.42 (1H, d, J=9.8 Hz), 5.37-5.32 (2H, m), 5.16-5.10 (1H, m), 4.80 (1H, d, J=11.7 Hz), 4.64 (1H, d, J=12.1 Hz), 4.26-4.22 (2H, m), 4.17-4.12 (1H, m), 4.09-4.03 (1H, m), 3.46-3.43 (1H, m), 2.10 (3H, s), 2.05 (3H, s), 2.02 (3H, s).

(1-1B) Synthesis of [(2R,3S,4R,5R,6S)-3,4-diacetoxy-6-(2,2,2-trichloroethanimidoyl)oxy-5-(2,2,2-trichloroethoxycarbonylamino)tetrahydropyran-2-yl] methyl Acetate (Compound 1-1B: Compound of the Following Formula)

[Formula 40]

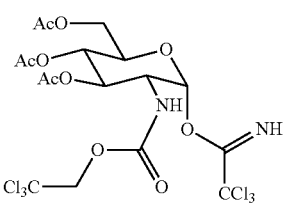

The compound 1-1A (5.00 g, 10.4 mmol) was dissolved in dichloromethane (35 mL). To the solution, trichloroacetonitrile (10.4 mL, 104 mmol) and diazabicycloundecene (0.467 mL, 3.12 mmol) were added at 0° C. The reaction solution was heated to room temperature and stirred for 40 minutes. The solvent was distilled off under reduced pressure to obtain a crude product. This product was purified by silica gel column chromatography (hexane:ethyl acetate=75: 25-50:50, v/v) to obtain the title compound 1-1B as a colorless oil (3.70 g, yield: 57%).

$^1$H-NMR (CDCl$_3$) δ: 8.81 (1H, s), 6.43 (1H, d, J=3.9 Hz), 5.37-5.34 (1H, m), 5.27-5.22 (2H, m), 4.72 (2H, dd, J=16.2, 11.9 Hz), 4.32-4.26 (2H, m), 4.16-4.10 (2H, m), 2.09 (3H, s), 2.06 (6H, s).

(1-1C) Synthesis of benzyl (2S)-3-[(2R,3R,4R,5S,6R)-3-acetamido-4,5-diacetoxy-6-(acetoxymethyl) tetrahydropyran-2-yl]oxy-2-(tert-butoxycarbonylamino)propanoate (Compound 1-1C: Compound of the Following Formula)

[Formula 41]

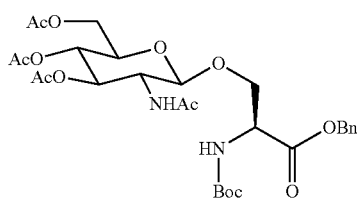

The compound 1-1B (2.77 g, 4.44 mmol) was dissolved in dichloromethane (50 mL). To the solution, benzyl (2S)-2-(tert-butoxycarbonylamino)-3-hydroxypropanoate (1.31 g, 4.44 mmol) and trimethylsilyl trifluoromethanesulfonate (8.0 µL, 0.0444 mmol) were added at room temperature, and the mixture was stirred for 1 hour. Triethylamine (0.1 mL) was added thereto, and the solvent was distilled off under reduced pressure to obtain a crude product. This product was purified by silica gel column chromatography (hexane:ethyl acetate=75:25-33:67, v/v) to obtain a crude product of the intermediate as a white solid (2.01 g).

The obtained crude product (2.01 g) of the intermediate was dissolved in acetic anhydride (50 mL). To the solution, zinc (1.5 g, 22.9 mmol), washed with 0.1 N hydrochloric acid, methanol, and diethyl ether in this order and dried, was added at room temperature, and the mixture was stirred for 6 hours. The reaction solution was filtered through celite, and the solvent was distilled off under reduced pressure to obtain a crude product. This product was purified twice by silica gel column chromatography (hexane:ethyl acetate=50: 50-0:100, v/v) to obtain the title compound 1-1C as a colorless solid (0.846 g, yield through 2 steps: 31%).

$^1$H-NMR (CDCl$_3$) δ: 7.40-7.33 (5H, m), 5.52-5.43 (2H, m), 5.29-5.15 (3H, m), 5.04 (1H, t, J=9.6 Hz), 4.70 (1H, d, J=8.2 Hz), 4.49-4.46 (1H, m), 4.27-4.23 (2H, m), 4.11-4.07 (1H, m), 3.84 (1H, dd, J=10.6, 3.5 Hz), 3.75-3.73 (1H, m), 3.64-3.62 (1H, m), 2.07 (3H, s), 2.03 (3H, s), 2.02 (3H, s), 1.94 (3H, s), 1.46 (9H, s).

(1-1D) Synthesis of (2S)-3-[(2R,3R,4R,5S,6R)-3-acetamido-4,5-diacetoxy-6-(acetoxymethyl)tetrahydropyran-2-yl]oxy-2-(tert-butoxycarbonylamino)propanoic Acid (Compound 1-1D: Compound of the Following Formula)

[Formula 42]

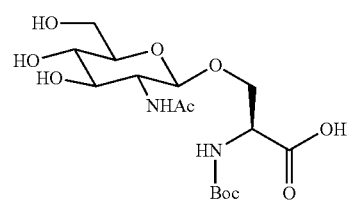

To the compound 1-1C (846 mg, 1.35 mmol), 10% palladium-carbon (approximately 50% water-wetted product) (150 mg), ethyl acetate (5 mL), and ethanol (5 mL) were added, and the mixture was stirred at room temperature for 3 hours under hydrogen atmosphere. The reaction solution was filtered, and the solvent was distilled off under reduced pressure to obtain a crude product of the intermediate as a colorless oil (740 mg).

The obtained crude product (740 mg) of the intermediate was dissolved in methanol (10 mL). To the solution, a 0.5 M solution of sodium methoxide in methanol (14 mL, 7.0 mmol) was added, and the mixture was stirred at room temperature for 20 hours. Dowex-50 was added to the reaction solution until the reaction solution became weakly acidic. Then, the mixture was filtered, and the solvent was distilled off under reduced pressure to obtain the title compound 1-1D as a light brown solid (543 mg, yield through 2 steps: 98%).

$^1$H-NMR (CD$_3$OD) δ: 4.44 (1H, d, J=8.8 Hz), 4.28-4.25 (1H, m), 4.16 (1H, dd, J=10.4, 4.4 Hz), 3.87 (1H, dd, J=12.0, 2.0 Hz), 3.80 (1H, dd, J=10.4, 4.4 Hz), 3.68 (1H, dd, J=12.0, 5.6 Hz), 3.62-3.58 (1H, m), 3.45 (1H, dd, J=10.5, 8.5 Hz), 3.29-3.24 (2H, m), 2.00 (3H, s), 1.44 (9H, s).

FAB-MS: Calcd for $C_{16}H_{28}N_2O_{10}$: [M+H]$^+$ 409, Found 409.

Example 1-2

(1-2A) Synthesis of benzyl 2-[(2R,3R,4R,5S,6R)-3-acetamido-4,5-diacetoxy-6-(acetoxymethyl)tetrahydropyran-2-yl]oxyacetate (Compound 1-2A: Compound of the Following Formula)

[Formula 43]

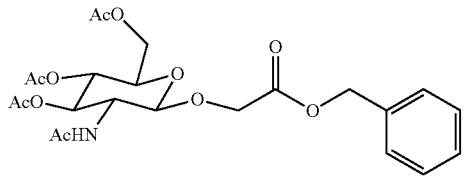

4',5'-Dihydro-2'-methyloxazolo[5',4':1,2]-3,4,6-tri-O-acetyl-1,2-dideoxy-α-glucopyranose (4.30 g, 13.1 mmol) produced according to the description of Bull. Chem. Soc. Jpn., 2003, 76, 485-500 was dissolved in dichloroethane (50 ml). To the solution, benzyl glycolate (5.56 ml, 39.1 mmol) and pyridinium p-toluenesulfonate (1.64 g, 6.53 mmol) were added at room temperature, and the mixture was heated to reflux for 3 hours. The reaction solution was cooled and then added to a saturated aqueous solution of sodium bicarbonate under ice cooling, and the organic matter was extracted with dichloromethane. The organic layer was washed with a 1 N aqueous hydrochloric acid solution, a saturated aqueous solution of sodium bicarbonate, and saturated saline, then dried over anhydrous sodium sulfate, and filtered, and the solvent was distilled off under reduced pressure to obtain a crude product. This product was purified by silica gel column chromatography (hexane:ethyl acetate=60:40-0:100, v/v) to obtain the title compound 1-2A as a colorless solid (3.45 g, yield: 53%).

$^1$H-NMR (CDCl$_3$) δ: 7.37-7.34 (5H, m), 5.85 (1H, d, J=8.8 Hz), 5.16-5.08 (4H, m), 4.66 (1H, d, J=8.3 Hz), 4.33 (2H, s), 4.22 (1H, dd, J=12.2, 4.4 Hz), 4.09 (1H, dd, J=12.2, 2.4 Hz), 4.07-4.02 (1H, m), 3.64-3.62 (1H, m), 2.05 (3H, s), 2.01 (3H, s), 1.99 (3H, s), 1.91 (3H, s).

(1-2B) Synthesis of 2-[(2R,3R,4R,5S,6R)-3-acetamido-4,5-diacetoxy-6-(acetoxymethyl)tetrahydropyran-2-yl]oxyacetatic Acid (Compound 1-2B: Compound of the Following Formula)

[Formula 44]

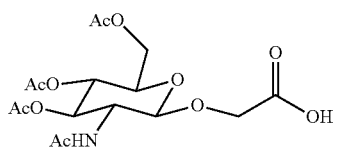

The compound 1-2A (3.45 g, 6.96 mmol) was dissolved in methanol (54 ml). To the solution, 20% palladium hydroxide-carbon (690 mg) was added, and the mixture was stirred at room temperature for 3.0 hours under hydrogen atmosphere. The reaction mixture was filtered through celite, and the solvent was distilled off under reduced pressure. The solid obtained by the addition of diisopropyl ether was collected by filtration to obtain the title compound 1-2B as a colorless solid (2.72 g, yield: 96%).

$^1$H-NMR (CDCl$_3$) δ: 6.36 (1H, d, J=8.8 Hz), 5.21-5.10 (2H, m), 4.70 (1H, d, J=8.8 Hz), 4.39 (1H, d, J=16.9 Hz), 4.32 (1H, d, J=16.9 Hz), 4.28 (1H, dd, J=12.2, 4.9 Hz), 4.15 (1H, dd, J=12.2, 2.4 Hz), 4.11-4.05 (1H, m) 3.72-3.70 (1H, m), 2.10 (3H, s), 2.07 (3H, s), 2.04 (3H, s), 1.97 (3H, s).

(1-2C) Synthesis of 2-[(2R,3R,4R,5S,6R)-3-acetamido-4,5-dihydroxy-6-(hydroxymethyl)tetrahydropyran-2-yl]oxyacetic Acid (Compound 1-2C: Compound of the Following Formula)

[Formula 45]

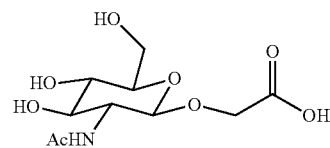

The compound 1-2B (2.72 g, 6.73 mmol) was dissolved in methanol (42 ml). To the solution, a 5 mol/L solution of sodium methoxide in methanol (2 ml, 10 mmol) was added at room temperature, and then the mixture was stirred overnight at room temperature. After the completion of the reaction, distilled water (4 ml) was added thereto, and then an ion-exchange resin (Dowex 50w×8) was added to the mixture to adjust its pH to 3. The reaction solution was filtered, and the solvent was distilled off under reduced pressure. The solid obtained by the addition of diisopropyl ether was collected by filtration to obtain the title compound 1-2C as a colorless solid (2.72 g, yield: 96%).

$^1$H-NMR (D$_2$O, TMSP) δ: 4.57 (1H, d, J=8.6 Hz), 4.17 (2H, s), 3.91 (1H, dd, J=12.5, 1.6 Hz), 3.77-3.72 (2H, m), 3.56-3.41 (3H, m), 2.05 (3H, s).

ESI-LC-MS: Calcd for C$_{10}$H$_{17}$NO$_3$: [M+H]$^+$ 280, Found 280.

Example 1-3

(1-3A) Synthesis of 3-[2[2[2[2[[2-[(2R,3R,4R,5S,6R)-3-acetamido-4,5-dihydroxy-6-(hydroxymethyl)tetrahydropyran-2-yl]oxyacetyl]amino]ethoxy]ethoxy]ethoxy]ethoxy]propanoic Acid (Compound 1-3A: Compound of the Following Formula)

[Formula 46]

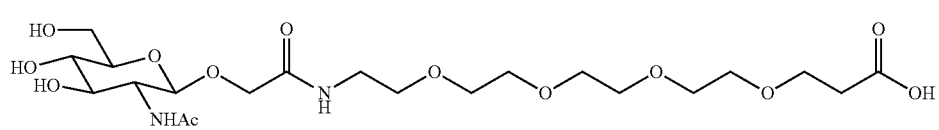

A 1.20 mmol/g 2-chlorotrityl chloride resin (694 mg, 0.833 mmol) was placed in a column for solid-phase synthesis. Dichloromethane (5 mL) was added thereto, and the mixture was shaken for 5 minutes. After filtration, a solution of 3-[2[2[2[2-(9H-fluoren-9-ylmethoxycarbonylamino)ethoxy]ethoxy]ethoxy]ethoxy]propan oic acid (488 mg, 1 mmol) and N,N-diisopropylethylamine (730 μL, 4.17 mmol) in dichloromethane (5 mL) was added thereto, and the mixture was stirred at room temperature for 2 hours. After filtration, the resin was washed with a dichloromethane mixed solution (dichloromethane:methanol:N,N-diisopropylethylamine=85:10:5, v/v) three times, dichloromethane three times, and N,N-dimethylformamide three times. A 20% solution of piperidine in N,N-dimethylformamide (5 mL) was added thereto, and the mixture was shaken for 5 minutes, followed by filtration. This operation was carried out 4 times. The resin was washed with N,N-dimethylformamide three times, dichloromethane three times, and diethyl ether three times and dried in a vacuum pump. An aliquot (200 mg) of the obtained resin (800 mg) was placed in a column for solid-phase synthesis, and N,N-dimethylformamide (2.5 mL), triethylamine (406 μL, 2.92 mmol), and water (0.5 mL) were added thereto. A solution obtained by the stirring of the compound 1-2C (174 mg, 0.625 mmol), N,N-dimethylformamide (3 mL), triethylamine (174 μL, 1.25 mmol), and dimethylthiophosphonoyl chloride (80 mg, 0.625 mmol) at room temperature for 1 hour was added thereto. The mixture was stirred at room temperature for 2 hours and then filtered, and the resin was washed with N,N-dimethylformamide three times and dichloromethane three times. A 1% solution of trifluoroacetic acid in dichloromethane (2 mL) was added thereto, and the mixture was shaken for 2 minutes, followed by the recovery of the filtrate. This operation was carried out 10 times. The solvent in the recovered solution was distilled off under reduced pressure to obtain a crude product. The crude product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents to obtain the title compound 1-3A as a white solid (25 mg).

ESI-LC-MS: Calcd for $C_{21}H_{38}N_2O_{13}$: $[M+H]^+$ 526, Found 526.

Example 1-4

(1-4A) Synthesis of 3-[2-[2-[2-[2-[2-[2-[2-[2-[2-[2-(2-aminoethoxy)ethoxy]ethoxy]ethoxy]ethoxy]ethoxy]eth oxy]ethoxy]ethoxy]ethoxy]ethoxy]propanoic Acid (Compound 1-4A: Compound of the Following Formula)

[Formula 47]

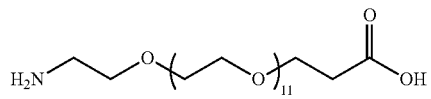

3-[2-[2-[2-[2-[2-[2-[2-[2-[2-[2-[2-(9H-Fluoren-9-ylmethoxycarbonylamino)ethoxy]ethoxy]ethoxy]ethoxy]ethoxy]ethoxy]ethoxy]ethoxy]ethoxy]ethoxy]ethoxy]propanoic acid (320 mg, 0.38 mmol) was dissolved in methanol (2 ml) and distilled water (2 ml). To the solution, a 1 N aqueous sodium hydroxide solution (1 ml) was added at 0° C., and the mixture was stirred at room temperature for 1.5 hours. 1 N hydrochloric acid (1 ml) was added thereto at 0° C., and the organic solvent was distilled off under reduced pressure. To the residue, distilled water (10 ml) was added, and the resulting product was washed with dichloromethane, then separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents, and lyophilized to obtain the title compound 1-4A as a colorless oil (233.5 mg, 99%).

$^1$H-NMR (CDCl$_3$) δ: 7.63 (2H, br s), 3.79 (2H, t, J=5.1 Hz), 3.75 (2H, t, J=5.9 Hz), 3.70-3.68 (2H, m), 3.65-3.61 (42H, m), 3.21-3.17 (2H, m), 2.58 (2H, t, J=5.9 Hz).

(1-4B) Synthesis of 3-[2-[2-[2-[2-[2-[2-[2-[2-[2-[2-[2-[2-[[2-[(2R,3R,4R,5S,6R)-3-acetamido-4,5-dihydroxy-6-(hydroxymethyl)tetrahydropyran-2-yl]oxyacetyl]amino]ethoxy]ethoxy]ethoxy]ethoxy]ethoxy]ethoxy]ethoxy]ethoxy]ethoxy]ethoxy]ethoxy]propanoic Acid (Compound 1-4B: Compound of the Following Formula)

[Formula 48]

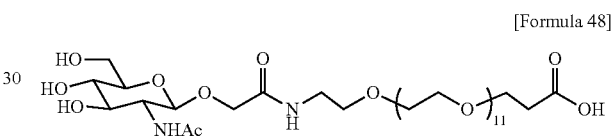

The compound 1-2C (36.6 mg, 0.13 mmol) was dissolved in dimethylformamide (500 μl). To the solution, triethylamine (45.7 μl, 0.33 mmol) was added at room temperature, then a solution of dimethylthiophosphinoyl chloride (16.9 mg, 0.13 mmol) in dimethylformamide (500 μl) was added at 0° C., and the mixture was stirred at 0° C. for 0.5 hours.

The compound 1-4A (67.5 mg, 0.11 mmol) was dissolved in dimethylformamide (500 μl). To the solution, prepared active ester was added at 0° C., and the mixture was stirred at room temperature for 6 hours. Distilled water (3 ml) and acetic acid (100 μl) were added thereto, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound 1-4B as a colorless oil (31.0 mg, 32%).

$^1$H-NMR (CDCl$_3$) δ: 7.62 (1H, d, J=6.8 Hz), 7.40 (1H, t, J=5.4 Hz), 4.47 (1H, d, J=8.3 Hz), 4.27 (1H, d, J=16.1 Hz), 4.22 (1H, d, J=16.1 Hz), 3.90 (1H, dd, J=12.0, 3.2 Hz), 3.81 (1H, dd, J=12.2, 4.9 Hz), 3.77 (2H, t, J=6.1 Hz), 3.74-3.52 (54H, m), 3.39-3.34 (2H, m), 2.59 (2H, t, J=6.1 Hz), 2.08 (3H, s). MALDI-TOF-MS: Calcd for $C_{37}H_{70}N_2O_{21}$: $[M+Na]^+$ 901, Found 901.

Example 1-5

(1-5A) Synthesis of 3-[2-[2-[2-[2-[[(2S)-4-[[(2R,3R,4R,5S,6R)-3-acetamido-4,5-dihydroxy-6-(hydroxymethyl)tetrahydropyran-2-yl]amino-2-(tert-butoxycarbonylamino)-4-oxobutanoyl]amino]ethoxy]ethoxy]ethoxy]ethoxy]propanoic Acid (Compound 1-5A: Compound of the Following Formula)

[Formula 49]

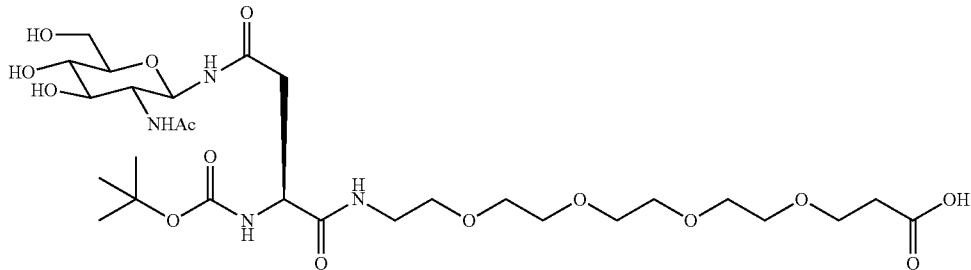

3-[2-[2-[2-[2-(tert-Butoxycarbonylamino) ethoxy]ethoxy]ethoxy]ethoxy]propanoic acid (200 mg, 0.547 mmol) was dissolved in a solution of 4 N hydrochloric acid in dioxane (2 mL), and the solution was stirred at room temperature for 1 hour. The solvent was distilled off under reduced pressure, and the residue was dried in a vacuum pump to obtain a crude product of the intermediate as a light brown oil (165 mg).

(2S)-4-[[(2R,3R,4R,5S,6R)-3-Acetamido-4,5-dihydroxy-6-(hydroxymethyl)tetrahydropyran-2-yl]amino]-2-(tert-butoxycarbonylamino)-4-oxobutanoic acid (158 mg, 0.364 mmol) produced according to the approach of J. Am. Chem. Soc., 1999, 121, 284-290 and HATU (138 mg, 0.364 mmol) were dissolved in N,N-dimethylformamide (3 mL). To the solution, N,N-diisopropylethylamine (128 µL, 0.728 mmol) was added, and the mixture was stirred at room temperature for 1 minute. This solution was added to the obtained crude product (54.9 mg) of the intermediate, further N,N-diisopropylethylamine (128 µL, 0.728 mmol) was added, and the mixture was stirred at room temperature for 0.5 hours. The reaction solution was diluted with water, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents to obtain the title compound 1-5A as a white solid (53 mg, yield through 2 steps: 43%).

ESI-LC-MS: Calcd for $C_{28}H_{50}N_4O_{15}$: $[M+H]^+$ 683, Found 683.

(1-5B) Synthesis of 3-[2-[2-[2-[2-[[(2S)-4-[[(2R,3R,4R,5S,6R)-3-acetamido-4,5-dihydroxy-6-(hydroxymethyl)tetrahydropyran-2-yl]amino]-2-[[2-[(2R,3R,4R,5S,6R)-3-acetamido-4,5-dihydroxy-6-(hydroxymethyl)tetrahydropyran-2-yl]oxyacetyl]amino]-4-oxobutanoyl]amino]ethoxy]ethoxy]ethoxy]ethoxy]propanoic Acid (Compound 1-5B: Compound of the Following Formula)

[Formula 50]

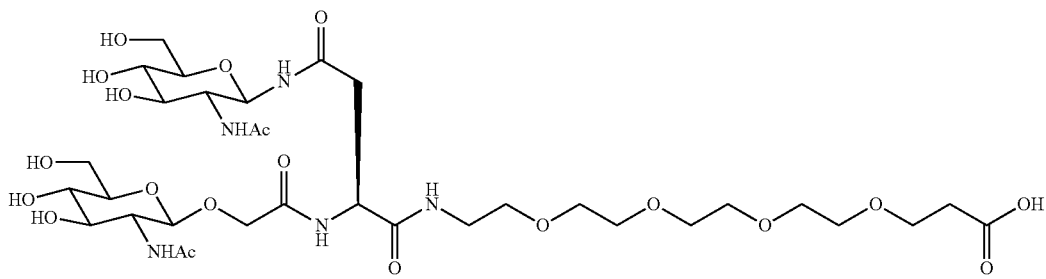

To the compound 1-5A (53 mg, 0.0777 mmol), a 30% aqueous trifluoroacetic acid solution was added, and the mixture was stirred at room temperature for 7 hours. The reaction solution was diluted with water and lyophilized to obtain a crude product of the intermediate as a light brown oil (45 mg).

The compound 1-2C (65.1 mg, 0.233 mmol) and triethylamine (65 µL, 0.466 mmol) were dissolved in N,N-dimethylformamide (0.5 mL). To the solution, a solution of dimethylthiophosphonoyl chloride (30 mg, 0.233 mmol) in N,N-dimethylformamide (0.5 mL) was added at 0° C. The mixture was heated to room temperature and stirred for 1 hour. This solution was cooled to 0° C., and a mixed solution of the obtained crude product (45 mg) of the intermediate, triethylamine (152 μL, 1.088 mmol), N,N-dimethylformamide (2.5 mL), and water (0.5 mL) was added thereto. The mixture was heated to room temperature and stirred for 8 hours. The reaction solution was diluted with water, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents to obtain the title compound 1-5B as a white solid (9.25 mg, yield through 2 steps: 14%). MALDI-TOF-MS: Calcd for $C_{33}H_{57}N_5O_{20}$: $[M+H]^+$ 844, Found 844.

Example 1-6

(1-6A) Synthesis of [(2R,3S,4R,5R,6R)-5-acetamido-3,4-diacetoxy-6-[2-(4-nitrophenyl)ethoxy]tetrahydropyran-2-yl]methyl Acetate (Compound 1-6A: Compound of the Following Formula)

[Formula 51]

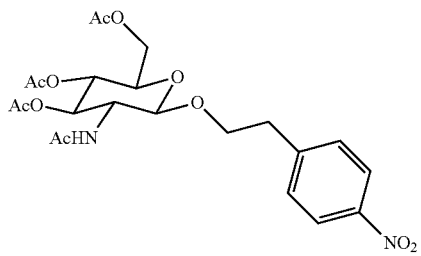

4,5-Dihydro-2-methyloxazolo[5',4':1,2]-3,4,6-tri-O-acetyl-1,2-dideoxy-α-glucopyranose (1.00 g, 3.04 mmol) produced according to the description of Bull. Chem. Soc. Jpn., 2003, 76, 485-500 was dissolved in dichloroethane (10 ml). To the solution, molecular sieve 4A (312 mg), 2-(4-nitrophenyl)-ethanol (2.54 g, 15.2 mmol), and (+)-camphorsulfonic acid (0.78 g, 3.34 mmol) were added at room temperature, and the mixture was stirred at 60° C. for 3 hours. The reaction solution was added to a saturated aqueous solution of sodium bicarbonate, and the organic matter was extracted with ethyl acetate. The organic layer was washed with saturated saline, then dried over anhydrous sodium sulfate, and filtered, and the solvent was distilled off under reduced pressure to obtain a crude product. This product was purified by silica gel column chromatography (hexane:ethyl acetate=67:33-0:100, v/v) to obtain the title compound 1-6A as a colorless solid (1.51 g, yield: 65%).

$^1$H-NMR (CDCl$_3$) δ: 8.14 (2H, d, J=8.9 Hz), 7.38 (2H, d, J=9.0 Hz), 5.32 (1H, d, J=8.6 Hz), 5.21 (1H, dd, J=10.6, 9.4 Hz), 5.07 (1H, t, J=9.6 Hz), 4.63 (1H, d, J=8.2 Hz), 4.25 (1H, dd, J=12.1, 4.7 Hz), 4.20-4.12 (2H, m), 3.88 (1H, dt, J=10.6, 8.6 Hz), 3.72-3.64 (2H, m), 3.06-2.93 (2H, m), 2.09 (3H, s), 2.03 (3H, s), 2.03 (3H, s), 1.84 (3H, s).

(1-6B) Synthesis of [(2R,3S,4R,5R,6R)-5-acetamido-3,4-diacetoxy-6-[2-(4-aminophenyl)ethoxy]tetrahydropyran-2-yl]methyl Acetate (Compound 1-6B: Compound of the Following Formula)

[Formula 52]

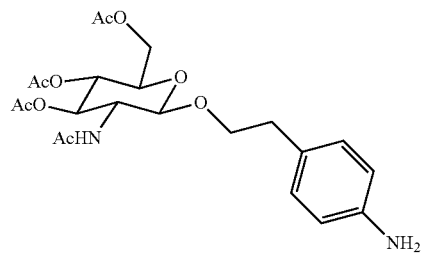

The compound 1-6A (982.0 mg, 1.98 mmol) was dissolved in ethyl acetate (12 ml) and ethanol (12 ml). To the solution, 10% palladium-carbon (250 mg) was added, and the mixture was stirred at room temperature for 1.5 hours under hydrogen atmosphere. The reaction mixture was filtered through celite, and the solvent was distilled off under reduced pressure to obtain the title compound 1-6B as a colorless solid (758 mg, yield: 82%).

$^1$H-NMR (CDCl$_3$) δ: 6.99 (2H, d, J=8.6 Hz), 6.61 (2H, d, J=8.6 Hz), 5.32 (1H, d, J=9.0 Hz), 5.24 (1H, dd, J=10.6, 9.4 Hz), 5.06 (1H, t, J=9.6 Hz), 4.60 (1H, d, J=8.2 Hz), 4.26 (1H, dd, J=12.1, 4.7 Hz), 4.15-4.04 (3H, m), 3.84 (1H, dt, J=10.6, 8.4 Hz), 3.68-3.58 (4H, m), 2.78-2.77 (2H, m), 2.09 (3H, s), 2.02 (3H, s), 2.02 (3H, s), 1.88 (3H, s).

(1-6C) Synthesis of [(2R,3S,4R,5R,6R)-5-acetamido-3,4-diacetoxy-6-[2-[4-[(ethoxycarbonylamino)carbamoylamino]phenyl]ethoxy]tetrahydropyran-2-yl]methyl Acetate (Compound 1-6C: Compound of the Following Formula)

[Formula 53]

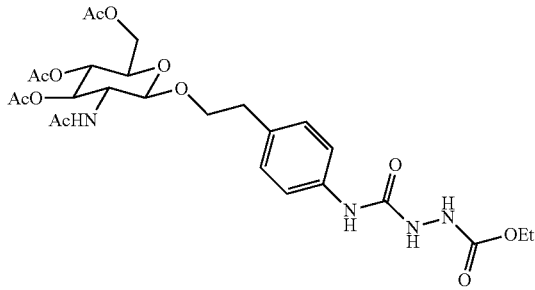

The compound 1-6B (568.0 mg, 1.22 mmol) was dissolved in tetrahydrofuran (22 ml). To the solution, triethylamine (424 μl, 3.04 mmol) was added at room temperature, then 4-nitrophenyl chloroformate (441.8 mg, 2.19 mmol) was added at −10° C., and the mixture was stirred at room temperature for 1.5 hours. Triethylamine (424 μl, 3.04 mmol) was added thereto at room temperature, then ethyl carbazate (228.2 mg, 2.19 mmol) was added, and the mixture was stirred at room temperature for 30 minutes. The reaction solution was added to water, and the organic matter was extracted with ethyl acetate twice. The organic layer was washed with saturated saline, then dried over anhydrous sodium sulfate, and filtered, and the solvent was distilled off under reduced pressure to obtain a crude product. This product was purified by silica gel column chromatography (dichloromethane:methanol=100:0-90:10, v/v) to obtain the title compound 1-6C as a colorless foam (650.4 mg, yield: 90%).

$^1$H-NMR (CDCl$_3$) δ: 7.88 (1H, br s), 7.24 (2H, s), 7.02 (2H, d, J=8.2 Hz), 6.58 (1H, br s), 5.27 (1H, t, J=10.0 Hz), 5.04 (1H, t, J=10.0 Hz), 4.64 (1H, d, J=8.6 Hz), 4.27-4.05 (5H, m), 3.90-3.81 (1H, m), 3.73-3.68 (1H, m), 3.61-3.55 (1H, m), 3.49 (2H, d, J=4.3 Hz), 2.85-2.70 (2H, m), 2.07 (3H, s), 2.00 (6H, s), 1.82 (3H, s), 1.27 (3H, t, J=9.4 Hz).

(1-6D) Synthesis of N-[(2R,3S,4R,5R,6R)-3-acet-amido-2-[2-[4-(3,5-dioxo-1,2,4-triazolidin-4-yl)phenyl]ethoxy]-4,5-dihydroxy-6-(hydroxymethyl)tetrahydropyran-3-yl]acetamide (Compound 1-6D: Compound of the Following Formula)

[Formula 54]

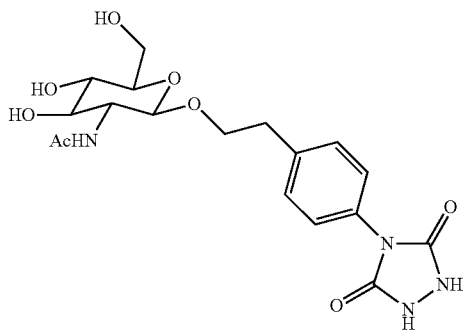

The compound 1-6C (650.0 mg, 1.09 mmol) was dissolved in methanol (30 ml). To the solution, potassium carbonate (451.8 mg, 3.27 mmol) was added at room temperature, and the mixture was stirred at 60° C. for 9.5 hours. After cooling to room temperature, the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound 1-6D as a colorless solid (462.4 mg, 85%).

$^1$H-NMR (CD$_3$OD) δ: 7.35 (4H, dd, J=13.1, 8.8 Hz), 4.36 (1H, d, J=8.2 Hz), 4.17 (1H, dt, J=11.0, 4.8 Hz), 3.87 (1H, dd, J=11.9, 2.2 Hz), 3.70-3.62 (3H, m), 3.39 (1H, dd, J=10.2, 8.6 Hz), 3.28-3.22 (2H, m), 2.90 (2H, t, J=6.3 Hz).

ESI-TOF-MS: Calcd for C$_{18}$H$_{24}$N$_4$O$_8$: [M+H]$^+$ 425, Found 425.

Example 1-7

(1-7A) Synthesis of 2-[(2R,3R,4R,5S,6R)-3-acet-amido-4,5-diacetoxy-6-(acetoxymethyl)tetrahydropyran-2-yl]oxyethylamine (Compound 1-7A: Compound of the Following Formula)

[Formula 55]

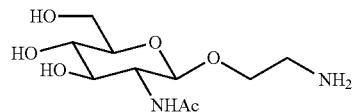

N-[(2R,3R,4R,5S,6R)-3-Acetamido-4,5-dihydroxy-6-(hydroxymethyl)tetrahydropyran-2-yl]oxyethylazide (500 mg, 1.72 mmol) was dissolved in ethanol (20 ml). To the solution, 10% palladium-carbon (200 mg) was added, and the mixture was stirred at room temperature for 3 hours under hydrogen atmosphere. The reaction mixture was filtered through celite, and the solvent was distilled off under reduced pressure to obtain the title compound 1-7A as a colorless solid (460 mg, yield: quant).

$^1$H-NMR (CD$_3$OD) δ: 4.38 (1H, d, J=8.3 Hz), 3.90-3.82 (2H, m), 3.69-3.55 (2H, m), 3.46-3.40 (1H, m), 2.80-2.73 (2H, m), 1.98 (3H, s).

(1-7B) Synthesis of N-[2-[(2R,3R,4R,5S,6R)-3-acetamido-4,5-dihydroxy-6-(hydroxymethyl)tetrahydropyran-2-yl]oxyethyl]-3-(2,5-dioxopyrrol-1-yl)propanamide (compound 1-7B: Compound of the Following Formula)

[Formula 56]

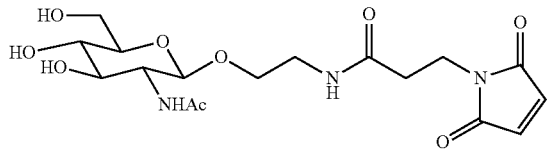

The compound 1-7A (100 mg, 0.378 mmol) was dissolved in N,N-dimethylformamide. To the solution, 2,5-dioxopyrrolidin-1-yl 3-(2,5-dioxopyrrol-1-yl)propanoate (0.126 mg, 0.473 mmol) was added, and the mixture was stirred at room temperature for 3 hours. The reaction solution was diluted with water, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents to obtain the title compound 1-7B as a white solid (93 mg, yield: 59%).

$^1$H-NMR (CD$_3$OD) δ: 6.82 (2H, s), 4.38 (1H, d, J=8.6 Hz), 3.89-3.87 (1H, m), 3.78-3.75 (3H, m), 3.66-3.62 (3H, m), 3.44-3.38 (1H, m), 2.67 (4H, s), 2.46 (2H, t, J=7.0 Hz), 1.98 (3H, s).

ESI-LC-MS: Calcd for C$_{17}$H$_{25}$N$_3$O$_9$: [M+H]$^+$ 416, Found 416.

Example 1-8

(1-8A) Synthesis of 2-[[(2R)-2-[[2-[[(2R)-2-[[2-[[(2R)-2-[[2-[[(2R)-2-[[2-[[(2R)-2-acetamido-3-tritylsulfanylpropanoyl]amino]acetyl]amino]-3-tritylsulfanylpropanoyl]amino]acetyl]amino]-3-tritylsulfanylpropanoyl]amino]acetyl]amino]-3-tritylsulfanylpropanoyl]amino]acetyl]amino]-3-tritylsulfanylpropanoyl]amino]acetic Acid (Compound 1-8A: Compound of the Following Formula)

[Formula 57]

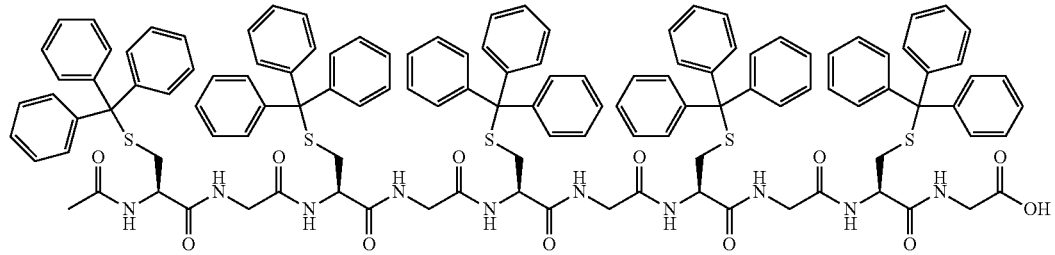

A 1.20 mmol/g 2-chlorotrityl chloride resin (833 mg, 1.00 mmol) was placed in a column for solid-phase synthesis. Dichloromethane (7.5 mL) was added thereto, and the mixture was shaken for 10 minutes. After filtration, a solution of 2-(9H-fluoren-9-ylmethoxycarbonylamino) acetic acid (594 mg, 2 mmol) and N,N-diisopropylethylamine (0.86 mL, 5 mmol) in dichloromethane (7.5 mL) was added thereto, and the mixture was stirred at room temperature for 2 hours. After filtration, the resin was washed with a dichloromethane mixed solution (dichloromethane:methanol:N,N-diisopropylethylamine=85:10:5, v/v) three times, dichloromethane three times, and diethyl ether three times. The resin was dried in a vacuum pump and recovered (1.83 g). An aliquot (1.37 g) of the recovered resin was placed in a column for solid-phase synthesis. A 20% solution of piperidine in N,N-dimethylformamide (20 mL) was added thereto, and the mixture was shaken for 5 minutes, followed by the filtration of the reaction solution. This operation was carried out 4 times. After washing with N,N-dimethylformamide 4 times, a solution of (2R)-2-(9H-fluoren-9-ylmethoxycarbonylamino)-3-tritylsulfanyl]propanoic acid (1.32 g, 2.25 mmol), HATU (856 mg, 2.25 mmol), and N,N-diisopropylethylamine (582 μL, 4.50 mmol) in N,N-dimethylformamide (15 mL) was added thereto, and the mixture was shaken at room temperature for 30 minutes. After filtration, the resin was washed with N,N-dimethylformamide 4 times. A 20% solution of piperidine in N,N-dimethylformamide (20 mL) was added thereto, and the mixture was shaken for 5 minutes, followed by filtration of the reaction solution. This operation was carried out 4 times. After washing with N,N-dimethylformamide 4 times, a solution of 2-(9H-fluoren-9-ylmethoxycarbonylamino) acetic acid (669 mg, 2.25 mmol), HATU (856 mg, 2.25 mmol), and N,N-diisopropylethylamine (582 μL, 4.50 mmol) in N,N-dimethylformamide (15 mL) was added thereto, and the mixture was shaken at room temperature for 30 minutes. After filtration, the resin was washed with N,N-dimethylformamide 4 times. A 20% solution of piperidine in N,N-dimethylformamide (20 mL) was added thereto, and the mixture was shaken for 5 minutes, followed by filtration of the reaction solution. This operation was carried out 4 times. After washing with N,N-dimethylformamide 4 times, a solution of (2R)-2-(9H-fluoren-9-ylmethoxycarbonylamino)-3-tritylsulfanyl]propanoic acid (1.32 g, 2.25 mmol), HATU (856 mg, 2.25 mmol), and N,N-diisopropylethylamine (582 μL, 4.50 mmol) in N,N-dimethylformamide (15 mL) was added thereto, and the mixture was shaken at room temperature for 30 minutes. After filtration, the resin was washed with N,N-dimethylformamide 4 times. A 20% solution of piperidine in N,N-dimethylformamide (20 mL) was added thereto, and the mixture was shaken for 5 minutes, followed by filtration of the reaction solution. This operation was carried out 4 times. After washing with N,N-dimethylformamide 4 times, a solution of 2-(9H-fluoren-9-ylmethoxycarbonylamino) acetic acid (669 mg, 2.25 mmol), HATU (856 mg, 2.25 mmol), and N,N-diisopropylethylamine (582 μL, 4.50 mmol) in N,N-dimethylformamide (15 mL) was added thereto, and the mixture was shaken at room temperature for 30 minutes. After filtration, the resin was washed with N,N-dimethylformamide 4 times. A 20% solution of piperidine in N,N-dimethylformamide (20 mL) was added thereto, and the mixture was shaken for 5 minutes, followed by filtration of the reaction solution. This operation was carried out 4 times. After washing with N,N-dimethylformamide 4 times, a solution of (2R)-2-(9H-fluoren-9-ylmethoxycarbonylamino)-3-tritylsulfanyl]propanoic acid (1.32 g, 2.25 mmol), HATU (856 mg, 2.25 mmol), and N,N-diisopropylethylamine (582 μL, 4.50 mmol) in N,N-dimethylformamide (15 mL) was added thereto, and the mixture was shaken at room temperature for 30 minutes. After filtration, the resin was washed with N,N-dimethylformamide 4 times. A 20% solution of piperidine in N,N-dimethylformamide (20 mL) was added thereto, and the mixture was shaken for 5 minutes, followed by filtration of the reaction solution. This operation was carried out 4 times. After washing with N,N-dimethylformamide 4 times, a solution of 2-(9H-fluoren-9-ylmethoxycarbonylamino) acetic acid (669 mg, 2.25 mmol), HATU (856 mg, 2.25 mmol), and N,N-diisopropylethylamine (582 μL, 4.50 mmol) in N,N-dimethylformamide (15 mL) was added, and the mixture was shaken at room temperature for 30 minutes. After filtration, the resin was washed with N,N-dimethylformamide 4 times. A 20% solution of piperidine in N,N-dimethylformamide (20 mL) was added thereto, and the mixture was shaken for 5 minutes, followed by filtration of the reaction solution. This operation was carried out 4 times. After washing with N,N-dimethylformamide 4 times, a solution of (2R)-2-(9H-fluoren-9-ylmethoxycarbonylamino)-3-tritylsulfanyl]propanoic acid (1.32 g, 2.25 mmol), HATU (856 mg, 2.25 mmol), and N,N-diisopropylethylamine (582 μL, 4.50 mmol) in N,N-dimethylformamide (15 mL) was added thereto, and the mixture was shaken at room temperature for 30 minutes. After filtration, the resin was washed with N,N-dimethylformamide 4 times. A 20% solution of piperidine in N,N-dimethylformamide (20 mL) was added thereto, and the mixture was shaken for 5 minutes, followed by filtration of the reaction solution. This operation was carried out 4 times. After washing with N,N-dimethylformamide 4 times, a solution of 2-(9H-fluoren-9-ylmethoxycarbonylamino) acetic acid (669 mg, 2.25 mmol), HATU (856 mg, 2.25 mmol), and N,N-diisopropylethylamine (582 μL, 4.50 mmol) in N,N-dimethylformamide (15 mL) was added thereto, and the mixture was shaken at room temperature for 30 minutes. After filtration, the resin was washed with N,N-dimethylformamide 4 times. A 20% solution of piperidine in N,N-dimethylformamide (20 mL) was added thereto, and the mixture was shaken for 5 minutes, followed by filtration of the reaction solution. This operation was carried out 4 times. After washing with N,N-dimethylformamide 4 times, a solution of (2R)-2-(9H-fluoren-9-ylmethoxycarbonylamino)-3-tritylsulfanyl]propanoic acid (1.32 g, 2.25 mmol), HATU (856 mg, 2.25 mmol), and N,N-diisopropylethylamine (582 μL, 4.50 mmol) in N,N-dimethylformamide (15 mL) was added thereto, and the mixture was shaken at room temperature for 30 minutes. After filtration, the resin was washed with N,N-dimethylformamide 4 times. A 20% solution of piperidine in N,N-dimethylformamide (20 mL) was added thereto, and the mixture was shaken for 5 minutes, followed by filtration of the reaction solution. This operation was carried out 4 times. The resin was washed with N,N-dimethylformamide 4 times and washed with dichloromethane 4 times and diethyl ether 4 times. The resin was dried in a vacuum pump and recovered (1.83 g). An aliquot (360 mg) of the recovered resin was placed in a column for solid-phase synthesis. A solution of acetic acid (27 mg, 0.45 mmol), HATU (171 mg, 0.45 mmol), and N,N-diisopropylethylamine (154 μL, 0.90 mmol) in N,N-dimethylformamide (5 mL) was added thereto, and the mixture was shaken at room temperature for 30 minutes. After filtration, the resin was washed with N,N-dimethylformamide 4 times and dichloromethane 4 times. A mixed solution of 1,1,1,3,3,3-hexafluoro-2-propanol (1 mL) and dichloromethane (3 mL) was added thereto, and the mixture was shaken at room temperature for 1.5 hours. The resin was filtered off, and the filtrate was concentrated under reduced pressure. The concentrate was subjected to azeotropy with dichloromethane three times and dried in a vacuum pump to obtain the title compound 1-8A as a brown solid (176 mg).

MALDI-TOF-MS: Calcd for $C_{122}H_{114}N_{10}O_{12}S_5$: [M+Na]$^+$ 2094, Found 2094.

Example 1-9

(1-9A) Synthesis of benzyl 2-[[(2S)-2,6-bis(tert-butoxycarbonylamino)hexanoyl]amino]acetate (Compound 1-9A: Compound of the Following Formula)

[Formula 58]

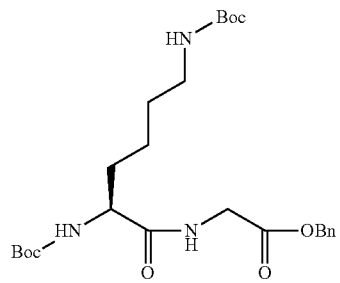

To a solution of (2S)-2,6-bis(tert-butoxycarbonylamino) hexanoic acid (1.70 g, 5.00 mmol), benzyl 2-aminoacetate (1.00 g, 5.00 mmol), and HATU (2.90 g, 7.50 mmol) in N,N-dimethylformamide (25 mL), N,N-diisopropylethylamine (2.60 mL, 15.0 mmol) was added, and the mixture was stirred at room temperature for 20 hours. The reaction solution was added to water, and the organic matter was extracted with ethyl acetate. The organic layer was washed with saturated saline, then dried over anhydrous sodium sulfate, and filtered, and the solvent was distilled off under reduced pressure to obtain a crude product. This product was purified by silica gel column chromatography (hexane:ethyl acetate=90:10-0:100, v/v) to obtain the title compound 1-9A as a pale yellow oil (2.30 g, yield: 93%).

$^1$H-NMR (CDCl$_3$) δ: 7.40-7.33 (5H, m), 6.63 (1H, s), 5.18 (2H, s), 5.11 (1H, s), 4.63 (1H, s), 4.15-4.03 (3H, m), 3.16-3.06 (2H, m), 1.91-1.81 (1H, m), 1.70-1.59 (1H, m), 1.53-1.24 (22H, m).

MS (ESI): Calcd for $C_{25}H_{40}N_3O_7$: [M+H]$^+$ 494, Found 494.

(1-9B) Synthesis of benzyl 2-[[(2S)-2,6-bis(tert-butoxycarbonylamino)hexanoyl]amino]acetate (Compound 1-9B: Compound of the Following Formula)

[Formula 59]

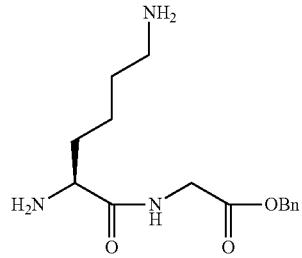

The compound 1-9A (250 mg, 0.507 mmol) was dissolved in dichloromethane (3.0 ml). To the solution, trifluoroacetic acid (1.0 mL) was added, and the mixture was stirred at room temperature for 1 hour. The solvent was distilled off under reduced pressure to obtain the title compound 1-9B as a pale yellow oil (247 mg, yield: 100%).

$^1$H-NMR (DMSO-d$_5$) δ: 8.95 (1H, t, J=5.9 Hz), 8.18 (2H, s), 7.71 (2H, s), 7.42-7.34 (5H, m), 5.16 (2H, d, J=12.5 Hz), 4.12-3.96 (2H, m), 3.87-3.78 (1H, m), 2.78-2.66 (2H, m), 1.76-1.66 (2H, m), 1.54-1.47 (2H, m), 1.40-1.31 (2H, m).

(1-9C) Synthesis of benzyl 2-[[(2S)-2,6-bis[[2-[(2R,3R,4R,5S,6R)-3-acetamido-4,5-dihydroxy-6-(hydroxymethyl)tetrahydropyran-2-yl]oxyacetyl]amino]hexanoyl]amino]acetate (Compound 1-9C: Compound of the Following Formula)

[Formula 60]

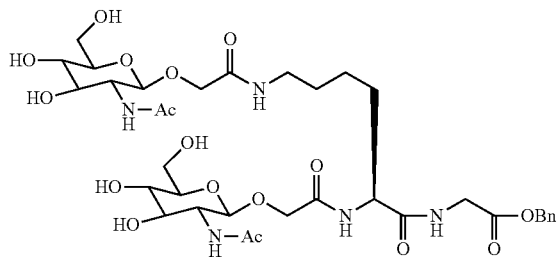

The title compound 1-9C was obtained as a colorless foam (180 mg, yield: 88%) according to the same method as in (1-5B) using the compounds 1-9B (93.0 mg, 0.190 mmol) and 1-2C (160 mg, 0.573 mmol).

$^1$H-NMR (CD$_3$OD) δ: 7.39-7.29 (5H, m), 5.16 (2H, s), 4.94-4.84 (2H, m), 4.46-4.39 (3H, m), 4.33-4.27 (2H, m), 4.13-4.00 (3H, m), 3.94 (1H, d, J=17.6 Hz), 3.91-3.84 (2H, m), 3.78-3.66 (4H, m), 3.50-3.42 (2H, m), 3.38-3.28 (2H, m), 3.22 (2H, t, J=6.6 Hz), 2.03 (3H, s), 2.01 (3H, s), 1.88-1.81 (1H, m), 1.78-1.67 (1H, m), 1.58-1.50 (2H, m), 1.48-1.35 (2H, m).

(1-9D) Synthesis of 2-[[(2S)-2,6-bis[[2-[(2R,3R,4R,5S,6R)-3-acetamido-4,5-dihydroxy-6-(hydroxymethyl)tetrahydropyran-2-yl]oxyacetyl]amino]hexanoyl]amino]acetic Acid (Compound 1-9D: Compound of the Following Formula)

[Formula 61]

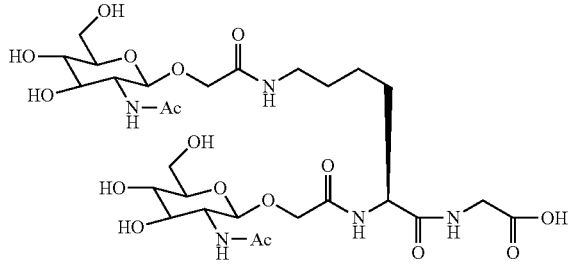

The compound 1-9C (180 mg, 0.221 mmol) was dissolved in methanol (50 ml). To the solution, 10% palladium-carbon (180 mg) was added, and the mixture was stirred at room temperature for 2 hours under hydrogen atmosphere. The reaction mixture was filtered through celite, and the solvent was distilled off under reduced pressure to obtain the title compound 1-9D as a pale yellow foam (160 mg, yield: 100%).

MS (ESI): Calcd for C$_{28}$H$_{48}$N$_5$O$_{17}$: [M+H]$^+$ 726, Found 726.

Example 1-10

(1-10A) Synthesis of 2-[[(2R)-2-[[2-[[(2R)-2-[[2-[[(2R)-2-acetamido-3-sulfanylpropanoyl]amino]acetyl]amino]-3-sulfanylpropanoyl]amino]acetyl]amino]-3-sulfanylpropanoyl]amino]acetic acid (Compound 1-10A: Compound of the Following Formula)

[Formula 62]

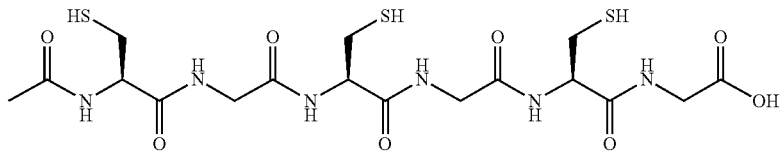

A 1.20 mmol/g 2-chlorotrityl chloride resin (208 mg, 0.25 mmol) was placed in a column for solid-phase synthesis. Dichloromethane (2.5 mL) was added thereto, and the mixture was shaken for 10 minutes. After filtration, a solution of 2-(9H-fluoren-9-ylmethoxycarbonylamino)acetic acid (149 mg, 0.5 mmol) and N,N-diisopropylethylamine (219 μL, 1.25 mmol) in dichloromethane (2.5 mL) was added thereto, and the mixture was stirred at room temperature for 2 hours. After filtration, the resin was washed with a dichloromethane mixed solution (dichloromethane:methanol:N,N-diisopropylethylamine=85:10:5, v/v) three times, dichloromethane three times, and N,N-dimethylformamide three times. The obtained resin was loaded in a peptide synthesizer (433A Peptide Synthesizer manufactured by Applied Biosystems, Inc.) and subjected to deprotection, condensation, deprotection, condensation, deprotection, condensation, deprotection, condensation, deprotection, condensation, deprotection, and condensation in the synthesizer to elongate the peptide chain. For the deprotection, piperidine and N-methylpyrrolidone were used. For the condensation reactions, HATU, N,N-diisopropylethylamine, N-methylpyrrolidone, and various carboxylic acids were used. The carboxylic acids were used in each condensation reaction in the order of (2R)-2-(9H-fluoren-9-ylmethoxycarbonylamino)-3-tritylsulfanyl]propanoic acid, 2-(9H-fluoren-9-ylmethoxycarbonylamino)acetic acid, (2R)-2-(9H-fluoren-9-ylmethoxycarbonylamino)-3-tritylsulfanyl]propanoic acid, 2-(9H-fluoren-9-ylmethoxycarbonylamino)acetic acid, (2R)-2-(9H-fluoren-9-ylmethoxycarbonylamino)-3-tritylsulfanyl]propanoic acid, and acetic acid. A half (450 mg) of the amount of the obtained resin (900 mg) was placed in a column for solid-phase synthesis, and a mixed solution of trifluoroacetic acid (2.64 mL), water (0.27 mL), phenol (0.06 g), and triisopropylsilane (0.03 mL) was added thereto. The mixture was shaken at room temperature for 2 hours, and trifluoroacetic acid was distilled off. The reaction solution was diluted with water, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents to obtain the title compound 1-10A as a white solid (11 mg, yield: 16%).

ESI-LC-MS: Calcd for $C_{17}H_{28}N_6O_8S_3$: $[M+H]^+$ 541, Found 541.

(1-10B) Synthesis of 2-[[(2R)-2-[[2-[[(2R)-2-[[2-[[(2R)-2-acetamido-3-[1-[3-[2-[(2R,3R,4R,5S,6R)-3-acetamido-4,5-dihydroxy-6-(hydroxymethyl)tetrahydropyran-2-yl]oxyethylamino]-3-oxopropyl]-2,5-dioxopyrrolidin-3-yl]sulfanylpropanoyl]amino]acetyl]amino]-3-[1-[3-[2-[(2R,3R,4R,5S,6R)-3-acetamido-4,5-dihydroxy-6-(hydroxymethyl)tetrahydropyran-2-yl]oxyethylamino]-3-oxopropyl]-2,5-dioxopyrrolidin-3-yl]sulfanylpropanoyl]amino]acetyl]amino]-3-[1-[3-[2-[(2R,3R,4R,5S,6R)-3-acetamido-4,5-dihydroxy-6-(hydroxymethyl)tetrahydropyran-2-yl]oxyethylamino]-3-oxopropyl]-2,5-dioxopyrrolidin-3-yl]sulfanylpropanoyl]amino]acetic Acid (Compound 1-10B: Compound of the Following Formula)

[Formula 63]

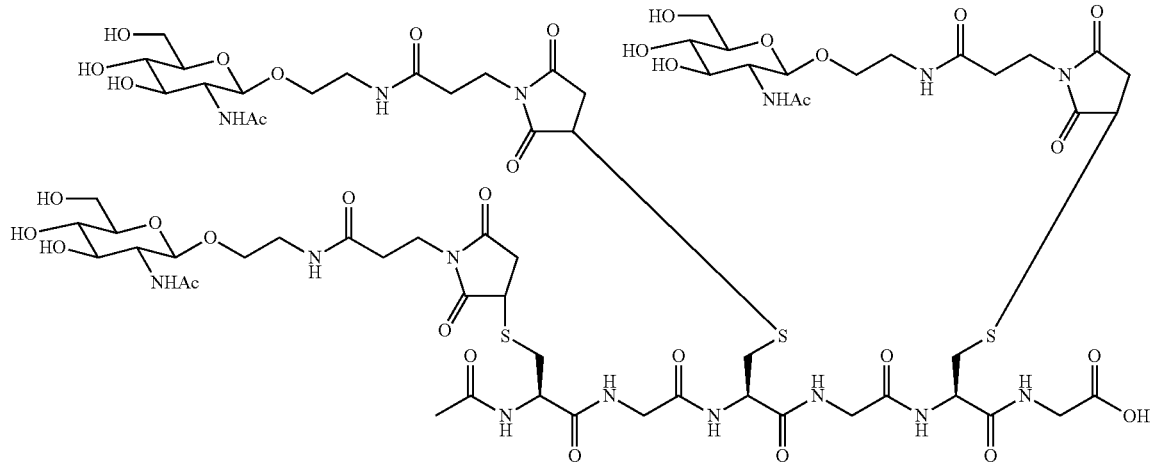

The compounds 1-10B (11 mg, 0.0203 mmol) and 1-7B (33 mg, 0.0794 mmol) were dissolved in a mixed solution of acetonitrile (1 mL) and a 0.2 M phosphate buffer of pH 6.75 (1 mL), and the solution was stirred at room temperature for 2 hours. The reaction solution was diluted with water, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents to obtain the title compound 1-10B as a white solid (27 mg, yield: 74%).

MALDI-TOF-MS: Calcd for $C_{68}H_{103}N_{15}O_{35}S_3$: $[M-H]^+$ 1784, Found 1784.

Example 1-11

(1-11A) Synthesis of N-[(2R,3R,4R,5S,6R)-3-acet-amido-4,5-dihydroxy-6-(hydroxymethyl)tetrahydro-pyran-2-yl]oxyethylamine Trifluoroacetate (Compound 1-11A: Compound of the Following Formula)

[Formula 64]

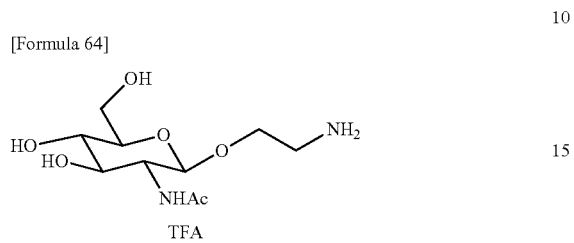

TFA

The compound 1-7A (120 mg) was dissolved in distilled water (6 ml). To the solution, trifluoroacetic acid (48 µl) was then added, and the mixture was lyophilized. The obtained amorphous solid 1-11A was used without being purified.

(1-11B) Synthesis of SG-NH$_2$ (Compound 1-11B: Compound of the Following Formula)

[Formula 65]

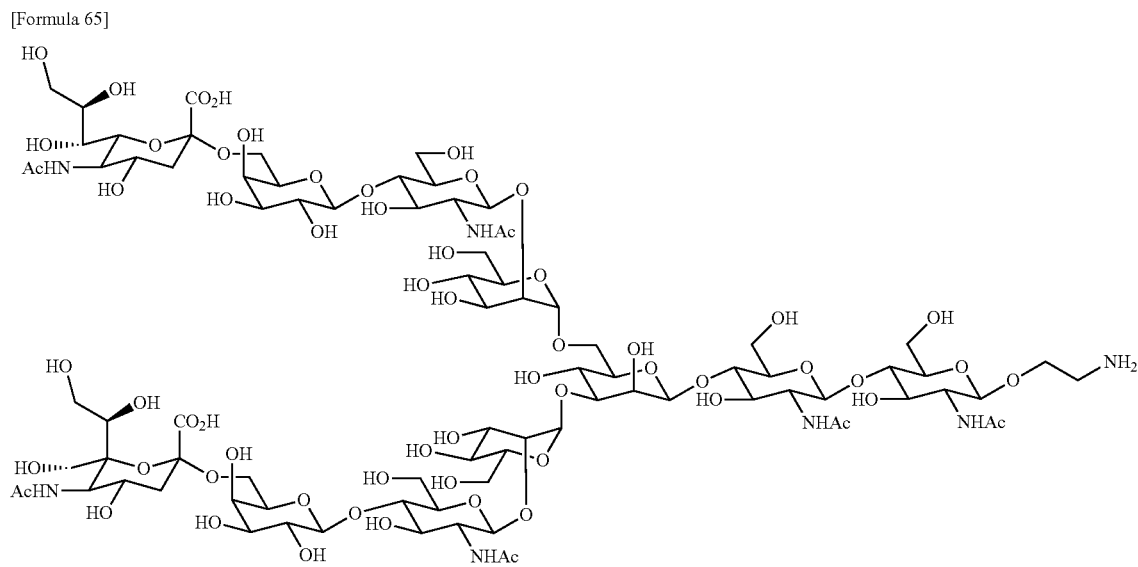

Sialylglycopeptide (60 mg) was dissolved in a 0.2 M phosphate buffer solution (pH 6.25) (260 µl). To the solution, an aqueous solution (100 µl) of glycosynthase (Endo-M-N175Q, Tokyo Chemical Industry Co., Ltd., 1 U/ml) was then added. The compound 1-11A (28 mg) in a 0.2 M phosphate buffer solution (pH 6.25) (160 µl) was further added thereto, and the mixture was reacted at 28° C. for 72 hours. The reaction was terminated by the addition of a 0.2% aqueous trifluoroacetic acid solution (2480 µl) to the reaction solution, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound SG-NH$_2$ (28.5 mg). ESI-TOF-MS: Calcd for $C_{86}H_{143}N_7O_{62}$: [M–H]$^-$ 2264.8, Found 2264.8

(1-11C) Synthesis of SG-I (Compound 1-11C: Compound of the Following Formula)

[Formula 66]

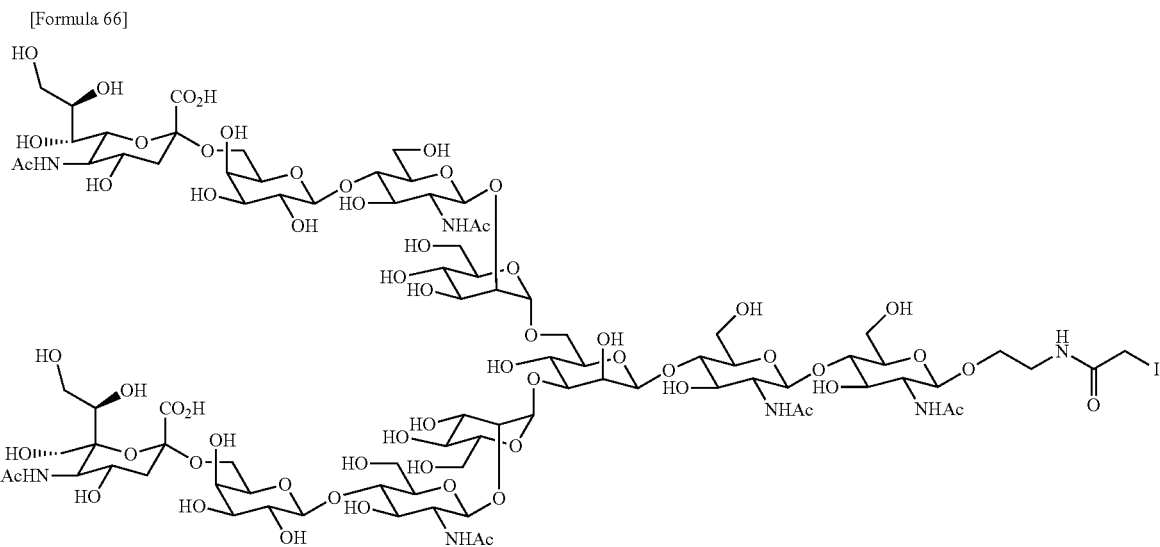

The compound SG-NH$_2$ (15.0 mg) produced in (1-11B) was dissolved in a 43 mM aqueous sodium bicarbonate solution (750 µl). To the solution, a 30 mM solution of iodoacetic acid N-hydroxysuccinimide ester in acetone (250 µl) was added under ice cooling, and the mixture was stirred at room temperature for 1 hour. The reaction was terminated by the addition of acetic acid (1.8 µl) to the reaction solution, and the organic solvent was removed under reduced pressure. The resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound SG-I (13.4 mg). ESI-TOF-MS: Calcd for $C_{88}H_{44}IN_7O_{63}$: $[M+2H]^{2+}$ 1218.5 (ave.), Found 1218.3

Example 1-12

(1-12A) Synthesis of SG-Oxa (Compound 1-12A: Compound of the Following Formula)

[Formula 67]

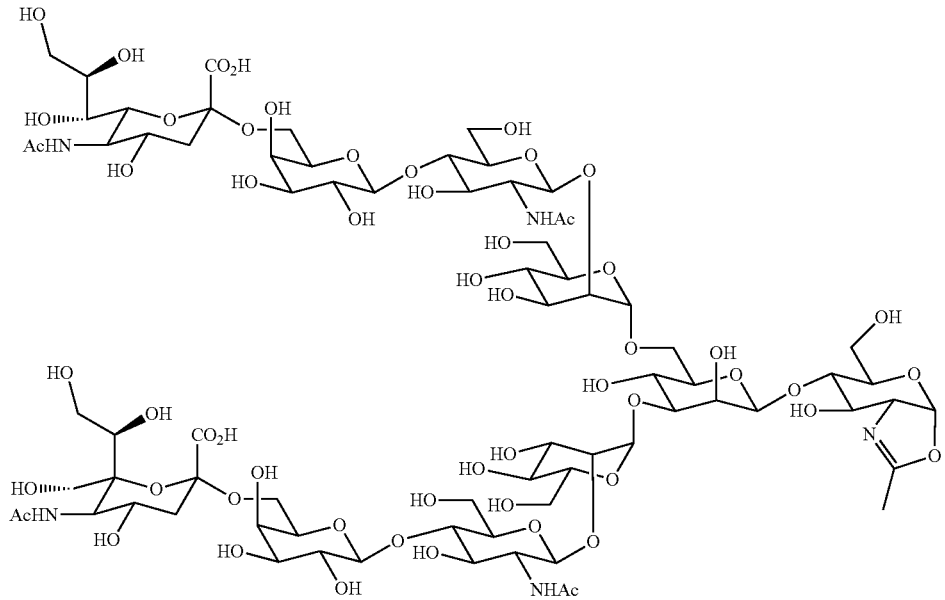

Disialooctasaccharide (Tokyo Chemical Industry Co., Ltd., 26.0 mg, 12.8 μmol) was dissolved in distilled water (210 μl). To the solution, triethylamine (80.7 μl, 579 μmol) was added at room temperature. An aqueous solution (52 l) of 2-chloro-1,3-dimethylimidazolium chloride (32.6 mg, 192 μmol) was added thereto at 0° C., and the mixture was stirred at 0° C. for 2 hours. The resulting product was purified with Sephadex G15 (0.03% aqueous $NH_3$ solution). A 0.1 N aqueous sodium hydroxide solution (100 μl) was added thereto, and the mixture was lyophilized to obtain the title compound SG-Oxa as a colorless solid (24.6 mg, 95%).

NMR (in D2O) (chart of FIG. 1).

Example 1-13

(1-13A) Synthesis of SG-M (Compound 1-13A: Compound of the Following Formula)

[Formula 68]

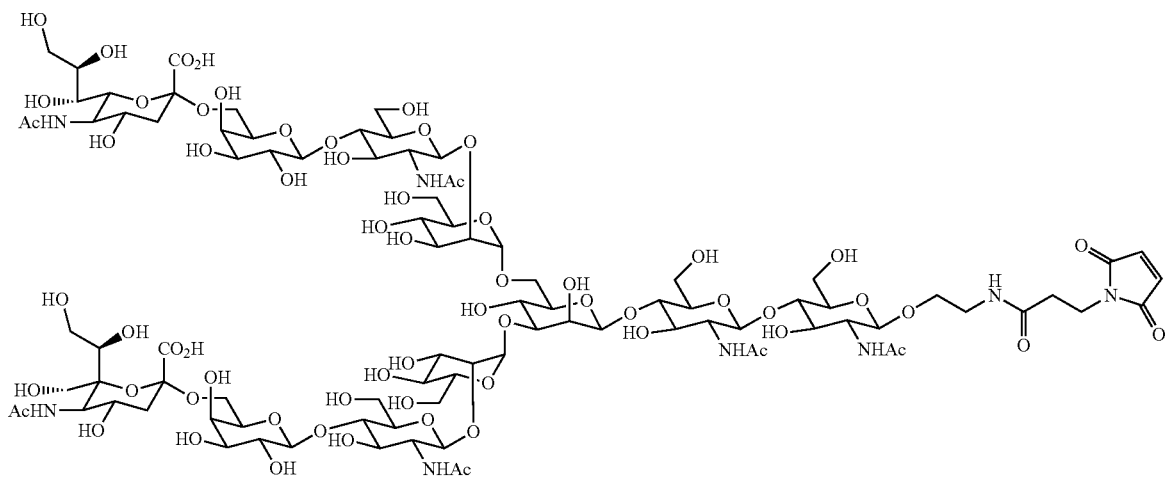

The compound $SG-NH_2$ (30.0 mg) produced in (1-11B) was dissolved in a 43 mM aqueous sodium bicarbonate solution (1500 ul). To the solution, a 13.9 mM solution of 3-(2,5-dioxopyrrol-1-yl)butyric acid N-hydroxysuccinimide ester in acetone (500 ul) was added under ice cooling, and the mixture was stirred at room temperature for 1 hour. The reaction was terminated by the addition of acetic acid (3.6 ul) to the reaction solution, and the organic solvent was removed under reduced pressure. The resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound SG-M (29 mg).

ESI-TOF-MS: Calcd for $C_{93}H_{148}N_8O_{65}$: $[M+2H]^{2+}$ 1209.4, Found 1209.4

Example 1-14

(1-14A) Synthesis of 2-[(2R,3R,4R,5S,6R)-3-acetamido-4,5-dihydroxy-6-(hydroxymethyl)tetrahydropyran-2-yl]oxyacetatic Acid Ammonium Salt (Compound 1-14A: Compound of the Following Formula)

[Formula 69]

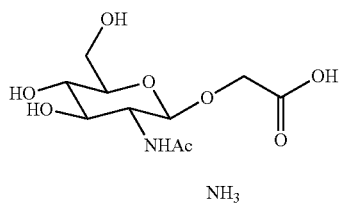

The compound 1-2C (200 mg) was dissolved in distilled water (2 ml). To the solution, 28 to 30% ammonia water (100 μl) was then added, and the mixture was lyophilized. The obtained amorphous solid 1-14A was used without being purified.

(1-14B) Synthesis of SG-A (Compound 1-14B: Compound of the Following Formula)

[Formula 70]

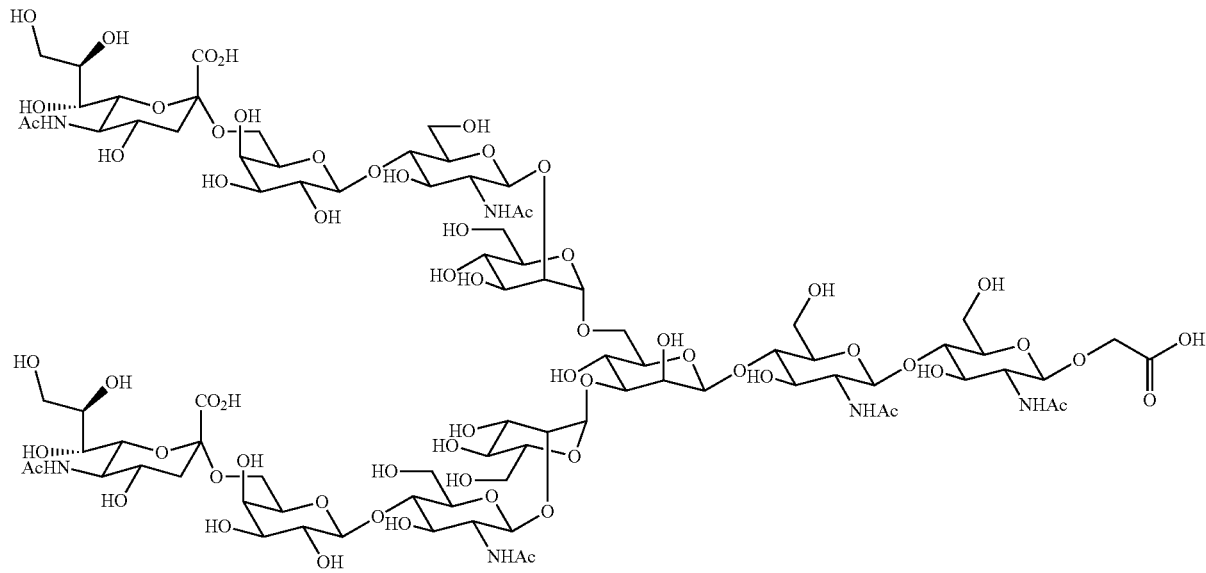

Sialylglycopeptide (58 mg) was dissolved in a 0.2 M phosphate buffer solution (pH 6.25) (254 µl). To the solution, an aqueous solution (100 µl) of glycosynthase (Endo-M-N175Q, Tokyo Chemical Industry Co., Ltd., 1 U/ml) was then added. The compound 1-14A (24 mg) in a 0.2 M phosphate buffer solution (pH 6.25) (152 µl) was further added thereto, and the mixture was reacted at 28° C. for 72 hours. The reaction was terminated by the addition of a 0.2% aqueous trifluoroacetic acid solution (3000 µl) to the reaction solution, and the resulting product was separated and purified by reverse-phase HPLC (Shiseido Co., Ltd., Proteonavi) using a 0.1% aqueous trifluoroacetic acid solution and a 0.1% solution of trifluoroacetic acid in acetonitrile as eluents and lyophilized to obtain the title compound SG-A (19.5 mg).

ESI-TOF-MS: Calcd for $C_{86}H_{140}N_6O_{64}$: $[M+2H]^{2+}$ 1142.0 (ave.), Found 1141.4

Example 1-15

(1-15A) Synthesis of Di-Tert-Butyl (2S)-2-[3-(2,5-dioxopyrrol-1-yl)propanoylamino]pentanedicarboxylate (Compound 1-15A: Compound of the Following Formula)

[Formula 71]

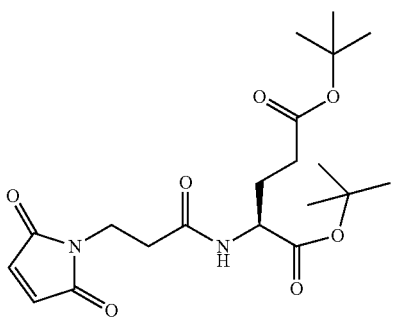

A solution of di-tert-butyl (2S)-2-aminopentanedicarboxylate hydrochloride (295 mg, 1.00 mmol) in N,N-dimethylformamide (5.0 mL) was cooled to 0° C. N,N-Diisopropylethylamine (0.510 mL, 3.00 mmol) and (2,5-dioxopyrrolidin-1-yl) 3-(2,5-dioxopyrrol-1-yl)propanoate (293 mg, 1.10 mmol) were added thereto in this order, and the mixture was stirred at 0° C. for 1 hour, further heated to room temperature, and stirred at room temperature for 18 hours. Ethyl acetate was added to the reaction solution. The organic layer was washed with 1 M hydrochloric acid and saturated saline in this order, then dried over anhydrous sodium sulfate, and filtered, and the solvent was distilled off under reduced pressure to obtain a crude product. This product was purified by silica gel column chromatography (hexane:ethyl acetate=95:5-0:100, v/v) to obtain the title compound 1-15A as a pale yellow oil (400 mg, yield: 98%).

$^1$H-NMR (CDCl$_3$) δ: 6.70 (2H, s), 6.22 (1H, d, J=7.8 Hz), 4.48-4.42 (1H, m), 3.91-3.79 (2H, m), 2.60-2.52 (2H, m), 2.35-2.18 (2H, m), 2.13-2.04 (1H, m), 1.93-1.84 (1H, m), 1.46 (9H, s), 1.44 (9H, s).

(1-15B) Synthesis of (2S)-2-[3-(2,5-dioxopyrrol-1-yl)propanoylamino]pentanedicarboxylic Acid (Compound 1-15B: Compound of the Following Formula)

[Formula 72]

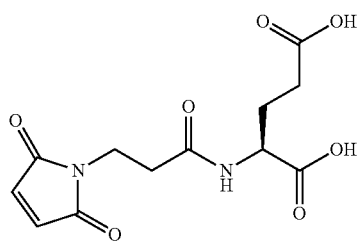

The title compound 1-15B (260 mg, yield: 89%) was obtained according to the same approach as in (1-9B) using the compound 1-15A (400 mg, 0.976 mmol).

MS (ESI): Calcd for $C_{12}H_{15}N_2O_7$: $[M+H]^+$ 299, Found 299.

(1-15C) Synthesis of SG-(SG-Gln*)-Mal (Compound 1-15C: Compound of the Following Formula)

[Formula 73]

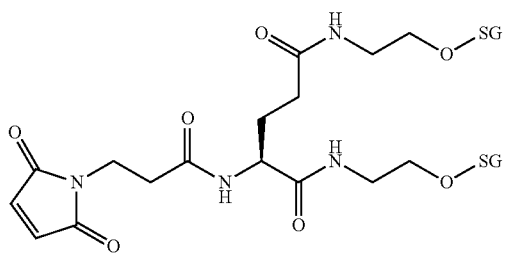

A solution of the compound 1-15B (30.0 mg, 0.101 mmol) and N-hydroxysuccinimide (58.0 mg, 0.504 mmol) in dichloromethane (0.400 mL) was cooled to 0° C. Pyridine (0.200 mL, 2.48 mmol) and trifluoroacetic anhydride (70.0 μL, 0.500 mmol) were added thereto in this order, and the mixture was stirred at 0° C. for 10 minutes. The reaction mixture was heated to room temperature and further stirred at room temperature for 30 minutes. Dichloromethane was added to the reaction solution. The organic layer was washed with 1 M hydrochloric acid, then dried over anhydrous sodium sulfate, and filtered, and the solvent was distilled off under reduced pressure to obtain a crude product. This product was purified by silica gel column chromatography (dichloromethane:ethyl acetate=25:75-0:100, v/v) to obtain a pale yellow foam (25 mg).

Subsequently, an aliquot (2.00 mg) of the obtained product was dissolved in N,N-dimethylformamide (200 μL). The solution was added to a solution of the compound SG-NH$_2$ (20.0 mg, 8.41 μmol) produced in (1-11B) and N,N-diisopropylethylamine (15 μL, 88.0 μmol) in N,N-dimethylformamide (600 μL), and the mixture was stirred at room temperature for 2 hours. A 0.2% aqueous trifluoroacetic acid solution (2.0 mL) was added to the reaction solution, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound SG-(SG-Gln*)-Mal (15.0 mg, yield: 76%).

ESI-TOF-MS: Calcd for $C_{184}H_{299}N_{16}O_{129}$: $[M+3H]^{3+}$ 1599.7 (ave.), Found 1599.6.

Example 1-16

(1-16A) Synthesis of di-tert-butyl (2S)-2-[3-[2-[2-[2-[2-[3-(2,5-dioxopyrrol-1-yl)propanoylamino]ethoxy]ethoxy]ethoxy]ethoxy]propanoylamino]pentanedicarboxylate (Compound 1-16A: Compound of the Following Formula)

[Formula 74]

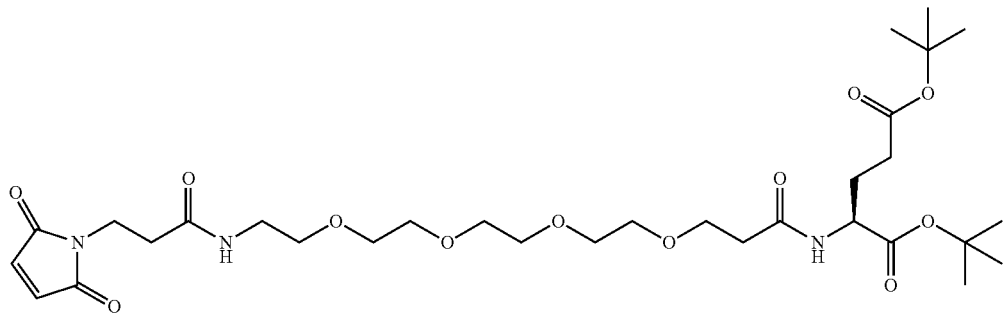

A solution of di-tert-butyl (2S)-2-aminopentanedicarboxylate hydrochloride (58.0 mg, 0.196 mmol) in N,N-dimethylformamide (1.0 mL) was cooled to 0° C. N,N-Diisopropylethylamine (0.100 mL, 0.588 mmol) and (2,5-dioxopyrrolidin-1-yl) 3-[2-[2-[2-[2-[3-(2,5-dioxopyrrol-1-yl)propanoylamino]ethoxy]ethoxy]ethoxy]ethoxy]propanoate (100 mg, 0.195 mmol) were added thereto in this order, and the mixture was stirred at 0° C. for 1 hour, further heated to room temperature, and stirred at room temperature for 20 hours. Ethyl acetate was added to the reaction solution. The organic layer was washed with 1 M hydrochloric acid and saturated saline in this order, then dried over anhydrous sodium sulfate, and filtered, and the solvent was distilled off under reduced pressure to obtain a crude product. This product was purified by silica gel column chromatography (dichloromethane:methanol=98:2-90:10, v/v) to obtain the title compound 1-16A as a pale yellow oil (100 mg, yield: 78%).

$^1$H-NMR (CDCl$_3$) δ: 6.84 (1H, br s), 6.70 (2H, s), 6.46 (1H, br s), 4.53-4.45 (1H, m), 3.85 (2H, t, J=7.2 Hz), 3.80-3.71 (2H, m), 3.68-3.60 (12H, m), 3.54 (2H, t, J=5.1 Hz), 3.42 (2H, q, J=5.1 Hz), 2.54-2.49 (4H, m), 2.37-2.21 (2H, m), 2.16-2.07 (1H, m), 1.92-1.83 (1H, m), 1.46 (9H, s), 1.43 (9H, s).

MS (ESI): Calcd for $C_{31}H_{52}N_3O_{12}$: $[M+H]^+$ 658, Found 658.

(1-16B) Synthesis of (2S)-2-[3-[2-[2-[2-[2-[3-(2,5-dioxopyrrol-1-yl)propanoylamino]ethoxy]ethoxy]ethoxy]ethoxy]propanoylamino]pentanedioic Acid (Compound 1-16B: Compound of the Following Formula)

[Formula 75]

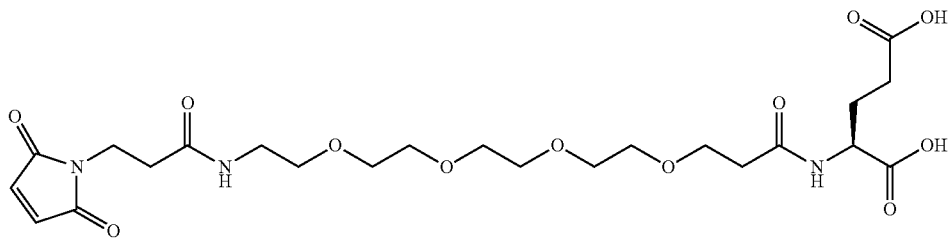

The title compound 1-16B (83 mg, yield: 100%) was obtained according to the same approach as in (1-9B) using the compound 1-16 (100 mg, 0.152 mmol).

MS (ESI): Calcd for $C_{23}H_{36}N_3O_{12}$: $[M+H]^+$ 546, Found 546.

(1-16C) Synthesis of SG-(SG-Gln*)-PEG(3)-Mal (Compound 1-16C: Compound of the Following Formula)

[Formula 76]

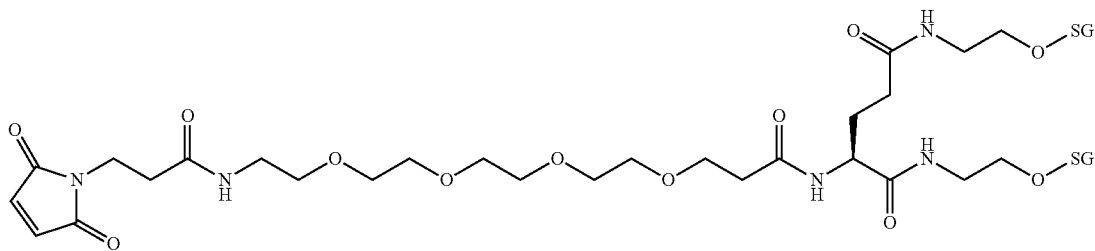

A solution of the compound 1-16B (32.0 mg, 58.7 μmol) and N-hydroxysuccinimide (34.0 mg, 0.295 mmol) in dichloromethane (0.400 mL) was cooled to 0° C. Pyridine (0.200 mL, 2.48 mmol) and trifluoroacetic anhydride (42.0 μL, 0.300 mmol) were added thereto in this order, and the mixture was stirred at 0° C. for 30 minutes. The reaction mixture was heated to room temperature and further stirred at room temperature for 2 hours. Dichloromethane was added to the reaction solution. The organic layer was washed with 1 M hydrochloric acid, then dried over anhydrous sodium sulfate, and filtered, and the solvent was distilled off under reduced pressure to obtain a crude product (35 mg). Subsequently, an aliquot (0.31 mg) of the obtained crude product was dissolved in N,N-dimethylformamide (20 μL). The solution was added to a solution of the compound SG-NH$_2$ (2.0 mg, 0.88 μmol) produced in (1-11B) and N,N-diisopropylethylamine (1.5 μL, 8.8 μmol) in N,N-dimethylformamide (30 μL), and the mixture was stirred at room temperature for 18 hours. A 0.2% aqueous trifluoroacetic acid solution (2.0 mL) was added to the reaction solution, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound SG-(SG-Gln*)-PEG(3)-Mal (0.60 mg, yield: 28%).

ESI-TOF-MS: Calcd for $C_{195}H_{320}N_{17}O_{134}$: $[M+3H]^{3+}$ 1682.2 (ave.), Found 1682.2.

Example 1-17

(1-17A) Synthesis of AG(9)—P (Compound 1-17A: Compound 1 of the Following Formula)

[Formula 77]

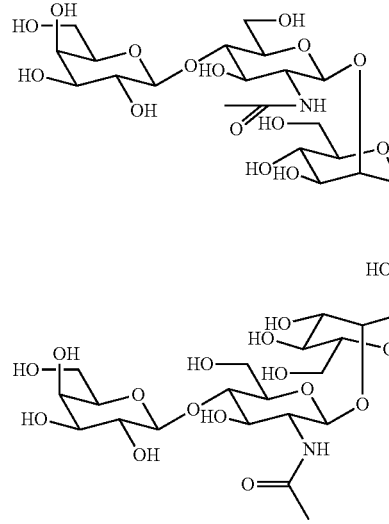
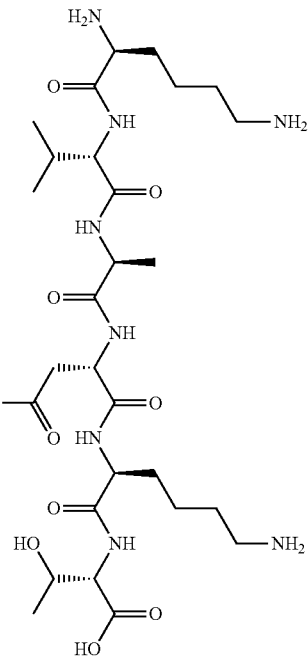

Sialylglycopeptide (200 mg) was dissolved in a 0.2 M acetate buffer solution (pH 5.0) (1000 μl). To the solution, an aqueous solution (1000 μl) of neuraminidase ([E.C.3.2.1.18], Nacalai Tesque, Inc., 1 U/ml) was then added, and the mixture was reacted at 37° C. for 17 hours. After the completion of the reaction, a 0.2% aqueous trifluoroacetic acid solution (2000 μl) was added thereto. Two lots of this reaction were combined, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound AG(9)-P (307 mg).

ESI-TOF-MS: Calcd for $C_{90}H_{155}N_{13}O_{54}$: $[M+2H]^{2+}$ 1142.6 (ave.), Found 1142.0

(1-17B) Synthesis of AG(7)-P (Compound 1-17B: Compound of the Following Formula)

[Formula 78]

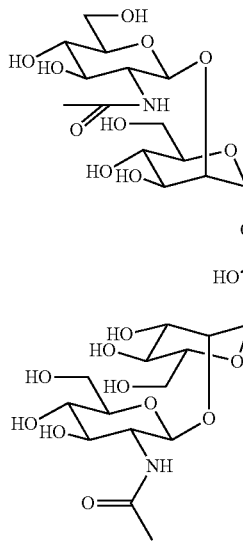
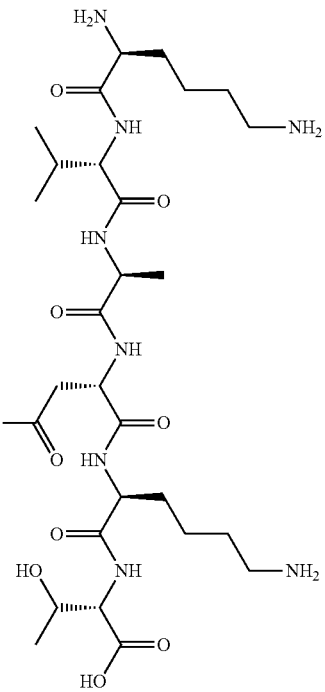

The compound AG(9)-P (100 mg) produced in (1-17A), magnesium sulfate (0.48 mg), and β-D-galactosidase (Wako Pure Chemical Industries, Ltd., 600 U/mg) (2 mg) were dissolved in a 0.2 M phosphate buffer solution (pH 7.0) (2000 μl), and the solution was reacted at 37° C. for 24 hours. β-D-galactosidase (Wako Pure Chemical Industries, Ltd., 600 U/mg) (1 mg) was added thereto, and the mixture was further reacted for 24 hours. After the completion of the reaction, a 0.2% aqueous trifluoroacetic acid solution (2000 μl) was added thereto. Two lots of this reaction were combined, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound AG(7)-P (158 mg). ESI-TOF-MS: Calcd for [M+H]$^+$ $C_{78}H_{135}N_{13}O_{44}$ 1959.0 (ave.), Found 1958.9

(1-17C) Synthesis of AG(5)-P (Compound 1-17C: Compound of the Following Formula)

[Formula 79]

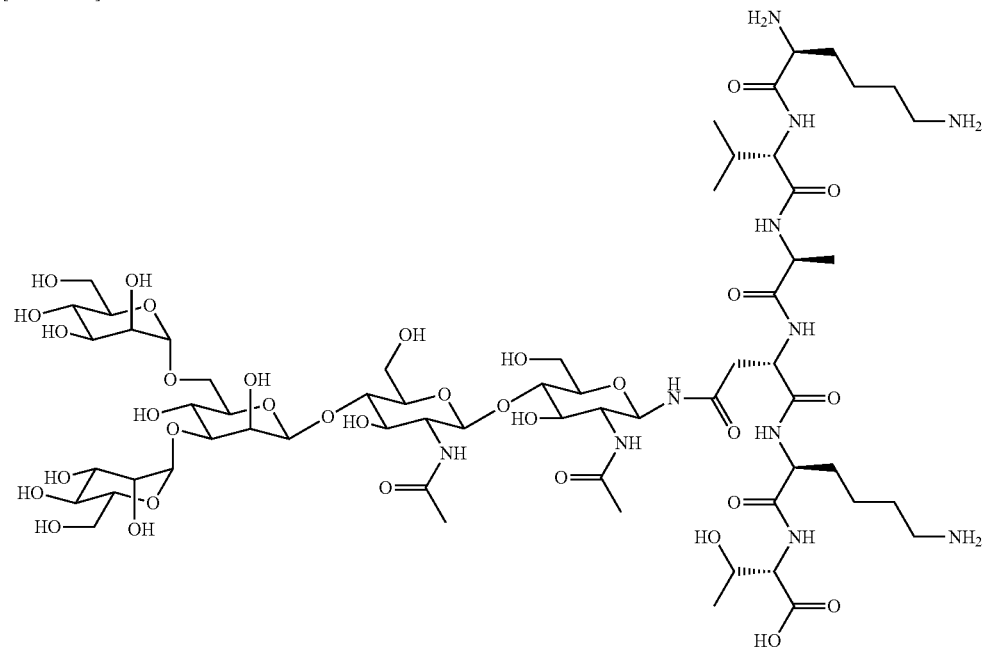

The compound AG(7)-P (100 mg) produced in (1-17B) was dissolved in a 0.2 M phosphate buffer solution (pH 6.25) (3150 μl). To the solution, 100×BSA (New England BioLabs Japan Inc.) (43 μl) and β-N-acetylglucosaminidase (New England BioLabs Japan Inc., 4000 U/ml) (100 μl) were added, and the mixture was reacted at 37° C. for 20 hours. After the completion of the reaction, a 0.2% aqueous trifluoroacetic acid solution (1000 μl) was added thereto. The resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound AG(5)-P (73.8 mg).

ESI-TOF-MS: Calcd for $[M+2H]^{2+}$ $C_{62}H_{109}N_{11}O_{34}$ 777.3 (ave.), Found 777.3

Example 1-18

(1-18A) Synthesis of SG-$N_3$ (Compound 1-18A: Compound of the Following Formula)

[Formula 80]

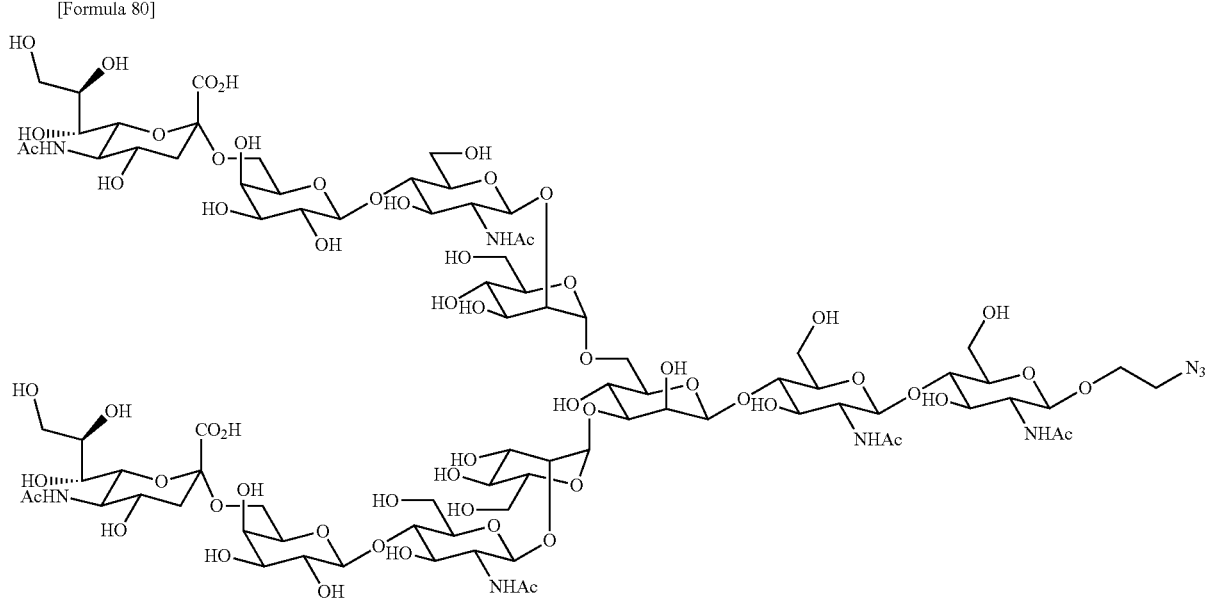

Sialylglycopeptide (76 mg) was dissolved in a 0.2 M phosphate buffer solution (pH 6.25) (330 µl). To the solution, an aqueous solution (100 µl) of glycosynthase (Endo-M-N175Q, Tokyo Chemical Industry Co., Ltd., 1 U/ml) was then added. N-[(2R,3R,4R,5S,6R)-3-Acetamido-4,5-dihydroxy-6-(hydroxymethyl)tetrahydropyran-2-yl]oxyethylazide (23 mg) in a 0.2 M phosphate buffer solution (pH 6.25) (230 µl) was further added thereto, and the mixture was reacted at 28° C. for 96 hours. The reaction was terminated by the addition of a 0.2% aqueous trifluoroacetic acid solution (3000 µl) to the reaction solution, and the resulting product was separated and purified by reverse-phase HPLC (Shiseido Co., Ltd., Proteonavi) using a 0.1% aqueous trifluoroacetic acid solution and a 0.1% solution of trifluoroacetic acid in acetonitrile as eluents and lyophilized to obtain a solid composed mainly of the title compound. Subsequently, the obtained solid was dissolved in distilled water (3000 µl), and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound SG-$N_3$ (34.4 mg).

ESI-TOF-MS: Calcd for $C_{86}H_{41}N_9O_{62}$: $[M+2H]^{2+}$ 1147.5, Found 1147.4

Example 1-19

(1-19A) Synthesis of tert-butyl N-[2-[2-[2-[2-[3-[2-[(2R,3R,4R,5S,6R)-3-acetamido-4,5-dihydroxy-6-(hydroxymethyl)tetrahydropyran-2-yl]oxyethylamino]-3-oxo-propoxy]ethoxy]ethoxy]ethoxy]ethyl] carbamate (Compound 1-19A: Compound of the Following Formula)

[Formula 81]

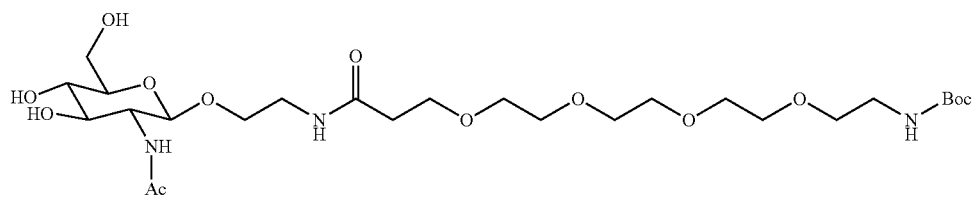

The title compound 1-19A was obtained as a pale yellow foam (150 mg, yield: 90%) according to the same method as in (1-9A) using 3-[2-[2-[2-[2-(tert-butoxycarbonylamino)ethoxy]ethoxy]ethoxy]ethoxy]propanoic acid (100 mg, 0.274 mmol) and the compound 1-7A (110 mg, 0.291 mmol).

MS (ESI): Calcd for $C_{26}H_{49}N_3O_{13}$: $[M+H]^+$ 612, Found 612.

(1-19B) Synthesis of N-[2-[(2R,3R,4R,5S,6R)-3-acetamido-4,5-dihydroxy-6-(hydroxymethyl)tetrahydropyran-2-yl]oxyethyl]-3-[2-[2-[2-(2-aminoethoxy)ethoxy]ethoxy]ethoxy]propanamide (Compound 1-19B: Compound of the Following Formula)

[Formula 82]

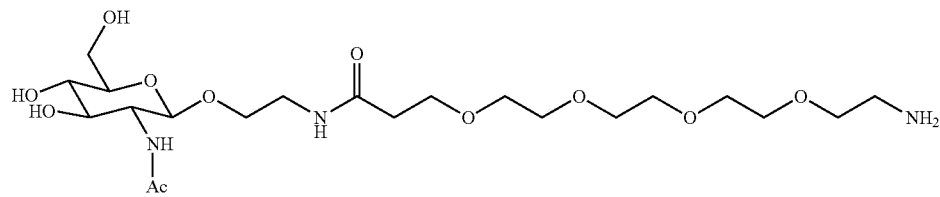

The compound 1-19A (150 mg, 0.245 mmol) was dissolved in dichloromethane (2.0 ml). To the solution, trifluoroacetic acid (2.0 mL) was added, and the mixture was stirred at room temperature for 2 hours. The solvent was distilled off under reduced pressure, and the obtained residue was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound 1-19B (70 mg, 55%) as a colorless oil.

MS (ESI): Calcd for $C_{21}H_{41}N_3O_{11}$: $[M+H]^+$ 512, Found 512.

Example 1-20

(1-20A) Synthesis of 3-[2-[2-[2-[2-[[(2S)-2,6-bis(tert-butoxycarbonylamino)hexanoyl]amino]ethoxy]ethoxy]ethoxy]ethoxy]propanoic Acid (Compound 1-20A: Compound of the Following Formula)

[Formula 83]

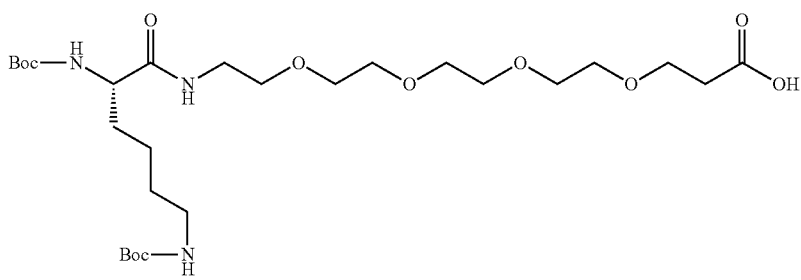

To a solution of (2S)-2,6-bis(tert-butoxycarbonylamino)hexanoic acid (210 mg, 607 µmol) and HATU (220 mg, 579 µmol) in N,N-dimethylformamide (2.0 mL), N,N-diisopropylethylamine (0.410 mL, 2.41 mmol) was added, and the mixture was stirred at room temperature for 2 minutes. The obtained reaction solution was added to a solution of 3-[2-[2-[2-(2-aminoethoxy)ethoxy]ethoxy]ethoxy]propanoic acid (150 mg, 497 µmol) produced according to the approach of (1-5A) and N,N-diisopropylethylamine (0.260 mL, 1.53 mmol) in N,N-dimethylformamide (0.50 mL), and the mixture was stirred at room temperature for 2 hours. The solvent was distilled off under reduced pressure, and the obtained residue was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound 1-20A (240 mg, 80%) as a pale yellow oil.

MS (ESI): Calcd for $C_{27}H_{52}N_3O_{11}$: $[M+H]^+$ 594, Found 594.

Example 1-21

(1-21A) Synthesis of 2-[[(2S)-2-[[2-[[(2S)-2-[[2-[[(2S)-2-amino-3-tert-butoxy-propanoyl]amino]acetyl]amino]-3-tert-butoxy-propanoyl]amino]acetyl]amino]-3-tert-butoxy-propanoyl]amino]acetic Acid (Compound 1-21A: Compound of the Following Formula)

[Formula 84]

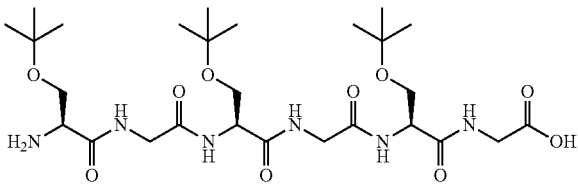

A 1.20 mmol/g 2-chlorotrityl chloride resin (166 mg, 0.200 mmol) was placed in a column for solid-phase synthesis. Dichloromethane (3 mL) was added thereto, and the mixture was shaken for 10 minutes. After filtration, a solution of 2-(9H-fluoren-9-ylmethoxycarbonylamino)acetic acid (119 mg, 0.400 mmol) and N,N-diisopropylethylamine (171 µL, 1.00 mmol) in dichloromethane (3 mL) was added thereto, and the mixture was stirred at room temperature for 2 hours. After filtration, the resin was washed with a dichloromethane mixed solution (dichloromethane:methanol:N,N-diisopropylethylamine=85:10:5, v/v) three times, dichloromethane three times, and N,N-dimethylformamide three times. The obtained resin was loaded in a peptide synthesizer (433A Peptide Synthesizer manufactured by Applied Biosystems, Inc.) and subjected to deprotection, condensation, deprotection, condensation, deprotection, condensation, deprotection, condensation, deprotection, condensation, and deprotection in the synthesizer to elongate the peptide chain. For the deprotection, piperidine and N-methylpyrrolidone were used. For the condensation reactions, HATU, N,N-diisopropylethylamine, N-methylpyrrolidone, and various carboxylic acids were used. The carboxylic acids were used in each condensation reaction in the order of (2S)-3-tert-butoxy-2-(tert-butoxycarbonylamino) propanoic acid, 2-(9H-fluoren-9-ylmethoxycarbonylamino)acetic acid, (2S)-3-tert-butoxy-2-(tert-butoxycarbonylamino)propanoic acid, 2-(9H-fluoren-9-ylmethoxycarbonylamino)acetic acid, and (2S)-3-tert-butoxy-2-(tert-butoxycarbonylamino)propanoic acid. The obtained resin was placed in a column for solid-phase synthesis. A mixed solution of hexafluoroisopropanol (1 mL) and dichloromethane (3 mL) was added thereto, and the mixture was shaken at room temperature for 2 hours. The resin was filtered off, and the obtained filtrate was concentrated under reduced pressure. The concentrate was subjected to azeotropy with dichloromethane 6 times and dried in a vacuum pump to obtain the title compound 1-21A as a white solid (120 mg, yield: 97%).

MALDI-TOF-MS: Calcd for $C_{27}H_{50}N_6O_{10}$: $[M+H]^+$ 619.4, Found 619.4.

(1-21B) Synthesis of 2-[[(2S)-2-[[2-[[(2S)-2-[[2-[[(2S)-2-[[(2S)-4-[[(2R,3R,4R,5S,6R)-3-acetamido-4,5-dihydroxy-6-(hydroxymethyl)tetrahydropyran-2-yl]amino]-2-[[2-[[(2R,3R,4R,5S,6R)-3-acetamido-4,5-dihydroxy-6-(hydroxymethyl)tetrahydropyran-2-yl]amino]acetyl]amino]-4-oxobutanoyl]amino]-3-tert-butoxy-propanoyl]amino]acetyl]amino]-3-tert-butoxy-propanoyl]amino]acetyl]amino]-3-tert-butoxy-propanoyl]amino]acetic Acid (Compound 1-21B: Compound of the Following Formula)

(2S)-4-[[(2R,3R,4R,5S,6R)-3-acetamido-4,5-dihydroxy-6-(hydroxymethyl)tetrahydropyran-2-yl]amino]-2-(tert-butoxycarbonylamino)-4-oxobutanoic acid (84.5 mg, 0.194 mmol) produced according to the approach of J. Am. Chem. Soc., 1999, 121, 284-290 and HATU (73.8 mg, 0.194 mmol) were dissolved in N,N-dimethylformamide (5 mL). To the solution, N,N-diisopropylethylamine (66 µL, 0.388 mmol) was added, and the mixture was stirred at room temperature for 3 minutes. This solution was added to the compound 1-21A (100 mg, 0.162 mmol), and the mixture was stirred at room temperature for 0.5 hours. The reaction solution was diluted with water, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents. To the obtained compound, a mixed solution of trifluoroacetic acid (0.1 mL) and water (0.9 mL) was added, and the mixture was stirred overnight. The reaction solution was diluted with water, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents to obtain the intermediate as a white solid (14.7 mg, 10%).

The compound 1-2C (5.91 mg, 0.0212 mmol) and HATU (8.04 mg, 0.0212 mmol) were dissolved in N,N-dimethylformamide (1 mL). To the solution, N,N-diisopropylethylamine (9.05 µL, 0.0529 mmol) was added, and the mixture was stirred at room temperature for 3 minutes. This solution was added to a solution of the obtained intermediate (16.5 mg, 0.0176 mmol) in N,N-dimethylformamide (1 mL), and the mixture was stirred at room temperature for 0.5 hours. The reaction solution was diluted with water, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents to obtain the title compound 1-21B as a white solid (14.0 mg, yield: 66%).

MALDI-TOF-MS: Calcd for $C_{49}H_{85}N_{11}O_{23}$: $[M+H]^+$ 1197.6, Found 1197.5.

[Formula 85]

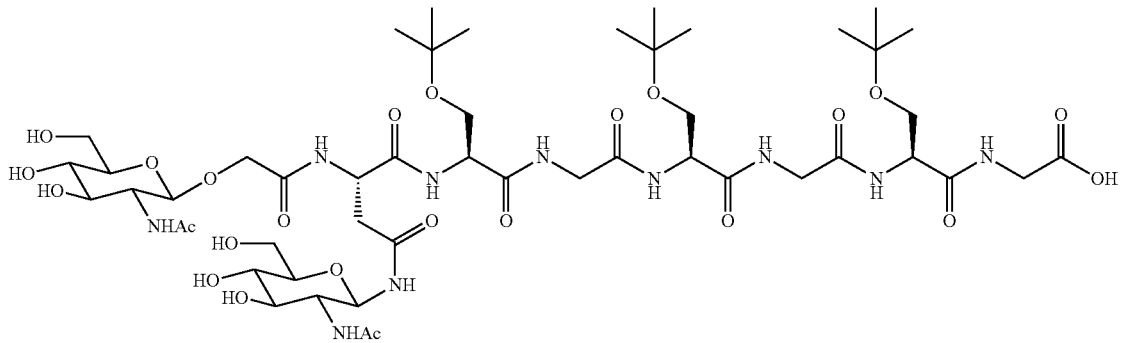

Example 1-22

(1-22A) Synthesis of (2S)-2,6-bis[3-[2-[2-[2-[2-[3-(2,5-dioxopyrrol-1-yl)propanoylamino]ethoxy]ethoxy]ethoxy]ethoxy]propanoylamino]hexanoic Acid (Compound 1-22A: Compound of the Following Formula)

[Formula 86]

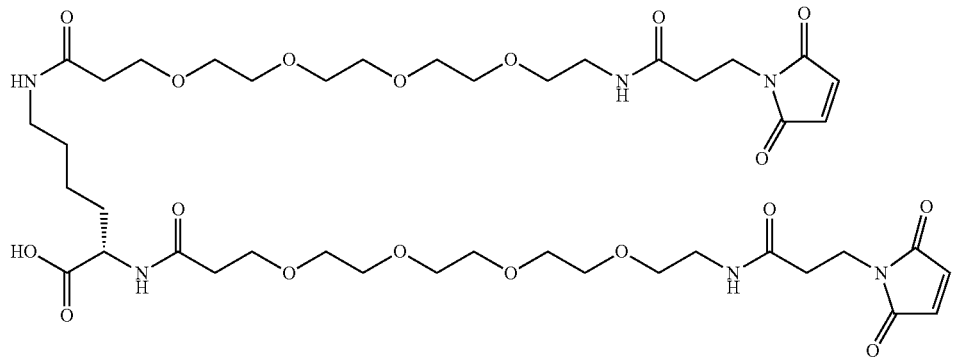

Lysine (26.0 mg, 0.178 mmol) was dissolved in a 0.10 M phosphate buffer (pH 7.0) (0.40 ml). To the solution, a solution of (2,5-dioxopyrrolidin-1-yl) 3-[2-[2-[2-[2-[3-(2,5-dioxopyrrol-1-yl)propanoylamino]ethoxy]ethoxy]ethoxy]ethoxy]propanoate (200 mg, 0.390 mmol) in N,N-dimethylformamide (0.40 mL) was added, and the mixture was stirred at room temperature for 3 hours. A 0.2% aqueous trifluoroacetic acid solution (2.0 mL) was added to the reaction solution, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound 1-22A (106 mg, yield: 63%).

MS (ESI): Calcd for $C_{42}H_{65}N_6O_{18}$: $[M-H]^-$ 941, Found 941.

(1-22B) Synthesis of SG-Lys*-[PEG(3)-Mal]$_2$ (Compound 1-22B: Compound of the Following Formula)

[Formula 87]

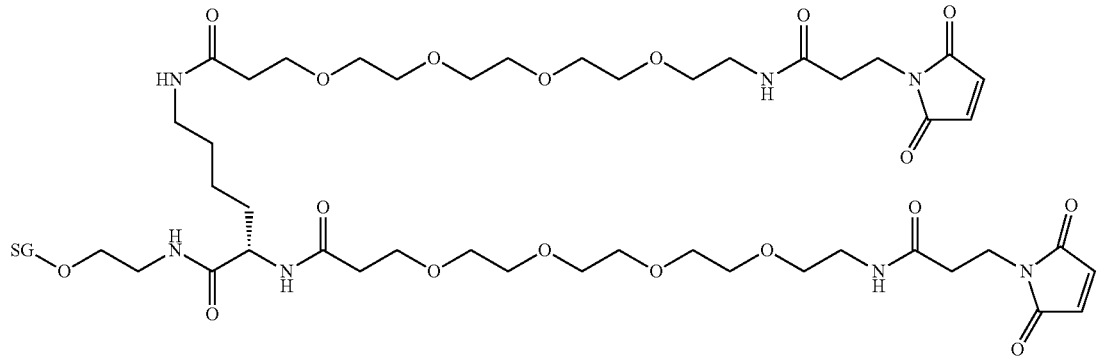

To a solution of the compound 1-22A (10.0 mg, 10.6 μmol) thus produced, the compound SG-NH$_2$ (19.4 mg, 8.13 μmol) produced in (1-11B), and HATU (4.00 mg, 10.6 μmol) in N,N-dimethylformamide (1.0 mL), N,N-diisopropylethylamine (8.80 μL, 51.7 μmol) was added, and the mixture was stirred at room temperature for 1 hour. The reaction solution was added to a 0.5% aqueous trifluoroacetic acid solution (6.0 mL), and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound SG-Lys*-[PEG(3)-Mal]$_2$ (10.0 mg, yield: 25%).

ESI-TOF-MS: Calcd for $C_{128}H_{205}N_{13}O_{79}$: $[M-2H]^{2-}$ 1595.0 (ave.), Found 1595.0.

Example 1-23

(1-23A) Synthesis of (2S)-2,6-bis[3-[2-[2-[2-[2-[2-[2-[2-[2-[2-[2-[3-(2,5-dioxopyrrol-1-yl)propanoylamino]ethoxy]ethoxy]ethoxy]ethoxy]ethoxy]ethoxy]ethoxy]ethoxy]ethoxy]ethoxy]propanoylamino]hexanoic Acid (Compound 1-23A: Compound of the Following Formula)

[Formula 88]

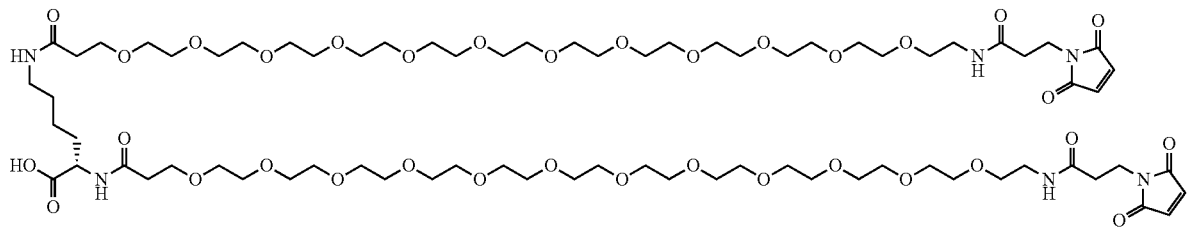

The title compound 1-23A was obtained as a colorless oil (36.0 mg, yield: 41%) according to the same method as in (1-22A) using lysine (7.70 mg, 52.7 μmol) and (2,5-dioxopyrrolidin-1-yl) 3-[2-[2-[2-[2-[2-[2-[2-[2-[2-[2-[3-(2,5-dioxopyrrol-1-yl)propanoylamino]ethoxy]ethoxy]ethoxy]ethoxy]ethoxy]ethoxy]ethoxy]ethoxy]ethoxy]ethoxy]propanoate (100 mg, 115 μmol).

MS (ESI): Calcd for $C_{74}H_{129}N_6O_{34}$: $[M-H]^-$ 1645, Found 1645.

(1-23B) Synthesis of SG-Lys*-[PEG(11)-Mal]$_2$ (Compound 1-23B: Compound of the Following Formula)

[Formula 89]

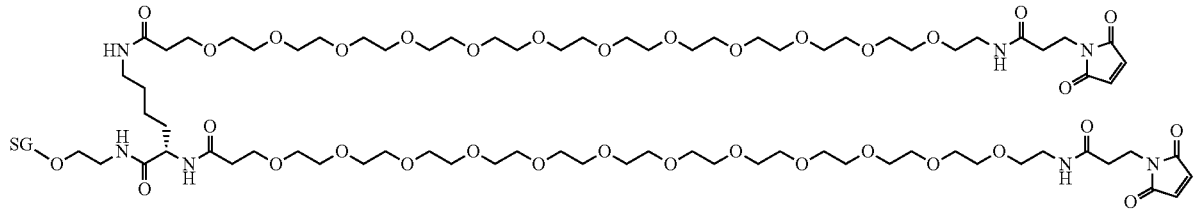

The title compound SG-Lys*-[PEG(11)-Mal]$_2$ was obtained as a colorless oil (14.0 mg, yield: 34%) according to the same method as in (1-22B) using the compound 1-23A (19.0 mg, 11.5 μmol) and the compound SG-NH$_2$ (25.0 mg, 10.5 μmol) produced in (1-11B).

ESI-TOF-MS: Calcd for $C_{180}H_{269}N_{13}O_{95}$: $[M-2H]^{2-}$ 1947.4 (ave.), Found 1947.3.

Example 1-24

(1-24A) Synthesis of Benzyl 2-[[2-[(2R,3R,4S,5R,6R)-3,4,5-triacetoxy-6-(acetoxymethyl)tetrahydropyran-2-yl]oxyacetic acid]amino]acetate (Compound 1-24A: Reaction Product of the Following Formula)

[Formula 90]

-continued

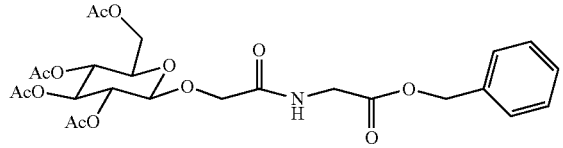

A known compound 2-[[2-[(2R,3R,4S,5R,6R)-3,4,5-triacetoxy-6-(acetoxymethyl)tetrahydropyran-2-yl]oxyacetic acid (Tetrahedron Asymmetry, 2008, 19, 1919-1933) (670 mg) was dissolved in DMF (6 ml). To the solution, HATU (630 mg) and DIPEA (0.57 ml) were added, and the mixture was stirred at room temperature for 4 minutes. Then, glycine benzyl ester hydrochloride (370 mg) was added thereto, and the mixture was stirred at room temperature for 1 hour. The reaction solution was diluted with ethyl acetate and washed with 10% saline twice and 1 N hydrochloric acid once. After drying over anhydrous sodium sulfate and filtration, the solvent was distilled off under reduced pressure to obtain a crude product. This product was purified by silica gel column chromatography (hexane:ethyl acetate=60:40-20:80, v/v) to obtain the title compound 1-24A (840 mg, yield: 62%) in an amorphous form.

$^1$H-NMR (CDCl$_3$) δ: 7.38-7.35 (5H, m), 6.99-6.98 (1H, br m), 5.23-5.21 (3H, m), 5.11-5.04 (2H, m), 4.56 (1H, d, J=7.8 Hz), 4.34 (1H, d, J=15.1 Hz), 4.20-4.09 (5H, m), 3.73-3.71 (1H, m), 2.08 (3H, s), 2.07 (3H, s), 2.04 (3H, s), 2.03 (3H, s).

ESI-LC-MS: Calcd for C$_{25}$H$_{31}$NO$_{13}$: [M+H]$^+$ 554, Found 554.

(1-24B) Synthesis of 2-[[2-[(2R,3R,4S,5R,6R)-3,4,5-triacetoxy-6-(acetoxymethyl)tetrahydropyran-2-yl]oxyacetic acid]amino]acetic Acid (Compound 1-24B: Reaction Product of the Following Formula)

[Formula 91]

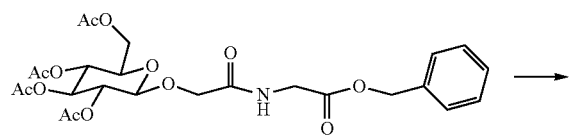

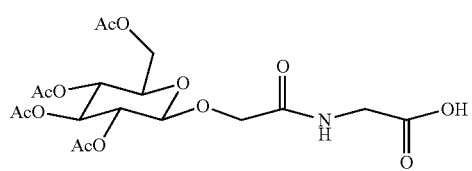

The title compound 1-24B (700 mg, yield: quant.) was obtained in an amorphous form according to the same approach as in (1-2B) using the compound 1-24A (840 mg). ESI-LC-MS: Calcd for C$_{18}$H$_{25}$NO$_{13}$: [M−H]$^-$ 462, Found 462.

$^1$H-NMR (CDCl$_3$) δ: 7.05-7.04 (1H, br m), 5.24 (1H, t, J=9.5 Hz), 5.12-5.05 (2H, m), 4.58 (1H, d, J=7.8 Hz), 4.35 (1H, d, J=15.6 Hz), 4.27-4.05 (6H, m), 3.76-3.75 (1H, m), 2.08-2.04 (12H, m).

(1-24C) Synthesis of 2-[[2-[(2R,3R,4S,5R,6R)-3,4,5-trihydroxy-6-(hydroxymethyl)tetrahydropyran-2-yl]oxyacetic acid]amino]acetic Acid (Compound 1-24C: Reaction Product of the Following Formula)

[Formula 92]

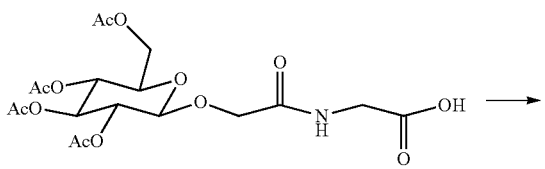

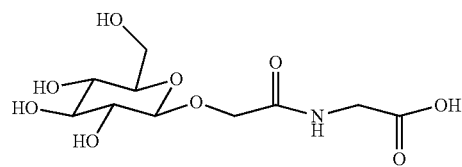

The title compound 1-24C (286 mg, yield: quant.) was obtained in an amorphous form according to the same approach as in (1-2C) using the compound 1-24B (450 mg). This compound was used directly in the next reaction.

$^1$H-NMR (D$_2$O, TMSP) δ: 4.54 (1H, d, J=7.8 Hz), 4.43 (1H, d, J=15.6 Hz), 4.31 (1H, d, J=15.6 Hz), 3.91-3.89 (3H, m), 3.73 (1H, dd, J=12.2, 5.4 Hz), 3.53-3.37 (4H, m). ESI-LC-MS: Calcd for C$_{10}$H$_{17}$NO$_9$: [M−H]$^-$ 294, Found 294.

(1-24D) Synthesis of 2-[[2-[(2R,3R,4S,5R,6R)-3,4,5-trihydroxy-6-(hydroxymethyl)tetrahydropyran-2-yl]oxyacetic acid]amino]acetic Acid Ammonium Salt (Compound 1-24D: Compound of the Following Formula)

[Formula 93]

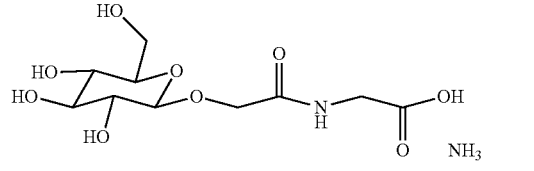

The title compound 1-24D (325 mg) was obtained in an amorphous form according to the same approach as in (1-14A) using the compound 1-24C (286 mg). This compound was used without being purified.

(1-24E) Synthesis of SG(Glc)-Gly-A (Compound 1-24E: Compound of the Following Formula)

[Formula 94]

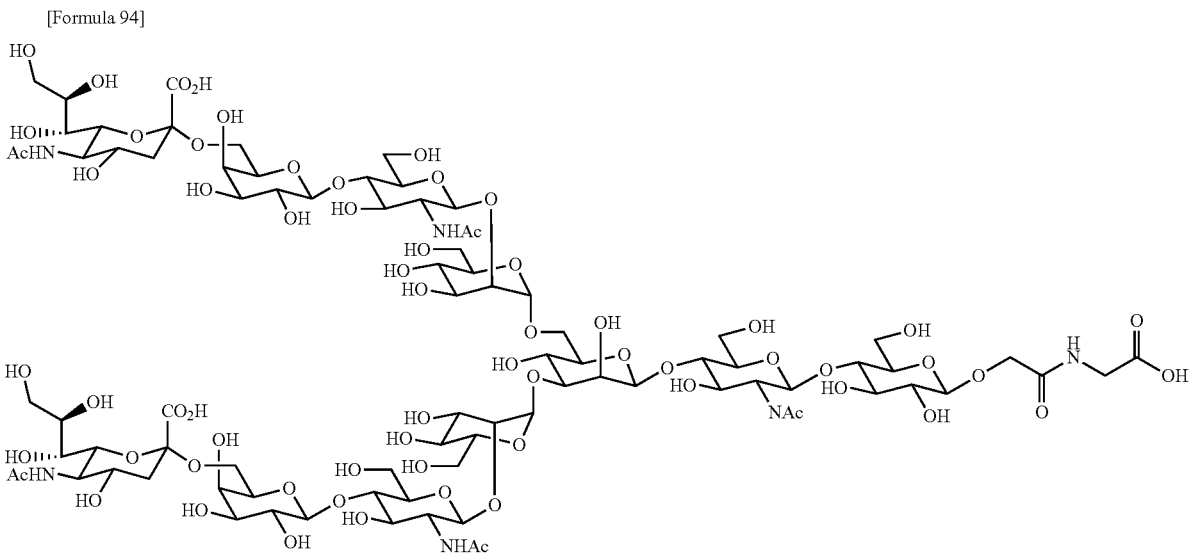

Sialylglycopeptide (191 mg) was dissolved in a 0.2 M phosphate buffer solution (pH 6.25) (1000 µl). To the solution, an aqueous solution (300 µl) of glycosynthase (Endo-M-N175Q, Tokyo Chemical Industry Co., Ltd., 1 U/ml) was then added. The compound 1-24D (125 mg) in a 0.2 M phosphate buffer solution (pH 6.25) (370 µl) was further added thereto, and the mixture was reacted at 28° C. for 72 hours. The reaction was terminated by the addition of a 0.2% aqueous trifluoroacetic acid solution (3000 µl) to the reaction solution, and the resulting product was separated and purified by reverse-phase HPLC (Inertsil ODS-3, GL Sciences Inc.) using a 0.1% aqueous trifluoroacetic acid solution and a 0.1% solution of trifluoroacetic acid in acetonitrile as eluents and lyophilized to obtain the title compound SG(Glc)-Gly-A (88 mg).

ESI-TOF-MS: Calcd for $C_{86}H_{140}N_6O_{65}$: $[M+4H]^{4+}$ 1149.4 (ave.), Found 1149.4

Also, a compound derived from the compound 1-24D by the replacement of the sugar structure with a sugar other than Glc (e.g., Man or Gal) can be synthesized with reference to the reaction of Example 1-24. A glycochain altered at the reducing end of SG(Man)-Gly, SG(Gal)-Gly, or the like can be synthesized through the same transglycosylation reaction as in (1-24E) by use of the compound thus synthesized as an acceptor compound.

In addition, a glycochain altered at the reducing end of SG-NH2, SG-I, SG-oxa, SG-A, or the like can be appropriately synthesized by the appropriate conversion of the sugar structure of the starting material (acceptor compound) to a desired one with reference to the reaction of Example 1-24 in the methods of Examples 1-11, 1-12, 1-13, and 1-14.

Example 2

Hereinafter, the simple term "hANP" in a structural formula represents that the hANP peptide in the modified peptide is hANP(1-28).

<Example 2-1> Synthesis of SG-hANP(1-28) (Compound 2-1)

(2-1A) Preparation of hANP-TFA Salt (Trifluoroacetate)

The hANP-TFA salt used in the reactions given below was prepared according to the following procedures:

Preparation Method 1

Carperitide acetate (hANP(1-28) acetate) (100 mg) was dissolved in distilled water (4000 µl), and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound (89.6 mg).

Preparation Method 2

Carperitide acetate (hANP(1-28) acetate) (250 mg) was dissolved in distilled water (30 ml). To the solution, trifluoroacetic acid (600 µl) was added, and the mixture was lyophilized. This compound was used directly without being further purified.

(2-1B) Synthesis of SG-hANP (1-28) (Compound 2-1: Compound of the Following Formula)

[Formula 95]

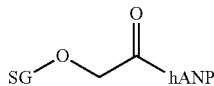

(2-1B-1) Synthesis of SG-hANP(1-28) (Compound 2-1) TFA Salt

To a solution of the compound SG-A (97.7 mg) synthesized in (1-14B) in N,N-dimethylformamide (1000 µl), a solution of HATU (16.3 mg) in N,N-dimethylformamide (1000 µl) was added, then diisopropylethylamine (30 µl) was added, and the mixture was stirred at room temperature for 5 minutes and immediately used in the next reaction.

The hANP-TFA salt (100 mg) prepared according to the procedures of (2-1A) was dissolved in N,N-dimethylformamide (1200 µl) and distilled water (320 µl). To the solution, diisopropylethylamine (22.5 µl) was added. To this solution, a solution containing active ester prepared beforehand in N,N-dimethylformamide (2000 µl) was added, and the mixture was stirred for 1 hour. After the completion of the reaction, a 0.2% aqueous trifluoroacetic acid solution (20 ml) was added thereto under ice cooling. Insoluble matter was dissolved by the addition of acetic acid (2 ml), and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound SG-hANP(1-28) (compound 2-1)-TFA salt (91.0 mg).

MALDI-TOF-MS: Calcd for $C_{213}H_{341}N_{51}O_{102}S_3$: [M+H]$^+$ 5342 0.2, Found 5342.2

(2-1B-2) Synthesis of SG-hANP(1-28) (Compound 2-1) Acetate

To a solution of the compound SG-A (790 mg) synthesized in (1-14B) in N,N-dimethylformamide (18 ml), a solution of TSTU (O—(N-succinimidyl)-N,N,N',N'-tetramethyluronium tetrafluoroborate) (104 mg) in N,N-dimethylformamide (2 ml) was added, then diisopropylethylamine (241 µl) was added, and the mixture was stirred at room temperature for 60 minutes and used in the next reaction.

Carperitide acetate (hANP(1-28) acetate) (1000 mg) was dissolved in N,N-dimethylformamide (12 ml) and distilled water (3.2 ml). To the solution, diisopropylethylamine (241 µl) was added. To this solution, a solution containing active ester prepared beforehand in N,N-dimethylformamide (20 ml) was added, and the mixture was stirred for 1 hour. After the completion of the reaction, acetonitrile (32 ml) was added thereto, and the precipitates were collected by filtration. After washing with N,N-dimethylformamide/acetonitrile (1/1) (30 ml) and acetonitrile (100 ml), the obtained solid matter was dried under reduced pressure. This solid matter was dissolved in distilled water, and the resulting product was separated and purified by reverse-phase HPLC (GL Sciences Inc., Inertsil ODS-3) using a 0.1% aqueous acetic acid solution and a 0.1% solution of acetic acid in acetonitrile as eluents and lyophilized to obtain the title compound SG-hANP(1-28) (compound 2-1)-acetate (1056 mg).

ESI-TOF-MS: Calcd for $C_{213}H_{341}N_{51}O_{102}S_3$: [M+4H]$^{4+}$ 1337.1 (ave.), Found 1337.0

As mentioned above, the modified peptide of interest is also synthesized as a salt of a type corresponding to the salt of the hANP peptide used as a starting material. In the Examples below, the TFA salt of the hANP peptide was adopted, and the modified peptide of interest was obtained as a TFA salt, unless otherwise specified. In these cases, the type of the salt is not particularly described. All title compounds can be synthesized as acetates by synthesis according to the procedures of (2-1B-2).

<Example 2-2> Synthesis of hANP(1-28)-SG (Compound 2-2) (2-2A) Synthesis of Boc-hANP(1-28) (Compound of the Following Formula)

[Formula 96]

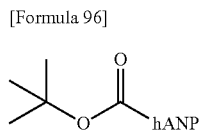

The hANP(1-28)-acetate (62.5 mg) was dissolved in distilled water (1.3 ml). To the solution, a solution of di-t-butyl dicarbonate (0.9 mg, 324.6 µmol) in t-butyl alcohol (400 µl) was added at room temperature, then an aqueous solution (200 µl) of triethylamine (13.6 µl) was added, and the mixture was stirred at room temperature for 3 hours. Insoluble matter was dissolved by the addition of distilled water (6 ml), acetonitrile (2 ml), and acetic acid (1 ml), and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound Boc-hANP(1-28) (59.9 mg).

MALDI-TOF-MS: Calcd for $C_{132}H_{211}N_{45}O_{41}S_3$: [M+H]$^+$ 3179.5, Found 3179.7

(2-2B) Synthesis of Boc-hANP(1-28)-GlcNAc (Compound of the Following Formula)

[Formula 97]

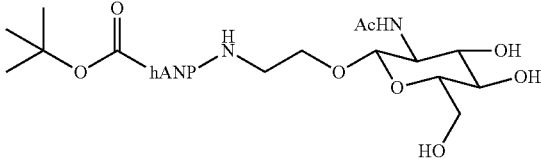

The Boc-hANP(1-28) (59.9 mg) produced in (2-2A) and the compound 1-7A (59.7 mg) were dissolved in distilled water (0.2 ml). To the solution, a solution of HATU (35.8 mg) in dimethylformamide (2.0 ml) and triethylamine (15.8 µl) were added at room temperature, and the mixture was stirred at room temperature for 2 hours. The reaction solution was added to an ice-cold aqueous solution (5 ml) of trifluoroacetic acid (8.7 µl), and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound Boc-hANP(1-28)-GlcNAc (38.7 mg).

MALDI-TOF-MS: Calcd for $C_{142}H_{229}N_{47}O_{46}S_3$: [M+H]$^+$ 3425.6, Found 3426.0

(2-2C) Synthesis of hANP(1-28)-GlcNAc (Compound of the Following Formula)

[Formula 98]

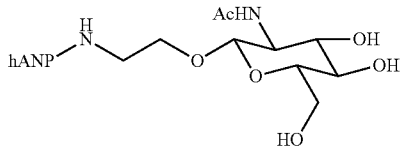

The Boc-hANP(1-28)-GlcNAc (38.7 mg) produced in (2-2B) was dissolved in a 20% aqueous trifluoroacetic acid solution (5 ml) and acetic acid (1 ml), and the solution was left standing at room temperature for 7 hours. Distilled water (10 ml) was added thereto, and the mixture was lyophilized. The resulting crude product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound hANP(1-28)-GlcNAc (21.8 mg).

MALDI-TOF-MS: Calcd for $C_{137}H_{221}N_{47}O_{44}S_3$: [M+H]$^+$ 3325.6, Found 3425.5

(2-2D) Synthesis of hANP(1-28)-SG (Compound 2-2: Compound of the Following Formula)

[Formula 99]

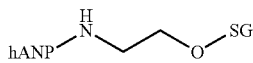

To the compound SG-Oxa produced in (1-12A) in a 0.2 M phosphate buffer solution (60 mM, 120 µl), glycosynthase (Endo-M-N175Q, Tokyo Chemical Industry Co., Ltd., 1 U/ml, 48 µl) was added at room temperature, then a solution of the hANP(1-28)-GlcNAc (6.0 mg, 1.8 µmol) produced in (2-2C) in dimethyl sulfoxide (72 µl) was added in two portions at an interval of 15 minutes at room temperature, and the mixture was shaken at 25° C. for 2 hours. The reaction was terminated by the addition of a 0.2% aqueous trifluoroacetic acid solution (1.5 ml) at room temperature, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound hANP(1-28)-SG (compound 2-2) (6.2 mg).

MALDI-TOF-MS: Calcd for $C_{213}H_{334}N_{52}O_{100}S_3$: [M+H]$^+$ 5327.3, Found 5326.7.

<Example 2-3> Synthesis of (SG-)Asn-hANP(1-28) (Compound 2-3) (2-3A) Synthesis of Boc-(GlcNAc-)Asn-hANP(1-28) (Compound of the Following Formula)

[Formula 100]

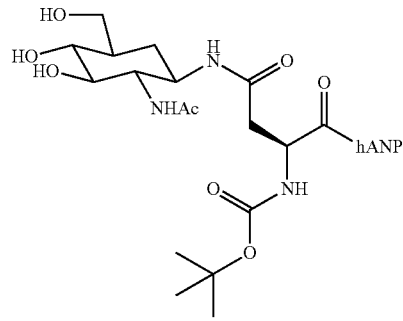

The title compound Boc-(GlcNAc-)Asn-hANP(1-28) (13.0 mg) was obtained according to the same approach as in (2-1B) using (2S)-4-[[(2R,3R,4R,5S,6R)-3-acetamido-4,5-dihydroxy-6-(hydroxymethyl)tetrahydropyran-2-yl]amino]-2-(tert-butoxycarbonylamino)-4-oxobutanoic acid (42.4 mg, 0.0976 mmol) synthesized according to the description of J. Am. Chem. Soc., 1999, 121, 284-290 and hANP(1-28)-TFA salt prepared from the hANP(1-28)-acetate (31.3 mg) by Preparation Method 2 of (2-1A).

MALDI-TOF-MS: Calcd for $C_{144}H_{230}N_{48}O_{48}S_3$: [M+H]$^+$ 3495.6, Found 3496.5

(2-3B) Synthesis of (GlcNAc-)Asn-hANP(1-28) (Compound of the Following Formula)

[Formula 101]

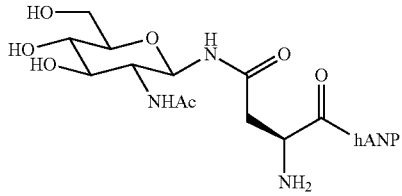

The title compound (GlcNAc-)Asn-hANP(1-28) (5.83 mg) was obtained according to the same approach as in (2-2C) from the Boc-(GlcNAc-)Asn-hANP(1-28) (13.0 mg) produced in (2-3A).

MALDI-TOF-MS: Calcd for $C_{139}H_{222}N_{48}O_{46}S_3$: [M+H]$^+$ 3396.6, Found 3396.6

(2-3C) Synthesis of (SG-)Asn-hANP(1-28) (Compound of the Following Formula: Compound 2-3)

[Formula 102]

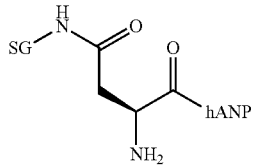

The title compound (GlcNAc-)Asn-hANP(1-28) (compound 2-3) (2.17 mg) was obtained according to the same approach as in (2-2D) from the (GlcNAc-)Asn-hANP(1-28) (4.90 mg) produced in (2-3B).
MALDI-TOF-MS: Calcd for $C_{215}H_{345}N_{53}O_{102}S_3$: $[M+H]^+$ 5398.3, Found 5398.4.

<Example 2-4> Synthesis of (SG-)Asn-hANP(2-28) (Compound 2-4)

(2-4A) Preparation of hANP(2-28)

The hANP(1-28)-acetate (100 mg) was dissolved in a mixed solution of 1.5% dimethylallylamine, 60% pyridine, and 38.5% water (10.4 mL). To the solution, phenyl isothiocyanate (1.04 mL) was added at room temperature, and the mixture was stirred at 50° C. for 30 minutes. The reaction mixture was cooled to room temperature, and water and acetic acid were added thereto. After washing with benzene three times, the aqueous layer was lyophilized. Trifluoroacetic acid (2.6 mL) was added thereto, and the mixture was stirred at 50° C. for 30 minutes. Then, trifluoroacetic acid was distilled off. To the residue, water and acetic acid were added. After washing with benzene three times, the aqueous layer was lyophilized. The dried product was dissolved in water and acetic acid, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents to obtain the title compound ANP(2-28) as a white solid (50 mg).
MALDI-TOF-MS: Calcd for $C_{124}H_{198}N_{44}O_{37}S_3$: $[M+H]^+$ 2992.4, Found 2992.0

(2-4B) Synthesis of Boc-(GlcNAc-)Asn-hANP(2-28) (Compound of the Following Formula)

[Formula 103]

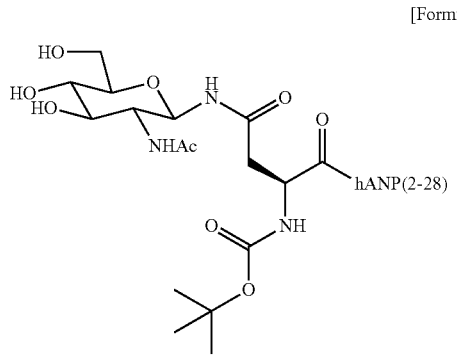

The title compound Boc-(GlcNAc-)Asn-hANP(2-28) (13.0 mg) was obtained according to the same approach as in (2-3A) using the hANP(2-28) (25.0 mg) produced in (2-4A) instead of the hANP(1-28).
MALDI-TOF-MS: Calcd for $C_{141}H_{225}N_{47}O_{46}S_3$: $[M+H]^+$ 3409.6, Found 3409.5

(2-4C) Synthesis of (GlcNAc-)Asn-hANP(2-28) (Compound of the Following Formula)

[Formula 104]

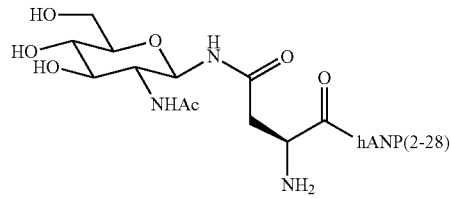

The title compound (GlcNAc-)Asn-hANP(2-28) (6.86 mg) was obtained according to the same approach as in (2-2C) from the Boc-(GlcNAc-)Asn-hANP(2-28) (13.0 mg) produced in (2-4B).
MALDI-TOF-MS: Calcd for $C_{136}H_{217}N_{47}O_{44}S_3$: $[M+H]^+$ 3309.5, Found 3309.5

(2-4D) Synthesis of (SG-)Asn-hANP(2-28) (Compound 2-4: Compound of the Following Formula)

[Formula 105]

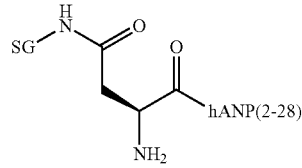

The title compound (SG-)Asn-hANP(2-28) (compound 2-4) (3.80 mg) was obtained according to the same approach as in (2-2D) from the (GlcNAc-)Asn-hANP(2-28) (5.75 mg) produced in (2-4C).
MALDI-TOF-MS: Calcd for $C_{212}H_{340}N_{52}O_{100}S_3$: $[M+H]^+$ 5313.4 (ave.), Found 5314.7.

<Example 2-5> Synthesis of (SG-)Ser-hANP(2-28) (Compound 2-5)

(2-5A) Synthesis of Boc-(GlcNAc-)Ser-hANP(2-28) (Compound of the Following Formula)

[Formula 106]

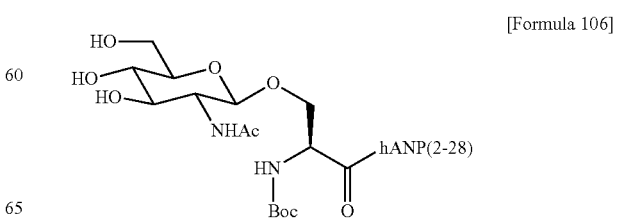

The title compound Boc-(GlcNAc-)Ser-hANP(2-28) (13.0 mg) was obtained according to the same approach as in (2-3A) using the compound 1-1D (40.8 mg) and the hANP(2-28) (25.0 mg) produced in (2-4A).

MALDI-TOF-MS: Calcd for $C_{140}H_{224}N_{46}O_{46}S_3$: $[M+H]^+$ 3382.6, Found 3382.7

(2-5B) Synthesis of (GlcNAc-)Ser-hANP(2-28) (Compound of the Following Formula)

[Formula 107]

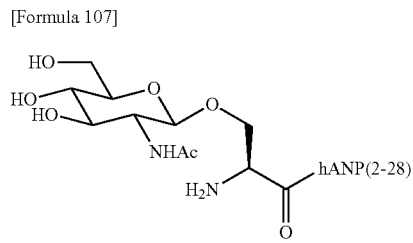

The title compound (GlcNAc-)Ser-hANP(2-28) (6.36 mg) was obtained by the removal of Boc according to the same approach as in (2-2C) using the Boc-(GlcNAc-)Ser-hANP (2-28) (13.0 mg) produced in (2-5A).

MALDI-TOF-MS: Calcd for $C_{135}H_{216}N_{46}O_{44}S_3$: $[M+H]^+$ 3282.5, Found 3282.6

(2-5C) Synthesis of (SG-Ser)-hANP(2-28) (Compound 2-5: Compound of the Following Formula)

[Formula 108]

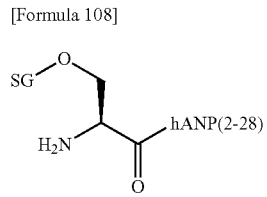

The title compound (SG-)Ser-hANP(2-28) (compound 2-5) (4.40 mg) was obtained according to the same approach as in (2-2D) using the (GlcNAc-)Ser-hANP(2-28) (5.47 mg) produced in (2-5B).

MALDI-TOF-MS: Calcd for $C_{211}H_{339}N_{51}O_{100}S_3$: $[M+H]^+$ 5284.2, Found 5284.4.

<Example 2-6> Synthesis of hANP(1-27)-(SG-)Tyr (Compound 2-6)

(2-6A) Synthesis of hANP(1-27)-(GlcNAc-)Tyr (Compound of the Following Formula)

[Formula 109]

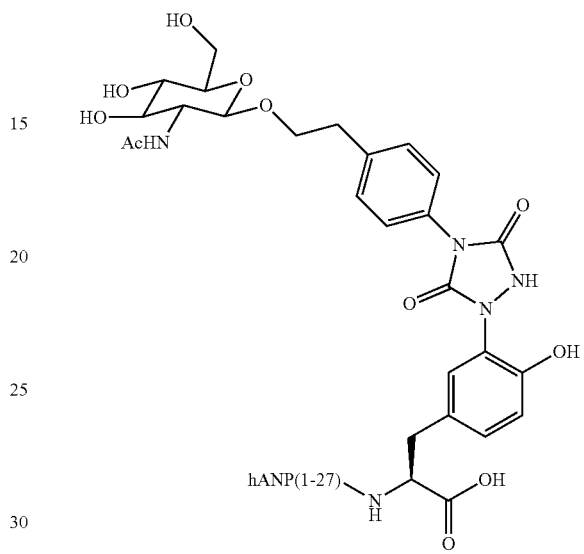

The compound 1-6D (30.6 mg) was dissolved in dimethylformamide (200 μl). To the solution, a solution of N-bromosuccinimide (11.5 mg) and pyridine (5.2 μl) in dimethylformamide (125 μl) was added at 0° C., and the mixture was stirred for 5 minutes.

The hANP(1-28)-acetate (50.0 mg) was dissolved in a 0.1 M phosphate buffer solution (pH 7.0, 1 ml). To the solution, a solution of a triazoledione derivative prepared in advance in dimethylformamide (325 μl) was added at 0° C. The mixture was left standing at room temperature for 5 hours, and then, the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound hANP(1-27)-(GlcNAc-)Tyr (9.8 mg).

MALDI-TOF-MS: Calcd for $C_{145}H_{225}N_{49}O_{47}S_3$: $[M+H]^+$ 3501.6, Found 3501.6

(2-6B) Synthesis of hANP(1-27)-(SG-)Tyr (Compound 2-6: Compound of the Following Formula)

[Formula 110]

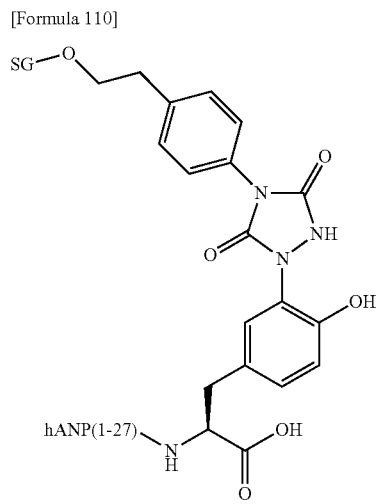

The title compound hANP(1-27)-(SG-)Tyr (compound 2-6) (6.3 mg) was obtained according to the same approach as in (2-2D) using the hANP(1-27)-(GlcNAc-)Tyr (8.3 mg) produced in (2-6A).

MALDI-TOF-MS: Calcd for $C_{221}H_{348}N_{54}O_{103}S_3$: [M+H]$^+$ 5503.3, Found 5502.8.

<Example 2-7> Synthesis of SG-hANP(1-28)-SG (Compound 2-7)

(2-7A) Synthesis of GlcNAc-hANP(1-28) (Compound of the Following Formula)

[Formula 111]

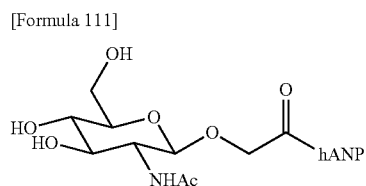

The compound 1-2C (25.0 mg) was dissolved in dimethylformamide (0.5 ml). To the solution, triethylamine (34 ml) was added at room temperature, then a solution of dimethylthiophosphinoyl chloride (12.0 mg) in dimethylformamide (0.5 ml) was added under ice cooling, and then the mixture was stirred at room temperature for 1 hour. Meanwhile, hANP(1-28)-acetate (25 mg) was dissolved in dimethylformamide (1 ml) and distilled water (0.32 ml). To the solution, triethylamine (25.3 µl) was added at room temperature, then a solution of activated ester prepared in advance in dimethylformamide (433 µl) was added under ice cooling, and the mixture was stirred at room temperature for 2 hours. The reaction solution was added to an ice-cold 0.5% aqueous trifluoroacetic acid solution (5 ml), and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound GlcNAc-hANP(1-28) (17.8 mg).

MALDI-TOF-MS: Calcd for $C_{137}H_{218}N_{46}O_{46}S_3$: [M+H]$^+$ 3340.5, Found 3340.5

(2-7B) Synthesis of GlcNAc-hANP(1-28)-GlcNAc (Compound of the Following Formula)

[Formula 112]

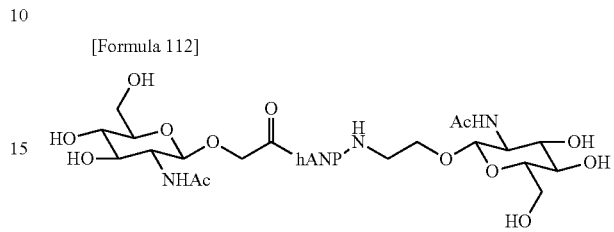

The title compound GlcNAc-hANP(1-28)-GlcNAc (10.0 mg) was obtained by the linking of GlcNAc to the C terminus of hANP according to the same approach as in (2-2B) using the GlcNAc-hANP(1-28) (30.0 mg) produced in (2-7A) and the compound 1-7A.

MALDI-TOF-MS: Calcd for $C_{147}H_{236}N_{48}O_{51}S_3$: [M+H]$^+$ 3586.7, Found 3586.7

(2-7C) Synthesis of SG-hANP(1-28)-SG (Compound 2-7: Compound of the Following Formula)

[Formula 113]

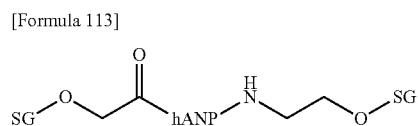

The title compound SG-hANP(1-28)-SG (compound 2-7) (13.0 mg) was obtained according to the same approach as in (2-2D) using the GlcNAc-hANP(1-28)-GlcNAc (6.0 mg) produced in (2-7B).

MALDI-TOF-MS: Calcd for $C_{299}H_{482}N_{58}O_{163}S_3$: [M+H]$^+$ 7590.0, Found 7589.0.

<Example 2-8> Synthesis of (SG-)Asn-hANP(3-28) (Compound 2-8) (2-8A) Synthesis of (GlcNAc-)Asn-hANP(3-28) (Compound of the Following Formula)

[Formula 114]

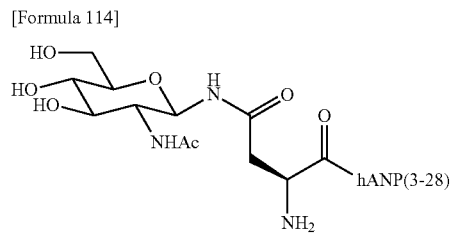

The N-terminal amino acid of the hANP(2-28) (32.0 mg) produced in (2-4A) was removed by the method of (2-4A), again, to obtain hANP(3-28). The title compound (GlcNAc-)Asn-hANP(3-28) (3.5 mg) was obtained according to the same approach as in Example 2-4 using the obtained hANP (3-28) instead of hANP(2-28).

MALDI-TOF-MS: Calcd for $C_{130}H_{206}N_{46}O_{43}S_3$: [M+H]$^+$ 3196.5, Found 3196.7

(2-8B) Synthesis of (SG-)Asn-hANP(3-28) (Compound of the Following Formula: Compound 2-8)

[Formula 115]

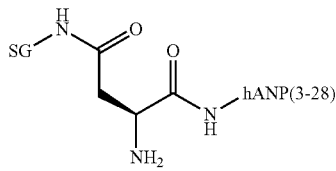

The title compound (SG-)Asn-hANP(3-28) (compound 2-8) ((2.5 mg) was obtained according to the same approach as in (2-2D) using the GlcNAc-Asn-hANP(3-28) (3.5 mg) produced in (2-8A).

MALDI-TOF-MS: Calcd for $C_{206}H_{329}N_{51}O_{99}S_3$: [M+H]$^+$ 5198.1, Found 5198.3

<Example 2-9> Synthesis of SG-(SG-)Asn-hANP (1-28) (Compound 2-9)

(2-9A) Synthesis of GlcNAc-(GlcNAc-)Asn-hANP (1-28) (Compound of the Following Formula)

[Formula 116]

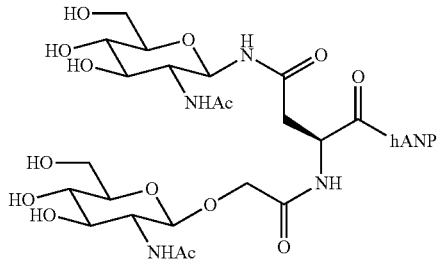

The title compound GlcNAc-(GlcNAc-)Asn-hANP(1-28) (6.15 mg) was obtained by the linking of GlcNAc to the amino group of Asp according to the same approach as in (1-5B) using the (GlcNAc-)Asn-hANP(1-28) (16.0 mg) produced in (2-3B).

MALDI-TOF-MS: Calcd for $C_{149}H_{237}N_{49}O_{53}S_3$: [M+H]$^+$ 3657.7, Found 3658.1

(2-9B) Synthesis of SG-(SG-)Asn-hANP(1-28) (Compound 2-9: Compound of the Following Formula)

[Formula 117]

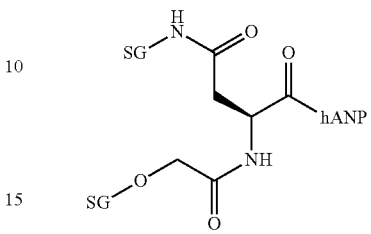

The title compound SG-(SG-)Asn-hANP(1-28) (compound 2-9) (6.7 mg) was obtained by the same approach as in 2-2D using the compound SG-Oxa produced in (1-12A) in a 0.2 M phosphate buffer solution (60 mM, 168 µl), glycosynthase (Endo-M-N175Q, Tokyo Chemical Industry Co., Ltd., 1 U/ml, 67 µl), and the GlcNAc-(GlcNAc-)Asn-hANP(1-28) (6.15 mg) produced in (2-9A).

MALDI-TOF-MS: Calcd for $C_{301}H_{483}N_{59}O_{165}S_3$: [M+H]$^+$ 7661.0, Found 7660.7.

<Example 2-10> Synthesis of AG(9)-hANP(1-28) (Compound 2-10)

(2-10A) Synthesis of AG(9)-hANP(1-28) (Compound 2-10: Compound of the Following Formula)

[Formula 118]

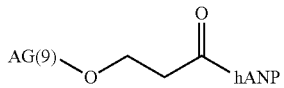

The SG-hANP(1-28) (21 mg) synthesized in (2-1B) was dissolved in a 0.2 M acetate buffer solution (pH 5.0) (1000 µl). To the solution, an aqueous solution (1000 µl) of neuraminidase ([E.C.3.2.1.18], Nacalai Tesque, Inc., 1 U/ml) was then added, and the mixture was reacted at 37° C. for 17 hours. After the completion of the reaction, a 0.2% aqueous trifluoroacetic acid solution (2000 µl) was added thereto. Insoluble matter was dissolved by the addition of acetic acid (200 µl). Two lots of this reaction solution were combined, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound AG(9)-hANP(1-28) (compound 2-10) (33.8 mg).

MALDI-TOF-MS: Calcd for $C_{191}H_{307}N_{49}O_{86}S_3$: [M+H]$^+$ 4760.0, Found 4760.4.

<Example 2-11> Synthesis of AG(7)-hANP(1-28)

(2-11A) Synthesis of AG(7)-hANP(1-28) (Compound 2-11: Compound of the Following Formula)

[Formula 119]

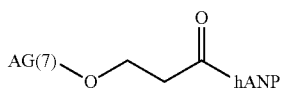

The AG(9)-hANP(1-28) (16 mg) synthesized in (2-10A) was dissolved in distilled water (1425 μl). To the solution, a 0.2 M phosphate buffer solution (pH 6.25) (1500 μl) and an aqueous solution (75 μl) of β1-4 galactosidase (New England BioLabs Japan Inc., 8000 U/ml) were then added, and the mixture was reacted at 37° C. for 24 hours. After the completion of the reaction, a 0.2% aqueous trifluoroacetic acid solution (3000 ul) was added thereto. Insoluble matter was dissolved by the addition of acetic acid (300 μl), and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound AG(7)-hANP(1-28) (compound 2-11) (11.7 mg).

MALDI-TOF-MS: Calcd for $C_{179}H_{287}N_{49}O_{76}S_3$: [M+H]+ 4435.9, Found 4435.8.

<Example 2-12> Synthesis of SG-triazole-hANP(1-28) (Compound 2-12)

(2-12A) Synthesis of Pentynoyl-hANP(1-28) (Compound of the Following Formula)

[Formula 120]

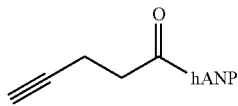

The title compound Pentynoyl-hANP(1-28) (26.0 mg) was obtained according to the same method as in (2-7A) using the hANP(1-28)-acetate (50.0 mg) and 4-pentynoic acid (10.0 mg, 101 μmol).

MALDI-TOF-MS: Calcd for $C_{132}H_{207}N_{45}O_{40}S_3$: [M]+ 3158.4, Found 3158.0.

(2-12B) Synthesis of GlcNAC-triazole-hANP(1-28) (Compound of the Following Formula)

[Formula 121]

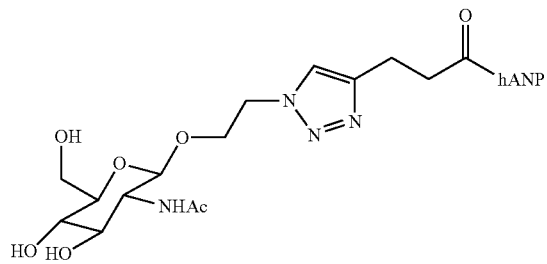

To the Pentynoyl-hANP(1-28) (22.0 mg) produced in (2-12A), a 30 mM aqueous N-[(2R,3R,4R,5S,6R)-2-(2-azidoethoxy)-4,5-dihydroxy-6-(hydroxymethyl)tetrahydropyran-3-yl]acetamide solution (0.37 mL, 11.1 μmol), a 30 mM aqueous sodium ascorbate solution (0.26 mL, 7.8 μmol), a 10 mM aqueous copper sulfate solution (0.15 mL, 1.5 μmol), and a 0.1 M phosphate buffer (pH 7.0) were added in this order, and the mixture was stirred at room temperature for 4 hours. A 0.2% aqueous trifluoroacetic acid solution (12 mL) was added to the reaction solution, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound GlcNAc-triazole-hANP(1-28) (15.0 mg).

MALDI-TOF-MS: Calcd for $C_{142}H_{225}N_{49}O_{46}S_3$: [M+H]+ 3449.6, Found 3449.6.

(2-12C) Synthesis of SG-triazole-hANP(1-28) (Compound 2-12: Compound of the Following Formula)

[Formula 122]

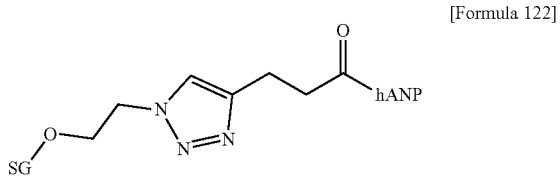

The title compound SG-triazole-hANP(1-28) (compound 2-12) (9.3 mg) was obtained according to the same approach as in (2-2D) using the GlcNAc-triazole-hANP(1-28) (8.0 mg) produced in (2-12B).

MALDI-TOF-MS: Calcd for $C_{218}H_{348}N_{54}O_{102}S_3$: [M+H]+ 5451.3, Found 5451.1.

<Example 2-13> Synthesis of SG-(SG-)Asn-PEG (3)-hANP(1-28) (Compound 2-13)

(2-13A) Synthesis of GlcNAc-(GlcNAc-Asn)-PEG (3)-hANP(1-28) (Compound of the Following Formula)

[Formula 123]

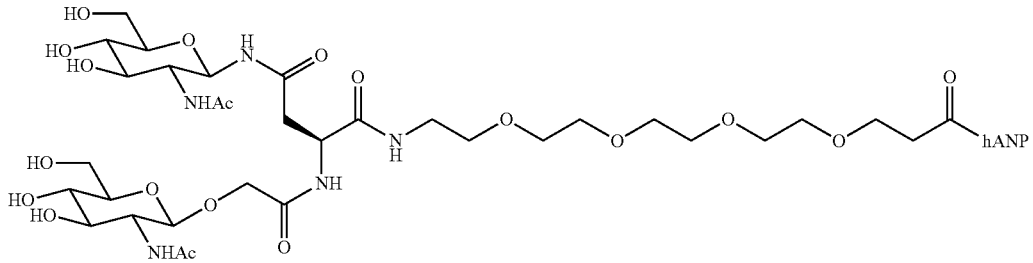

The title compound GlcNAc-(GlcNAc-)Asn-PEG(3)-hANP(1-28) (12.0 mg) was obtained according to the same approach as in (2-1B) from the compound 1-5B (9 mg) and the hANP-TFA salt (16.6 mg) prepared by Preparation Method 2 of (2-1A).

MALDI-TOF-MS: Calcd for $C_{160}H_{258}N_{50}O_{58}S_3$: $[M+H]^+$ 3904.8, Found 3904.5

(2-13B) Synthesis of SG-(SG-)Asn-PEG(3)-hANP (1-28) (Compound 2-13: Compound of the Following Formula)

[Formula 124]

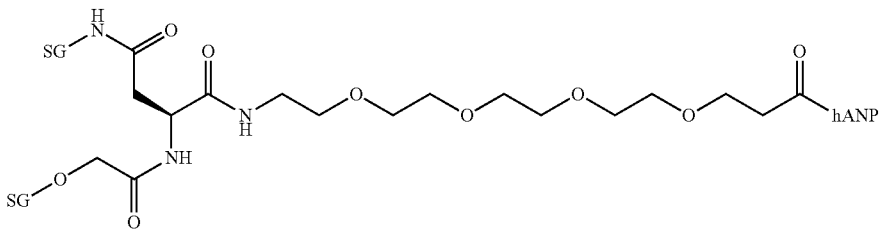

The title compound SG-(SG-)Asn-PEG(3)-hANP(1-28) (compound 2-13) (6.40 mg) was obtained according to the same approach as in (2-9B) using the GlcNAc-(GlcNAc-)Asn-PEG(3)-hANP(1-28) (6.00 mg) produced in (2-13A). ESI-TOF-MS: Calcd for $C_{312}H_{504}N_{60}O_{170}S_3$: $[M+4H]^{4+}$ 1979.0 (ave.), Found 1978.5.

<Example 2-14> Synthesis of SG-(SG-)Lys-Gly-hANP(1-28) (Compound 2-14)

(2-14A) Synthesis of GlcNAc-(GlcNAc-)Lys-Gly-hANP(1-28) (Compound of the Following Formula)

[Formula 125]

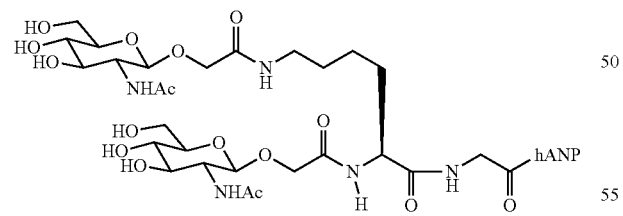

The title compound GlcNAc-(GlcNAc-)Lys-Gly-hANP (1-28) (14.9 mg) was obtained according to the same method as in (2-7A) using the hANP(1-28)-acetate (50.0 mg) and the compound 1-9D (29.0 mg, 40.0 µmol).

MALDI-TOF-MS: Calcd for $C_{155}H_{249}N_{50}O_{55}S_3$: $[M+H]^+$ 3786.7, Found 3786.8.

(2-14B) Synthesis of SG-(SG-)Lys-Gly-hANP(1-28) (Compound 2-14: Compound of the Following Formula)

[Formula 126]

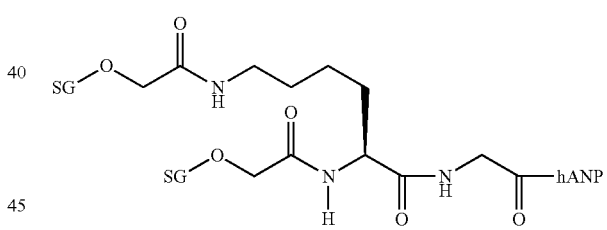

The title compound SG-(SG-)Lys-Gly-hANP(1-28) (compound 2-14) (7.6 mg) was obtained according to the same approach as in (2-2D) using the GlcNAc-(GlcNAc-)Lys-Gly-hANP(1-28) (6.0 mg) produced in (2-14A).

ESI-TOF-MS: Calcd for $C_{307}H_{498}N_{60}O_{167}S_3$: $[M+4H]^{4+}$ 1949.4 (ave.), Found 1949.2.

<Example 2-15> Synthesis of [(SG-)Cys-Gly]₃-hANP(1-28) (Compound 2-15)

(2-15A) Synthesis of [(GlcNAc-)Cys-Gly]₃-hANP(1-28) (Compound of the Following Formula)

[Formula 127]

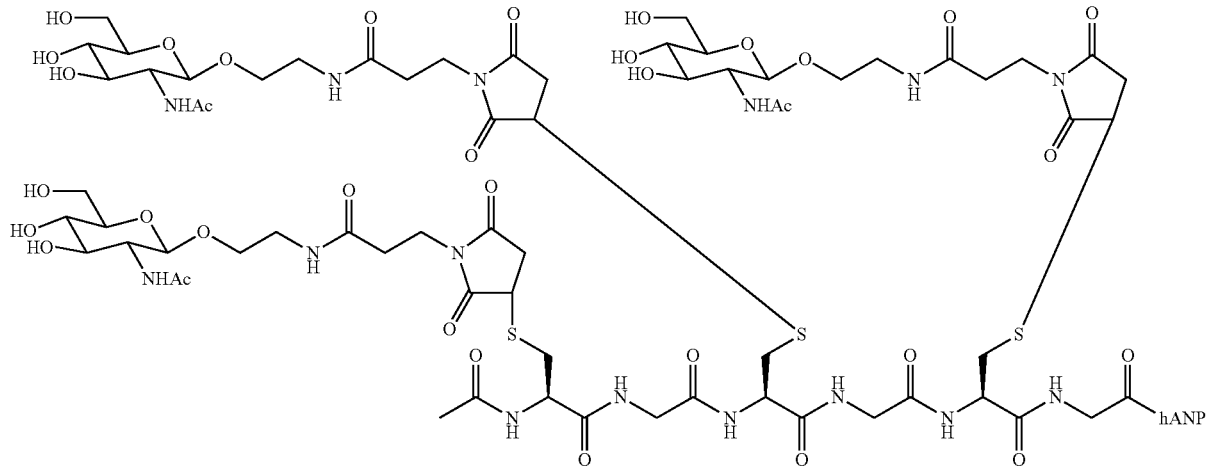

The title compound [(GlcNAc-)Cys-Gly]₃-hANP(1-28) (18.4 mg) was obtained according to the same approach as in (2-1B) using the compound 1-10B (27 mg).

MALDI-TOF-MS: Calcd for $C_{195}H_{304}N_{60}O_{73}S_6$: [M+H]⁺ 4847.0, Found 4847.2

(2-15B) Synthesis of [(SG-)Cys-Gly]₃-hANP(1-28) (Compound 2-15: Compound of the Following Formula)

[Formula 128]

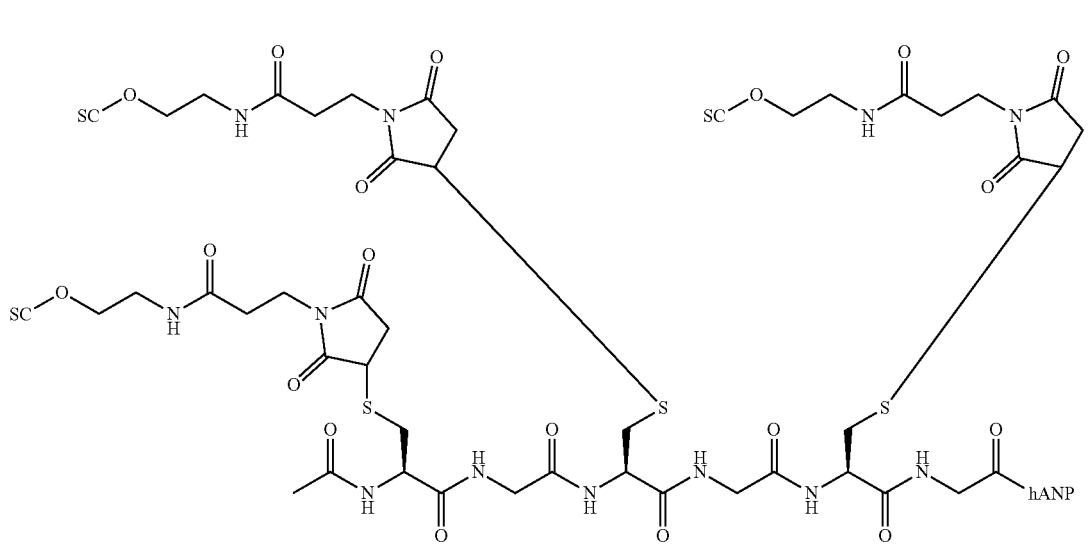

The title compound [(SG-)Cys-Gly]₃-hANP(1-28) (compound 2-15) (5.23 mg) was obtained by the same approach as in 2-2D using the compound SG-Oxa produced in (1-12A) in a 0.2 M phosphate buffer solution (60 mM, 118 µl), glycosynthase (Endo-M-N175Q, Tokyo Chemical Industry Co., Ltd., 1 U/ml, 47 µl), and the [(GlcNAc-)Cys-Gly]₃-hANP(1-28) produced in (2-15A).

ESI-TOF-MS: Calcd for $C_{423}H_{673}N_{75}O_{241}S_6$: [M+5H]⁵⁺ 2172.5 (ave.), Found 2172.4

<Example 2-16> Synthesis of SG-PEG(3)-(SG-)-Asn-hANP(1-28) (Compound 2-16) (2-16A) Synthesis of GlcNAc-PEG(3)-(GlcNAc-)Asn-hANP(1-28) (Compound of the Following Formula)

[Formula 129]

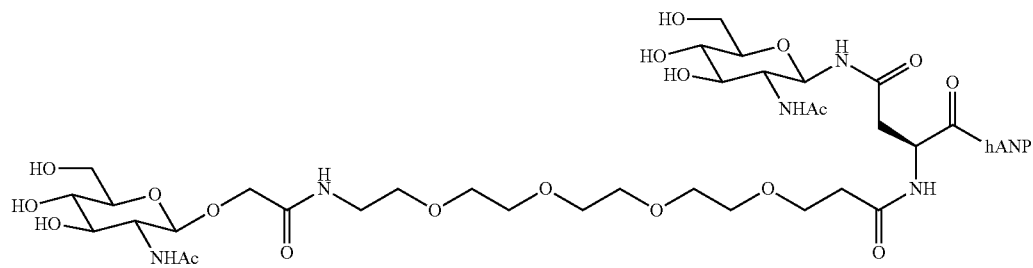

The title compound GlcNAc-PEG(3)-(GlcNAc-)Asn-hANP(1-28) (9.10 mg) was obtained according to the same approach as in (2-7A) from the (GlcNAc-)Asn-hANP (19.0 mg) produced in (2-3B) and the compound 1-3A (8.8 mg).
MALDI-TOF-MS: Calcd for $C_{160}H_{258}N_{50}O_{58}S_3$: [M+H]$^+$ 3904.8, Found 3904.4

(2-16B) Synthesis of SG-PEG(3)-(SG-)Asn-hANP(1-28) (Compound 2-16: Compound of the Following Formula)

[Formula 130]

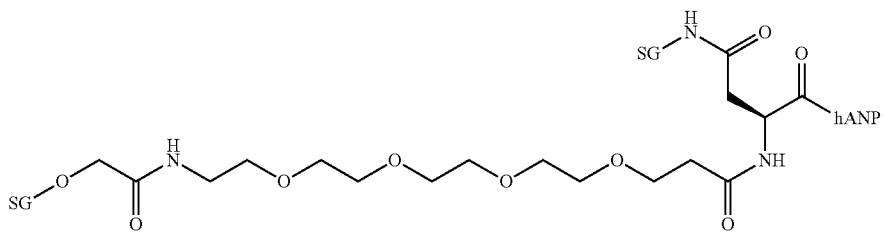

The title compound SG-PEG(3)-(SG-)Asn-hANP(1-28) (compound 2-16) (3.10 mg) was obtained according to the same approach as in (2-9B) using the GlcNAc-PEG(3)-(GlcNAc-)Asn-hANP(1-28) (3.50 mg) produced in (2-16A) at room temperature.
ESI-TOF-MS: Calcd for $C_{312}H_{504}N_{60}O_{170}S_3$: [M+4H]$^{4+}$ 1978.1 (ave.), Found 1978.8.

<Example 2-17> Synthesis of [(SG-)Cys-Gly]$_5$-hANP(1-28) (Compound 2-17)

(2-17A) Synthesis of [Cys-Gly]$_5$-hANP(1-28) (Compound of the Following Formula)

[Formula 131]

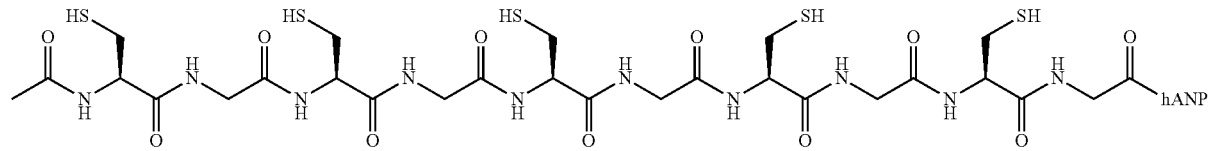

The intermediate (13.0 mg) was obtained according to the same approach as in (2-1B) from the compound 1-8A (50.6 mg) and hANP-TFA salt prepared from the hANP-acetate (47.0 mg) by Preparation Method 2 of (2-1A).

To the obtained intermediate (13.0 mg), a mixed solution of trifluoroacetic acid (1.9 mL), water (0.05 mL), and triisopropylsilane (0.05 mL) was added. The mixture was shaken at room temperature for 1 hour. The reaction solution was diluted with water, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents to obtain the title compound [Cys-Gly]$_5$-hANP(1-28) as a white solid (3.2 mg).

MALDI-TOF-MS: Calcd for $C_{154}H_{245}N_{55}O_{50}S_8$: [M+H]$^+$ 3921.6, Found 3921.9

(2-17B) Synthesis of [(SG-)Cys-Gly]$_5$-hANP(1-28) (Compound 2-17: Compound of the Following Formula)

[Formula 132]

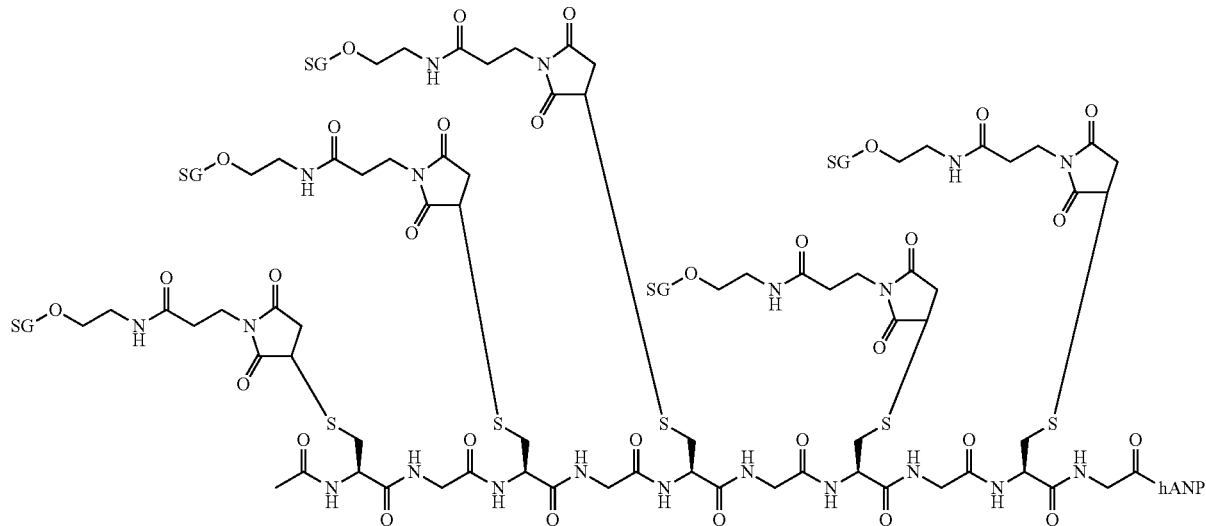

The [Cys-Gly]$_5$-hANP(1-28) (3.00 mg) produced in (2-17A) and the compound SG-M (9.94 mg) produced in (1-13A) were dissolved in a mixed solution of acetonitrile (0.25 mL) and a 0.2 M phosphate buffer of pH 6.75 (0.25 mL), and the solution was stirred at room temperature for 2 hours. The reaction solution was diluted with water, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents to obtain the title compound [(SG-)Cys-Gly]$_5$-hANP(1-28) (compound 2-17) (8.19 mg).

ESI-TOF-MS: Calcd for $C_{619}H_{985}N_{95}O_{375}S_8$: [M+6H]$^{6+}$ 2670.1 (ave.), Found 2670.1.

<Example 2-18> Synthesis of [(SG$_2$-)Cys-Gly]$_5$-hANP(1-28) (Compound 2-18)

(2-18A) Synthesis of Tert-Butyl N-[(1R)-1-(prop-2-ynylcarbamoyl)but-3-ynyl]carbamate (Compound of the Following Formula)

[Formula 133]

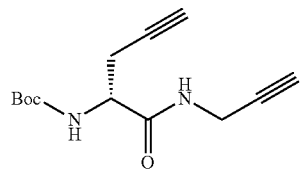

The title compound was obtained as a pale yellow solid (480 mg, yield: 96%) according to the same method as in (1-9A) using (2R)-2-(tert-butoxycarbonylamino)-4-pentynoic acid (430 mg, 2.02 mmol) and propargylamine (140 mg, 2.54 mmol).

MS (ESI): Calcd for $C_{13}H_{19}N_2O_3$: [M+H]$^+$ 251, Found 251.

(2-18B) Synthesis of (2R)-2-amino-N-prop-2-ynyl-pent-4-enamide Trifluoroacetate (Compound of the Following Formula)

[Formula 134]

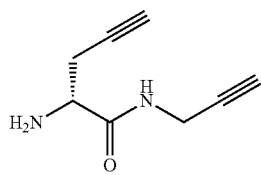

The title compound was obtained as a pale yellow oil (270 mg, yield: 100%) according to the same method as in (1-9B) using the title compound (250 mg, 1.00 mmol) obtained in (2-18A).

$^1$H-NMR (CD$_3$OD) δ: 4.11-3.96 (3H, m), 2.87-2.74 (2H, m), 2.68-2.65 (2H, m).

(2-18C) Synthesis of (2R)-2-[3-(2,5-dioxopyrrol-1-yl)propanoylamino]-N-prop-2-ynyl-pent-4-enamide (Compound of the Following Formula)

[Formula 135]

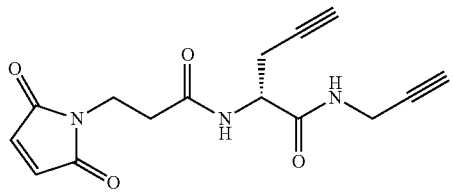

The title compound was obtained as a pale yellow solid (220 mg, yield: 73%) according to the same method as in (1-15A) using the title compound (270 mg, 1.00 mmol) obtained in (2-18B).

MS (ESI): Calcd for C$_{15}$H$_{14}$N$_3$O$_4$: [M−H]$^-$ 300, Found 300.

(2-18D) Synthesis of [(SG$_2$-)Cys-Gly]$_5$-hANP(1-28) (Compound 2-18: Compound of the Following Formula)

The compound SG-N$_3$ (20.0 mg, 8.73 μmol) produced in (1-18A) was dissolved in a 0.10 M phosphate buffer (pH 8.0) (0.840 ml). To the solution, a 3.3 mM solution of the title compound obtained in (2-18C) in tert-butanol (1.06 mL, 3.50 μmol), a 50 mM aqueous sodium ascorbate solution (0.420 mL, 21.0 μmol), and a 10 mM aqueous copper sulfate solution (0.420 mL, 4.20 μmol) were added in this order, and the mixture was stirred at room temperature for 1 hour and 30 minutes. A 0.2% aqueous trifluoroacetic acid solution (12 mL) was added to the reaction solution, and the resulting product was separated and purified by reverse-phase HPLC (Shiseido Co., Ltd., Proteonavi) using a 0.1% aqueous trifluoroacetic acid solution and a 0.1% solution of trifluoroacetic acid in acetonitrile as eluents and lyophilized to obtain the intermediate (6.20 mg, 36%).

The title compound [(SG$_2$-)Cys-Gly]$_5$-hANP(1-28) (compound 2-18) (8.42 mg) was obtained according to the same approach as in (2-17B) from the (Cys-Gly)$_5$-hANP(1-28) (1.76 mg) produced in (2-17A) and the synthesized intermediate (10.3 mg).

ESI-TOF-MS: Calcd for C$_{1089}$H$_{1730}$N$_{160}$O$_{690}$S$_8$: [M−10H]$^{10-}$ 2835 0.1 (ave.), Found 2834.9.

[Formula 136]

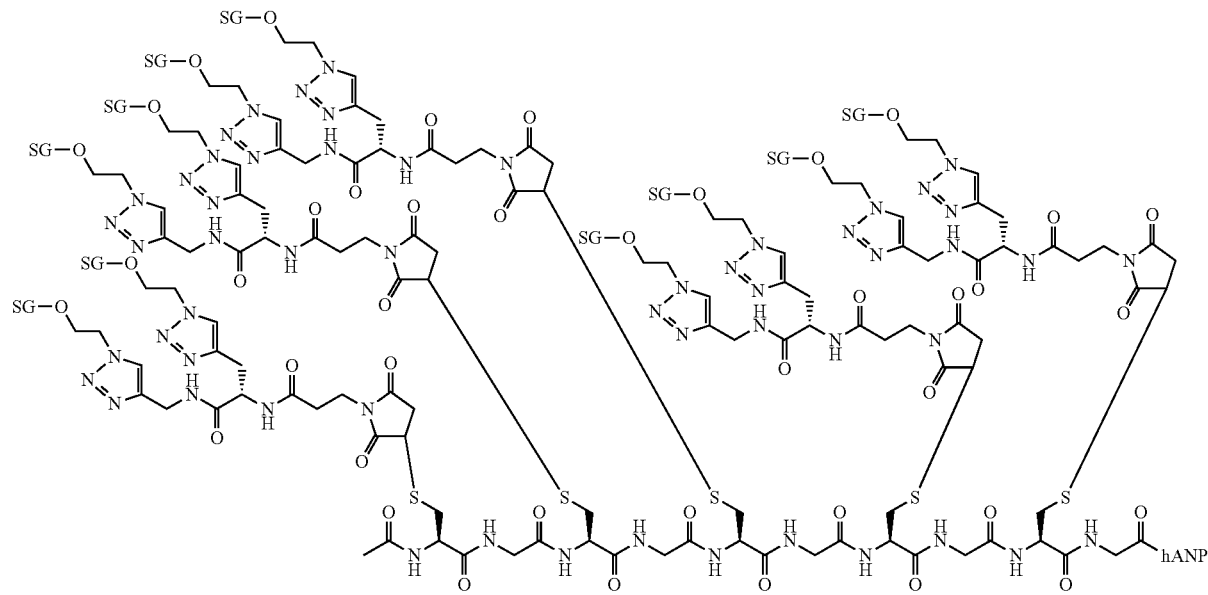

<Example 2-19> Synthesis of SG-(SG-)Lys-[SG-(SG-)Lys-]Lys-PEG(3)-hANP(1-28) (Compound 2-19)

(2-19A) Synthesis of TrS-(TrS-)Lys-[TrS-(TrS-)Lys-]Lys-PEG(3) (Compound of the Following Formula)

[Formula 137]

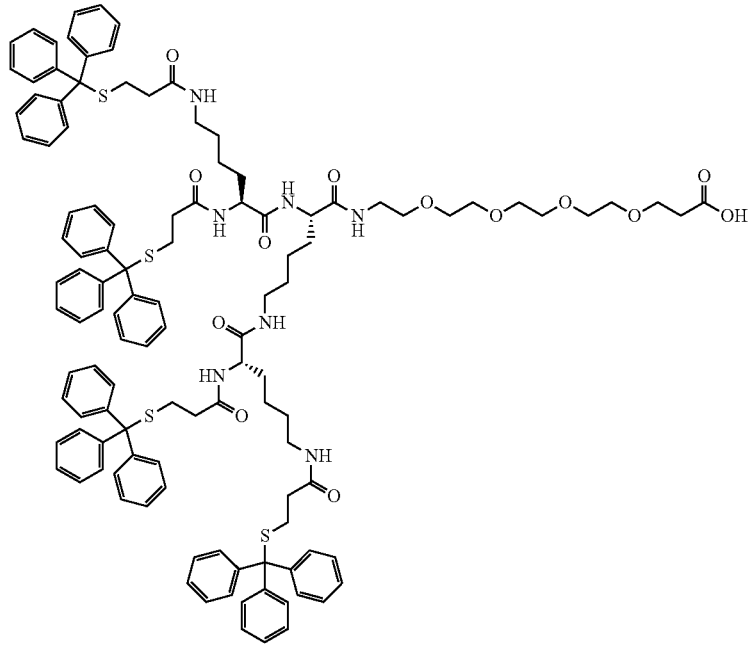

A 1.20 mmol/g 2-chlorotrityl chloride resin (250 mg, 0.300 mmol) was placed in a column for solid-phase synthesis. Dichloromethane (5 mL) was added thereto, and the mixture was shaken for 10 minutes. After filtration, a solution of 3-[2[2[2[2-(9H-fluoren-9-ylmethoxycarbonylamino)ethoxy]ethoxy]ethoxy]ethoxy]propionic acid (175 mg, 0.360 mmol) and N,N-diisopropylethylamine (257 μL, 1.50 mmol) in dichloromethane (5 mL) was added thereto, and the mixture was stirred at room temperature for 2 hours. After filtration, the resin was washed with a dichloromethane mixed solution (dichloromethane:methanol:N,N-diisopropylethylamine=85:10:5, v/v) three times, dichloromethane three times, and N,N-dimethylformamide three times. A 20% solution of piperidine in N,N-dimethylformamide (10 mL) was added thereto, and the mixture was shaken for 5 minutes, followed by filtration. This operation was carried out 4 times. The resin was washed with N,N-dimethylformamide 4 times. A solution of (2S)-2,6-bis(9H-fluoren-9-ylmethoxycarbonylamino)hexanoic acid (532 mg, 0.900 mmol), HATU (342 mg, 0.900 mmol), and N,N-diisopropylethylamine (308 μL, 1.80 mmol) in N,N-dimethylformamide (10 mL) was added to the resin, and the mixture was shaken at room temperature for 30 minutes. After filtration, the resin was washed with N,N-dimethylformamide three times. A 20% solution of piperidine in N,N-dimethylformamide (10 mL) was added thereto, and the mixture was shaken for 5 minutes, followed by filtration. This operation was carried out 4 times. The resin was washed with N,N-dimethylformamide 4 times. A solution of (2S)-2,6-bis(9H-fluoren-9-ylmethoxycarbonylamino)hexanoic acid (1060 mg, 1.80 mmol), HATU (684 mg, 1.80 mmol), and N,N-diisopropylethylamine (616 μL, 3.60 mmol) in N,N-dimethylformamide (10 mL) was added to the resin, and the mixture was shaken at room temperature for 1 hour. After filtration, the resin was washed with N,N-dimethylformamide 4 times. A 20% solution of piperidine in N,N-dimethylformamide (10 mL) was added thereto, and the mixture was shaken for 5 minutes, followed by filtration. This operation was carried out 5 times. The resin was washed with N,N-dimethylformamide 4 times. A ⅓ amount (corresponding to 0.100 mmol) of the obtained resin was placed in a column for solid-phase synthesis. A solution of 3-tritylsulfanylpropionic acid (418 mg, 1.20 mmol), HATU (456 mg, 1.20 mmol), and N,N-diisopropylethylamine (411 μL, 2.40 mmol) in N,N-dimethylformamide (10 mL) was added thereto, and the mixture was shaken at room temperature for 1 hour. After filtration, a solution of 3-tritylsulfanylpropionic acid (418 mg, 1.20 mmol), HATU (456 mg, 1.20 mmol), and N,N-diisopropylethylamine (411 μL, 2.40 mmol) in N,N-dimethylformamide (10 mL) was added again to the resin, and the mixture was shaken at room temperature for 1 hour. After filtration, the resin was washed with N,N-dimethylformamide 4 times and dichloromethane three times. A mixed solution of 1,1,1,3,3,3-hexafluoro-2-propanol (2.5 mL) and dichloromethane (7.5 mL) was added thereto, and the mixture was shaken at room temperature for 1.5 hours. The resin was filtered off, and the filtrate was concentrated under reduced pressure. The concentrate was subjected to azeotropy with dichloromethane 6 times and dried in a vacuum pump to obtain the title compound TrS-(TrS-)Lys-[TrS-(TrS-)Lys-]Lys-PEG(3) as a brown solid (170 mg).

(2-19B) Synthesis of HS-(HS-)Lys[HS-(HS-)Lys-]Lys-PEG(3)-hANP(1-28) (Compound of the Following Formula)

[Formula 138]

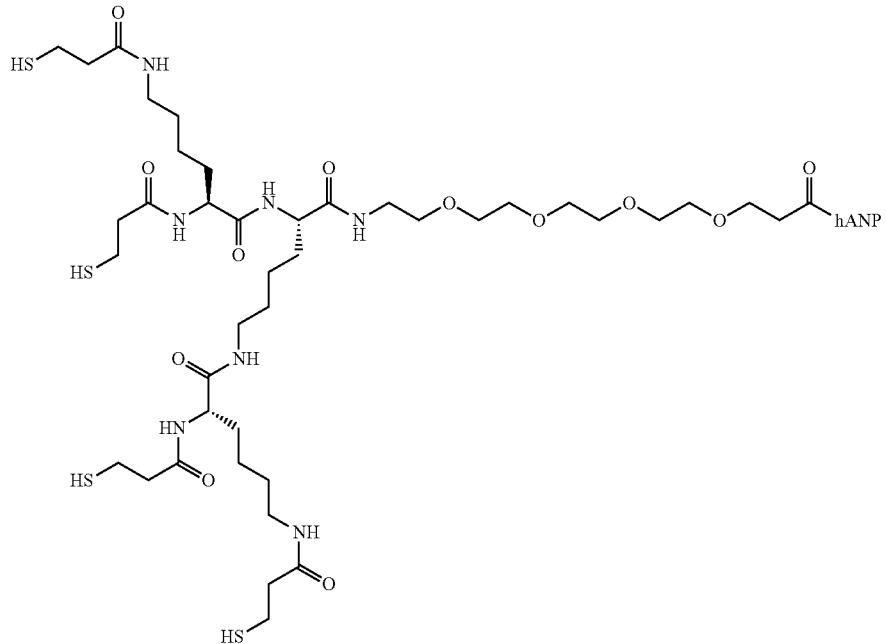

The intermediate (40 mg) was obtained according to the same approach as in (2-17A) from the compound (66.1 mg) produced in (2-19A).

The title compound HS-(HS-)Lys[HS-(HS-)Lys-]Lys-PEG(3)-hANP(1-28) (2.3 mg) was obtained according to the same approach as in (2-17A) from the obtained intermediate (7.0 mg).

MALDI-TOF-MS: Calcd for $C_{168}H_{276}N_{52}O_{51}S_7$: $[M+H]^+$ 4062.9, Found 4062.8

(2-19C) Synthesis of SG-(SG-)Lys-[SG-(SG-)-Lys-]Lys-PEG(3)-hANP(1-28) (Compound of the Following Formula: Compound 2-19)

[Formula 139]

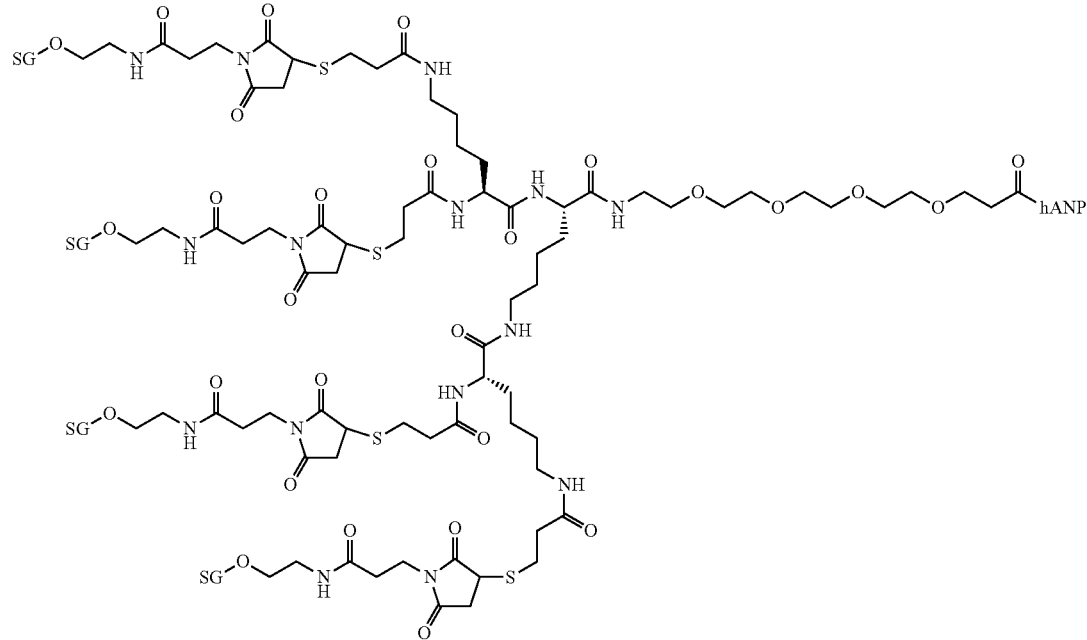

The title compound [SG-(SG-)Lys-[SG-(SG-)-Lys-]Lys-PEG(3)-hANP(1-28) (compound 2-19) (5.31 mg) was obtained according to the same approach as in (2-17B) from HS(HS-)-Lys-[HS-(HS-)Lys-]Lys-PEG(3)-hANP(1-28) (2.90 mg) produced by the approach of (2-19B).

ESI-TOF-MS: Calcd for $C_{540}H_{868}N_{84}O_{311}S_7$: $[M+7H]^{7+}$ 1963.4 (ave.), Found 1963.4.

<Example 2-20> Synthesis of [SG$_2$-(SG$_2$-)Lys-[SG$_2$-(SG$_2$-) -Lys-]Lys-PEG(3)-hANP(1-28) (Compound 2-20)

(2-20A) Synthesis of SG$_2$-(SG$_2$-)Lys-[SG$_2$-(SG$_2$-)-Lys-]Lys-PEG(3)-hANP(1-28) (compound 2-20: Compound of the Following Formula)

[Formula 140]

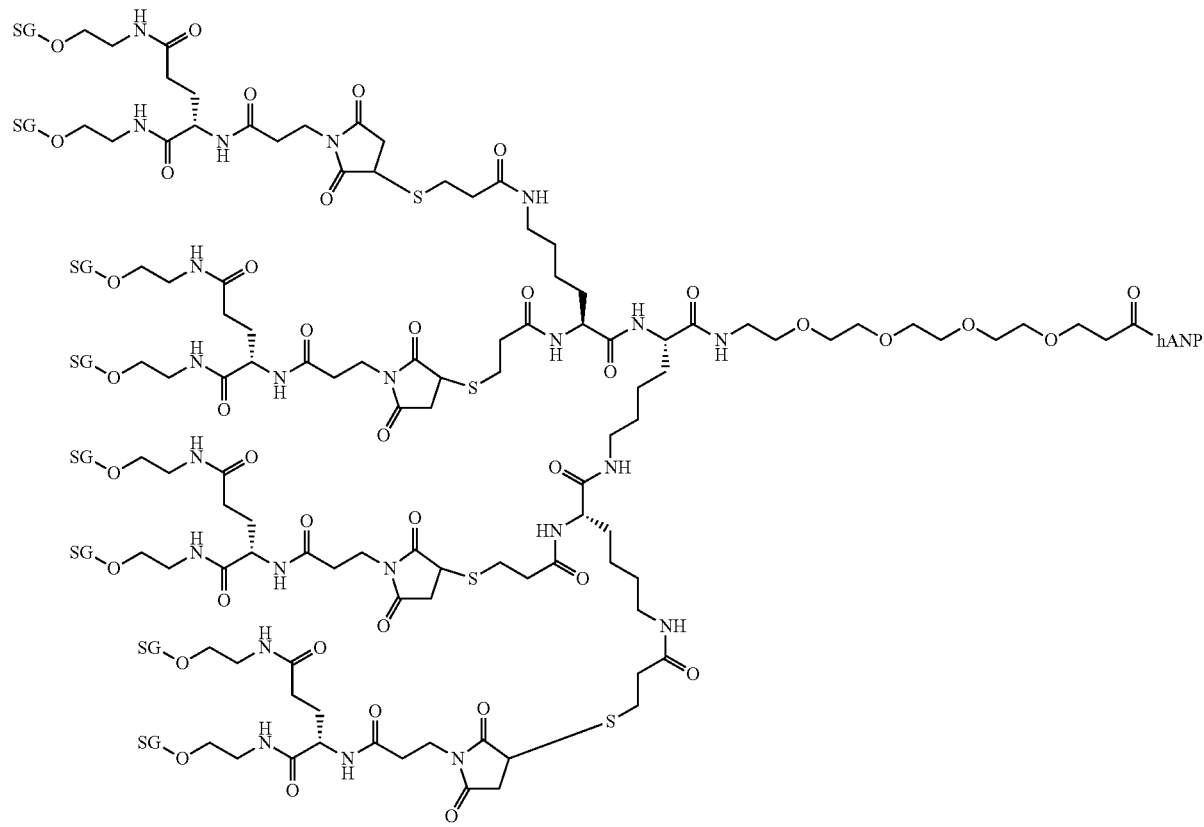

The title compound SG$_2$-(SG$_2$-)Lys-[SG$_2$-(SG$_2$-) -Lys-]Lys-PEG(3)-hANP(1-28) (compound 2-20) (4.79 mg) was obtained according to the same approach as in (2-17B) from the HS(HS-)-Lys-[HS-(HS-)Lys-]Lys-PEG(3)-hANP(1-28) (2.20 mg) produced in (2-19B) and the compound SG-(SG-)Gln*-Mal (12.1 mg) produced in (1-15C).

ESI-TOF-MS: Calcd for $C_{904}H_{1460}N_{116}O_{567}S_7$: $[M+8H]^{8+}$ 2907.3 (ave.), Found 2907.

<Example 2-21> Synthesis of AG(9)-(AG(9)-)Asn-PEG(3)-hANP(1-28) (Compound 2-21)

(2-21A) Synthesis of AG(9)-(AG(9)-)Asn-PEG(3)-hANP(1-28) (Compound 2-21: Compound of the Following Formula)

[Formula 141]

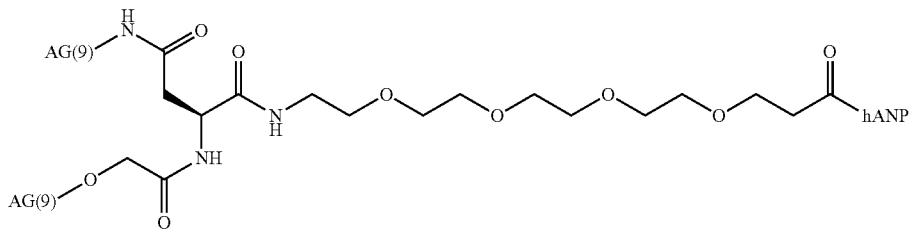

The title compound AG(9)-(AG(9)-)Asn-PEG(3)-hANP (1-28) (compound 2-21) (8.2 mg) was obtained according to the same approach as in (2-10A) using the SG-(SG-Asn)-PEG-hANP(1-28) (16 mg) synthesized in (2-13B).
ESI-TOF-MS: Calcd for $C_{268}H_{436}N_{56}O_{138}S_3$: $[M+4H]^{4+}$ 1687.7, Found 1687.4.

<Example 2-22> Synthesis of AG(7)-(AG(7)-)Asn-PEG(3)-hANP(1-28) (Compound 2-22)

(2-22A) Synthesis of AG(7)-(AG(7)-)Asn-PEG(3)-hANP(1-28) (Compound 2-22: Compound of the Following Formula)

[Formula 142]

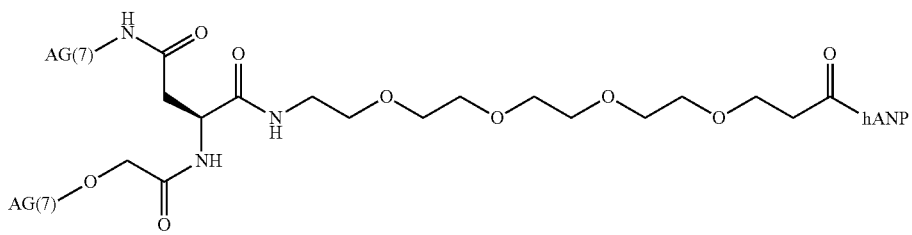

The title compound AG(7)-(AG(7)-)Asn-PEG(3)-hANP (1-28) (compound 2-22) (6.6 mg) was obtained according to the same approach as in (2-11A) using the AG(9)-(AG(9)-)Asn-PEG(3)-hANP(1-28) (8 mg) synthesized in (2-21A).
ESI-TOF-MS: Calcd for $C_{244}H_{396}N_{56}O_{118}S_3$: $[M+4H]^{4+}$ 1525.6, Found 1525.4.

<Example 2-23> Synthesis of SG-Mal-(SG-Mal-)Lys-[SG-Mal-(SG-Mal-)Lys-]Lys-PEG(11)-hANP(1-28) (Compound 2-23)

(2-23A) Synthesis of TrS-(TrS-)Lys-[TrS-(TrS-)Lys-]Lys-PEG(11)-CO₂H (Compound of the Following Formula)

[Formula 143]

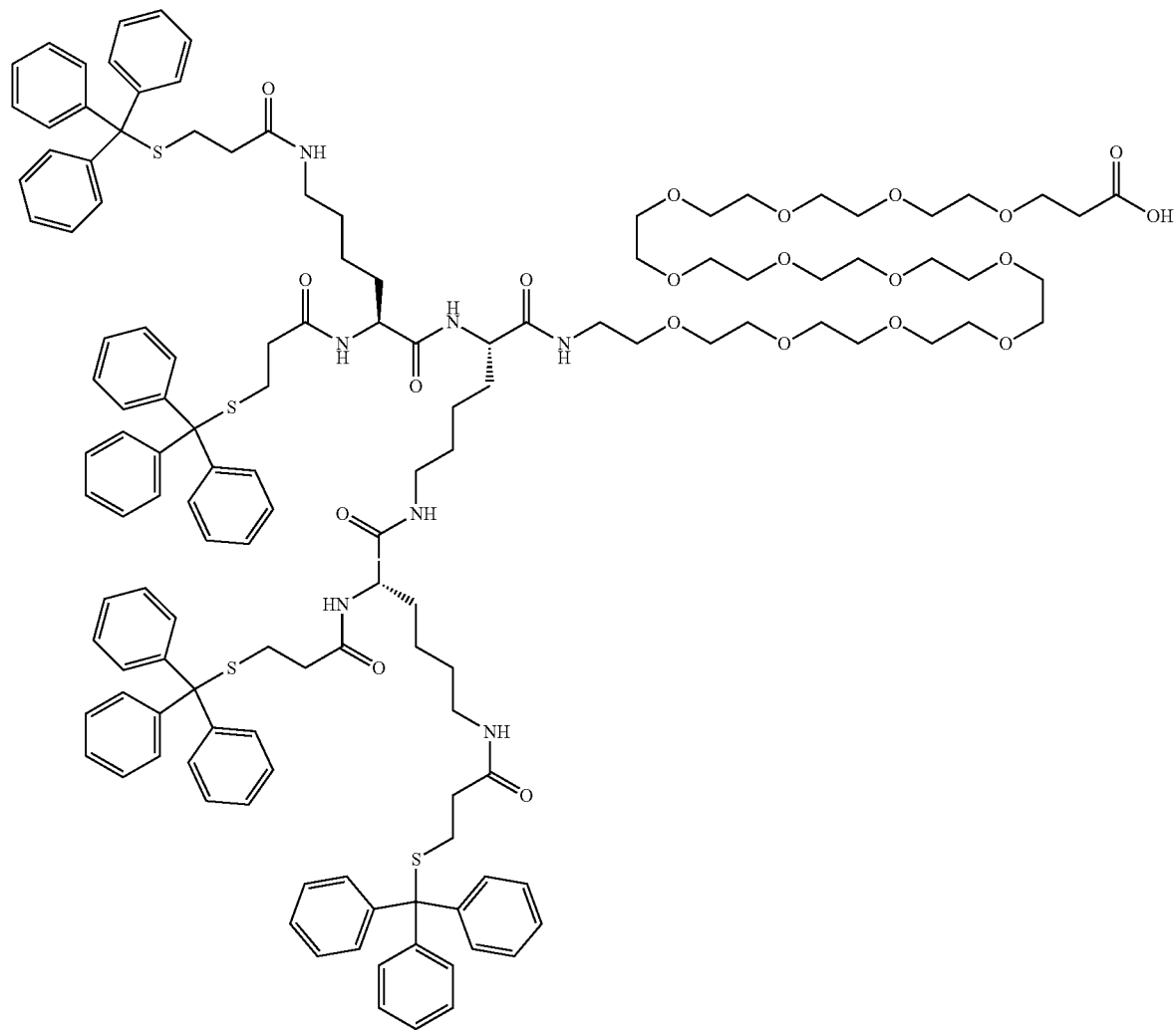

The title compound TrS-(TrS-)Lys-[TrS-(TrS-)Lys-]Lys-PEG(11)-CO₂H (135 mg) was obtained according to the same approach as in (2-19A) from 3-[2-[2-[2-[2-[2-[2-[2-[2-[2-[2-[2-(9H-fluoren-9-ylmethoxycarbonylamino)ethoxy]ethoxy]ethoxy]ethoxy]ethoxy]ethoxy]ethoxy]ethoxy]ethoxy]ethoxy]ethoxy]propionic acid (202 mg).

(2-23B) Synthesis of HS-(HS-)Lys-[HS-(HS-)Lys-]Lys-PEG(11)-hANP(1-28) (Compound of the Following Formula)

[Formula 144]

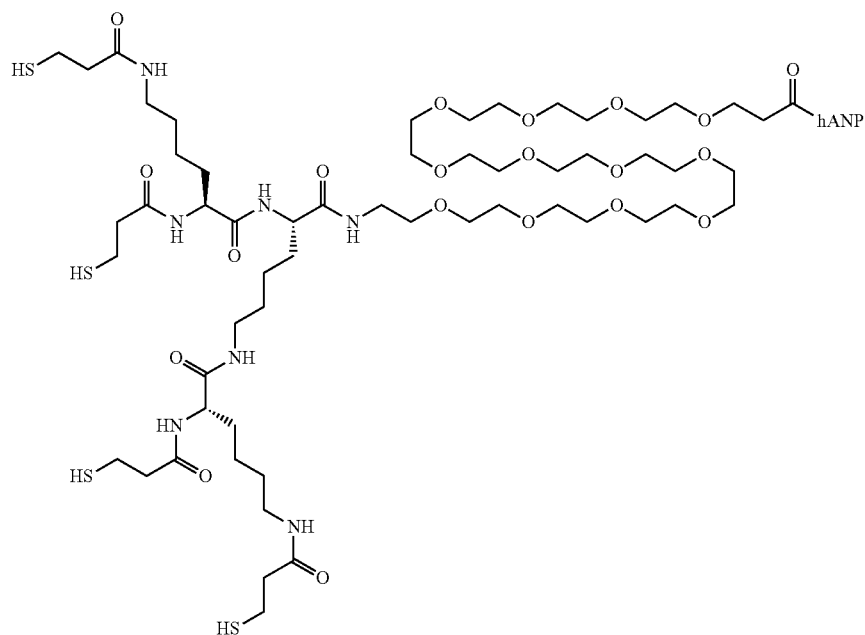

The title compound HS-(HS-)Lys-[HS-(HS-)Lys-]Lys-PEG(11)-hANP(1-28) (12.0 mg) was obtained according to the same approach as in (2-17A) from the TrS-(TrS-)Lys-[TrS-(TrS-) Lys-]Lys-PEG (11)-CO$_2$H (45.3 mg) produced in (2-23A).

MALDI-TOF-MS: Calcd for $C_{184}H_{308}N_{52}O_{59}S_7$: [M+H]$^+$ 4415.1, Found 4416.1

(2-23C) Synthesis of SG$_4$-Lys$_3$-PEG(11)-hANP(1-28) (Compound 2-23: Compound of the Following Formula)

[Formula 145]

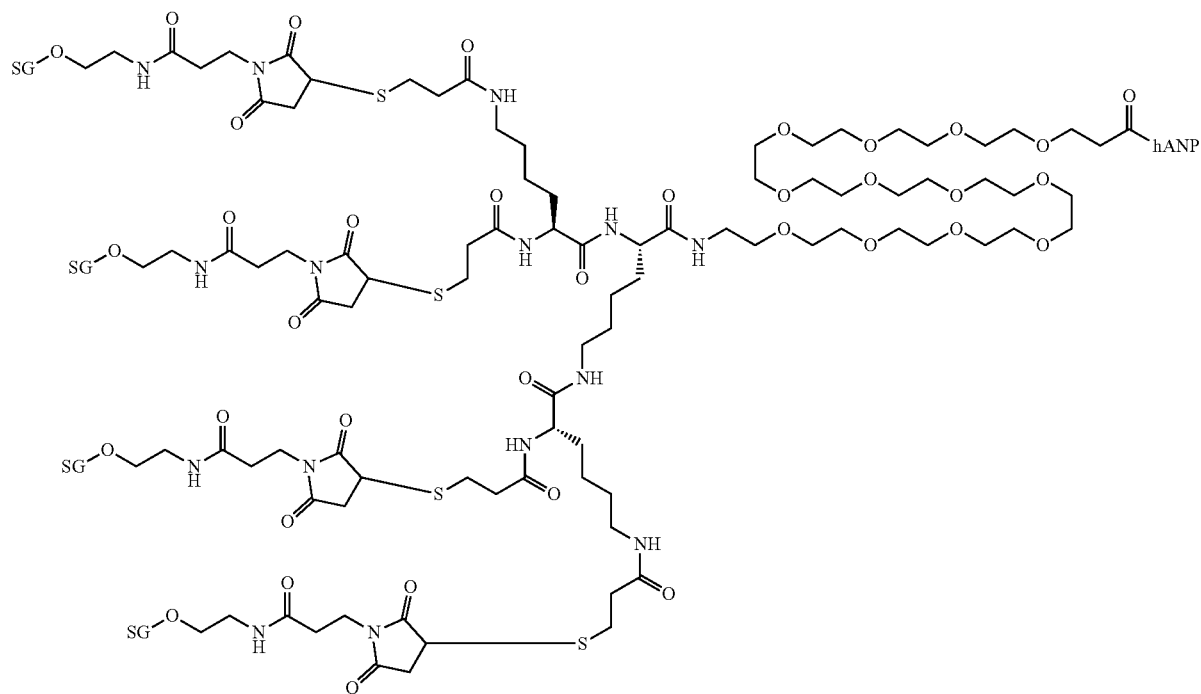

The title compound SG-Mal-(SG-Mal-)Lys-[SG-Mal-(SG-Mal-)Lys-]Lys-PEG(11)-hANP(1-28) (compound 2-23) (4.40 mg) was obtained according to the same approach as in (2-17B) from the HS-(HS-)Lys-[HS-(HS-)Lys-]Lys-PEG(11)-hANP(1-28) (3.16 mg) produced in (2-23B).

ESI-TOF-MS: Calcd for $C_{556}H_{900}N_{84}O_{319}S_7$: $[M+6H]^{6+}$ 2349.3 (ave.), Found 2349.2.

<Example 2-24> Synthesis of SG-PEG(3)-hANP(1-28)-PEG(3)-SG (Compound 2-24)

(2-24A) Synthesis of GlcNAc-PEG(3)-hANP(1-28) (Compound of the Following Formula)

[Formula 146]

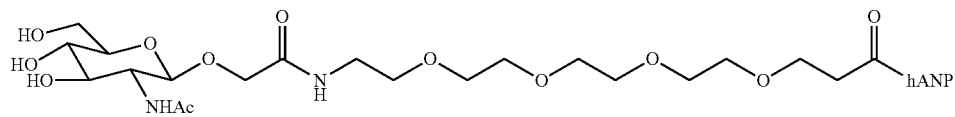

The title compound GlcNAc-PEG(3)-hANP(1-28) (25.0 mg) was obtained according to the same method as in (2-7A) using the hANP(1-28)-TFA salt (33.0 mg) produced in (2-1A) and the compound 1-3A(13.0 mg, 24.7 μmol).

MALDI-TOF-MS: Calcd for $C_{148}H_{240}N_{47}O_{51}S_3$: $[M+H]^+$ 3587.7, Found 3587.6.

(2-24B) Synthesis of GlcNAc-PEG(3)-hANP(1-28)-PEG(3)-GlcNAc (Compound of the Following Formula)

[Formula 147]

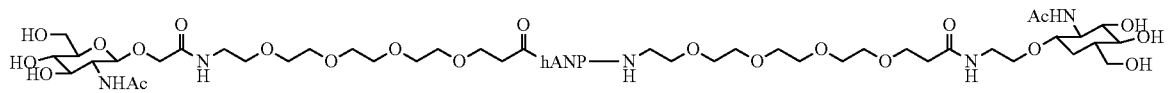

The title compound GlcNAc-PEG(3)-hANP(1-28)-PEG(3)-GlcNAc (3.0 mg) was obtained according to the same method as in (2-2B) using the GlcNAc-PEG(3)-hANP(1-28) (21.0 mg) produced in (2-24A) and the compound 1-19B (46 mg, 73.6 μmol).

MALDI-TOF-MS: Calcd for $C_{169}H_{278}N_{50}O_{61}S_3$: $[M+H]^+$ 4080.9, Found 4080.9.

(2-24C) Synthesis of SG-PEG(3)-hANP(1-28)-PEG(3)-SG (Compound 2-24: Compound of the Following Formula)

[Formula 148]

The title compound SG-PEG(3)-hANP(1-28)-PEG(3)-SG (compound 2-24) (5.5 mg) was obtained according to the same approach as in (2-2D) using the GlcNAc-PEG(3)-hANP(1-28)-PEG(3)-GlcNAc (4.0 mg) produced in (2-24B). ESI-TOF-MS: Calcd for $C_{321}H_{528}N_{60}O_{173}S_3$: $[M+4H]^{4+}$ 2023.0 (ave.), Found 2022.8.

<Example 2-25> Synthesis of SG-thioacetamide-hANP(1-28) (Compound 2-25)

(2-25A) Synthesis of TrS-hANP(1-28) (Compound of the Following Formula)

[Formula 149]

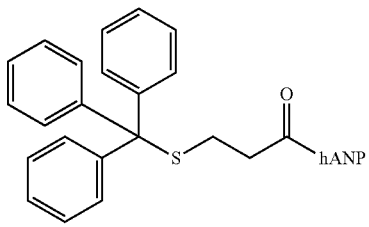

3-Tritylsulfanylpropionic acid (2.24 mg, 6.43 μmol) was dissolved in dimethylformamide (100 μl). To the solution, triethylamine (1.79 μl, 12.8 μmol) was added at room temperature, then a solution of dimethylthiophosphinoyl chloride (0.83 mg, 6.46 μmol) in dimethylformamide (60 μl) was added under ice cooling, and then the mixture was stirred at room temperature for 1 hour. Meanwhile, the hANP(1-28)-TFA salt (10 mg) was dissolved in dimethylformamide (200 μl) and distilled water (60 μl). To the solution, triethylamine (4.2 μl) was added at room temperature, then a solution of active ester prepared in advance in dimethylformamide (160 μl) was added under ice cooling, and the mixture was stirred at room temperature for 5 hours. The reaction solution was added to an ice-cold 0.5% aqueous trifluoroacetic acid solution (2 ml), and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound TrS-hANP(1-28) (5.77 mg).

ESI-TOF-MS: Calcd for $C_{149}H_{221}N_{45}O_{40}S_4$: $[M+3H]^{3+}$ 1138.0 (ave.), Found 1137.8

(2-25B) Synthesis of HS-hANP(1-28) (Compound of the Following Formula)

[Formula 150]

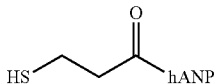

The TrS-hANP(1-28) (5.77 mg) synthesized in (2-25A) was dissolved in a trifluoroacetic acid/distilled water/triisopropylsilane (90/5/5) solution, and the solution was stirred at room temperature for 1 hour. After the completion of the reaction, insoluble matter was dissolved by the addition of a distilled water/acetic acid (10/1) solution (3 ml), and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound HS-hANP(1-28) (2.88 mg).

MALDI-TOF-MS: Calcd for $C_{130}H_{207}N_{45}O_{40}S_4$: $[M+H]^+$ 3167.4, Found 3167.7

(2-25C) Synthesis of SG-thioacetamide-hANP(1-28) (Compound 2-25: Compound of the Following Formula)

[Formula 151]

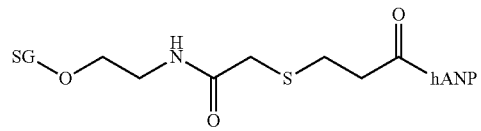

The HS-hANP(1-28) (2.88 mg) synthesized in (2-25B) and the compound SG-I (2.66 mg) synthesized in (1-11C) were dissolved in dimethylformamide (300 μl). To the solution, diisopropylethylamine (0.77 μl) was added, and the mixture was stirred at room temperature for 1 hour. After the completion of the reaction, insoluble matter was dissolved by the addition of a distilled water/acetic acid (10/1) solution (3 ml), and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound SG-thioacetamide-hANP(1-28) (compound 2-25) (2.90 mg). ESI-TOF-MS: Calcd for $C_{218}H_{350}N_{52}O_{103}S_4$: $[M+4H]^{4+}$ 1369.9 (ave.), Found 1369.6.

<Example 2-26> Synthesis of AG(5)-hANP(1-28) (Compound 2-26)

(2-26A) Synthesis of AG(5)-hANP(1-28) (Compound 2-26: Compound of the Following Formula)

[Formula 152]

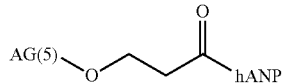

Trifluoroacetate of the GlcNAc-hANP synthesized in (2-7A) was replaced with another salt by use of an ion-exchange resin (Dowex 1×8), and the resulting GlcNAc-hANP acetate was used in the next reaction.

The compound AG(5)-P (18 mg) synthesized in (1-17C) was dissolved in a 0.2 M phosphate buffer solution (pH 6.75, 160 μl). To the solution, a solution of glycosynthase (Endo-M-N175Q, Tokyo Chemical Industry Co., Ltd., 1 U/ml, 64 μl) and acetate (8.0 mg) of the hANP-GlcNAc synthesized in (2-7A) in dimethyl sulfoxide (96 μl) was then added, and the mixture was reacted at 25° C. for 3 hours. The reaction was terminated by the addition of a 0.2% aqueous trifluoroacetic acid solution (1.5 ml) at room temperature, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound AG(5)-hANP(1-28) (compound 2-26) (5.6 mg).

ESI-TOF-MS: Calcd for $C_{163}H_{261}N_{47}O_{66}S_3$: $[M+3H]^{3+}$ 1345.1 (ave.), Found 1344.6.

135

<Example 2-27> Synthesis of SG-(SG-)Asn-PEG (11)-hANP(1-28) (Compound 2-27)

(2-27A) Synthesis of Boc-(GlcNAc-)Asn-PEG(11)-CO₂H (Compound of the Following Formula)

[Formula 153]

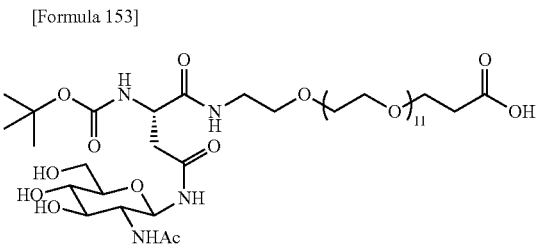

(2S)-4-[[(2R,3R,4R,5S,6R)-3-Acetamido-4,5-dihydroxy-6-(hydroxymethyl)tetrahydropyran-2-yl]amino]-2-(tert-butoxycarbonylamino)-4-oxobutanoic acid (187 mg, 0.43 mmol) produced according to the description of J. Am. Chem. Soc., 1999, 121, 284-290 and HATU (163 mg, 0.43 mmol) were dissolved in N,N-dimethylformamide (3.0 ml). To the solution, diisopropylethylamine (150 μl, 0.86 mmol) was added at room temperature, and the mixture was stirred for 3 minutes. This reaction solution was added to the 3-[2-[2-[2-[2-[2-[2-[2-[2-[2-[2-[2-(2-aminoethoxy)ethoxy]ethoxy]ethoxy]ethoxy]ethoxy]ethoxy]ethoxy]ethoxy]ethoxy]ethoxy]propanoic acid (0.22 g, 0.36 mmol) produced in (1-4A), and the mixture was stirred at room temperature for 3 hours. This reaction mixture was added dropwise to an ice-cold mixed solvent of distilled water (3 ml) and acetic acid (100 μl) and dissolved therein, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound Boc-(GlcNAc-Asn)-PEG(11)—CO₂H (210 mg).

MALDI-TOF-MS: Calcd for $C_{44}H_{82}N_4O_{23}$: [M+K]⁺ 1073.6, Found 1073.5

136

(2-27B) Synthesis of Boc-(GlcNAc-)Asn-PEG(11)-hANP(1-28) (Compound of the Following Formula)

[Formula 154]

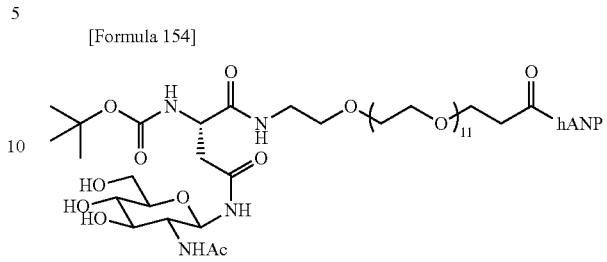

The Boc-(GlcNAc-)Asn-PEG(11)-CO₂H (7.3 mg, 7.1 μmol) produced in (2-27A) was dissolved in N,N-dimethylformamide (150 μl). To the solution, a solution of triethylamine (5.9 μl, 43 μmol) and dimethylthiophosphinoyl chloride (1.7 mg, 21 μmol) in N,N-dimethylformamide (50 μl) was added under ice cooling. This reaction solution was heated to room temperature while stirred for 1.5 hours. This reaction solution was added under ice cooling to a solution of the hANP-TFA salt (36 mg, 60 w/w %, 7.1 μmol) prepared according to the procedures of (2-1A) and triethylamine (14 μl, 99 μmol) dissolved in a mixed solvent of N,N-dimethylformamide (1500 μl) and distilled water (300 μl), and the mixture was heated to room temperature while stirred for 1 day. This reaction solution was added to an ice-cold 0.2 v/v % aqueous trifluoroacetic acid solution (8.3 ml), and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound GlcNAc-(GlcNAc-)Asn-PEG (11)-CO₂H (14.8 mg).

ESI-TOF-MS: Calcd for $C_{171}H_{283}N_{49}O_{61}S_3$: [M+2H]²⁺ 2049.8 (ave.), Found 2049.5

(2-27C) Synthesis of GlcNAc-(GlcNAc-)Asn-PEG (11)-hANP(1-28) (Compound of the Following Formula)

[Formula 155]

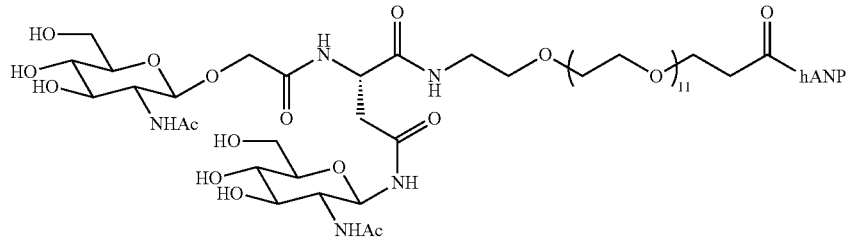

The Boc-(GlcNAc-)Asn-PEG(11)-hANP(1-28) (14.8 mg) produced in (2-27B) was dissolved in a 33 v/v % aqueous trifluoroacetic acid solution (1.0 ml), and the solution was left standing at room temperature for 3 hours. This reaction solution was added to an ice-cold mixed solvent of distilled water (9.5 ml) and acetic acid (0.5 ml), and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the intermediate (10.2 mg).

The 2-[(2R,3R,4R,5S,6R)-3-acetamido-4,5-dihydroxy-6-(hydroxymethyl)tetrahydropyran-2-yl]oxyacetic acid (1.4 mg, 5.1 µmol) produced in (1-2C) was dissolved in N,N-dimethylformamide (150 µl). To the solution, triethylamine (2.1 µl, 15 µmol) and dimethylthiophosphinoyl chloride (0.98 mg, 7.7 µmol) were added under ice cooling. This reaction solution was heated to room temperature while stirred for 1.5 hours. This reaction solution was added under ice cooling to a solution of the obtained intermediate (10 mg, 2.6 µmol) and triethylamine (5.0 µl, 36 µmol) dissolved in a mixed solvent of N,N-dimethylformamide (1500 µl) and distilled water (3 00 µl), and the mixture was heated to room temperature while stirred for 3 days. This reaction solution was added to an ice-cold 0.2 v/v % aqueous trifluoroacetic acid solution (8.5 ml), and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound GlcNAc-(GlcNAc-)Asn-PEG(11)-hANP(1-28) (9.0 mg).

ESI-TOF-MS: Calcd for $C_{176}H_{290}N_{50}O_{66}S_3$: $[M-2H]^{2-}$ 2128.3 (ave.), Found 2128.0

(2-27D) Synthesis of SG-(SG-Asn)-PEG(11)-hANP (1-28) (Compound 2-27: Compound of the Following Formula)

[Formula 156]

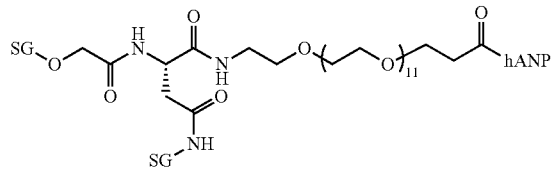

To the compound SG-Oxa produced in (1-12A) in a 0.2 M phosphate buffer solution (60 mM, 188 µl), Endo-M-N175Q (1 U/ml, 100 µl) was added at room temperature, then a solution of the hANP-GlcNAc (8.0 mg, 1.9 µmol) produced in (2-27D) in dimethyl sulfoxide (120 µl) was added in two portions at an interval of 15 minutes at room temperature, and the mixture was shaken at 25° C. for 1 day. The reaction was terminated by the addition of a mixed solvent of a 0.2% aqueous trifluoroacetic acid solution (4.5 ml) and acetic acid (0.5 ml) at room temperature, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound SG-(SG-)Asn-PEG(11)-hANP(1-28) (compound 2-27) (3.4 mg). ESI-TOF-MS: Calcd for $C_{328}H_{536}N_{60}O_{178}S_3$: $[M+5H]^{5+}$ 1653.8 (ave.), Found 1653.7.

<Example 2-28> Synthesis of SG-(SG-)Asn-PEG (11)-PEG(11)-hANP(1-28) (Compound 2-28)

(2-28A) Synthesis of Fmoc-PEG(11)-PEG(11)-CO₂H (Compound of the Following Formula)

[Formula 157]

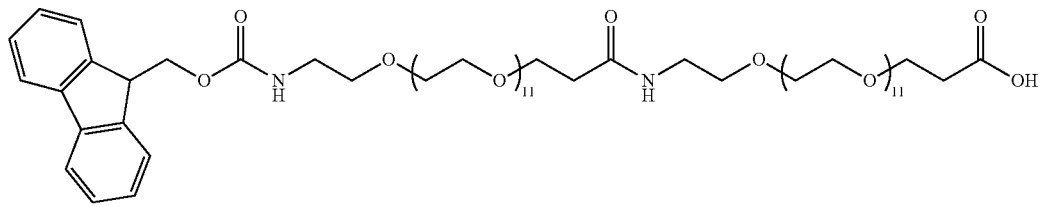

3-[2-[2-[2-[2-[2-[2-[2-[2-[2-[2-[2-[2-(9H-Fluoren-9-yl-methoxycarbonylamino)ethoxy]ethoxy]ethoxy]ethoxy] ethoxy]ethoxy]ethoxy]ethoxy]ethoxy]ethoxy]ethoxy] ethoxy]propanoic acid (350 mg, 0.42 mmol) and HATU (192 mg, 0.50 mmol) were dissolved in N,N-dimethylformamide (3.0 ml). To the solution, diisopropylethylamine (176 µl, 1.01 mmol) was added at room temperature, and the mixture was stirred for 3 minutes. This reaction solution was added to the 3-[2-[2-[2-[2-[2-[2-[2-[2-[2-[2-[2-(2-aminoethoxy)ethoxy]ethoxy]ethoxy]ethoxy]ethoxy]ethoxy] ethoxy]ethoxy]ethoxy]ethoxy]propanoic acid (259 mg, 0.42 mmol) produced in (1-4A), and the mixture was stirred at room temperature for 3 hours. This reaction mixture was added dropwise to an ice-cold mixed solvent of distilled water (3 ml) and acetic acid (117 µl) and dissolved therein, and the solution was further diluted with a mixed solvent of N,N-dimethylformamide (3.0 ml) and distilled water (15 ml). The resulting product was separated and purified from the solution by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound Fmoc-PEG(11)-PEG(11)-CO₂H (399 mg).

ESI-TOF-MS: Calcd for $C_{69}H_{118}N_2O_{29}$: $[M-H]^-$ 1437.8, Found 1437.8

(2-28B) Synthesis of H₂N-PEG(11)-PEG(11)-CO₂H (Compound of the Following Formula)

[Formula 158]

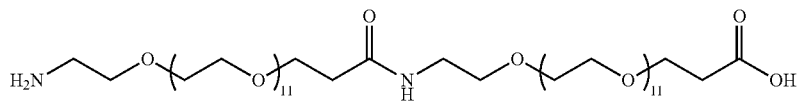

The title compound H₂N-PEG(11)-PEG(11)-CO₂H (77 mg) was obtained according to the same approach as in (1-4A) from the Fmoc-PEG(11)-PEG(11)-CO₂H (250 mg) produced in (2-28A).

MALDI-TOF-MS: Calcd for $C_{54}H_{08}N_2O_{27}$: $[M+H]^+$ 1217.7, Found 1217.9

(2-28C) Synthesis of Boc-(GlcNAc-)Asn-PEG(11)-PEG(11)-CO₂H (Compound of the Following Formula)

[Formula 159]

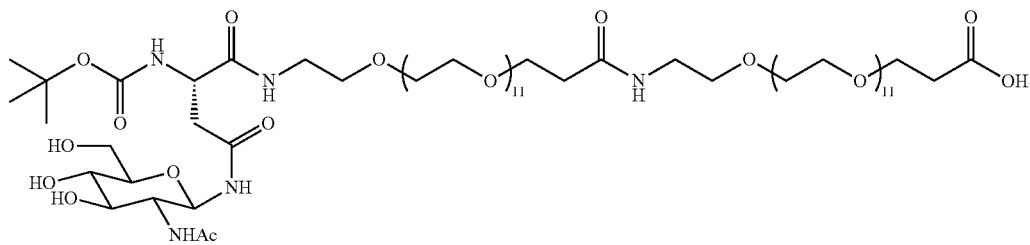

The title compound Boc-(GlcNAc-)Asn-PEG(11)-PEG(11)-CO₂H (58 mg) was obtained according to the same approach as in (2-27A) from (2S)-4-[[(2R,3R,4R,5S,6R)-3-acetamido-4,5-dihydroxy-6-(hydroxymethyl)tetrahydropyran-2-yl]amino]-2-(tert-butoxycarbonylamino)-4-oxobutanoic acid (32 mg, 74 μmol) produced according to the description of J. Am. Chem. Soc., 1999, 121, 284-290 and the H₂N-PEG(11)-PEG(11)-CO₂H (76 mg) produced in (2-28B).

MALDI-TOF-MS: Calcd for $C_{71}H_{35}N_5O_{36}$: $[M+K]^+$ 1673.0, Found 1672.9

(2-28D) Synthesis of Boc-(GlcNAc)-Asn-PEG(11)-PEG(11)-hANP(1-28) (Compound of the Following Formula)

[Formula 160]

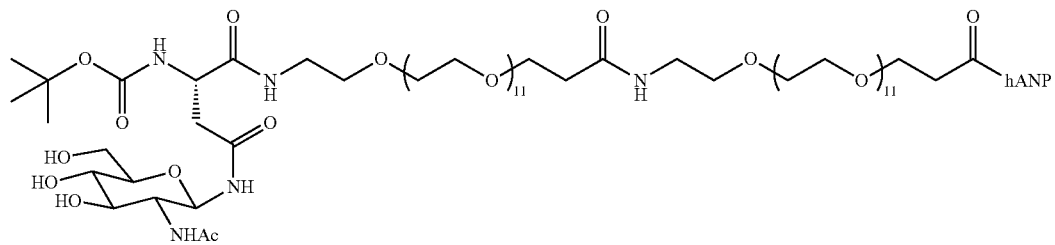

The title compound Boc-(GlcNAc-)Asn-PEG(11)-PEG(11)-hANP(1-28) (35 mg) was obtained according to the same approach as in (2-27B) using the Boc-(GlcNAc-Asn)-PEG(11)-PEG(11)-COOH (29 mg, 18 μmol) produced in (2-28C) and the hANP(1-28)-TFA salt (50 mg, 60 w/w %, 9.7 μmol) produced in (2-1A).

MALDI-TOF-MS: Calcd for $C_{198}H_{336}N_{50}O_{74}S_3$: [M+H]$^+$ 4695.3, Found 4697.5

(2-28E) Synthesis of GlcNAc-(GlcNAc-Asn)-PEG(11)-PEG(11)-hANP(1-28) (Compound of the Following Formula)

[Formula 161]

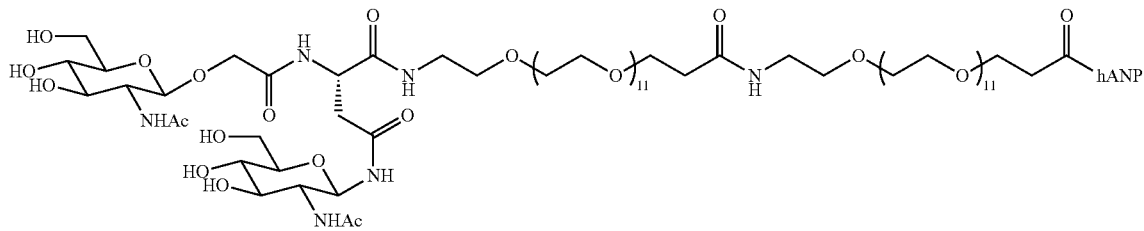

The title compound GlcNAc-(GlcNAc-)Asn-PEG(11)-PEG(11)-hANP(1-28) (16 mg) was obtained according to the same approach as in (2-27C) from the Boc-(GlcNAc-Asn)-PEG(11)-PEG(11)-hANP(1-28) (35 mg, 7.4 μmol) produced in (2-28D).

MALDI-TOF-MS: Calcd for $C_{203}H_{343}N_{51}O_{79}S_3$: [M+H]$^+$ 4859.4 (ave.), Found 4858.4

TOF-MS: Calcd for $C_{203}H_{343}N_{51}O_{79}S_3$: [M+H]$^+$ 4859.4 (ave.), Found 4858.4

(2-28F) Synthesis of SG-(SG-Asn)-PEG(11)-PEG(11)-hANP(1-28) (Compound 2-28: Compound of the Following Formula)

[Formula 162]

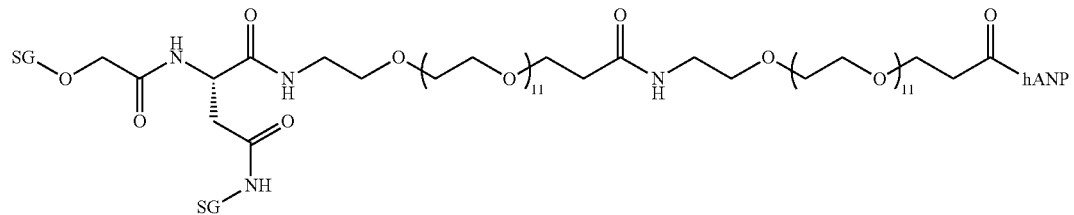

The title compound SG-(SG-Asn)-PEG(11)-PEG(11)-hANP(1-28) (compound 2-28) (13 mg) was obtained according to the same approach as in (2-27D) from the compound SG-Oxa produced in (1-12A) in a 0.2 M phosphate buffer solution (60 mM, 190 μl) and the GlcNAc-(GlcNAc)-Asn-PEG(11)-PEG(11)-hANP(1-28) (16 mg, 3.2 μmol) produced in (2-28F).

ESI-TOF-MS: Calcd for $C_{355}H_{589}N_{61}O_{191}S_3$: [M+4H]$^{4+}$ 2217.0 (ave.), Found 2216.9.

Example 2-29> Synthesis of SG-PEG(3)-hANP(1-28) (Compound 2-29)

(2-29A) Synthesis of SG-PEG(3)-hANP(1-28) (Compound 2-29: Compound of the Following Formula)

[Formula 163]

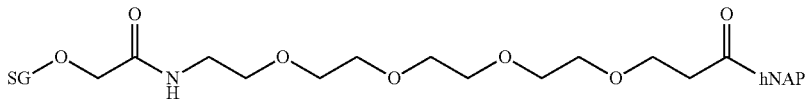

The title compound SG-PEG(3)-hANP(1-28) (compound 2-29) (12.32 mg) was obtained according to the same approach as in (1-14B) from the GlcNAc-PEG(3)-hANP(1-28) (15.0 mg) produced in (2-24A).
ESI-TOF-MS: Calcd for $C_{224}H_{362}N_{52}O_{107}S_3$: $[M+4H]^{4+}$ 1399.0 (ave.), Found 1398.3.

<Example 2-30> Synthesis of SG-PEG(11)-hANP(1-28) (Compound 2-30)

(2-30A) Synthesis of GlcNAc-PEG(11)-hANP(1-28) (Compound of the Following Formula)

[Formula 164]

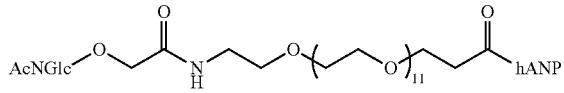

The title compound GlcNAc-PEG(11)-hANP(1-28) (33.7 mg) was obtained according to the same approach as in (2-7A) using the hANP(1-28)-TFA salt (43.9 mg) and the compound 1-4B (15.0 mg).
MALDI-TOF-MS: Calcd for $C_{164}H_{271}N_{47}O_{59}S_3$: $[M+H]^+$ 3939.9, Found 3939.8

(2-30B) Synthesis of SG-PEG(11)-hANP(1-28) (Compound 2-30; Compound of the following formula)

[Formula 165]

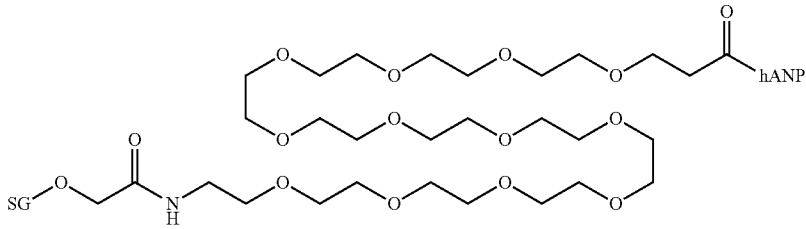

The title compound SG-PEG(11)-hANP(1-28) (compound 2-30) (11.52 mg) was obtained according to the same approach as in (1-14B) using the GlcNAc-PEG(11)-hANP(1-28) (15.0 mg) produced in (2-30A).
ESI-TOF-MS: Calcd for $C_{240}H_{394}N_{52}O_{115}S_3$: $[M+5H]^{5+}$ 1189.8 (ave.), Found 1189.3.

<Example 2-31> Synthesis of SG-(SG-)Gln*-Mal-PEG(3)-hANP(1-28) (compound 2-31)

(2-31A) Synthesis of $H_2N$-PEG(3)-hANP(1-28) (Compound of the Following Formula)

[Formula 166]

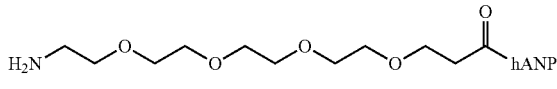

Boc-PEG(3)-hANP(1-28) (12.7 mg) was obtained according to the same approach as in (2-1B) using 3-[2-[2-[2-[2-(tert-butoxycarbonylamino) ethoxy]ethoxy]ethoxy]propionic acid (11.7 mg) and hANP(1-28)-TFA salt prepared from the hANP(1-28)-acetate (41.0 mg) by Preparation Method 2 of (2-1A).
The title compound $H_2N$-PEG(3)-hANP(1-28) (12.0 mg) was obtained according to the same approach as in (2-2C) using the obtained Boc-PEG(3)-hANP(1-28) (12.7 mg).
MALDI-TOF-MS: Calcd for $C_{138}H_{224}N_{46}O_{44}S_3$: $[M+H]^+$ 3326.6, Found 3326.6

(2-31B) Synthesis of HS-PEG(3)-hANP(1-28) (Compound of the Following Formula)

[Formula 167]

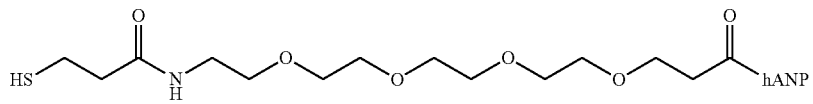

The title compound HS-PEG(3)-hANP(1-28) (5.00 mg) was obtained according to the same approach as in (2-25A) and (2-25B) using the H₂N-PEG(3)-hANP(1-28) (12.0 mg) produced in (2-31A).

MALDI-TOF-MS: Calcd for $C_{141}H_{228}N_{46}O_{45}S_4$: [M+H]$^+$ 3414.6, Found 3414.7

(2-31C) Synthesis of SG-(SG-)Gln\*-Mal-PEG(3)-hANP(1-28) (Compound of the Following Formula: Compound 3-31)

[Formula 168]

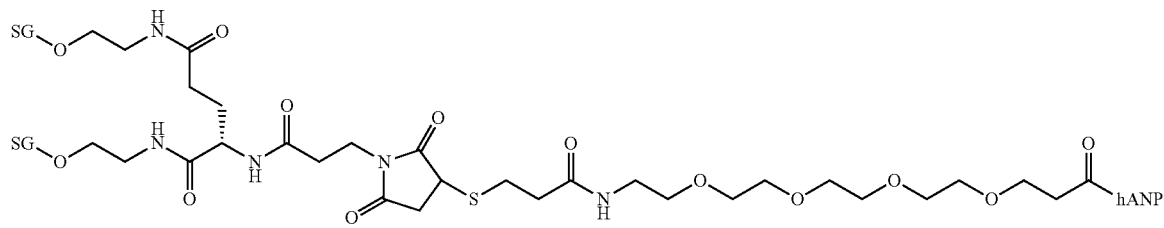

The title compound SG-(SG-)Gln\*-Mal-PEG(3)-hANP (1-28) (compound 2-31) (2.09 mg) was obtained according to the same approach as in (2-17B) using the HS-PEG(3)-hANP(1-28) (4.00 mg) produced in (2-31C) and the SG-(SG-)G1n\*-Mal (7.43 mg) produced in (1-15C).

ESI-TOF-MS: Calcd for $C_{325}H_{524}N_{62}O_{174}S_4$: [M+5H]$^{5+}$ 1643.4 (ave.), Found 1643.2.

<Example 2-32> Synthesis of SG-(SG-)G1n\*-PEG (3)-Mal-hANP(1-28) (Compound 2-32: Compound of the Following Formula)

[Formula 169]

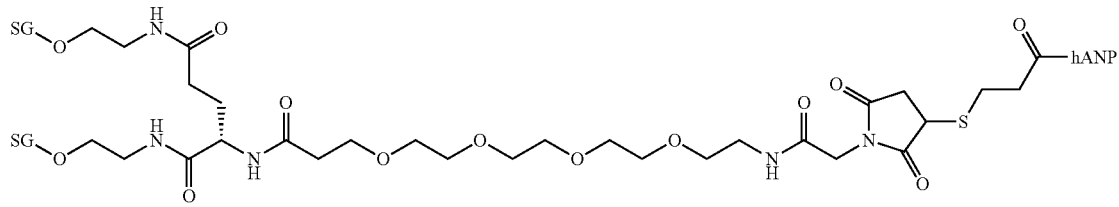

The HS-hANP(1-28) (2.3 mg) produced in (2-25B) and the SG-(SG-)Gln*-PEG(3)-Mal (4.0 mg) produced in (1-16C) were dissolved in a mixed solvent of a 0.2 M acetate buffer (pH 5.0) (0.10 mL) and dimethyl sulfoxide (0.10 mL), and the solution was stirred at room temperature for 5 hours. A 0.2% aqueous trifluoroacetic acid solution (2.0 mL) was added to the reaction solution, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain the title compound SG-(SG-)Gln*-PEG(3)-Mal-hANP(1-28) (compound 2-32) (3.5 mg).

ESI-TOF-MS: Calcd for $C_{325}H_{528}N_{62}O_{174}S_4$: $[M+4H]^{4+}$ 2054.0 (ave.), Found 2053.8.

<Example 2-33> Synthesis of SG-Mal-(SG-Mal-)Lys-hANP(1-28) (Compound 2-33)

(2-33A) Synthesis of TrS-(TrS-)Lys-PEG(3)-CO₂H (Compound of the Following Formula)

[Formula 170]

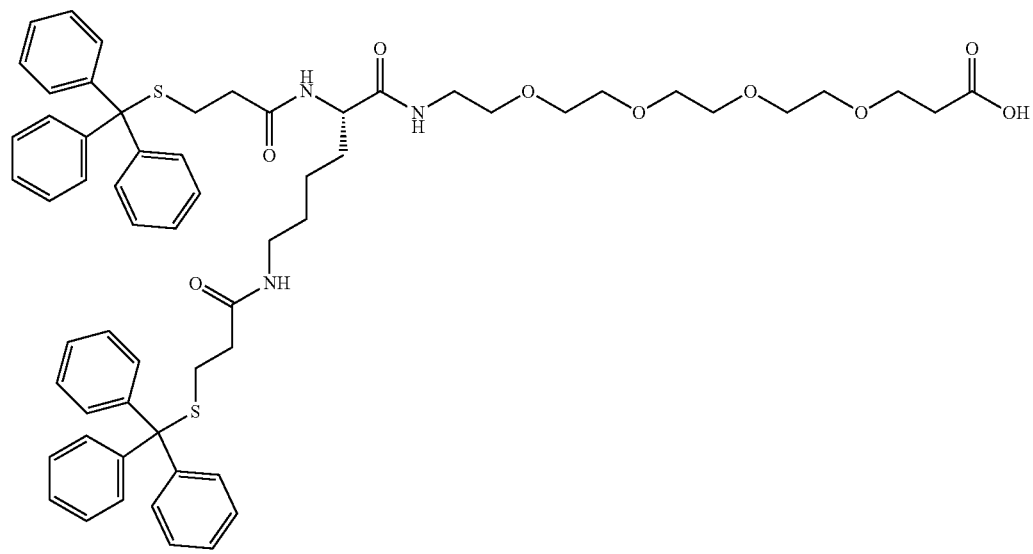

A 1.20 mmol/g 2-chlorotrityl chloride resin (83 mg, 0.100 mmol) was placed in a column for solid-phase synthesis. Dichloromethane (2 mL) was added thereto, and the mixture was shaken for 10 minutes. After filtration, a solution of 3-[2[2[2[2-(9H-fluoren-9-ylmethoxycarbonylamino)ethoxy]ethoxy]ethoxy]propionic acid (97.5 mg, 0.200 mmol) and N,N-diisopropylethylamine (85.6 µL, 0.500 mmol) in dichloromethane (2 mL) was added thereto, and the mixture was shaken at room temperature for 2 hours. After filtration, the resin was washed with a dichloromethane mixed solution (dichloromethane:methanol:N,N-diisopropylethylamine=85:10:5, v/v) three times, dichloromethane three times, and N,N-dimethylformamide three times. A 20% solution of piperidine in N,N-dimethylformamide (2 mL) was added thereto, and the mixture was shaken for 5 minutes, followed by filtration. This operation was carried out 4 times. The resin was washed with N,N-dimethylformamide 4 times. A solution of (2S)-2,6-bis(9H-fluoren-9-ylmethoxycarbonylamino)hexanoic acid (177 mg, 0.300 mmol), HATU (114 mg, 0.300 mmol), and N,N-diisopropylethylamine (103 µL, 0.600 mmol) in N,N-dimethylformamide (2 mL) was added to the resin, and the mixture was shaken at room temperature for 30 minutes. After filtration, the resin was washed with N,N-dimethylformamide 4 times. A 20% solution of piperidine in N,N-dimethylformamide (2 mL) was added thereto, and the mixture was shaken for 5 minutes, followed by filtration. This operation was carried out 4 times. The resin was washed with N,N-dimethylformamide 4 times. A solution of 3-tritylsulfanylpropionic acid (209 mg, 0.600 mmol), HATU (228 mg, 0.600 mmol), and N,N-diisopropylethylamine (205 µL, 1.20 mmol) in N,N-dimethylformamide (2 mL) was added thereto, and the mixture was shaken at room temperature for 1 hour. After filtration, the resin was washed with N,N-dimethylformamide 4 times and dichloromethane 4 times. A mixed solution of 1,1,1,3,3,3-hexafluoro-2-propanol (0.5 mL) and dichloromethane (1.5 mL) was added thereto, and the mixture was shaken at room temperature for 2 hours. The resin was filtered off, and the filtrate was concentrated under reduced pressure. The concentrate was subjected to azeotropy with dichloromethane 6 times and dried in a vacuum pump to obtain the title compound TrS-(TrS-)Lys-PEG(3)-CO₂H as a brown solid (105 mg).

(2-33B) Synthesis of TrS-(TrS-)Lys-PEG-(3)-hANP (1-28) (Compound of the Following Formula)

[Formula 171]

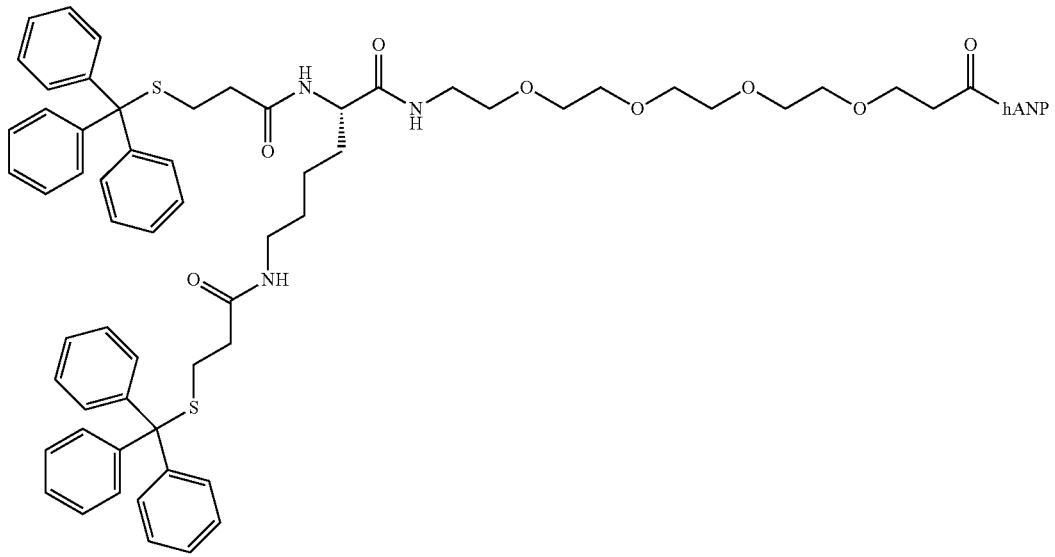

The title compound TrS-(TrS-)Lys-PEG-(3)-hANP(1-28) (30 mg) was obtained according to the same approach as in (2-17A) from the TrS-(TrS-)Lys-PEG(3)-CO$_2$H (27.4 mg) produced in (2-33A).

MALDI-TOF-MS: Calcd for $C_{188}H_{272}N_{48}O_{47}S_5$: [M+H]$^+$ 4114.9, Found 4115.1

(2-33C) Synthesis of HS-(HS-)Lys-PEG-(3)-hANP (1-28) (Compound of the Following Formula)

[Formula 172]

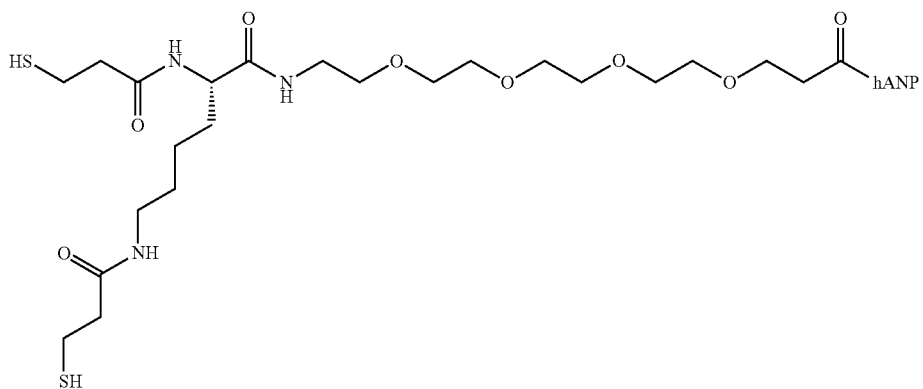

The title compound HS-(HS-)Lys-PEG-(3)-hANP(1-28) (15.3 mg) was obtained according to the same approach as in (2-17B) from the TrS-(TrS-)Lys-PEG-(3)-hANP(1-28) (30.0 mg) produced in (2-33B).

MALDI-TOF-MS: Calcd for $C_{150}H_{244}N_{48}O_{47}S_5$: [M+H]$^+$ 3630.7, Found 3631.0

(2-33D) Synthesis of SG-Mal-(SG-Mal-)Lys-PEG-(3)-hANP(1-28) (Compound 2-33: Compound of the Following Formula)

[Formula 173]

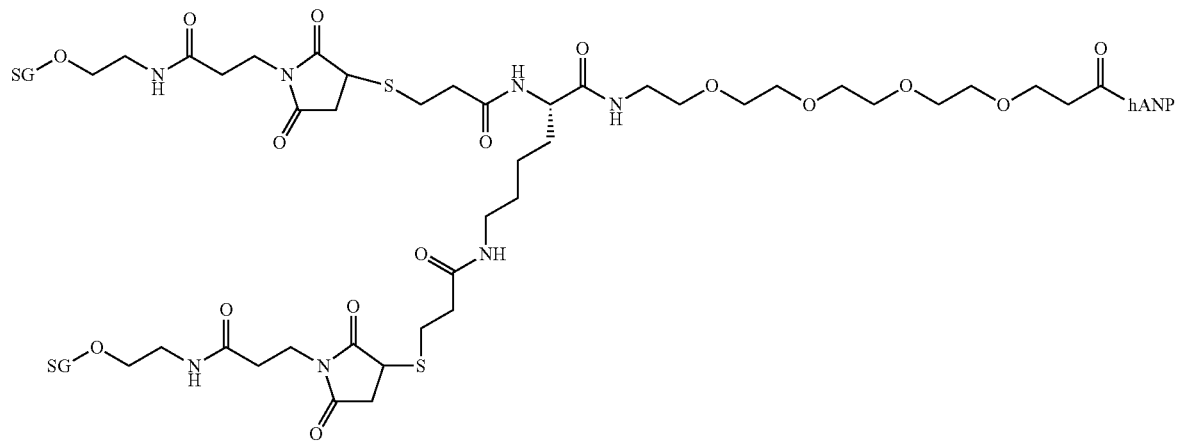

The title compound SG-Mal-(SG-Mal-)Lys-PEG-(3)-hANP(1-28) (compound 2-33) (8.55 mg) was obtained according to the same approach as in (2-17C) from the HS-(HS-)Lys-PEG-(3)-hANP(1-28) (5.00 mg) produced by the approach of (2-33C).

ESI-TOF-MS: Calcd for $C_{336}H_{540}N_{64}O_{177}S_5$: $[M+5H]^{5+}$ 1694.7 (ave.), Found 1694.5.

<Example 2-34> Synthesis of SG-thioacetamide-(SG-thioacetamide-)Lys-PEG-(3)-hANP(1-28) (compound 2-34) (2-34A) Synthesis of SG-thioacetamide-(SG-thioacetamide-)Lys-PEG-(3)-hANP(1-28) (Compound of the Following Formula)

[Formula 174]

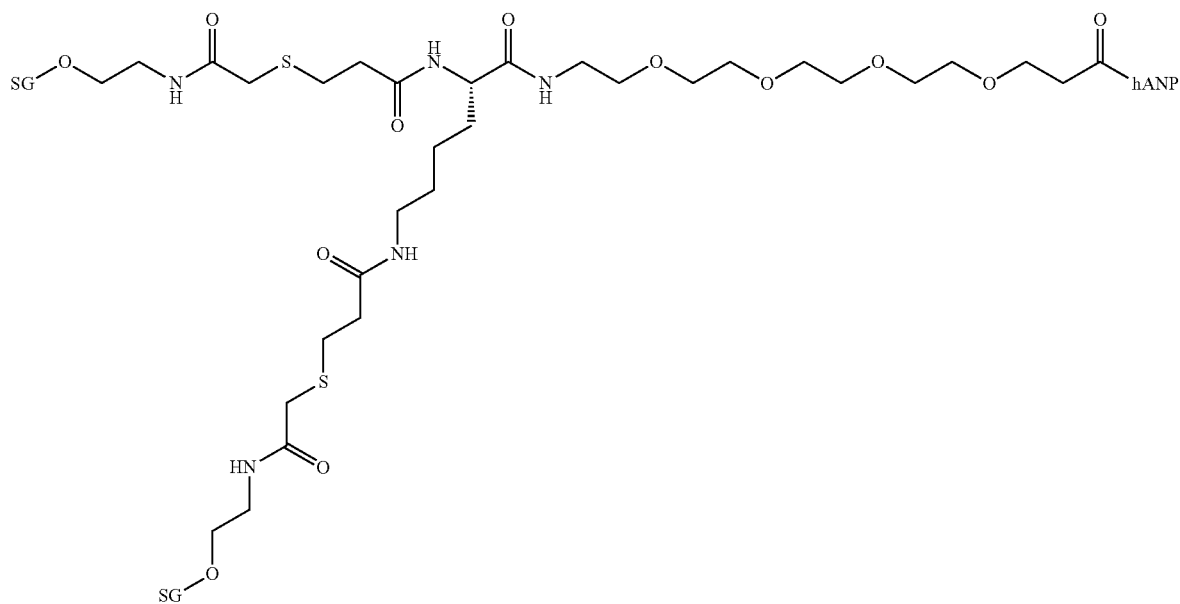

The title compound SG-thioacetamide-(SG-thioacetamide-)Lys-PEG-(3)-hANP(1-28) (compound 2-34) (4.74 mg) was obtained according to the same approach as in (2-25C) using the HS-(HS-)Lys-PEG-(3)-hANP(1-28) (4.14 mg) produced in (2-33C) and the compound SG-I (7.40 mg) produced in (1-19D).

ESI-TOF-MS: Calcd for $C_{326}H_{530}N_{62}O_{173}S_5$: $[M+5H]^{5+}$ 1650.3 (ave.), Found 1650.2.

<Example 2-35> Synthesis of SG-(SG-)Lys-PEG (3)-hANP(1-28) (Compound 2-35)

(2-35A) Synthesis of Lys-PEG(3)-hANP(1-28) (Compound of the Following Formula)

[Formula 175]

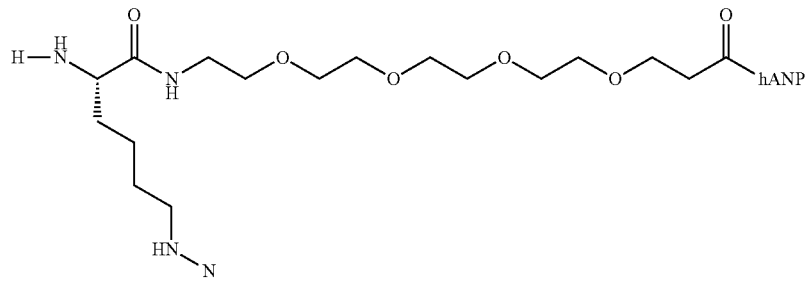

To a solution of the compound 1-20A (4.40 mg, 7.42 μmol) and HATU (2.6 mg, 6.84 μmol) in N,N-dimethylformamide (94 μL), N,N-diisopropylethylamine (5.0 μL, 29.4 μmol) was added, and the mixture was stirred at room temperature for 3 minutes. The obtained reaction solution was added to a mixed solution of hANP(1-28)-TFA salt (25 mg) and N,N-diisopropylethylamine (13 μL, 76.4 μmol) in N,N-dimethylformamide/water (5:1, v/v) (0.60 mL), and the mixture was stirred at room temperature for 2 hours. A 0.2% aqueous trifluoroacetic acid solution (3 mL) was added to the reaction solution, and the resulting product was separated and purified by reverse-phase HPLC (GL Sciences Inc., Inertsil ODS-3) using a 0.1% aqueous trifluoroacetic acid solution and a 0.1% solution of trifluoroacetic acid in acetonitrile as eluents and lyophilized to obtain Boc-(Boc-)Lys-PEG(3)-hANP(1-28) (18.0 mg).

The title compound Lys-PEG(3)-hANP(1-28) (12.0 mg) was obtained according to the same approach as in (2-2C) using the obtained Boc-(Boc-)Lys-PEG(3)-hANP(1-28) (18.0 mg).

MALDI-TOF-MS: Calcd for $C_{144}H_{237}N_{48}O_{45}S_3$: $[M+H]^+$ 3454.7, Found 3454.7.

(2-35C) Synthesis of SG-(SG-)Lys-PEG(3)-hANP (1-28) (compound 2-35: Compound of the Following Formula)

[Formula 176]

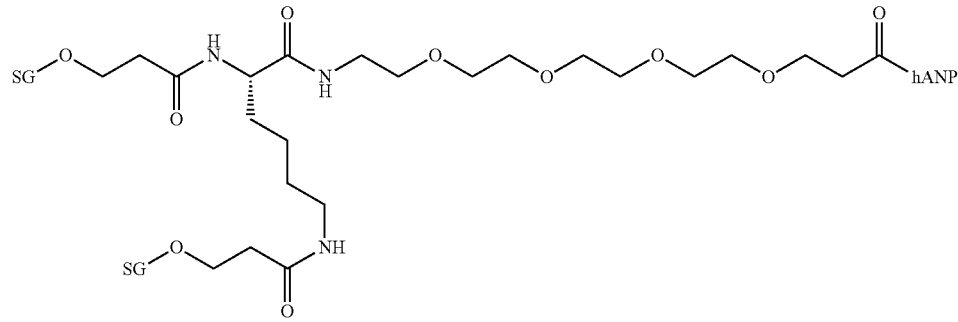

The title compound SG-(SG-)Lys-PEG(3)-hANP(1-28) (compound 2-35) (6.4 mg) was obtained according to the same approach as in (2-1B) using the Lys-PEG(3)-hANP(1-28) (6.0 mg) produced in (2-35B).
ESI-TOF-MS: Calcd for $C_{316}H_{507}N_{60}O_{171}S_3$: $[M-5H]^{5-}$ 1595.7 (ave.), Found 1595.6.

<Example 2-36> Synthesis of SG-(SG-)Asn-(Ser-Gly)$_3$-hANP(1-28) (compound 2-36)

(2-36A) Synthesis of GlcNAc-(GlcNAc-)Asn-(tBuSer-Gly)$_3$-hANP(1-28) (Compound of the Following Formula)

[Formula 177]

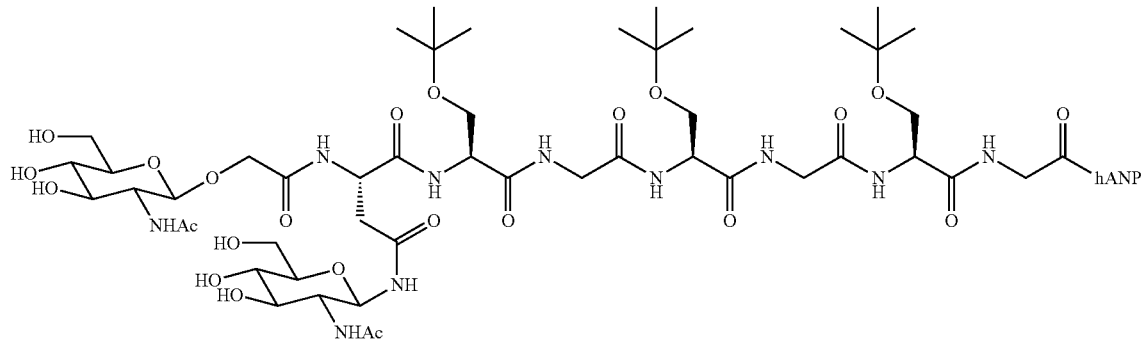

The title compound GlcNAc-(GlcNAc-)Asn-(tBuSer-Gly)$_3$-hANP(1-28) (27.0 mg) was obtained according to the same approach as in (2-1B) using the compound 1-21B (13.8 mg) and hANP(1-28)-TFA salt prepared from the hANP-acetate (37.1 mg) by Preparation Method 2 of (2-1A). MALDI-TOF-MS: Calcd for $C_{176}H_{286}N_{56}O_{61}S_3$: $[M+H]^+$ 4258.0, Found 4257.8

(2-36B) Synthesis of GlcNAc-(GlcNAc-Asn)-(Ser-Gly)$_3$-hANP(1-28) (Compound of the Following Formula)

[Formula 178]

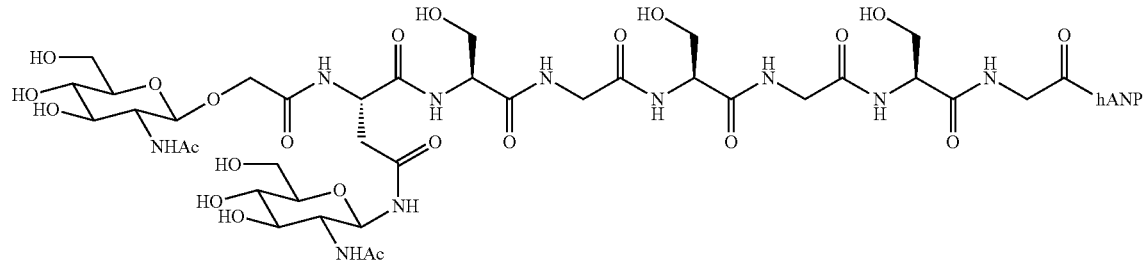

The title compound GlcNAc-(GlcNAc-Asn)-(Ser-Gly)$_3$-hANP(1-28) (4.66 mg) was obtained according to the same approach as in (2-17A) from the GlcNAc-(GlcNAc-Asn)-(tBuSer-Gly)$_3$-hANP(1-28) (27.0 mg) produced in (2-36A). MALDI-TOF-MS: Calcd for $C_{164}H_{262}N_{56}O_{61}S_3$: $[M+H]^+$ 4089.8, Found 4090.1

(2-36C) Synthesis of SG-(SG-Asn)-(Ser-Gly)₃-hANP(1-28) (compound 2-36: compound of the following formula)

[Formula 179]

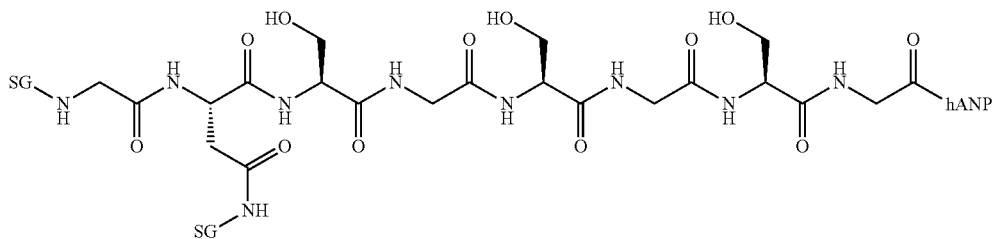

The title compound SG-(SG-)Asn-(Ser-Gly)₃-hANP(1-28) (compound 2-36) (3.24 mg) was obtained according to the same approach as in (2-2D) from the GlcNAc-(GlcNAc-)Asn-(Ser-Gly)₃-hANP(1-28) (3.50 mg) produced in (2-36B).

ESI-TOF-MS: Calcd for $C_{316}H_{508}N_{66}O_{173}S_3$: $[M+4H]^{4+}$ 2025.0 (ave.), Found 2025.0.

<Example 2-37> Synthesis of SG-(SG-)Asn-Gly₆-hANP(1-28) (Compound 2-37)

(2-37A) Synthesis of Gly₃-hANP(1-28) (compound of the following formula)

[Formula 180]

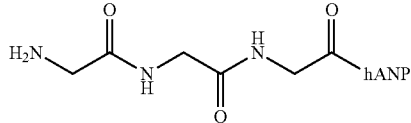

Boc-Gly₃-hANP(1-28) (196 mg) was obtained according to the same approach as in (2-1B) using 2-[[2-[[2-(tert-butoxycarbonylamino)acetyl]amino]acetyl]amino]acetic acid (27.7 mg) and hANP-TFA salt prepared from hANP-acetate (246 mg) by Preparation Method 2 of (2-1A). The title compound Gly₃-hANP(1-28) (190 mg) was obtained according to the same approach as in (2-2C) from the obtained Boc-Gly₃-hANP(1-28) (196 mg).

MALDI-TOF-MS: Calcd for $C_{133}H_{212}N_{48}O_{42}S_3$: $[M+H]^+$ 3250.5, Found 3250.6

(2-37B) Synthesis of Gly₆-hANP(1-28) (Compound of the Following Formula)

[Formula 181]

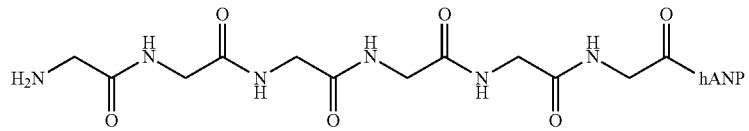

Boc-Gly$_6$-hANP(1-28) (115 mg) was obtained according to the same approach as in (2-1B) from the Gly$_3$-hANP(1-28) (190 mg) produced in (2-37A) and 2-[[2-[[2-(tert-butoxycarbonylamino)acetyl]amino]acetyl]amino]acetic acid (13.4 mg).

The title compound Gly$_6$-hANP(1-28) (115 mg) was obtained according to the same approach as in (2-2C) from the obtained Boc-Gly$_6$-hANP(1-28) (115 mg).

MALDI-TOF-MS: Calcd for $C_{139}H_{221}N_{51}O_{45}S_3$: [M+H]$^+$ 3421.6, Found 3421.5

(2-37C) Synthesis of Boc-(GlcNAc-)Asn-Gly$_6$-hANP(1-28) (Compound of the Following Formula)

[Formula 182]

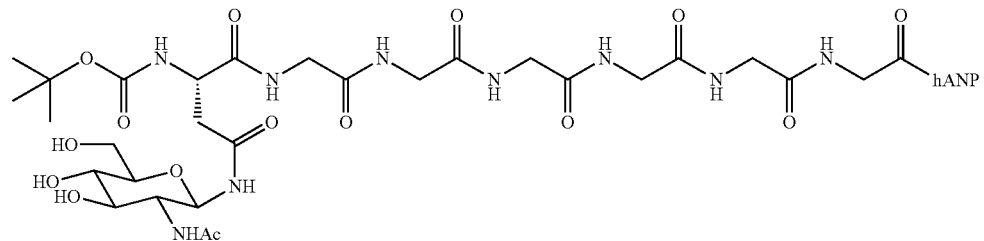

The title compound Boc-(GlcNAc-)Asn-Gly$_6$-hANP(1-28) (23.0 mg) was obtained according to the same approach as in (1-5A) from the Gly$_6$-hANP(1-28) (60.0 mg) produced in (2-37B).

MALDI-TOF-MS: Calcd for $C_{156}H_{248}N_{54}O_{54}S_3$: [M+H]$^+$ 3838.7, Found 3839.0

(2-37D) Synthesis of GlcNAc-(GlcNAc-)Asn-Gly$_6$-hANP (1-28) (Compound of the Following Formula)

[Formula 183]

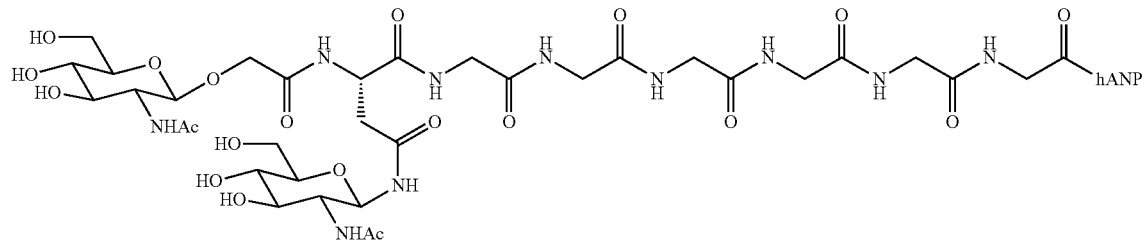

The title compound GlcNAc-(GlcNAc-)Asn-Gly$_6$-hANP (1-28) was obtained as a white solid (6.77 mg) according to the same approach as in (1-5B) from the Boc-(GlcNAc-Asn)-Gly$_6$-hANP(1-28) (23.0 mg) produced in (2-37C).

MALDI-TOF-MS: Calcd for $C_{161}H_{255}N_{55}O_{59}S_3$: [M+H]$^+$ 3999.8, Found 4000.1

(2-37E) Synthesis of SG-(SG-)Asn-Gly$_6$-hANP(1-28) (Compound 2-37: Compound of the Following Formula)

[Formula 184]

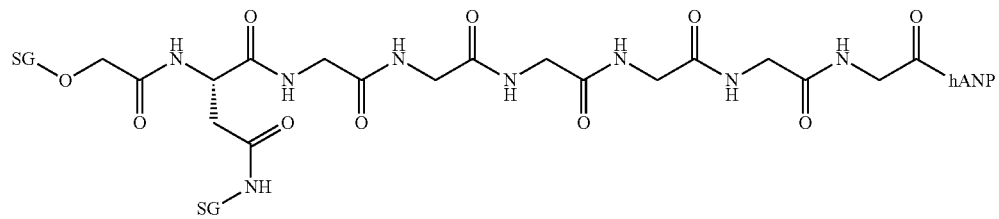

The title compound SG-(SG-) Asn-Gly$_6$-hANP (1-28) (compound 2-37) (4.32 mg) was obtained according to the same approach as in (2-2D) from the GlcNAc-(GlcNAc-)Asn-Gly$_6$-hANP(1-28) (3.40 mg) produced in (2-37D). ESI-TOF-MS: Calcd for $C_{313}H_{501}N_{65}O_{171}S_3$: $[M+4H]^{4+}$ 2002.7 (ave.), Found 2002.5.

<Example 2-38> Synthesis of SG-Lys*-[PEG(3)-Mal-hANP(1-28)]$_2$ (Compound 2-38: Compound of the Following Formula)

[Formula 185]

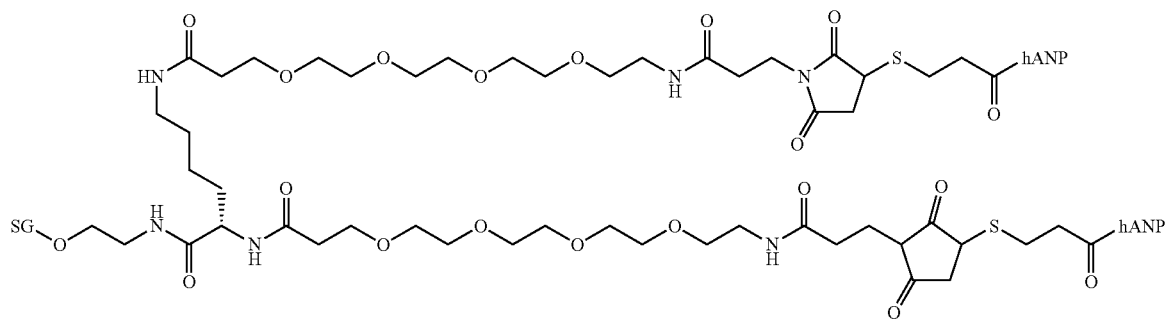

The title compound SG-Lys*-[PEG(3)-Mal-hANP(1-28)]$_2$ (compound 2-38) (7.0 mg) was obtained according to the same method as in (2-32A) using the SG-Lys-[PEG(3)-Mal]$_2$ (3.0 mg, 0.94 μmol) produced in (1-22B).

ESI-TOF-MS: Calcd for $C_{388}H_{616}N_{103}O_{159}S_8$: $[M-5H]^{5-}$ 1904.8 (ave.), Found 1904.8.

<Example 2-39> Synthesis of SG-Lys*-[PEG(11)-Mal-hANP(1-28)]$_2$ (Compound 2-39: Compound of the Following Formula)

[Formula 186]

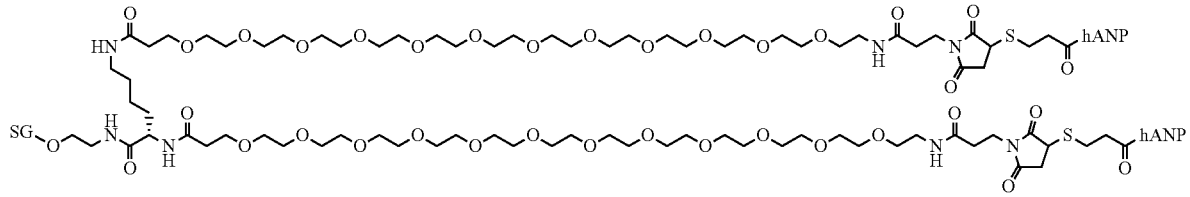

The title compound SG-Lys*-[PEG(11)-Mal-hANP(1-28)]₂ (compound 2-39) (7.0 mg) was obtained according to the same method as in (2-32A) using the SG-Lys*-[PEG(11)-Mal]₂ (3.7 mg, 0.95 μmol) produced in (1-23B).

ESI-TOF-MS: Calcd for $C_{420}H_{680}N_{103}O_{175}S_8$: $[M-5H]^{5-}$ 2045.8 (ave.), Found 2045.8.

<Example 2-40> Synthesis of SG(Glc)-Gly-A-hANP(1-28) (Compound 2-40: Compound of the Following Formula)

[Formula 187]

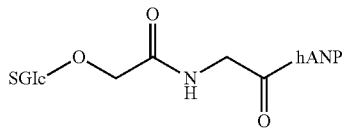

The title compound SG(Glc)-Gly-A-hANP(1-28) (compound 2-40) (34.2 mg) was obtained according to the same approach as in (2-1B) using the SG(Glc)-Gly-A (30 mg) synthesized in (1-24E).

ESI-TOF-MS: Calcd for $C_{213}H_{341}N_{51}O_{103}S_3$: $[M+4H]^{4+}$ 1341.1 (ave.), Found 1341.0

Also, modified hANP containing a glycochain altered at the reducing end as the glycochain can be appropriately produced by use of various glycochains altered at the reducing end synthesized according to the methods of Example 1-11, 1-12, 1-13, or 1-14 and Example 1-24 in the production of each modified hANP of Example 2.

TEST EXAMPLES

<Test Example 1> Test on cGMP Elevating Activity of Glyco-Modified Peptide

The cGMP elevating activity of each modified peptide prepared in Example 2 was measured by the following method:

CHO/human GC-A cells, which are CHO cells constitutively expressing human GC-A, were suspended at $2\times10^5$ cells/ml in α-MEM, 10% FBS, and 1% penicillin-streptomycin, inoculated at 20 μl/well ($4\times10^3$ cells/well) onto a 384-well plate (Corning, 3826), and cultured overnight in a $CO_2$ incubator. On the next day, the medium was removed from this plate, and then, 1.6 mM IBMX/KRB buffer was added thereto at 10 μl/well. The mixture was stirred on a plate shaker and then incubated at room temperature for 10 minutes. Next, a test substance (each modified peptide and native hANP(1-28) (Peptide Institute, Inc.); dilution series were prepared such that the final concentration range involved 0.01, 0.1, 1, 10, and 100 nM) prepared at a concentration 3 times the final concentration by dissolution in water was added thereto at 5 μl/well. The mixture was stirred on a plate shaker and then incubated for 15 minutes in a $CO_2$ incubator. Thereafter, a lysis buffer (50 mM phosphate buffer, pH 7.0, and 1% Triton X-100) was added thereto at 5 μl/well. The cells were lysed by stirring for 10 minutes on a plate shaker. Subsequently, the cGMP levels in the cell lysates were measured by use of a cGMP kit (manufactured by Cisbio Bioassays). Specifically, to a 384-well plate (Greiner, 784076), 5 μl/well of a diluent attached to the kit, 5 μl/well of the cell lysate, 5 μl/well of cGMP-d2, and 5 μl/well of anti cGMP-Cryptate were added. The mixture was stirred on a plate shaker and then incubated overnight at 4° C. in the dark, followed by the measurement of homogeneous time-resolved fluorescence using RubyStar (manufactured by BMG LABTECH JAPAN Ltd.). The activity value (T/C) of the test substance at each concentration was calculated when the activity value of a well supplemented with only a solvent was defined as 0 and the activity value of a well supplemented with 1 nM ANP was defined as 1. T/C at each concentration was plotted, and the maximum T/C value in the measurement concentration range was determined as $E_{max}$ from the obtained sigmoid curve with the value of T/C=0.5 defined as $EC_{50}$ (Table 1).

From the results of Table 1, all of the modified peptides were shown to exhibit 50% or more cGMP elevating activity compared with hANP (Emax>0.5) and to maintain cGMP elevating activity. The compounds 2-17, 2-18, and 2-20 were prone to have low Emax on the order of 0.6 to 0.7, whereas the other modified peptides had Emax of 0.95 or higher and maintained a cGMP elevating effect equivalent to that of the native hANP.

cGMP elevating activity of test compound

TABLE 1

| Compound No. of test substance | EC50 (nM) | Emax |
|---|---|---|
| Native hANP | 0.022 | |
| 2-1 | 0.04 | 1.02 |
| 2-2 | 0.1 | 1.01 |
| 2-3 | 0.12 | 1.02 |
| 2-4 | 0.08 | 1.04 |
| 2-5 | 0.082 | 1.04 |
| 2-6 | 1.7 | 1.00 |
| 2-7 | 1.7 | 0.99 |
| 2-8 | 0.2 | 1.01 |
| 2-9 | 1.1 | 1.00 |
| 2-10 | 0.03 | 1.02 |
| 2-11 | 0.048 | 1.01 |
| 2-12 | 0.69 | 1.01 |
| 2-13 | 0.34 | 1.01 |
| 2-14 | 0.6 | 0.95 |
| 2-15 | 3.1 | 0.98 |
| 2-16 | 0.98 | 1.01 |
| 2-17 | 35 | 0.70 |
| 2-18 | 48 | 0.63 |
| 2-19 | 9.8 | 0.90 |
| 2-20 | 64 | 0.59 |
| 2-21 | 0.097 | 1.02 |
| 2-22 | 0.08 | 1.02 |
| 2-23 | 2.4 | 0.98 |
| 2-24 | 0.54 | 1.01 |
| 2-25 | 0.054 | 1.02 |
| 2-26 | 0.024 | 1.01 |
| 2-27 | 0.26 | 1.02 |
| 2-28 | 0.31 | 1.01 |
| 2-29 | 0.1 | 1.01 |
| 2-30 | 0.12 | 1.01 |
| 2-31 | 0.31 | 1.00 |
| 2-32 | 0.41 | 1.00 |
| 2-33 | 0.4 | 1.01 |
| 2-34 | 0.53 | 1.01 |
| 2-35 | 0.31 | 1.00 |
| 2-36 | 0.39 | 1.00 |
| 2-37 | 0.4 | 1.00 |
| 2-38 | 0.016 | 1.01 |
| 2-39 | 0.0077 | 1.00 |
| 2-40 | 0.05 | 1.03 |

<Test Example 2> Test on NEP Degradation of Modified Peptide

The resistance of each modified peptide prepared in Example 2 to degradation by neutral endopeptidase (generic name: neprilysin) was examined by the following method:

Neprilysin (R&D systems, Inc.) was added at 1 µg/ml into a solution of a test substance (each glyco-modified ANP and native hANP(1-28)), followed by pretreatment at 37° C. for 30 minutes. The neprilysin-treated solution was used to examine the cGMP elevating activity of the test substance by the method of Test Example 1.

As a result, the native hANP lost its activity by the NEP treatment, whereas the modified peptide of the present invention maintained cGMP elevating activity at the same level as in Test Example 1 even after the NEP treatment, demonstrating that the modified peptide is insusceptible to degradation by NEP.

The main mechanism underlying the rapid disappearance of the naturally occurring ANP from the blood of animals is considered to be the degradation by NEP. The modified peptide of the present invention maintained cGMP elevating activity even after the NEP treatment, demonstrating that the modified peptide is insusceptible to degradation by NEP even in the bodies of animals and, when administered in an effective amount, can exert cGMP elevating activity over a long time after the administration.

<Test Example 3> Test on Duration Time of Modified Peptide in Blood of Rat

The duration time (the effect of persistently elevating cGMP in blood and the time for which a test substance was detectable in blood) of each modified peptide prepared in Example 2 in the blood of rats was examined by the following method:
(1) Preparation of Plasma Sample
Isoflurane: Japanese pharmacopoeia isoflurane Needle and syringe for blood collection: Terumo Syringe 25G×1 SR for Tuberculin
Tube for blood collection: CAPIJECT Micro Collection Tube EDTA-2Na 500 µL
Tube for sample storage: MTARIX 4170 Sample Tracking Tube 0.75 mL Each 8-week-old male Slc:SD rat was subjected to isoflurane inhalation anesthesia ((inhalation of an Escain inhalation anesthetic kept at a concentration of 1 to 2%). A solution of a test substance (each modified peptide and native hANP(1-28) (Peptide Institute, Inc.)) prepared at a concentration of 100 µM by dissolution in water was rapidly intravenously injected at a dose of 100 nmol/kg (1 mL/kg) into the jugular vein of the rat.

Before the administration and 15, 30, 60, 90, 120, 180, and 240 minutes after the administration, blood was sampled (200 µL/sampling) over time from the jugular vein. The blood samples were immediately left on ice.

The collected blood samples were centrifuged at 5000 rpm at 4° C. for 5 minutes by use of a centrifuge (Sigma 4K15, rotor: Nr12130-H). The separated plasma samples were divided into two types (samples for PK measurement and for cGMP measurement) and stored at −80° C. until measurement.
(2) Measurement of cGMP Concentration in Plasma The cGMP concentration in plasma was measured using Amersham cGMP Enzyme Immunoassay Biotrak™ (EIA) System (dual range) according to the protocol attached thereto. The results were plotted with the cGMP concentration on the ordinate vs. the elapsed time (min) after the administration on the abscissa to calculate AUC of 0 minutes to 240 minutes (AUC0-240) and AUC of 60 to 240 minutes after the administration (AUC60-240) (Table 2).

(3) Detection of Test Substance in Plasma Sample

An internal standard (20 µL (500 nM) of a stable isotope of hANP) and an acetic acid mixed solvent (AcOH/distilled water/DMSO=5/3/2, v/v/v) were added to 50 µL of each rat plasma sample prepared in (1) and then mixed therewith. The mixture was transferred to Amicon Ultra-0.5 50K (Millipore Corp., MA) and centrifuged at 14000 rpm at 15° C. for 30 minutes. The obtained filtrate was transferred to Amicon Ultra-0.5 3K (Millipore Corp., MA) and centrifuged again under the aforementioned conditions. The solution remaining on the filter was recovered and transferred to a 96-well deep well plate. The content of the test substance was measured by LC-MS/MS (LC: Shimadzu LC-10ADVP (Shimadzu Corp.), MS/MS: API 4000 QTrap (AB SCIEX)) to calculate the concentration in plasma. The time at which the test substance was finally detected is shown in the rightmost column of Table 2.
Evaluation of Duration Time in Blood of Rat

TABLE 2

| Compound No. of test substance | All values integrated * AUC [(pmol/ml)*h] 0-240 | All values integrated * AUC [(pmol/ml)*h] 60-240 | Pre-value and higher values integrated ** AUC [(pmol/ml)*h] 60-240 | Maximum time of detection after administration (hr) |
|---|---|---|---|---|
| Native hANP | 13.90 | −33.86 | 0.00 | 0 |
| 2-1 | 488.98 | 188.59 | 191.43 | 3 |
| 2-3 | 340.97 | 116.61 | 136.00 | 2 |
| 2-10 | 735.39 | 323.59 | 323.59 | 1.5 |
| 2-11 | 874.06 | 397.08 | 399.13 | 2 |
| 2-12 | 581.28 | 193.48 | 198.16 | 1.5 |
| 2-13 | 268.64 | 72.88 | 75.73 | 3 |
| 2-14 | 179.61 | 35.76 | 43.03 | 1.5 |
| 2-15 | 47.20 | 7.14 | 36.06 | 1.5 |
| 2-16 | 173.71 | 33.08 | 8.66 | 2 |
| 2-25 | 524.33 | 205.83 | 207.18 | 2 |
| 2-26 | 245.50 | 13.72 | 60.43 | 2 |
| 2-27 | 208.58 | 30.24 | 41.71 | 2 |
| 2-29 | 430.38 | 143.46 | 156.49 | 2 |
| 2-30 | 365.22 | 136.33 | 138.87 | 4 |

* AUC value obtained by using Pre-value (value at 0 minutes) as a baseline and integrating differences at all points on the curve from the baseline. Points on the curve under the baseline were calculated as negative values.
** AUC value obtained by using Pre-value (value at 0 minutes) as a baseline and integrating differences at only points on the curve above the baseline, from the baseline. Points on the curve under the baseline were excluded from the calculation.

*) AUC value obtained by using Pre-value (value at 0 minutes) as a baseline and integrating differences at all points on the curve from the baseline. Points on the curve under the baseline were calculated as negative values.

**) AUC value obtained by using Pre-value (value at 0 minutes) as a baseline and integrating differences at only points on the curve above the baseline, from the baseline. Points on the curve under the baseline were excluded from the calculation.

Although a transient upsurge in cGMP caused by the administration was observed in the native hANP, this cGMP level decreased 30 minutes after the administration to a level close to that before the start of the administration. The elevation of cGMP disappeared completely at 60 minutes or later. The native hANP therefore had AUC60-240 of 0 or lower and was thus confirmed to have no duration time in blood. In the detection of this test substance in plasma, the native hANP was no longer detected in the plasma sample even 15 minutes after the administration.

By contrast, the modified peptides of Example 2 exhibited a high value of AUC60-240. The cGMP concentration in plasma elevated by the administration of these test substances maintained a value higher than that before the start of the administration, even at 60 minutes or later after the administration (180 minutes later for the compounds 2-1 and 2-10, 120 minutes later for the compounds 2-12, 2-13, 2-14, and 2-16, and 60 minutes later for the compounds 2-11, 2-15, and 2-19). In addition, these test substances themselves were still detected from the plasma sample 1.5 hours or later after administration, demonstrating that the modified peptide stays in blood over a long time without being metabolized in vivo. From these results, the modified peptide of the present invention was shown to have a prolonged duration time in blood and to maintain cGMP elevating activity in this duration.

The invention claimed is:

1. A modified peptide or a pharmaceutically acceptable salt thereof, wherein the modified peptide has a structure of

[Formula 10]

(Compoumd 2-1)

wherein hANP is hANP(1-28) consisting of the amino acid sequence of SEQ ID NO: 1 and is bonded at the N terminus of the amino acid sequence to the linker structure through an amide bond; and SG is a sugar substance of following formula

[Formula 4]

Neu5Acα2-6Galβ1-4GlcNAcβ1-2Manα1⎯6

Neu5Acα2-6Galβ1-4GlcNAcβ1-2Manα1⎯3

Manβ1-4GlcNAcβ1-4Gxxβ1-(O/N-L)

wherein Gxx is GlcNAc and "O/N-L" represents binding to the linker structure through an O-glycosidic bond.

2. The modified peptide or pharmaceutically acceptable salt according to claim 1, wherein the pharmaceutically acceptable salt is a trifluoroacetate salt or an acetate salt.

3. A medicament comprising a modified peptide or a pharmaceutically acceptable salt according to claim 1.

4. The medicament according to claim 3, wherein the medicament is an agent for treating or alleviating a cardiovascular disease.

5. The medicament according to claim 4, wherein the medicament is an agent for management of a medical condition after the onset of acute heart failure.

6. A medicament comprising a modified peptide or a pharmaceutically acceptable salt according to claim 1.

7. The medicament according to claim 6, wherein the medicament is an agent for treating or alleviating a cardiovascular disease.

8. The medicament according to claim 7, wherein the medicament is an agent for management of a medical condition after the onset of acute heart failure.

9. A method for treating or alleviating a cardiovascular disease comprising
administering the modified peptide or a pharmaceutically acceptable salt according to claim 1 to a patient in need thereof.

10. A method for management of a medical condition after the onset of acute heart failure comprising
administering the modified peptide or pharmaceutically acceptable salt according to claim 1 to a patient in need thereof.

11. A method for treating or alleviating a cardiovascular disease comprising
administering the modified peptide or a pharmaceutically acceptable salt according to claim 2 to a patient in need thereof.

12. A method for management of a medical condition after the onset of acute heart failure comprising administering the modified peptide or pharmaceutically acceptable salt according to claim 2 to a patient in need thereof.

\* \* \* \* \*

SEQUENCE LISTING

```
<160> NUMBER OF SEQ ID NOS: 1

<210> SEQ ID NO 1
<211> LENGTH: 28
<212> TYPE: PRT
<213> ORGANISM: Homo sapiens
<220> FEATURE:
<223> OTHER INFORMATION: Inventor:Iwamoto, Mitsuhiro;Yamaguchi,
      Takahiro;Mori, Yutaka;Saito, Keiji;Honda, Takeshi; Nagayama, T
      akahiro

<400> SEQUENCE: 1

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25
```